(12) United States Patent
Friesen et al.

(10) Patent No.: US 9,468,604 B2
(45) Date of Patent: Oct. 18, 2016

(54) PHARMACEUTICAL COMPOSITIONS OF DISPERSIONS OF DRUG AND NEUTRAL POLYMERS

(71) Applicant: Bend Research, Inc., Bend, OR (US)

(72) Inventors: Dwayne T. Friesen, Bend, OR (US); Michael J. Gumkowski, Old Lyme, CT (US); Rodney James Ketner, Bend, OR (US); Douglas A. Lorenz, Bend, OR (US); James A. S. Nightingale, Bend, OR (US); Ravi M. Shanker, Groton, CT (US); James B. West, Bend, OR (US)

(73) Assignee: Bend Research, Inc., Bend, OR (US)

( * ) Notice: Subject to any disclaimer, the term of this patent is extended or adjusted under 35 U.S.C. 154(b) by 37 days.

(21) Appl. No.: 14/242,141

(22) Filed: Apr. 1, 2014

(65) Prior Publication Data

US 2014/0210117 A1    Jul. 31, 2014

Related U.S. Application Data

(63) Continuation of application No. 11/383,520, filed on May 16, 2006, now abandoned, which is a continuation of application No. 10/175,132, filed on Jun. 18, 2002, now abandoned.

(60) Provisional application No. 60/300,255, filed on Jun. 22, 2001.

(51) Int. Cl.
   *A61K 9/16*   (2006.01)
   *A61K 9/14*   (2006.01)

(52) U.S. Cl.
   CPC ............. *A61K 9/1682* (2013.01); *A61K 9/146* (2013.01)

(58) Field of Classification Search
   CPC .......................... A61K 9/146; A61K 9/1682
   USPC .......................................................... 264/5
   See application file for complete search history.

(56) References Cited

U.S. PATENT DOCUMENTS

| | | | |
|---|---|---|---|
| 4,540,602 A | 9/1985 | Motoyama et al. |
| 4,673,564 A | 6/1987 | Kawata et al. |
| 4,753,800 A | 6/1988 | Mozda |
| 4,894,235 A | 1/1990 | Kohne et al. |
| 4,916,138 A | 4/1990 | Ueda et al. |
| 4,983,593 A | 1/1991 | Miyajima et al. |
| 5,320,848 A | 6/1994 | Geyer et al. |
| 5,340,591 A | 8/1994 | Nakano et al. |
| 5,368,864 A | 11/1994 | Lahr et al. |
| 5,456,923 A | 10/1995 | Nakamichi et al. |
| 5,508,276 A | 4/1996 | Anderson et al. |
| 5,656,297 A | 8/1997 | Bernstein et al. |
| 5,684,040 A | 11/1997 | Grabowski et al. |
| 5,925,645 A | 7/1999 | Schmidt et al. |
| 5,935,939 A | 8/1999 | Kararli et al. |
| 5,939,099 A | 8/1999 | Grabowski et al. |
| 5,968,251 A | 10/1999 | Auweter et al. |
| 5,968,983 A | 10/1999 | Kaesemeyer |
| 6,068,856 A | 5/2000 | Sachs et al. |
| 6,077,541 A | 6/2000 | Chen et al. |
| 6,121,283 A | 9/2000 | Chang et al. |
| 6,127,383 A | 10/2000 | Schmidt et al. |
| 6,140,343 A | 10/2000 | DeNinno et al. |
| 6,147,089 A | 11/2000 | DeNinno et al. |
| 6,153,730 A | 11/2000 | Little, II |
| 6,184,230 B1 | 2/2001 | Watanabe et al. |
| 6,197,786 B1 | 3/2001 | DeNinno et al. |
| 6,221,368 B1 | 4/2001 | Breitenbach et al. |
| 6,254,889 B1 | 7/2001 | Kigoshi et al. |
| 6,264,981 B1 | 7/2001 | Zhang et al. |
| 6,310,075 B1 | 10/2001 | DeNinno et al. |
| 6,395,300 B1 | 5/2002 | Straub et al. |
| 6,423,345 B2 | 7/2002 | Bernstein et al. |
| 6,432,426 B2 | 8/2002 | Kessler |
| 6,645,528 B1 | 11/2003 | Straub et al. |
| 6,689,390 B2 | 2/2004 | Bernstein et al. |
| 6,706,283 B1 * | 3/2004 | Appel et al. ................... 424/473 |
| 6,973,741 B2 * | 12/2005 | Beyerinck et al. ............. 34/372 |
| 7,550,158 B2 * | 6/2009 | Appel et al. ................... 424/490 |
| 8,147,872 B2 * | 4/2012 | Crew et al. .................... 424/489 |
| 8,173,142 B2 * | 5/2012 | Crew et al. .................... 424/400 |
| 8,207,232 B2 * | 6/2012 | Babcock et al. ............... 514/781 |
| 8,257,739 B2 * | 9/2012 | Babcock et al. ............... 424/486 |
| 8,343,550 B2 * | 1/2013 | Beyerinck et al. ........... 424/490 |
| 8,828,442 B2 * | 9/2014 | Babcock et al. ............... 424/489 |
| 8,828,443 B2 * | 9/2014 | Beyerinck et al. ........... 424/489 |
| 8,883,209 B2 * | 11/2014 | Babcock et al. ............... 424/484 |
| 8,940,800 B2 * | 1/2015 | Babcock et al. ............... 514/781 |
| 2001/0036482 A1 | 11/2001 | Fredell et al. |

(Continued)

FOREIGN PATENT DOCUMENTS

| | | |
|---|---|---|
| DE | 19627419 | 1/1998 |
| DE | 19627430 | 1/1998 |

(Continued)

OTHER PUBLICATIONS

Chowdary et al., "Evaluation of water Soluble Cellulose Polymers as Carriers for Naproxen Solid Dispersions," *The Eastern Pharmacist*, (May 1991), pp. 129-131.

(Continued)

*Primary Examiner* — Blessing M Fubara

(74) *Attorney, Agent, or Firm* — Klarquist Sparkman, LLP

(57) ABSTRACT

In one aspect, pharmaceutical compositions comprising dispersions of an acid-sensitive drug and a neutral dispersion polymer are disclosed. The acid-sensitive drug has improved chemical stability relative to dispersions of the drug and acidic polymers. In another aspect, pharmaceutical compositions of low-solubility drugs and amphiphilic, hydroxy-functional vinyl copolymers are disclosed.

19 Claims, No Drawings

(56) References Cited

U.S. PATENT DOCUMENTS

| | | |
|---|---|---|
| 2001/0053778 A1 | 12/2001 | Hoover et al. |
| 2001/0053791 A1 | 12/2001 | Babcock et al. |
| 2001/0056127 A1 | 12/2001 | Kessler |
| 2007/0141150 A1 | 6/2007 | Kandarapu et al. |

FOREIGN PATENT DOCUMENTS

| | | |
|---|---|---|
| DE | 19627431 | 1/1998 |
| DE | 19704243 | 8/1998 |
| DE | 19704244 | 8/1998 |
| DE | 19709125 | 9/1998 |
| DE | 19741051 | 3/1999 |
| DE | 19741399 | 3/1999 |
| DE | 19741400 | 3/1999 |
| DE | 19832159 | 3/1999 |
| EP | 0344603 | 12/1989 |
| EP | 0371471 | 6/1990 |
| EP | 0462066 | 12/1991 |
| EP | 0580860 | 2/1994 |
| EP | 0232155 | 10/1994 |
| EP | 0784974 | 7/1997 |
| EP | 0818448 | 1/1998 |
| EP | 0852140 | 7/1998 |
| EP | 0872233 | 10/1998 |
| EP | 0901786 | 3/1999 |
| EP | 0987251 | 3/2000 |
| EP | 0988863 | 3/2000 |
| EP | 0992496 | 4/2000 |
| EP | 0796846 | 7/2000 |
| EP | 1027888 A2 | 8/2000 |
| EP | 1027887 | 2/2001 |
| EP | 1027888 | 2/2001 |
| EP | 1027886 | 3/2001 |
| EP | 0784974 A1 | 5/2003 |
| JP | 11049743 | 2/1999 |
| WO | WO9311749 | 6/1993 |
| WO | WO9638153 | 12/1996 |
| WO | WO9708950 | 3/1997 |
| WO | WO9744014 | 11/1997 |
| WO | WO9804528 | 2/1998 |
| WO | WO9835937 | 8/1998 |
| WO | WO9908660 | 2/1999 |
| WO | WO9914174 | 3/1999 |
| WO | WO9914204 | 3/1999 |
| WO | WO9914215 | 3/1999 |
| WO | WO9922738 | 5/1999 |
| WO | WO9932118 | 7/1999 |
| WO | WO9940061 | 8/1999 |
| WO | WO9941237 | 8/1999 |
| WO | WO0017164 | 3/2000 |
| WO | WO0017165 | 3/2000 |
| WO | WO0017166 | 3/2000 |
| WO | WO0018721 | 4/2000 |
| WO | WO0018723 | 4/2000 |
| WO | WO0018724 | 4/2000 |
| WO | WO0064414 | 11/2000 |
| WO | WO0115664 | 3/2001 |
| WO | WO0122938 | 4/2001 |
| WO | WO0130288 | 5/2001 |
| WO | WO0141536 | 6/2001 |
| WO | WO0142221 | 6/2001 |
| WO | WO0147498 | 7/2001 |
| WO | WO0185135 | 11/2001 |
| WO | WO0211710 | 2/2002 |

OTHER PUBLICATIONS

Chowdary et al., "Dissolution, Bioavailability and Ulcerogenic Studies on Solid Dispersions of Indomethacin in water Soluble Cellulose Polymers," *Drug Development and Industrial Pharmacy*, 20:5, pp. 799-813 (Jan. 1994).

Chowdary et al., "Solid Dispersions of Nimodipine: Physico-Chemical and Dissolution Rate Studies," *Indian Drugs*, 32:11, pp. 537-542 (Nov. 1995).

English translation of Patent Abstract of Japan publication No. 56-49314, <http://www.19.ipdl.inpit.go.jp/PA1/result/detail/main/wAAAsDaOMWDA35604931...2008/04/16>, 2008.

Jans-Frontini et al., "Stability of Drugs in Solid Dispersions: Effect of Glass Transition on Degradation Kinetics under Stress in Systems of Reserpine and PVP," *Eur. J. Pharm. Biopharm.*, vol. 42, No. 5, pp. 303-312 (1996).

Kai et al., "Oral Absorption Improvement of Poorly Soluble Drug Using Solid Dispersion Technique," *Pharmaceutical Society of Japan*, vol. 44, No. 3, pp. 568-571 (Mar. 1996).

Kohri et al, "Improving the Oral Bioavailability of Albendazole in Rabbits by the Solid Dispersion Technique," *J. Pharm. Pharmacol.*, vol. 51, No. 2, pp. 159-164 (Feb. 1999).

Leuner et al., "Improving drug solubility for oral delivery using solid dispersions," in *European Journal of Pharmaceutics and Biopharmaceutics*, vol. 50, pp. 47-50 (Jul. 2000).

Owusu-Ababio et al., "Polymers Applied in Solid Dispersion Technology," *Clin. Research & Reg. Affairs*, vol. 15, No. 1, pp. 25-45 (Jan. 1998).

Pavletich, Nikola P., "Mechanisms of Cyclin-dependent Kinase Regulation: Structures of Cdks, their Cyclin Activators, and Cip and INK4 Inhibitors," *J. Mol. Biol.*, vol. 287, No. 5, pp. 821-828 (Apr. 1999).

Sarisuta, N., "Physico-chemical characterization of interactions between erythromycin and various film polymers," *International J. of Pharmaceutics*, vol. 186, No. 2, pp. 109-118 (Sep. 1999).

Schmidt C. et al, "Incorporation of polymeric nanoparticles into solid forms," *J. of Controlled Release*, vol. 57, No. 2, pp. 115-125 (Feb. 1999).

Shah, J.C., "Preformulation study of etoposide: II. Increased solubility and dissolution rate by solid-solid dispersion," *International J. of Pharmaceutics*, vol. 113, No. 1 pp. 103-111 (Jan. 1995).

Snyder et al., "14.2 Measurement of Signals," in *Practical HPLC Method Development*, 2$^{nd}$ Edition, John Wiley & Sons, Inc., New York, NY, pp. 647-656 (Mar. 1997).

Suzuki et al., "Influence of water-Soluble Polymers on the Dissolution of Nifedipine Solid Dispersions with Combined Carriers," *Chem. Pharm. Bull.*, vol. 46, No. 3 pp. 482-487 (Mar. 1998).

Windholz, M. et al., "The Merck Index: An Encyclopedia of Chemicals, Drugs, and Biologicals", 10th Edition, pp. 531-532 (Dec. 1983).

Yono et al., "Improvement of Bioavailability of Poorly Water-Soluble Drug by Nanoparticles from a Solid Dispersion System," *Yakuzaigaku*, vol. 57, No. 2, pp. 95-101 (Jun. 1997).

\* cited by examiner

PHARMACEUTICAL COMPOSITIONS OF DISPERSIONS OF DRUG AND NEUTRAL POLYMERS

This is a Continuation of U.S. patent application Ser. No. 11/383,520, filed May 16, 2006, which in turn is a Continuation of U.S. patent application Ser. No. 10/175,132, filed Jun. 18, 2002, now abandoned, which application claim the benefit of U.S. Provisional Patent Application No. 60/300,255, filed Jun. 22, 2001, entitled Pharmaceutical Compositions of Dispersions of Drugs and Neutral Polymers, all of which are incorporated herein by reference.

BACKGROUND OF THE INVENTION

This invention relates to pharmaceutical compositions comprised of amorphous dispersions of drugs and neutral polymers that provide either improved chemical stability, concentration-enhancement, or both improved chemical stability and concentration-enhancement.

It is sometimes desired to form a solid amorphous dispersion of a drug and a polymer. One reason for forming dispersions is that the aqueous concentration of a poorly soluble drug may be improved by forming an amorphous dispersion of the drug and a polymer. For example, Curatolo, et al., EP 0 901 786 A2 disclose forming pharmaceutical spray dried dispersions of sparingly soluble drugs and the polymer hydroxypropyl methyl cellulose acetate succinate. The spray dried dispersions disclosed in Curatolo et al. provide superior aqueous concentration relative to dispersions formed from other methods and relative to the crystalline drug alone.

Similarly, others have recognized the enhancement in aqueous concentration afforded by dispersing a drug in a polymer. Nakamichi, et al., U.S. Pat. No. 5,456,923 disclose solid dispersions formed by twin-screw extrusion of low solubility drugs and various polymers.

Another reason for forming an amorphous dispersion is that it may be desired to use a particular process for forming a pharmaceutical composition, such as a spray-coating or wet granulation process which results in the formation of amorphous drug, in whole or in part, rather than pure crystalline drug. Thus, amorphous dispersions may be formed of drugs which are not low-solubility drugs.

However, regardless of whether the drug is poorly soluble, the inventors have determined that for some drug and polymer dispersions, the drug is not chemically stable in the dispersion. In particular, the inventors have observed that for dispersions containing certain drugs and polymers, the drug degrades in the dispersion over time, resulting in a loss of potency for the composition. The inventors have found this problem to arise especially for acid-sensitive drugs.

Drug degradation within the dispersion is a particular problem for low-solubility, acid-sensitive drugs, since the increase in aqueous concentration of the drug provided by the dispersion is offset by decreasing drug purity. In general, the greatest concentration-enhancement is often observed through the use of acidic dispersion polymers, especially acidic, cellulosic enteric polymers. However, the use of such acidic polymers within the dispersion is precluded due to the acid-sensitive nature of the drug.

Accordingly, there is still a need for pharmaceutical compositions of dispersions containing acid-sensitive drugs that are chemically stable over time. Likewise, there is also a continuing need to provide concentration-enhancement for low-solubility drugs.

BRIEF SUMMARY OF INVENTION

The present invention relates to, in a first aspect, pharmaceutical compositions comprising a solid amorphous dispersion of an acid-sensitive drug and a neutral dispersion polymer, wherein said composition provides improved chemical stability relative to a control acidic dispersion comprising an equivalent quantity of said drug and an acidic polymer.

In a preferred embodiment, the acid-sensitive drug has one or more functional groups selected from the group consisting of sulfonyl ureas, hydroxamic acids, hydroxy amides, carbamates, acetals, hydroxy ureas, esters, and amides.

In another preferred embodiment, the acid-sensitive drug when present in a control acidic dispersion and stored for a period of six months at 40° C. and 75% relative humidity has a degree of degradation of at least 0.01%, preferably at least 0.1%.

In another preferred embodiment, the drug is quinoxaline-2-carboxylic acid [4(R)-carbamoyl-1(S)-3-fluorobenzyl-2(S),7-dihydroxy-7-methyl-octyl]amide; quinoxaline-2-carboxylic acid [1-benzyl-4-(4,4-difluoro-cyclohexyl)-2-hydroxy-4-hydroxycarbamoyl-butyl]-amide; quinoxaline-2-carboxylic acid [1-benzyl-4-(4,4-difluoro-1-hydroxy-cyclohexyl)-2-hydroxy-4-hydroxycarbamoyl-butyl]-amide; (+)-N-{3-[3-(4-fluorophenoxy)phenyl]-2-cyclopenten-1-yl}-N-hydroxyurea; omeprazole; etoposide; famotidine; erythromycin; quinapril; lansoprazole; or progabide.

In another preferred embodiment, the drug in said composition has a relative degree of improvement in chemical stability of at least 1.25, preferably at least 3, more preferably at least 10. Preferably, drug in said composition has a relative degree of improvement in chemical stability of at least 1.25 when stored at 40° C. and 75% relative humidity for a period of six months.

In another preferred embodiment, the dispersion polymer is ionizable, non-ionizable, cellulosic, or non-cellulosic. Preferred cellulosic dispersion polymers include hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose. Preferred non-cellulosic dispersion polymers include vinyl polymers and copolymers having one or more substituents comprising hydroxyl-containing repeat units, alkylacyloxy-containing repeat units, or cyclicamido-containing repeat units; polyvinyl alcohols that have at least a portion of their repeat units in the unhydrolyzed form; polyvinyl alcohol polyvinyl acetate copolymers; polyethylene glycol, polyethylene glycol polypropylene glycol copolymers, polyvinyl pyrrolidone; polyethylene polyvinyl alcohol copolymers, and polyoxyethylene-polyoxypropylene block copolymers. Preferrably, the non-cellulosic dispersion polymer comprising a vinyl copolymer having: (1) hydroxyl-containing repeat units; and (2) hydrophobic repeat units.

In another preferred embodiment, the acid-sensitive drug is also a low-solubility drug and said dispersion polymer is concentration-enhancing. Preferably, the drug has a minimum solubility in aqueous solution in the absence of said dispersion polymer of less than 1 mg/mL at any pH of from about 1 to about 8, more preferably the minimum aqueous solubility is less than 0.01 mg/mL.

In another preferred embodiment, the drug has a dose-to-aqueous-solubility ratio of at least 10 mL.

In yet another preferred embodiment, the dispersion polymer is present in an amount sufficient to provide a maximum concentration of said acid-sensitive drug in a use environment that is at least 1.25-fold, preferably at least 2-fold, that provided by a second control composition comprising an equivalent quantity of said acid-sensitive drug and free from said dispersion polymer.

In another preferred embodiment, the dispersion polymer is present in a sufficient amount so that said dispersion provides in a use environment an area under the concentration versus time curve for any period of at least 90 minutes between the time of introduction into the use environment and about 270 minutes following introduction to the use environment that is at least 1.25-fold, preferably at least 2-fold, that provided by a second control composition comprising an equivalent quantity of said acid-sensitive drug and free from said dispersion polymer.

In another preferred embodiment, the dispersion polymer is present in a sufficient amount so that said dispersion provides a relative bioavailability that is at least 1.25, preferably at least 2, relative to a second control composition comprising an equivalent quantity of said acid-sensitive drug and free from said polymer.

In yet another preferred embodiment, the drug is base-sensitive and said dispersion polymer is non-ionizable.

In another preferred embodiment, the dispersion comprising a buffer. Preferred buffers include sodium acetate, ammonium acetate, sodium carbonate, sodium bicarbonate, disodium hydrogen phosphate and trisodium phosphate. Preferably, the buffer comprises at least 10 wt % of said dispersion.

In another preferred embodiment, the dispersion has a pH from about 6 to about 10. Preferably, the composition comprising a base and the dispersion has a pH of from about 6 to about 10.

In still another preferred embodiment, the acid-sensitive drug is a low-solubility drug and the composition comprising a second polymer, said dispersion is free from at least a portion of said second polymer, and said second polymer is concentration-enhancing. Preferably, the second polymer has at least one hydrophobic portion and at least one hydrophilic portion. More preferably, the second polymer is a cellulosic, ionizable polymer, comprising hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Other more preferable second polymers are non-ionizable cellulosic polymers comprising hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose. Still other more preferably second polymers are ionizable, non-cellulosic polymers comprising carboxylic acid functionalized polymethacrylates, carboxylic acid functionalized polyacrylates, amine-functionalized polyacrylates, amine-functionalized polymethacrylates, proteins, and carboxylic acid functionalized starches.

Yet other more preferable second polymers are non-ionizable, non-cellulosic polymers comprising vinyl polymers and copolymers having one or more substituents such as hydroxyl-containing repeat units, alkylacyloxy-containing repeat units, or cyclicamido-containing repeat units; polyvinyl alcohols that have at least a portion of their repeat units in the unhydrolyzed form; polyvinyl alcohol polyvinyl acetate copolymers; polyethylene glycol, polyethylene glycol polypropylene glycol copolymers, polyvinyl pyrrolidone polyethylene polyvinyl alcohol copolymers, and polyoxyethylene-polyoxypropylene block copolymers. Within these vinyl copolymers, preferably the second polymer has (1) hydroxyl-containing repeat units; and (2) hydrophobic repeat units.

In another preferred embodiment, the drug in said composition has a relative degree of improvement in chemical stability of at least 1.25, preferably at least 3.

In another preferred embodiment, the dispersion is mixed with said second polymer. Another preferred embodiment, the dispersion and said second polymer occupy separate regions of said composition.

In still another preferred embodiment, the second polymer is present in an amount sufficient to provide a maximum concentration of said acid-sensitive drug in a use environment that is at least 1.25-fold, preferably at least 2-fold, that of a control composition comprising an equivalent quantity of said dispersion and free from said second polymer.

In another preferred embodiment, the second polymer is present in a sufficient amount so that said composition provides in a use environment an area under the concentration versus time curve for any period of at least 90 minutes between the time of introduction into the use environment and about 270 minutes following introduction to the use environment that is at least 1.25-fold, preferably at least 2-fold, that of a control composition comprising an equivalent quantity of said dispersion and free from said second polymer.

In another preferred embodiment, the second polymer is present in a sufficient amount so that said composition provides a relative bioavailability that is at least 1.25, preferably at least 2, relative to a control composition comprising an equivalent quantity of said dispersion and free from said second polymer.

A second aspect of the present invention relates to methods for treating a condition in an animal comprising by administering to an animal in need of such treatment a therapeutic amount of the above-described composition.

A third aspect of the present invention relates to methods of administering a pharmaceutical composition comprising co-administering to a patient: (a) a solid amorphous dispersion comprising an acid-sensitive drug and a neutral polymer; and (b) a second polymer, wherein said dispersion is substantially free from said second polymer and said second polymer is concentration-enhancing.

In one preferred embodiment, the second polymer is cellulosic, such as hydroxypropyl methyl cellulose acetate succinate, cellulose acetate phthalate, hydroxypropyl methyl cellulose phthalate, methyl cellulose acetate phthalate, cellulose acetate trimellitate, hydroxypropyl cellulose acetate phthalate, cellulose acetate terephthalate and cellulose acetate isophthalate.

In another preferred embodiment, the dispersion is administered separately from said second polymer. Preferably, the dispersion and said second polymer are administered at about the same time.

A fourth aspect of the present invention relates to pharmaceutical compositions that a solid amorphous dispersion of a low-solubility drug and a neutral dispersion polymer, wherein said neutral dispersion polymer comprising a vinyl copolymer having hydrophilic hydroxyl-containing repeat units and hydrophobic repeat units.

In one preferred embodiment, the hydrophobic repeat units include ester-linked alkylate or arylate substituents. More preferably, the hydrophobic repeat unit is an alkylate such as acetate, propionate, and butyrate. More preferably, the hydrophobic repeat units comprise the acetylated form of the hydroxyl-containing repeat units. Preferably, the acetylated form of the hydroxyl-containing repeat units comprise 0.5 to 30% of the repeat units of the polymer.

In another preferred embodiment, the hydroxyl-containing repeat unit is vinyl alcohol.

In another preferred embodiment, the dispersion polymer is a vinyl alcohol/vinyl acetate copolymer. Preferably, from about 0.5% to about 30% of the repeat units of said polymer are vinyl acetate.

A fifth aspect of the present invention relates to pharmaceutical compositions that include a solid amorphous dispersion comprising a low-solubility drug, a neutral dispersion polymer, and an excipient such as a base or a buffer.

In a preferred embodiment, the neutral dispersion polymer is concentration enhancing. Preferred neutral dispersion polymers are present in an amount sufficient to provide a maximum concentration of said low-solubility drug in a use environment that is at least 1.25-fold, preferably at least 2-fold, that provided by a second control composition comprising an equivalent quantity of said low-solubility drug and free from a concentration-enhancing polymer.

In another preferred embodiment, the neutral dispersion polymer is present in a sufficient amount so that said composition, when introduced to a use environment, provides an area under the concentration-versus time curve for any period of at least 90 minutes between the time of introduction to the use environment and about 270 minutes following introduction to the use environment that is at least 1.25-fold, preferably at least 2-fold, that of a second control composition comprising an equivalent quantity of said low-solubility drug and free from a concentration-enhancing polymer.

In another preferred embodiment, the neutral dispersion polymer is present in a sufficient amount so that said composition provides a relative bioavailability that is at least 1.25, preferably at least 2, relative to a second control composition comprising an equivalent quantity of said low-solubility drug and free from a concentration-enhancing polymer.

In another preferred embodiment, the drug in said composition has a relative degree of improvement in chemical stability of at least 1.25.

In yet another preferred embodiment, the composition provides improved chemical stability relative to a control composition, wherein said control comprising an equivalent quantity of a dispersion of said drug and said neutral dispersion polymer but free from said base and said buffer.

As described more fully below, the term "use environment" may refer to the in vivo environment of the gastrointestinal (GI) tract of an animal, particularly a human, or the in vitro environment of a test solution, such as phosphate buffered saline (PBS) or model fasted duodenal (MFD) solution.

The composition may be dosed in a variety of dosage forms, including both immediate release and controlled release dosage forms, the latter including both delayed and sustained release forms. The composition may include blends of polymers.

The various aspects of the present invention provide one or more of the following advantages. For those embodiments comprising an acid-sensitive drug, the inventors have recognized that a problem with forming dispersions of acid-sensitive drugs is that for some dispersions, the drug does not remain chemically stable in the dispersion over time. The inventors have found that acid-sensitive drugs dispersed in an acidic polymer, such as hydroxypropyl methyl cellulose acetate succinate (which has carboxylic acid functional groups), have a tendency to chemically degrade over time. It is believed that the presence of acidic ionic groups on the acidic polymer may either catalyze degradation of the drug or react directly with the drug. In any event, regardless of the particular degradation mechanism, the inventors have substantially reduced, if not eliminated the problem of drug degradation, by forming dispersions using neutral polymers, i.e. polymers that do not include acidic functional groups. Thus, the present invention is able to realize the advantages of forming dispersions of acid-sensitive drugs by improving the chemical stability of the acid-sensitive drug in the dispersion.

In addition, the invention in some embodiments further provides enhanced aqueous concentration and bioavailability for low-solubility drugs while at the same time minimizing the loss in potency and generation of impurities in the composition resulting from reaction or degradation of the drug when in the presence of an acidic species, such as an acidic dispersion polymer.

For those aspects comprising neutral vinyl copolymers of the present invention having hydroxyl-containing repeat units and hydrophobic repeat units, the compositions provide surprisingly effective concentration-enhancement. The polymers may be used with any low-solubility drug to improve the concentration of the drug in a use environment.

The foregoing and other objectives, features, and advantages of the invention will be more readily understood upon consideration of the following detailed description of the invention.

DETAILED DESCRIPTION OF THE INVENTION

The pharmaceutical compositions of the present invention comprise solid amorphous dispersions of a drug and a neutral dispersion polymer. The present invention finds utility anytime it is desired to improve either the chemical stability of an acid-sensitive drug, to improve the concentration or bioavailability of a low-solubility drug, or both. In one embodiment of the invention, the dispersions of the present invention improve the chemical stability of acid-sensitive drugs. Thus, the dispersions may be used to prevent degradation of the drug due to interactions with dispersion polymers, acidic dispersion species, or other acidic excipients present in the composition. In another embodiment, the dispersions improve the concentration or bioavailability of a low-solubility drug. Suitable acid-sensitive drugs, low-solubility drugs, neutral polymers and methods for making the dispersions are discussed in more detail below.

Acid-Sensitive Drugs

The term "drug" is conventional, denoting a compound having beneficial prophylactic and/or therapeutic properties when administered to an animal, especially humans. In one embodiment of the invention, the drug is an acid-sensitive drug, meaning that the drug either chemically reacts with or otherwise degrades in the presence of acidic species. Acid-sensitive drugs often include functional groups which are reactive under acidic conditions, such as sulfonyl ureas, hydroxamic acids, hydroxy amides, carbamates, acetals, hydroxy ureas, esters, and amides. Drugs which include such functional groups may be prone to reactions such as hydrolysis, lactonization, or transesterification in the presence of acidic species.

Acid-sensitive drugs may be identified experimentally by determining whether the drug chemically reacts or degrades when dispersed in an acidic polymer. In particular, as used herein, the term "acid-sensitive drug" refers to a drug which, when dispersed in a "control acidic dispersion," degrades when stored under controlled aging conditions either for long storage times at ambient storage conditions or for short storage times under elevated temperature and relative humidity conditions.

The "control acidic dispersion" used to determine whether a drug is acid-sensitive is a dispersion of the drug and a pharmaceutically acceptable acidic polymer. A convenient pharmaceutically acceptable acidic polymer for use as the acidic dispersion polymer is the HF grade of hydroxypropyl methyl cellulose acetate succinate (HPMCAS), which is an acidic, or so-called enteric polymer having carboxylic acid functional groups, and a $pK_a$ of about 5. The HPMCAS in the control acidic dispersion should have a minimum degree of substitution of succinate groups ($O(CO)CH_2CH_2(CO)OH$) of at least 4 wt % (or at least about 100 milliequivalents of carboxylic acid functional groups per mole of polymer). Alternatively, other acidic polymers which are at least as acidic as the HF grade of HPMCAS may be used, such as hydroxypropyl methyl cellulose acetate phthalate (HPMCP) or cellulose acetate phthalate (CAP). As with HPMCAS, such polymers should have at least about 100 milliequivalents of carboxylic acid functional groups per mole of polymer. The amount of acidic polymer present in the control acidic dispersion may vary, but should comprise at least 50 wt % or more of the control acidic dispersion. A drug is an acid-sensitive drug if it meets the drug degradation criteria described below in at least one control acidic dispersion comprised of 25 wt % drug and 75 wt % of the dispersion polymer HPMCAS, HPMCP or CAP.

In general, drug degradation may be measured using any conventional method for measuring the purity or potency of drug in a pharmaceutical composition. For example, the amount of active drug present in a dispersion may be measured initially using high-performance liquid chromatography (HPLC) or any other analytical technique well known in the art. Alternatively, the amount of drug initially present may be calculated from the amount of drug present in the dispersion formulation. The potency of the dispersion may then be measured after storage at controlled temperature and humidity conditions for an appropriate period of time. A decrease in potency indicates that a chemical reaction has occurred, leading to a decrease in the amount of active drug present in the dispersion, and is an indication of poor chemical stability.

An alternative method used to evaluate chemical stability is to analyze the rate of increase in the amount of drug degradant(s) in the dispersion, which would indicate reaction of the drug to form the degradant(s). An HPLC or other analytical technique may be used to determine the concentration of drug degradant(s) in a dispersion. The amount of the degradant(s) is measured before and after storage under controlled aging conditions. The amount of increase in the drug degradant(s) may be used to determine the amount of decrease in "percent drug purity." The "percent drug purity" is defined as 100 times the total amount of drug present divided by the total amount of drug initially present. Thus, a percent drug purity at a given time may be calculated by the formula $$\text{wt \% drug purity} = \left(\frac{\text{total } amt. \text{ of drug present}}{\text{total } amt. \text{ of drug } init. \text{ present}}\right) * 100$$

When the drug purity is calculated from the total amount of impurities, "percent drug purity" may be calculated by assuming that the "total amount of drug initially present," given in wt %, is equal to 100 wt % minus the wt % of total initial impurities, and that "total amount of drug present" is equal to 100 wt % minus the wt % of total impurities after storage, that is, at some later time. This method is equivalent to calculating "percent drug purity" by the formula $$\text{wt \% drug purity} = \left[1 - \left(\frac{\text{total } amt. \text{ of impurities}}{\text{total } amt. \text{ of drug } init. \text{ present}}\right)\right] * 100$$

The rate at which drug degradation occurs is generally dependent on the storage conditions. The drug, when formulated as a composition of the present invention, should be stable at ambient temperature and humidity conditions (e.g., relative humidities of 20% to 60%) for long periods of time, such as months or years. However, to expedite testing, the storage conditions may employ elevated temperature and/or humidity to simulate longer storage times at ambient conditions. The storage time may vary from a few days to weeks or months, depending on the reactivity of the drug and the storage conditions.

A "degree of degradation" of drug following storage may be determined by subtracting the final percent drug purity (either determined by measuring the decrease in drug present or an increase in the amount of drug degradants present) from the initial percent drug purity. For example, for a dispersion initially containing 100 mg drug, and no measurable impurities, the initial percent drug purity is 100 wt %. If, after storage, the amount of drug in the dispersion decreases to 95 mg, the final percent drug purity would be 95 wt % and the "degree of degradation" is 5 wt % (100 wt %-95 wt %). Alternatively, if 100 mg of drug substance were found to initially have 1 mg of impurities present, it would have an initial "percent drug purity" of 99 wt %. If, after storage, the total impurities present had increased to 6 wt %, the final percent drug purity would be 94 wt % and the "degree of degradation" would be 5 wt % (99 wt %-94 wt %).

Alternatively, "degree of degradation" can be determined by subtracting from the amount of one or more specific degradants initially present from the amount of that specific drug degradant present after storage. Such a measure is useful where there are several drug degradants, of which only one (or a few) is of concern. The degree of degradation may be calculated on the basis of only those degradants that are of concern, rather than all of the degradant. For example, if a drug initially contained a specific degradant at a concentration of 1 wt % and after storage the concentration of that degradant was 6 wt %, the degree of degradation would be 5 wt % (6 wt %-1 wt %).

Returning now to the determination of an acid-sensitive drug, as used herein an "acid-sensitive" drug is one in which the degree of degradation of the drug in a control acidic dispersion (as defined above) is at least 0.01 wt % in a six month period at 40° C. and 75% relative humidity (RH), or alternatively, in which the degree of degradation is at least 0.01 wt % in a one year period at 30° C. at 60% RH, or as defined below with respect to degradation of drug in an acidic aqueous solution. These storage conditions are conventional and well-known in the art, and are the ICH recommendations for storage conditions to be used to evaluate the stability of a drug after storage for two years at ambient temperature and humidity. A relative degree of improvement may become apparent within a shorter time, such as three to five days, and shorter storage times may be used for some very acid-sensitive drugs.

The need for the present invention will generally be greater when the drug's reactivity with or sensitivity to acidic species increases. Dispersions of the present invention are preferred for acid-sensitive drugs having a degree of degradation that is greater than the minimum level when in the presence of an acidic dispersion polymer. Thus, the dispersions of the present invention are preferred for "very acid-sensitive drugs." Very acid-sensitive drugs are those which, when dispersed in a control acidic dispersion, have a degree of degradation of at least 0.1 wt % when stored at 40° C./75% RH for six months. The dispersions are even more preferred for drugs which have a degree of degradation of at least 1 wt %, and are most preferred for drugs which have a degree of degradation of at least 5.0 wt % when stored at 40° C./75% RH for six months.

In addition, the acid-sensitive drug when present in the control acidic dispersion degrades at a rate that is greater than the rate at which pure drug in the amorphous form, or if the amorphous form is physically unstable, the crystalline form, degrades. A relative degree of degradation of the drug in a control acidic dispersion to the pure form of the drug may be determined by taking the ratio of the degree of degradation of the drug in the control acidic dispersion and the degree of degradation of the pure form of the drug under the same storage conditions for the same storage time period. For example, where the degree of degradation of the drug in the control acidic dispersion is 5 wt % and the degree of degradation of the pure amorphous form of the drug is 0.1 wt %, the relative degree of degradation of the drug in the control acidic dispersion to the pure form of the drug is 50 (5 wt %/0.1 wt %). An acid-sensitive drug is one in which the relative degree of degradation of the drug in the control composition to the pure form of the drug is at least 2. The invention finds increasing utility as the relative degree of degradation increases above this minimum level. Thus, the invention is preferred for drugs having a relative degree of degradation of about 3 or more, and more preferred for drugs having a relative degree of degradation of about 5 or more.

Alternatively, another test to determine whether a drug is an acid sensitive drug as used herein is to administer the drug to an acidic aqueous solution and plot drug concentration versus time. The acidic solution should have a pH of from 1-4. Drugs which are acid sensitive are those for which the drug concentration decreases by at least 1% within 24 hours of administration of the drug to the acidic solution. If the drug concentration changes by 1% in the 6-24 hour time period, then the drug is "slightly acid-sensitive." If the drug concentration changes by 1% in the 1-6 hour time period, then the drug is "moderately acid-sensitive." If the drug concentration changes by 1% in less than 1 hour, then the drug is "highly acid-sensitive." The present invention finds increasing utility for drugs which are slightly acid-sensitive, moderately acid-sensitive and highly acid-sensitive.

Specific examples of acid-sensitive drugs deliverable by the invention are set forth below, by way of example only. Each named drug should be understood to include the neutral form of the drug, pharmaceutically acceptable salts, and prodrugs. Examples of acid-sensitive drugs include quinoxaline-2-carboxylic acid [4(R)-carbamoyl-1(S)-3-fluorobenzyl-2(S),7-dihydroxy-7-methyl-octyl]amide; quinoxaline-2-carboxylic acid [1-benzyl-4-(4,4-difluoro-cyclohexyl)-2-hydroxy-4-hydroxycarbamoyl-butyl]-amide; quinoxaline-2-carboxylic acid [1-benzyl-4-(4,4-difluoro-1-hydroxy-cyclohexyl)-2-hydroxy-4-hydroxycarbamoyl-butyl]-amide; (+)-N-{3-[3-(4-fluorophenoxy)phenyl]-2-cyclopenten-1-yl}-N-hydroxyurea; omeprazole; etoposide; famotidine; erythromycin; quinapril; lansoprazole; and progabide.

Low-Solubility Drugs

In another embodiment of the invention, the drug is a "low-solubility drug," meaning that the drug may be either "substantially water-insoluble," which means that the drug has a minimum aqueous solubility at physiologically relevant pH (e.g., pH 1-8) of less than 0.01 mg/mL, "sparingly water-soluble," that is, has an aqueous solubility up to about 1 to 2 mg/mL, or even low to moderate aqueous-solubility, having an aqueous-solubility from about 1 mg/mL to as high as about 20 to 40 mg/mL. In general, it may be said that the drug has a dose-to-aqueous solubility ratio greater than 10 mL, and more typically greater than 100 mL, where the drug solubility (mg/mL) is the minimum value observed in any physiologically relevant aqueous solution (e.g., those with pH values between 1 and 8) including USP simulated gastric and intestinal buffers, and dose is in mg. The dose-to-aqueous-solubility-ratio may be determined by simply dividing the dose (in mg) by the aqueous solubility (in mg/mL).

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, and antiviral agents, glycogen phosphorylase inhibitors, and cholesterol ester transfer protein inhibitors.

Each named drug should be understood to include the neutral form of the drug, pharmaceutically acceptable salts, as well as prodrugs. Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl}-N-hydroxyurea; a specific example of a barbiturate is phenobarbital; specific examples of antivirals include acyclovir, nelfinavir, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethylphenoxy)-pyridin-4-yl]-(1-ethylpropyl)-amine, 3,5-dimethyl-4-(3'-pentoxy)-2-(2',4',6'-trimethylphenoxy)pyridine, pyroxidine, fluoxetine, paroxetine, venlafaxine and sertraline; specific examples of antibiotics include carbenicillin indanylsodium, bacampicillin hydrochloride, troleandomycin, doxycyline hyclate, ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, decarboethoxyloratadine and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R—(R*S*)]-5-chloro-N-[2-hydroxy-3-{methoxymethylamino}-3-oxo-1-(phenylmethyl) propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide; and specific examples of cholesterol ester transfer protein (CETP) inhibitors include [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, [2R,4S] 4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R,4S] 4-[(3,5-Bis-trifluoromethyl-benzyl)-methoxycarbonyl-amino]-2-ethyl-6-trifluoromethyl-3,4-dihydro-2H-quinoline-1-carboxylic acid isopropyl ester.

The invention is not limited by any particular structure or group of CETP inhibitors. Rather, the invention has general applicability to CETP inhibitors as a class, the class tending to be composed of compounds having low solubility. Compounds which may be the subject of the invention may be found in a number of patents and published applications, including DE 19741400 A1; DE 19741399 A1; WO 9914215 A1; WO 9914174; DE 19709125 A1; DE 19704244 A1; DE 19704243 A1; EP 818448 A1; WO 9804528 A2; DE 19627431 A1; DE 19627430 A1; DE 19627419 A1; EP 796846 A1; DE 19832159; DE 818197; DE 19741051; WO 9941237 A1; WO 9914204 A1; WO 9835937 A1; JP 11049743; WO 200018721; WO 200018723; WO 200018724; WO 200017164; WO 200017165; WO 200017166; EP 992496; and EP 987251, all of which are hereby incorporated by reference in their entireties for all purposes.

The invention is useful for CETP inhibitors that have sufficiently low aqueous solubility, low bioavailability or slow rate of absorption such that it is desirable to increase their concentration in an aqueous environment of use. Therefore, anytime one finds it desirable to raise the aqueous concentration of the CETP inhibitor in a use environment, the invention will find utility. The CETP inhibitor is "substantially water-insoluble" which means that the CETP inhibitor has a minimum aqueous solubility of less than about 0.01 mg/mL (or 10 µg/ml) at any physiologically relevant pH (e.g., pH 1-8) and at about 22° C. (Unless otherwise specified, reference to aqueous solubility herein and in the claims is determined at about 22° C.) Compositions of the present invention find greater utility as the solubility of the CETP inhibitors decreases, and thus are preferred for CETP inhibitors with solubilities less than about 2 µg/mL, and even more preferred for CETP inhibitors with solubilities less than about 0.5 µg/mL. Many CETP inhibitors have even lower solubilities (some even less than 0.1 µg/mL), and require dramatic concentration enhancement to be sufficiently bioavailable upon oral dosing for effective plasma concentrations to be reached at practical doses.

In general, it may be said that the CETP inhibitor has a dose-to-aqueous solubility ratio greater than about 100 mL, where the solubility (mg/mL) is the minimum value observed in any physiologically relevant aqueous solution (e.g., those with pH values from 1 to 8) including USP simulated gastric and intestinal buffers, and dose is in mg. Compositions of the present invention, as mentioned above, find greater utility as the solubility of the CETP inhibitor decreases and the dose increases. Thus, the compositions are preferred as the dose-to-solubility ratio increases, and thus are preferred for dose-to-solubility ratios greater than 1000 mL, and more preferred for dose-to-solubility ratios greater than about 5000 ml. The dose-to-solubility ratio may be determined by dividing the dose (in mg) by the aqueous solubility (in mg/ml).

Oral delivery of many CETP inhibitors is particularly difficult because their aqueous solubility is usually extremely low, typically being less than 2 μg/ml, often being less than 0.1 μg/ml. Such low solubilities are a direct consequence of the particular structural characteristics of species that bind to CETP and thus act as CETP inhibitors. This low solubility is primarily due to the hydrophobic nature of CETP inhibitors. Clog P, defined as the base 10 logarithm of the ratio of the drug solubility in octanol to the drug solubility in water, is a widely accepted measure of hydrophobicity. In general, Clog P values for CETP inhibitors are greater than 4 and are often greater than 5 to 7. Thus, the hydrophobic and insoluble nature of CETP inhibitors as a class pose a particular challenge for oral delivery. Achieving therapeutic drug levels in the blood by oral dosing of practical quantities of drug generally requires a large enhancement in drug concentrations in the gastrointestinal fluid and a resulting large enhancement in bioavailability. Such enhancements in drug concentration in gastrointestinal fluid typically need to be at least about 10-fold and often at least about 50-fold or even at least about 200-fold to achieve desired blood levels. Surprisingly, the dispersions of the present invention have proven to have the required large enhancements in drug concentration and bioavailability.

In contrast to conventional wisdom, the relative degree of enhancement in aqueous concentration and bioavailability generally improves for CETP inhibitors as solubility decreases and hydrophobicity increases. In fact, the inventors have recognized a subclass of these CETP inhibitors that are essentially aqueous insoluble, highly hydrophobic, and are characterized by a set of physical properties. This subclass exhibits dramatic enhancements in aqueous concentration and bioavailability when formulated using the compositions of the present invention.

The first property of this subclass of essentially insoluble, hydrophobic CETP inhibitors is extremely low aqueous solubility. By extremely low aqueous solubility is meant that the minimum aqueous solubility at physiologically relevant pH (pH of 1 to 8) is less than about 10 μg/ml and preferably less than about 1 μg/ml.

A second property is a very high does-to-solubility ratio. Extremely low solubility often leads to poor or slow absorption of the drug from the fluid of the gastrointestinal tract, when the drug is dosed orally in a conventional manner. For extremely low solubility drugs, poor absorption generally becomes progressively more difficult as the dose (mass of drug given orally) increases. Thus, a second property of this subclass of essentially insoluble, hydrophobic CETP inhibitors is a very high dose (in mg) to solubility (in mg/ml) ratio (ml). By "very high dose-to-solubility ratio" is meant that the dose-to-solubility ratio has a value of at least 1000 ml, and preferably at least 5,000 ml, and more preferably at least 10,000 ml.

A third property of this subclass of essentially insoluble, hydrophobic CETP inhibitors is that they are extremely hydrophobic. By extremely hydrophobic is meant that the Clog P value of the drug, has a value of at least 4.0, preferably a value of at least 5.0, and more preferably a value of at least 5.5.

A fourth property of this subclass of essentially insoluble CETP inhibitors is that they have a low melting point. Generally, drugs of this subclass will have a melting point of about 150° C. or less, and preferably about 140° C. or less.

Primarily, as a consequence of some or all of these four properties, CETP inhibitors of this subclass typically have very low absolute bioavailabilities. Specifically, the absolute bioavailability of drugs in this subclass when dosed orally in their undispersed state is less than about 10% and more often less than about 5%.

Turning now to the chemical structures of specific CETP inhibitors, one class of CETP inhibitors that finds utility with the present invention consists of oxy substituted 4-carboxyamino-2-methyl-1,2,3,4-tetrahydroquinolines having the Formula I

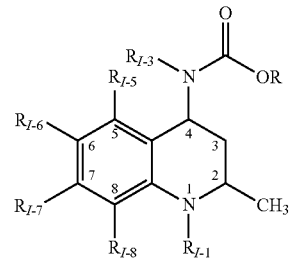

Formula I and pharmaceutically acceptable salts, enantiomers, or stereoisomers of said compounds;

wherein $R_{I-1}$ is hydrogen, $Y_I$, $W_I$—$X_I$, $W_I$—$Y_I$;

wherein $W_I$ is a carbonyl, thiocarbonyl, sulfinyl or sulfonyl;

$X_I$ is —O—$Y_I$, —S—$Y_I$, —N(H)—$Y_I$ or —N—$(Y_I)_2$;

wherein $Y_I$ for each occurrence is independently $Z_I$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_I$;

wherein $Z_I$ is a partially saturated, fully saturated or fully unsaturated three to eight membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_I$ substituent is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxyl, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with halo, hydroxy, $(C_1-C_6)$ alkoxy, $(C_1-C_4)$alkylthio, amino, nitro, cyano, oxo, carboxyl, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines;

$R_{I-3}$ is hydrogen or $Q_I$;

wherein $Q_I$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_I$;

wherein $V_I$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_I$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carbamoyl, mono-N— or di-N,N—$(C_1-C_6)$ alkylcarbamoyl, carboxyl, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxyl, $(C_1-C_6)$alkyloxycarbonyl, mono-N— or di-N,N—$(C_1-C_6)$alkylamino, said $(C_1-C_6)$alkyl or $(C_2-C_6)$alkenyl substituents are also optionally substituted with from one to nine fluorines;

$R_{I-4}$ is $Q_{I-1}$ or $V_{I-1}$ wherein $Q_{I-1}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_{I-1}$;

wherein $V_{I-1}$ is a partially saturated, fully saturated or fully unsaturated three to six membered ring optionally having one to two heteroatoms selected independently from oxygen, sulfur and nitrogen;

wherein said $V_{I-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein either $R_{I-3}$ must contain $V_I$ or $R_{I-4}$ must contain $V_{I-1}$; and $R_{I-5}$, $R_{I-6}$, $R_{I-7}$ and $R_{I-8}$ are each independently hydrogen, hydroxy or oxy wherein said oxy is substituted with $T_I$ or a partially saturated, fully saturated or fully unsaturated one to twelve membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $T_I$;

wherein $T_I$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $T_I$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines.

Compounds of Formula I and their methods of manufacture are disclosed in commonly assigned U.S. Pat. No. 6,140,342, U.S. Pat. No. 6,362,198, and European Patent publication 987251, all of which are incorporated herein by reference in their entireties for all purposes.

In a preferred embodiment, the CETP inhibitor is selected from one of the following compounds of Formula I:

[2R,4S] 4-[(3,5-dichloro-benzyl)-methoxycarbonyl-amino]-6,7-dimethoxy-2-methyl-3,4-dihydro-2H-quinoline-1-carboxylic acid ethyl ester;

[2R,4S] 4-[(3,5-dinitro-benzyl)-methoxycarbonyl-amino]-6,7-dimethoxy-2-methyl-3,4-dihydro-2H-quinoline-1-carboxylic acid ethyl ester;

[2R,4S] 4-[(2,6-dichloro-pyridin-4-ylmethyl)-methoxycarbonyl-amino]-6,7-dimethoxy-2-methyl-3,4-dihydro-2H-quinoline-1-carboxylic acid ethyl ester;

[2R,4S] 4-[(3,5-bis-trifluoromethyl-benzyl)-methoxycarbonyl-amino]-6,7-dimethoxy-2-methyl-3,4-dihydro-2H-quinoline-1-carboxylic acid ethyl ester;

[2R,4S] 4-[(3,5-bis-trifluoromethyl-benzyl)-methoxycarbonyl-amino]-6-methoxy-2-methyl-3,4-dihydro-2H-quinoline-1-carboxylic acid ethyl ester;

[2R,4S] 4-[(3,5-bis-trifluoromethyl-benzyl)-methoxycarbonyl-amino]-7-methoxy-2-methyl-3,4-dihydro-2H-quinoline-1-carboxylic acid ethyl ester,

[2R,4S] 4-[(3,5-bis-trifluoromethyl-benzyl)-methoxycarbonyl-amino]-6,7-dimethoxy-2-methyl-3,4-dihydro-2H-quinoline-1-carboxylic acid isopropyl ester;

[2R,4S] 4-[(3,5-bis-trifluoromethyl-benzyl)-ethoxycarbonyl-amino]-6,7-dimethoxy-2-methyl-3,4-dihydro-2H-quinoline-1-carboxylic acid ethyl ester;

[2R,4S] 4-[(3,5-bis-trifluoromethyl-benzyl)-methoxycarbonyl-amino]-6,7-dimethoxy-2-methyl-3,4-dihydro-2H-quinoline-1-carboxylic acid 2,2,2-trifluoro-ethylester;

[2R,4S] 4-[(3,5-bis-trifluoromethyl-benzyl)-methoxycarbonyl-amino]-6,7-dimethoxy-2-methyl-3,4-dihydro-2H-quinoline-1-carboxylic acid propyl ester;

[2R,4S] 4-[(3,5-bis-trifluoromethyl-benzyl)-methoxycarbonyl-amino]-6,7-dimethoxy-2-methyl-3,4-dihydro-2H-quinoline-1-carboxylic acid tert-butyl ester;

[2R,4S] 4-[(3,5-bis-trifluoromethyl-benzyl)-methoxycarbonyl-amino]-2-methyl-6-trifluoromethoxy-3,4-dihydro-2H-quinoline-1-carboxylic acid ethyl ester,

[2R,4S](3,5-bis-trifluoromethyl-benzyl)-(1-butyryl-6,7-dimethoxy-2-methyl-1,2,3,4-tetrahydro-quinolin-4-yl)-carbamic acid methyl ester;

[2R,4S](3,5-bis-trifluoromethyl-benzyl)-(1-butyl-6,7-dimethoxy-2-methyl-1,2,3,4-tetrahydro-quinolin-4-yl)-carbamic acid methyl ester; and

[2R,4S](3,5-bis-trifluoromethyl-benzyl)-[1-(2-ethyl-butyl)-6,7-dimethoxy-2-methyl-1,2,3,4-tetrahydro-quinolin-4-yl]-carbamic acid methyl ester, hydrochloride.

Another class of CETP inhibitors that finds utility with the present invention consists of 4-carboxyamino-2-methyl-1,2,3,4,-tetrahydroquinolines, having the Formula II

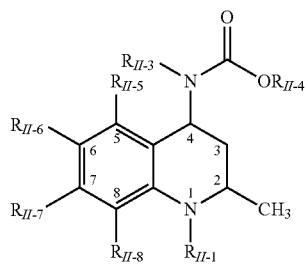

Formula II and pharmaceutically acceptable salts, enantiomers, or stereoisomers of said compounds;
wherein $R_{II-1}$ is hydrogen, $Y_{II}$, $W_{II}$—$X_{II}$, $W_{II}$—$Y_{II}$;
wherein $W_{II}$ is a carbonyl, thiocarbonyl, sulfinyl or sulfonyl;
$X_{II}$ is —O—$Y_{II}$, —S—$Y_{II}$, —N(H)—$Y_{II}$ or —N—$(Y_{II})_2$;
wherein $Y_{II}$ for each occurrence is independently $Z_{II}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{II}$;

$Z_{II}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{II}$ substituent is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl is also optionally substituted with from one to nine fluorines;
$R_{II-3}$ is hydrogen or $Q_{II}$;
wherein $Q_{II}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{II}$;

wherein $V_{II}$ is a partially saturated, fully saturated or fully unsaturated three to twelve membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{II}$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N, N—$(C_1-C_6)$ alkylcarboxamoyl, carboxy, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino or said $(C_1-C_6)$alkyl or $(C_2-C_6)$alkenyl substituents are optionally substituted with from one to nine fluorines;

$R_{II-4}$ is $Q_{II-1}$ or $V_{II-1}$
wherein $Q_{II-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{II-1}$;

wherein $V_{II-1}$ is a partially saturated, fully saturated or fully unsaturated three to six membered ring optionally having one to two heteroatoms selected independently from oxygen, sulfur and nitrogen;

wherein said $V_{II-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent is optionally substituted with from one to nine fluorines;

wherein either $R_{II-3}$ must contain $V_{II}$ or $R_{II-4}$ must contain $V_{II-1}$; and $R_{II-5}$, $R_{II-6}$, $R_{II-7}$ and $R_{II-8}$ are each independently hydrogen, a bond, nitro or halo wherein said bond is substituted with $T_{II}$ or a partially saturated, fully saturated or fully unsaturated $(C_1-C_{12})$ straight or branched carbon chain wherein carbon may optionally be replaced with one or two heteroatoms selected independently from oxygen, sulfur and nitrogen wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon is optionally mono-substituted with $T_{II}$;

wherein $T_{II}$ is a partially saturated, fully saturated or fully unsaturated three to twelve membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $T_{II}$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines; provided that at least one of substituents $R_{II-5}$, $R_{II-6}$, $R_{II-7}$ and $R_{II-8}$ is not hydrogen and is not linked to the quinoline moiety through oxy.

Compounds of Formula II and their methods of manufacture are disclosed in commonly assigned U.S. Pat. No. 6,147,090, U.S. patent application Ser. No. 09/671,400 filed Sep. 27, 2000, and PCT Publication No. WO00/17166, all of which are incorporated herein by reference in their entireties for all purposes.

In a preferred embodiment, the CETP inhibitor is selected from one of the following compounds of Formula II:

[2R,4S] 4-[(3,5-Bis-trifluoromethyl-benzyl)-methoxycarbonyl-amino]-2-methyl-7-trifluoromethyl-3,4-dihydro-2H-quinoline-1-carboxylic acid ethyl ester;

[2R,4S] 4-[(3,5-Bis-trifluoromethyl-benzyl)-methoxycarbonyl-amino]-7-chloro-2-methyl-3,4-dihydro-2H-quinoline-1-carboxylic acid ethyl ester;

[2R,4S] 4-[(3,5-Bis-trifluoromethyl-benzyl)-methoxycarbonyl-amino]-6-chloro-2-methyl-3,4-dihydro-2H-quinoline-1-carboxylic acid ethyl ester;

[2R,4S] 4-[(3,5-Bis-trifluoromethyl-benzyl)-methoxycarbonyl-amino]-2,6,7-trimethyl-3,4-dihydro-2H-quinoline-1-carboxylic acid ethyl ester;

[2R,4S] 4-[(3,5-Bis-trifluoromethyl-benzyl)-methoxycarbonyl-amino]-6,7-diethyl-2-methyl-3,4-dihydro-2H-quinoline-1-carboxylic acid ethyl ester;

[2R,4S] 4-[(3,5-Bis-trifluoromethyl-benzyl)-methoxycarbonyl-amino]-6-ethyl-2-methyl-3,4-dihydro-2H-quinoline-1-carboxylic acid ethyl ester;

[2R,4S] 4-[(3,5-Bis-trifluoromethyl-benzyl)-methoxycarbonyl-amino]-2-methyl-6-trifluoromethyl-3,4-dihydro-2H-quinoline-1-carboxylic acid ethyl ester; and

[2R,4S] 4-[(3,5-bis-trifluoromethyl-benzyl)-methoxycarbonyl-amino]-2-methyl-6-trifluoromethyl-3,4-dihydro-2H-quinoline-1-carboxylic acid isopropyl ester.

Another class of CETP inhibitors that finds utility with the present invention consists of annulated 4-carboxyamino-2-methyl-1,2,3,4,-tetrahydroquinolines, having the Formula III

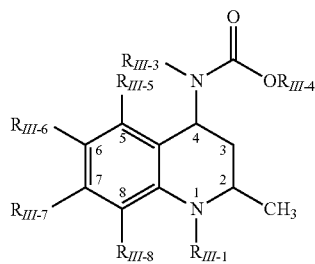

Formula III and pharmaceutically acceptable salts, enantiomers, or stereoisomers of said compounds;

wherein $R_{III-1}$, is hydrogen, $Y_{III}$, $W_{III}$—$X_{III}$, $W_{III}$—$Y_{III}$;

wherein $W_{III}$ is a carbonyl, thiocarbonyl, sulfinyl or sulfonyl;

$X_{III}$ is —O—$Y_{III}$, —S—$Y_{III}$, —N(H)—$Y_{III}$ or —N—$(Y_{III})_2$;

$Y_{III}$ for each occurrence is independently $Z_{III}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{III}$;

wherein $Z_{III}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{III}$ substituent is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl optionally substituted with from one to nine fluorines;

$R_{III-3}$ is hydrogen or $Q_{III}$;

wherein $Q_{III}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{III}$;

wherein $V_{III}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{III}$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N, N—$(C_1-C_6)$ alkylcarboxamoyl, carboxy, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino or said $(C_1-C_6)$alkyl or $(C_2-C_6)$alkenyl are optionally substituted with from one to nine fluorines;

$R_{III-4}$ is $Q_{III-1}$ or $V_{III-1}$;

wherein $Q_{III-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{III-1}$;

wherein $V_{III-1}$ is a partially saturated, fully saturated or fully unsaturated three to six membered ring optionally having one to two heteroatoms selected independently from oxygen, sulfur and nitrogen;

wherein said $V_{III-1}$ substituent is optionally mono-, di-, tri-, or tetra-substituted independently with halo, $(C_1-C_6)$ alkyl, $(C_1-C_6)$alkoxy, amino, nitro, cyano, $(C_1-C_6)$alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent optionally having from one to nine fluorines;

wherein either $R_{III-3}$ must contain $V_{III}$ or $R_{III-4}$ must contain $V_{III-1}$; and $R_{III-5}$ and $R_{III-6}$, or $R_{III-6}$ and $R_{III-7}$, and/or $R_{III-7}$ and $R_{III-8}$ are taken together and form at least one four to eight membered ring that is partially saturated or fully unsaturated optionally having one to three heteroatoms independently selected from nitrogen, sulfur and oxygen;

wherein said ring or rings formed by $R_{III-5}$ and $R_{III-6}$, or $R_{III-6}$ and $R_{III-7}$, and/or $R_{III-7}$ and $R_{III-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$ alkoxy, $(C_1-C_4)$alkylthio, amino, nitro, cyano, oxo, carboxy, $(C_1-C_6)$alkyloxycarbonyl, mono-N— or di-N,N—$(C_1-C_6)$ alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent optionally having from one to nine fluorines;

provided that the $R_{III-5}$, $R_{III-6}$, $R_{III-7}$ and/or $R_{III-8}$, as the case may be, that do not form at least one ring are each independently hydrogen, halo, $(C_1-C_6)$alkoxy or $(C_1-C_6)$ alkyl, said $(C_1-C_6)$alkyl optionally having from one to nine fluorines.

Compounds of Formula III and their methods of manufacture are disclosed in commonly assigned U.S. Pat. No. 6,147,089, U.S. Pat. No. 6,310,075, and European Patent Application No. 99307240.4 filed Sep. 14, 1999, all of which are incorporated herein by reference in their entireties for all purposes.

In a preferred embodiment, the CETP inhibitor is selected from one of the following compounds of Formula III:

[2R,4S] 4-[(3,5-bis-trifluoromethyl-benzyl)-methoxycarbonyl-amino]-2-methyl-2,3,4,6,7,8-hexahydro-cyclopenta[g]quinoline-1-carboxylic acid ethyl ester;

[6R,8S] 8-[(3,5-bis-trifluoromethyl-benzyl)-methoxycarbonyl-amino]-6-methyl-3,6,7,8-tetrahydro-1H-2-thia-5-aza-cyclopenta[b]naphthalene-5-carboxylic acid ethyl ester;

[6R,8S] 8-[(3,5-bis-trifluoromethyl-benzyl)-methoxycarbonyl-amino]-6-methyl-3,6,7,8-tetrahydro-2H-furo[2,3-g]quinoline-5-carboxylic acid ethyl ester;

[2R,4S] 4-[(3,5-bis-trifluoromethyl-benzyl)-methoxycarbonyl-amino]-2-methyl-3,4,6,8-tetrahydro-2H-furo[3,4-g]quinoline-1-carboxylic acid ethyl ester;

[2R,4S] 4-[(3,5-bis-trifluoromethyl-benzyl)-methoxycarbonyl-amino]-2-methyl-3,4,6,7,8,9-hexahydro-2H-benzo[g]quinoline-1-carboxylic acid propyl ester;

[7R,9S] 9-[(3,5-bis-trifluoromethyl-benzyl)-methoxycarbonyl-amino]-7-methyl-1,2,3,7,8,9-hexahydro-6-aza-cyclopenta[a]naphthalene-6-carboxylic acid ethyl ester; and

[6S,8R] 6-[(3,5-bis-trifluoromethyl-benzyl)-methoxycarbonyl-amino]-8-methyl-1,2,3,6,7,8-hexahydro-9-aza-cyclopenta[a]naphthalene-9-carboxylic acid ethyl ester.

Another class of CETP inhibitors that finds utility with the present invention consists of 4-carboxyamino-2-substituted-1,2,3,4,-tetrahydroquinolines, having the Formula IV

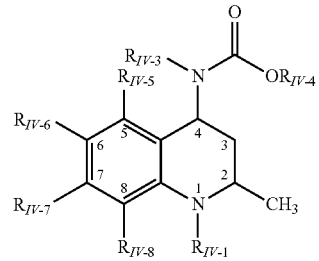

Formula IV and pharmaceutically acceptable salts, enantiomers, or stereoisomers of said compounds;

wherein $R_{IV-1}$ is hydrogen, $Y_{IV}$, $W_{IV}$—$X_{IV}$ or $W_{IV}$—$Y_{IV}$;

wherein $W_{IV}$ is a carbonyl, thiocarbonyl, sulfinyl or sulfonyl;

$X_{IV}$ is —O—$Y_{IV}$, —S—$Y_{IV}$, —N(H)—$Y_{IV}$ or —N—$(Y_{IV})_2$;

wherein $Y_{IV}$ for each occurrence is independently $Z_{IV}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{IV}$;

wherein $Z_{IV}$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{IV}$ substituent is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$ alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines;

$R_{IV-2}$ is a partially saturated, fully saturated or fully unsaturated one to six membered straight or branched carbon chain wherein the carbons, other than the connecting carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with oxo, said carbon is optionally mono-substituted with hydroxy, said sulfur is optionally mono- or di-substituted with oxo, said nitrogen is optionally mono- or di-substituted with oxo; or said $R_{IV-2}$ is a partially saturated, fully saturated or fully unsaturated three to seven membered ring optionally having one to two heteroatoms selected independently from oxygen, sulfur and nitrogen, wherein said $R_{IV-2}$ ring is optionally attached through $(C_1-C_4)$alkyl;

wherein said $R_{IV-2}$ ring is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$alkylthio, oxo or $(C_1-C_6)$alkyloxycarbonyl;

with the proviso that $R_{IV-2}$ is not methyl;

$R_{IV-3}$ is hydrogen or $Q_{IV}$;

wherein $Q_{IV}$ is a fully saturated, partially unsaturated or fully unsaturated one to six membered straight or branched carbon chain wherein the carbons other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{IV}$;

wherein $V_{IV}$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{IV}$ substituent is optionally mono-, di-, tri-, or tetra-substituted independently with halo, $(C_1-C_6)$alkyl, $(C_2-C_6)$alkenyl, hydroxy, $(C_1-C_5)$alkoxy, $(C_1-C_4)$alkylthio, amino, nitro, cyano, oxo, carboxamoyl, mono-N— or di-N,N—$(C_1-C_6)$ alkylcarboxamoyl, carboxy, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl or $(C_2-C_6)$alkenyl substituents are also optionally substituted with from one to nine fluorines;

$R_{IV-4}$ is $Q_{IV-1}$ or $V_{IV-1}$;

wherein $Q_{IV-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{IV-1}$;

wherein $V_{IV-1}$ is a partially saturated, fully saturated or fully unsaturated three to six membered ring optionally having one to two heteroatoms selected independently from oxygen, sulfur and nitrogen;

wherein said $V_{IV-1}$ substituent is optionally mono-, di-, tri-, or tetra-substituted independently with halo, $(C_1-C_6)$ alkyl, $(C_1-C_6)$alkoxy, amino, nitro, cyano, $(C_1-C_6)$alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein either $R_{IV-3}$ must contain $V_{IV}$ or $R_{IV-4}$ must contain $V_{IV-1}$;

$R_{IV-5}$, $R_{IV-6}$, $R_{IV-7}$ and $R_{IV-8}$ are each independently hydrogen, a bond, nitro or halo wherein said bond is substituted with $T_{IV}$ or a partially saturated, fully saturated or fully unsaturated $(C_1-C_{12})$ straight or branched carbon chain wherein carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon is optionally mono-substituted with $T_{IV}$;

wherein $T_{IV}$ is a partially saturated, fully saturated or fully unsaturated three to eight membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $T_{IV}$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines; and wherein $R_{IV-5}$ and $R_{IV-6}$, or $R_{IV-6}$ and $R_{IV-7}$, and/or $R_{IV-7}$ and $R_{IV-8}$ may also be taken together and can form at least one four to eight membered ring that is partially saturated or fully unsaturated optionally having one to three heteroatoms independently selected from nitrogen, sulfur and oxygen;

wherein said ring or rings formed by $R_{IV-5}$ and $R_{IV-6}$, or $R_{IV-6}$ and $R_{IV-7}$, and/or $R_{IV-7}$ and $R_{IV-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$ alkoxy, $(C_1-C_4)$alkylthio, amino, nitro, cyano, oxo, carboxy, $(C_1-C_6)$alkyloxycarbonyl, mono-N— or di-N,N—$(C_1-C_6)$ alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines; with the proviso that when $R_{IV-2}$ is carboxyl or $(C_1-C_4)$alkylcarbonyl, then $R_{IV-1}$ is not hydrogen.

Compounds of Formula IV and their methods of manufacture are disclosed in commonly assigned U.S. Pat. No. 6,197,786, U.S. application Ser. No. 09/685,3000 filed Oct. 10, 2000, and PCT Publication No. WO 00/17164, all of which are incorporated herein by reference in their entireties for all purposes.

In a preferred embodiment, the CETP inhibitor is selected from one of the following compounds of Formula IV:

[2S,4S] 4-[(3,5-bis-trifluoromethyl-benzyl)-methoxycarbonyl-amino]-2-isopropyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-6-chloro-2-cyclopropyl-3,4-dihydro-2H-quinoline-1-carboxylic acid isopropyl ester;

[2S,4S] 2-cyclopropyl-4-[(3,5-dichloro-benzyl)-methoxycarbonyl-amino]-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid tert-butyl ester;

[2R,4R] 4-[(3,5-bis-trifluoromethyl-benzyl)-methoxycarbonyl-amino]-2-cyclopropyl-6-trifluoromethyl-3,4-dihydro-2H-quinaline-1-carboxylic acid isopropyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-cyclobutyl-6-trifluoromethyl-3,4-dihydro-2H-quinoline-1-carboxylic acid isopropyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid 2-hydroxyethyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid propyl ester; and

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid propyl ester.

Another class of CETP inhibitors that finds utility with the present invention consists of 4-amino substituted-2-substituted-1,2,3,4,-tetrahydroquinolines, having the Formula V Formula V and pharmaceutically acceptable salts, enantiomers, or stereoisomers of said compounds;

wherein $R_{V-1}$ is $Y_V$, $W_V$—$X_V$ or $W_V$—$Y_V$;

wherein $W_V$ is a carbonyl, thiocarbonyl, sulfinyl or sulfonyl;

$X_V$ is —O—$Y_V$, —S—$Y_V$, —N(H)—$Y_V$ or —N—$(Y_V)_2$;

wherein $Y_V$ for each occurrence is independently $Z_V$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_V$;

wherein $Z_V$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_V$ substituent is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$ alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines;

$R_{V-2}$ is a partially saturated, fully saturated or fully unsaturated one to six membered straight or branched carbon chain wherein the carbons, other than the connecting carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with oxo, said carbon is optionally mono-substituted with hydroxy, said sulfur is optionally mono- or di-substituted with oxo, said nitrogen is optionally mono- or di-substituted with oxo; or said $R_{V-2}$ is a partially saturated, fully saturated or fully unsaturated three to seven membered ring optionally having one to two heteroatoms selected independently from oxygen, sulfur and nitrogen, wherein said $R_{V-2}$ ring is optionally attached through $(C_1-C_4)$alkyl;

wherein said $R_{V-2}$ ring is optionally mono-, di- or tri-substituted independently with halo, $(C_2-C_6)$alkenyl, $(C_1$-

$C_6$) alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$ alkylthio, oxo or $(C_1-C_6)$alkyloxycarbonyl;

$R_{V-3}$ is hydrogen or $Q_V$;

wherein $Q_V$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_V$;

wherein $V_V$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_V$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N,N—$(C_1-C_6)$ alkylcarboxamoyl, carboxy, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl or $(C_2-C_6)$alkenyl substituents are also optionally substituted with from one to nine fluorines;

$R_{V-4}$ is cyano, formyl, $W_{V-1}Q_{V-1}$, $W_{V-1}V_{V-1}$, $(C_1-C_4)$alkyleneV$_{V-1}$ or $V_{V-2}$;

wherein $W_{V-1}$ is carbonyl, thiocarbonyl, SO or $SO_2$, wherein $Q_{V-1}$ a fully saturated, partially unsaturated or fully unsaturated one to six membered straight or branched carbon chain wherein the carbons may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_{V-1}$;

wherein $V_{V-1}$ is a partially saturated, fully saturated or fully unsaturated three to six membered ring optionally having one to two heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{V-1}$ substituent is optionally mono-, di-, tri-, or tetra-substituted independently with halo, $(C_1-C_6)$alkyl, $(C_1-C_6)$alkoxy, hydroxy, oxo, amino, nitro, cyano, $(C_1-C_6)$ alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein $V_{V-2}$ is a partially saturated, fully saturated or fully unsaturated five to seven membered ring containing one to four heteroatoms selected independently from oxygen, sulfur and nitrogen;

wherein said $V_{V-2}$ substituent is optionally mono-, di- or tri-substituted independently with halo, $(C_1-C_2)$alkyl, $(C_1-C_2)$alkoxy, hydroxy, or oxo wherein said $(C_1-C_2)$alkyl optionally has from one to five fluorines; and wherein $R_{V-4}$ does not include oxycarbonyl linked directly to the $C^4$ nitrogen;

wherein either $R_{V-3}$ must contain $V_V$ or $R_{V-4}$ must contain $V_{V-1}$;

$R_{V-5}$, $R_{V-6}$, $R_{V-7}$ and $R_{V-8}$ are independently hydrogen, a bond, nitro or halo wherein said bond is substituted with $T_V$ or a partially saturated, fully saturated or fully unsaturated $(C_1-C_{12})$ straight or branched carbon chain wherein carbon may optionally be replaced with one or two heteroatoms selected independently from oxygen, sulfur and nitrogen, wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $T_V$;

wherein $T_V$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $T_V$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent also optionally has from one to nine fluorines;

wherein $R_{V-5}$ and $R_{V-6}$, or $R_{V-6}$ and $R_{V-7}$, and/or $R_{V-7}$ and $R_{V-8}$ may also be taken together and can form at least one ring that is a partially saturated or fully unsaturated four to eight membered ring optionally having one to three heteroatoms independently selected from nitrogen, sulfur and oxygen;

wherein said rings formed by $R_{V-5}$ and $R_{V-6}$, or $R_{V-6}$ and $R_{V-7}$, and/or $R_{V-7}$ and $R_{V-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent also optionally has from one to nine fluorines.

Compounds of Formula V and their methods of manufacture are disclosed in commonly assigned U.S. Pat. No. 6,140,343, U.S. patent application Ser. No. 09/671,221 filed Sep. 27, 2000, and PCT Publication No. WO 00/17165, all of which are incorporated herein by reference in their entireties for all purposes.

In a preferred embodiment, the CETP inhibitor is selected from one of the following compounds of Formula V:

[2S,4S] 4-[(3,5-bis-trifluoromethyl-benzyl)-formyl-amino]-2-cyclopropyl-6-trifluoromethyl-3,4-dihydro-2H-quinoline-1-carboxylic acid isopropyl ester;

[2S,4S] 4-[(3,5-bis-trifluoromethyl-benzyl)-formyl-amino]-2-cyclopropyl-6-trifluoromethyl-3,4-dihydro-2H-quinoline-1-carboxylic acid propyl ester;

[2S,4S] 4-[acetyl-(3,5-bis-trifluoromethyl-benzyl)-amino]-2-cyclopropyl-6-trifluoromethyl-3,4-dihydro-2H-quinoline-1-carboxylic acid tert-butyl ester;

[2R,4S] 4-[acetyl-(3,5-bis-trifluoromethyl-benzyl)-amino]-2-ethyl-6-trifluoromethyl-3,4-dihydro-2H-quinoline-1-carboxylic acid isopropyl ester;

[2R,4S] 4-[acetyl-(3,5-bis-trifluoromethyl-benzyl)-amino]-2-methyl-6-trifluoromethyl-3,4-dihydro-2H-quinoline-1-carboxylic acid ethyl ester;

[2S,4S] 4-[1-(3,5-bis-trifluoromethyl-benzyl)-ureido]-2-cyclopropyl-6-trifluoromethyl-3,4-dihydro-2H-quinoline-1-carboxylic acid isopropyl ester;

[2R,4S] 4-[acetyl-(3,5-bis-trifluoromethyl-benzyl)-amino]-2-ethyl-6-trifluoromethyl-3,4-dihydro-2H-quinoline-1-carboxylic acid ethyl ester;

[2S,4S] 4-[acetyl-(3,5-bis-trifluoromethyl-benzyl)-amino]-2-methoxymethyl-6-trifluoromethyl-3,4-dihydro-2H-quinoline-1-carboxylic acid isopropyl ester;

[2S,4S] 4-[acetyl-(3,5-bis-trifluoromethyl-benzyl)-amino]-2-cyclopropyl-6-trifluoromethyl-3,4-dihydro-2H-quinoline-1-carboxylic acid propyl ester;

[2S,4S] 4-[acetyl-(3,5-bis-trifluoromethyl-benzyl)-amino]-2-cyclopropyl-6-trifluoromethyl-3,4-dihydro-2H-quinoline-1-carboxylic acid ethyl ester;

[2R,4S] 4-[(3,5-bis-trifluoromethyl-benzyl)-formyl-amino]-2-ethyl-6-trifluoromethyl-3,4-dihydro-2H-quinoline-1-carboxylic acid isopropyl ester;

[2R,4S] 4-[(3,5-bis-trifluoromethyl-benzyl)-formyl-amino]-2-methyl-6-trifluoromethyl-3,4-dihydro-2H-quinoline-1-carboxylic acid ethyl ester;

[2S,4S] 4-[acetyl-(3,5-bis-trifluoromethyl-benzyl)-amino]-2-cyclopropyl-6-trifluoromethyl-3,4-dihydro-2H-quinoline-1-carboxylic acid isopropyl ester;

[2R,4S] 4-[(3,5-bis-trifluoromethyl-benzyl)-formyl-amino]-2-ethyl-6-trifluoromethyl-3,4-dihydro-2H-quinoline-1-carboxylic acid ethyl ester;

[2S,4S] 4-[(3,5-bis-trifluoromethyl-benzyl)-formyl-amino]-2-cyclopropyl-6-trifluoromethyl-3,4-dihydro-2H-quinoline-1-carboxylic acid ethyl ester;

[2R,4S] 4-[(3,5-bis-trifluoromethyl-benzyl)-formyl-amino]-2-methyl-6-trifluoromethyl-3,4-dihydro-2H-quinoline-1-carboxylic acid isopropyl ester; and

[2R,4S] 4-[acetyl-(3,5-bis-trifluoromethyl-benzyl)-amino]-2-methyl-6-trifluoromethyl-3,4-dihydro-2H-quinoline-1-carboxylic acid isopropyl ester.

Another class of CETP inhibitors that finds utility with the present invention consists of cycloalkano-pyridines having the Formula VI

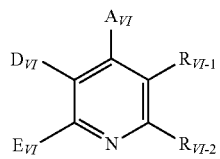

Formula VI and pharmaceutically acceptable salts, enantiomers, or stereoisomers of said compounds;

in which $A_{VI}$ denotes an aryl containing 6 to 10 carbon atoms, which is optionally substituted with up to five identical or different substituents in the form of a halogen, nitro, hydroxyl, trifluoromethyl, trifluoromethoxy or a straight-chain or branched alkyl, acyl, hydroxyalkyl or alkoxy containing up to 7 carbon atoms each, or in the form of a group according to the formula —$BNR_{VI-3}R_{VI-4}$, wherein $R_{VI-3}$ and $R_{VI-4}$ are identical or different and denote a hydrogen, phenyl or a straight-chain or branched alkyl containing up to 6 carbon atoms, $D_{VI}$ denotes an aryl containing 6 to 10 carbon atoms, which is optionally substituted with a phenyl, nitro, halogen, trifluoromethyl or trifluoromethoxy, or a radical according to the formula $R_{VI-5}$-$L_{VI}$-,

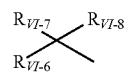

or $R_{VI-9}$-$T_{VI}$-$V_{VI}$—$X_{VI}$, wherein $R_{VI-5}$, $R_{VI-6}$ and $R_{VI-9}$ denote, independently from one another, a cycloalkyl containing 3 to 6 carbon atoms, or an aryl containing 6 to 10 carbon atom or a 5- to 7-membered, optionally benzo-condensed, saturated or unsaturated, mono-, bi- or tricyclic heterocycle containing up to 4 heteroatoms from the series of S, N and/or O, wherein the rings are optionally substituted, in the case of the nitrogen-containing rings also via the N function, with up to five identical or different substituents in the form of a halogen, trifluoromethyl, nitro, hydroxyl, cyano, carboxyl, trifluoromethoxy, a straight-chain or branched acyl, alkyl, alkylthio, alkylalkoxy, alkoxy or alkoxycarbonyl containing up to 6 carbon atoms each, an aryl or trifluoromethyl-substituted aryl containing 6 to 10 carbon atoms each, or an optionally benzo-condensed, aromatic 5- to 7-membered heterocycle containing up to 3 heteroatoms from the series of S, N and/or O, and/or in the form of a group according to the formula $BOR_{VI-10}$, —$SR_{VI-11}$, —$SO_2R_{VI-12}$ or $BNR_{VI-13}R_{VI-14}$, wherein $R_{VI-10}$, $R_{VI-11}$ and $R_{VI-12}$ denote, independently from one another, an aryl containing 6 to 10 carbon atoms, which is in turn substituted with up to two identical or different substituents in the form of a phenyl, halogen or a straight-chain or branched alkyl containing up to 6 carbon atoms, $R_{VI-13}$ and $R_{VI-14}$ are identical or different and have the meaning of $R_{VI-3}$ and $R_{VI-4}$ given above, or $R_{VI-5}$ and/or $R_{VI-6}$ denote a radical according to the formula

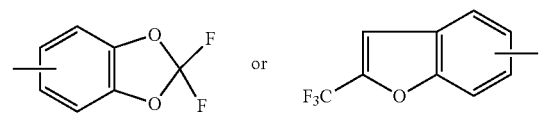

$R_{VI-7}$ denotes a hydrogen or halogen, and $R_{VI-8}$ denotes a hydrogen, halogen, azido, trifluoromethyl, hydroxyl, trifluoromethoxy, a straight-chain or branched alkoxy or alkyl containing up to 6 carbon atoms each, or a radical according to the formula

—$NR_{VI-15}R_{VI-16}$, wherein

R$_{VI-15}$ and R$_{VI-16}$ are identical or different and have the meaning of R$_{VI-3}$ and R$_{VI-4}$ given above, or R$_{V-17}$ and R$_{VI-8}$ together form a radical according to the formula =O or =NR$_{VI-17}$, wherein R$_{VI-17}$ denotes a hydrogen or a straight-chain or branched alkyl, alkoxy or acyl containing up to 6 carbon atoms each, L$_{VI}$ denotes a straight-chain or branched alkylene or alkenylene chain containing up to 8 carbon atoms each, which are optionally substituted with up to two hydroxyl groups, T$_{VI}$ and X$_{VI}$ are identical or different and denote a straight-chain or branched alkylene chain containing up to 8 carbon atoms, or T$_{VI}$ or X$_{VI}$ denotes a bond, V$_{VI}$ denotes an oxygen or sulfur atom or an BNR$_{VI-18}$ group, wherein R$_{VI-18}$ denotes a hydrogen or a straight-chain or branched alkyl containing up to 6 carbon atoms or a phenyl, E$_{VI}$ denotes a cycloalkyl containing 3 to 8 carbon atoms, or a straight-chain or branched alkyl containing up to 8 carbon atoms, which is optionally substituted with a cycloalkyl containing 3 to 8 carbon atoms or a hydroxyl, or a phenyl, which is optionally substituted with a halogen or trifluoromethyl, R$_{VI-1}$ and R$_{VI-2}$ together form a straight-chain or branched alkylene chain containing up to 7 carbon atoms, which must be substituted with a carbonyl group and/or a radical according to the formula

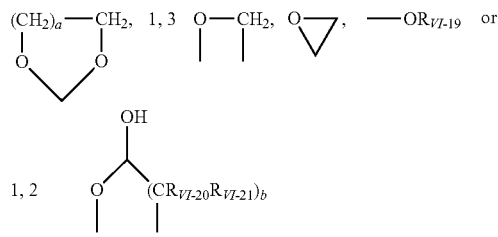

wherein a and b are identical or different and denote a number equaling 1, 2 or 3, R$_{VI-19}$ denotes a hydrogen atom, a cycloalkyl containing 3 to 7 carbon atoms, a straight-chain or branched silylalkyl containing up to 8 carbon atoms, or a straight-chain or branched alkyl containing up to 8 carbon atoms, which is optionally substituted with a hydroxyl, a straight-chain or a branched alkoxy containing up to 6 carbon atoms or a phenyl, which may in turn be substituted with a halogen, nitro, trifluoromethyl, trifluoromethoxy or phenyl or tetrazole-substituted phenyl, and an alkyl that is optionally substituted with a group according to the formula BOR$_{VI-22}$, wherein R$_{VI-22}$ denotes a straight-chain or branched acyl containing up to 4 carbon atoms or benzyl, or R$_{VI-19}$ denotes a straight-chain or branched acyl containing up to 20 carbon atoms or benzoyl, which is optionally substituted with a halogen, trifluoromethyl, nitro or trifluoromethoxy, or a straight-chain or branched fluoroacyl containing up to 8 carbon atoms, R$_{VI-20}$ and R$_{VI-21}$ are identical or different and denote a hydrogen, phenyl or a straight-chain or branched alkyl containing up to 6 carbon atoms, or R$_{VI-20}$ and R$_{VI-21}$ together form a 3- to 6-membered carbocyclic ring, and a the carbocyclic rings formed are optionally substituted, optionally also geminally, with up to six identical or different substituents in the form of trifluoromethyl, hydroxyl, nitrile, halogen, carboxyl, nitro, azido, cyano, cycloalkyl or cycloalkyloxy containing 3 to 7 carbon atoms each, a straight-chain or branched alkoxycarbonyl, alkoxy or alkylthio containing up to 6 carbon atoms each, or a straight-chain or branched alkyl containing up to 6 carbon atoms, which is in turn substituted with up to two identical or different substituents in the form of a hydroxyl, benzyloxy, trifluoromethyl, benzoyl, a straight-chain or branched alkoxy, oxyacyl or carboxyl containing up to 4 carbon atoms each and/or a phenyl, which may in turn be substituted with a halogen, trifluoromethyl or trifluoromethoxy, and/or the carbocyclic rings formed are optionally substituted, also geminally, with up to five identical or different substituents in the form of a phenyl, benzoyl, thiophenyl or sulfonylbenzyl, which in turn are optionally substituted with a halogen, trifluoromethyl, trifluoromethoxy or nitro, and/or optionally in the form of a radical according to the formula

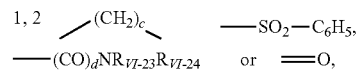

wherein c is a number equaling 1, 2, 3 or 4, d is a number equaling 0 or 1,

R$_{VI-23}$ and R$_{VI-24}$ are identical or different and denote a hydrogen, cycloalkyl containing 3 to 6 carbon atoms, a straight-chain or branched alkyl containing up to 6 carbon atoms, benzyl or phenyl, which is optionally substituted with up to two identical or different substituents in the form of halogen, trifluoromethyl, cyano, phenyl or nitro, and/or the carbocyclic rings formed are optionally substituted with a spiro-linked radical according to the formula

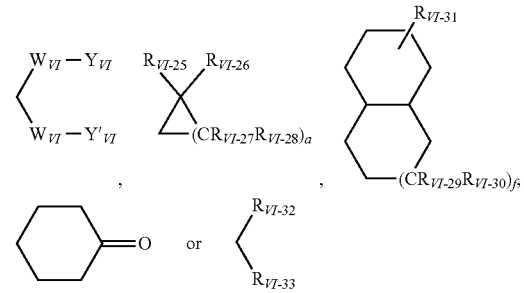

wherein

W$_{VI}$ denotes either an oxygen atom or a sulfur atom,

Y$_{VI}$ and Y=$_{VI}$ together form a 2- to 6-membered straight-chain or branched alkylene chain, e is a number equaling 1, 2, 3, 4, 5, 6 or 7, f is a number equaling 1 or 2, R$_{VI-25}$, R$_{VI-26}$, R$_{VI-27}$, R$_{VI-28}$, R$_{VI-29}$, R$_{VI-30}$ and R$_{VI-31}$ are identical or different and denote a hydrogen, trifluoromethyl, phenyl, halogen or a straight-chain or branched alkyl or alkoxy containing up to 6 carbon atoms each, or R$_{VI-25}$ and R$_{VI-26}$ or R$_{VI-27}$ and R$_{VI-28}$ each together denote a straight-chain or branched alkyl chain containing up to 6 carbon atoms or $R_{VI-25}$ and $R_{VI-26}$ or $R_{VI-27}$ and $R_{VI-28}$ each together form a radical according to the formula

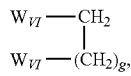

wherein $W_{VI}$ has the meaning given above, g is a number equaling 1, 2, 3, 4, 5, 6 or 7, $R_{VI-32}$ and $R_{VI-33}$ together form a 3- to 7-membered heterocycle, which contains an oxygen or sulfur atom or a group according to the formula SO, $SO_2$ or $BNR_{VI-34}$, wherein $R_{VI-34}$ denotes a hydrogen atom, a phenyl, benzyl, or a straight-chain or branched alkyl containing up to 4 carbon atoms, and salts and N oxides thereof, with the exception of 5(6H)-quinolones, 3-benzoyl-7,8-dihydro-2,7,7-trimethyl-4-phenyl.

Compounds of Formula VI and their methods of manufacture are disclosed in European Patent Application No. EP 818448 A1, U.S. Pat. No. 6,207,671 and U.S. Pat. No. 6,069,148, all of which are incorporated herein by reference in their entireties for all purposes.

In a preferred embodiment, the CETP inhibitor is selected from one of the following compounds of Formula VI:

2-cyclopentyl-4-(4-fluorophenyl)-7,7-dimethyl-3-(4-trifluoromethylbenzoyl)-4,6,7,8-tetrahydro-1H-quinolin-5-one;

2-cyclopentyl-4-(4-fluorophenyl)-7,7-dimethyl-3-(4-trifluoromethylbenzoyl)-7,8-dihydro-6H-quinolin-5-one;

[2-cyclopentyl-4-(4-fluorophenyl)-5-hydroxy-7,7-dimethyl-5,6,7,8-tetrahydroquinolin-3-yl]-(4-trifluoromethylphenyl)-methanone;

[5-(t-butyldimethylsilanyloxy)-2-cyclopentyl-4-(4-fluorophenyl)-7,7-dimethyl-5,6,7,8-tetrahydroquinolin-3-yl]-(4-trifluoromethylphenyl)-methanone;

[5-(t-butyldimethylsilanyloxy)-2-cyclopentyl-4-(4-fluorophenyl)-7,7-dimethyl-5,6,7,8-tetrahydroquinolin-3-yl]-(4-trifluoromethylphenyl)-methanol;

5-(t-butyldimethylsilanyloxy)-2-cyclopentyl-4-(4-fluorophenyl)-3-[fluoro-(4-trifluoromethylphenyl)-methyl]-7,7-dimethyl-5,6,7,8-tetrahydroquinoline; and 2-cyclopentyl-4-(4-fluorophenyl)-3-[fluoro-(4-trifluoromethylphenyl)-methyl]-7,7-dimethyl-5,6,7,8-tetrahydroquinolin-5-ol.

Another class of CETP inhibitors that finds utility with the present invention consists of substituted-pyridines having the Formula VII Formula VII

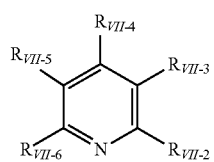

or a pharmaceutically acceptable salt or tautomer thereof, wherein $R_{VII-2}$ and $R_{VII-6}$ are independently selected from the group consisting of hydrogen, hydroxy, alkyl, fluorinated alkyl, fluorinated aralkyl, chlorofluorinated alkyl, cycloalkyl, heterocyclyl, aryl, heteroaryl, alkoxy, alkoxyalkyl, and alkoxycarbonyl; provided that at least one of $R_{VII-2}$ and $R_{VII-6}$ is fluorinated alkyl, chlorofluorinated alkyl or alkoxyalkyl;

$R_{VII-3}$ is selected from the group consisting of hydroxy, amido, arylcarbonyl, heteroarylcarbonyl, hydroxymethyl —CHO, —$CO_2R_{VII-7}$, wherein $R_{VII-7}$ is selected from the group consisting of hydrogen, alkyl and cyanoalkyl; and

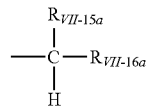

wherein $R_{VII-15a}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy and heterocyclyloxy, and $R_{VII-16a}$ is selected from the group consisting of alkyl, haloalkyl, alkenyl, haloalkenyl, alkynyl, haloalkynyl, aryl, heteroaryl, and heterocyclyl, arylalkoxy, trialkylsilyloxy;

$R_{VII-4}$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, hetereoarylalkenyl, heterocyclylalkenyl, alkoxy, alkenoxy, alkynoxy, aryloxy, heteroaryloxy, heterocyclyloxy, alkanoyloxy, alkenoyloxy, alkynoyloxy, aryloyloxy, heteroaroyloxy, heterocyclyloyloxy, alkoxycarbonyl, alkenoxycarbonyl, alkynoxycarbonyl, aryloxycarbonyl, heteroaryloxycarbonyl, heterocyclyloxycarbonyl, thio, alkylthio, alkenylthio, alkynylthio, arylthio, heteroarylthio, heterocyclylthio, cycloalkylthio, cycloalkenylthio, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclythioalkenyl, alkylamino, alkenylamino, alkynylamino, arylamino, heteroarylamino, heterocyclylamino, aryldialkylamino, diarylamino, diheteroarylamino, alkylarylamino, alkylheteroarylamino, arylheteroarylamino, trialkylsilyl, trialkenylsilyl, triarylsilyl, —CO(O)N($R_{VII-8a}R_{VII-8b}$), wherein $R_{VII-8a}$ and $R_{VII-8b}$ are independently selected from the group consisting of alkyl, alkenyl, alkynyl, aryl, heteroaryl and heterocyclyl, —$SO_2R_{VII-9}$, wherein $R_{VII-9}$ is selected from the group consisting of hydroxy, alkyl, alkenyl, alkynyl, aryl, heteroaryl and heterocyclyl, —OP(O)($OR_{VII-10a}$)($OR_{VII-10b}$), wherein $R_{VII-10a}$ and $R_{VII-10b}$ are independently selected from the group consisting of hydrogen, hydroxy, alkyl, alkenyl, alkynyl, aryl, heteroaryl and heterocyclyl, and —OP(S) ($OR_{VII-11a}$)($OR_{VII-11b}$), wherein $R_{VII-11a}$ and $R_{VII-11b}$ are independently selected from the group consisting of alkyl, alkenyl, alkynyl, aryl, heteroaryl and heterocyclyl;

$R_{VII-5}$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, alkoxy, alkenoxy, alkynoxy, aryloxy, heteroaryloxy, heterocyclyloxy, alkylcarbonyloxyalkyl, alkenylcarbonyloxyalkyl, alkynylcarbonyloxyalkyl, arylcarbonyloxyalkyl, heteroarylcarbonyloxyalkyl, heterocyclylcarbonyloxyalkyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, cycloalkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, alkoxyalkyl, alkenoxyalkyl, alkynoxyalkyl, aryloxyalkyl, heteroaryloxyalkyl, heterocyclyloxyalkyl, alkoxyalkenyl, alkenoxyalkenyl, alkynoxyalkenyl, aryloxyalkenyl, heteroaryloxyalkenyl, heterocyclyloxyalkenyl, cyano, hydroxymethyl, —$CO_2R_{VII-14}$, wherein $R_{VII-14}$ is selected from the group consisting of alkyl, alkenyl, alkynyl, aryl, heteroaryl and heterocyclyl;

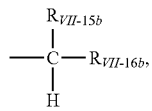

wherein $R_{VII-15b}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy, heterocyclyloxy, aroyloxy, and alkylsulfonyloxy, and $R_{VII-16b}$ is selected form the group consisting of alkyl, alkenyl, alkynyl, aryl, heteroaryl, heterocyclyl, arylalkoxy, and trialkylsilyloxy;

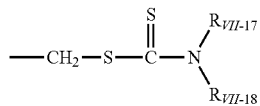

wherein $R_{VII-17}$ and $R_{VII-18}$ are independently selected from the group consisting of alkyl, cycloalkyl, alkenyl, alkynyl, aryl, heteroaryl and heterocyclyl;

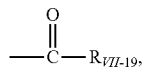

wherein $R_{VII-19}$ is selected from the group consisting of alkyl, cycloalkyl, alkenyl, alkynyl, aryl, heteroaryl, heterocyclyl, —$SR_{VII-20}$, —$OR_{VII-21}$, and $BR_{VII-22}CO_2R_{VII-23}$, wherein $R_{VII-20}$ is selected from the group consisting of alkyl, alkenyl, alkynyl, aryl, heteroaryl, heterocyclyl, aminoalkyl, aminoalkenyl, aminoalkynyl, aminoaryl, aminoheteroaryl, aminoheterocyclyl, alkylheteroarylamino, arylheteroarylamino, $R_{VII-21}$ is selected from the group consisting of alkyl, alkenyl, alkynyl, aryl, heteroaryl, and heterocyclyl, $R_{VII-22}$ is selected from the group consisting of alkylene or arylene, and $R_{VII-23}$ is selected from the group consisting of alkyl, alkenyl, alkynyl, aryl, heteroaryl, and heterocyclyl;

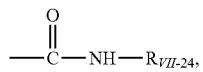

wherein $R_{VII-24}$ is selected from the group consisting of hydrogen, alkyl, cycloalkyl, alkenyl, alkynyl, aryl, heteroaryl, heterocyclyl, aralkyl, aralkenyl, and aralkynyl;

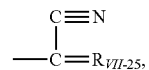

wherein $R_{VII-25}$ is heterocyclylidenyl;

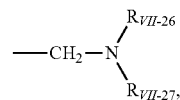

wherein $R_{VII-26}$ and $R_{VII-27}$ are independently selected from the group consisting of hydrogen, alkyl, cycloalkyl, alkenyl, alkynyl, aryl, heteroaryl, and heterocyclyl;

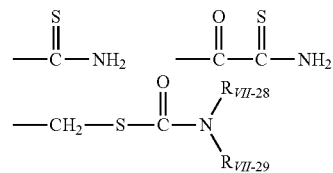

wherein $R_{VII-28}$ and $R_{VII-29}$ are independently selected from the group consisting of hydrogen, alkyl, cycloalkyl, alkenyl, alkynyl, aryl, heteroaryl, and heterocyclyl;

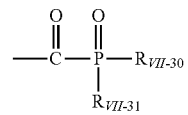

wherein $R_{VII-30}$ and $R_{VII-31}$ are independently alkoxy, alkenoxy, alkynoxy, aryloxy, heteroaryloxy, and heterocyclyloxy; and

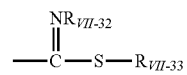

wherein $R_{VII-32}$ and $R_{VII-33}$ are independently selected from the group consisting of hydrogen, alkyl, cycloalkyl, alkenyl, alkynyl, aryl, heteroaryl, and heterocyclyl;

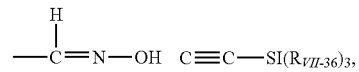

wherein $R_{VII-36}$ is selected from the group consisting of alkyl, alkenyl, aryl, heteroaryl and heterocyclyl;

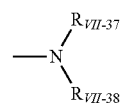

wherein $R_{VII-37}$ and $R_{VII-38}$ are independently selected from the group consisting of hydrogen, alkyl, cycloalkyl, alkenyl, alkynyl, aryl, heteroaryl, and heterocyclyl;

$$-N=C\begin{matrix}R_{VII-39}\\ \\R_{VII-40}\end{matrix}$$

wherein $R_{VII-39}$ is selected from the group consisting of hydrogen, alkoxy, alkenoxy, alkynoxy, aryloxy, heteroaryloxy, heterocyclyloxy, alkylthio, alkenylthio, alkynylthio, arylthio, heteroarylthio and heterocyclylthio, and $R_{VII-40}$ is selected from the group consisting of haloalkyl, haloalkenyl, haloalkynyl, haloaryl, haloheteroaryl, haloheterocyclyl, cycloalkyl, cycloalkenyl, heterocyclylalkoxy, heterocyclylalkenoxy, heterocyclylalkynoxy, alkylthio, alkenylthio, alkynylthio, arylthio, heteroarylthio and heterocyclylthio;

—N=$R_{VII-41}$, wherein $R_{VII-41}$ is heterocyclylidenyl;

$$-NR_{VII-42}-\overset{O}{\underset{\|}{C}}-R_{VII-43}$$

wherein $R_{VII-42}$ is selected from the group consisting of hydrogen, alkyl, alkenyl, alkynyl, aryl, heteroaryl, and heterocyclyl, and $R_{VII-43}$ is selected from the group consisting of hydrogen, alkyl, alkenyl, alkynyl, aryl, heteroaryl, heterocyclyl, cycloalkyl, cycloalkenyl, haloalkyl, haloalkenyl, haloalkynyl, haloaryl, haloheteroaryl, and haloheterocyclyl;

$$-NH-\overset{O}{\underset{\|}{C}}-NH-R_{VII-44}$$

wherein $R_{VII-44}$ is selected from the group consisting of hydrogen, alkyl, cycloalkyl, alkenyl, alkynyl, aryl, heteroaryl and heterocyclyl;

—N=S=O;

—N=C=S;

—N=C=O;

—N$_3$;

—S$R_{VII-45}$ wherein $R_{VII-45}$ is selected from the group consisting of hydrogen, alkyl, alkenyl, alkynyl, aryl, heteroaryl, heterocyclyl, haloalkyl, haloalkenyl, haloalkynyl, haloaryl, haloheteroaryl, haloheterocyclyl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, aminocarbonylalkyl, aminocarbonylalkenyl, aminocarbonylalkynyl, aminocarbonylaryl, aminocarbonylheteroaryl, and aminocarbonylheterocyclyl, —S$R_{VII-46}$, and —CH$_2R_{VII-47}$, wherein $R_{VII-46}$ is selected from the group consisting of alkyl, alkenyl, alkynyl, aryl, heteroaryl and heterocyclyl, and $R_{VII-47}$ is selected from the group consisting of hydrogen, alkyl, alkenyl, alkynyl, aryl, heteroaryl and heterocyclyl; and $$-S-CH\begin{matrix}R_{VII-48}\\ \\R_{VII-49}\end{matrix},$$

wherein $R_{VII-48}$ is selected from the group consisting of hydrogen, alkyl, cycloalkyl, alkenyl, alkynyl, aryl, heteroaryl and heterocyclyl, and $R_{VII-49}$ is selected from the group consisting of alkoxy, alkenoxy, alkynoxy, aryloxy, heteroaryloxy, heterocyclyloxy, haloalkyl, haloalkenyl, haloalkynyl, haloaryl, haloheteroaryl and haloheterocyclyl;

$$-S-\overset{O}{\underset{\|}{C}}-R_{VII-50},$$

wherein $R_{VII-50}$ is selected from the group consisting of hydrogen, alkyl, cycloalkyl, alkenyl, alkynyl, aryl, heteroaryl, heterocyclyl, alkoxy, alkenoxy, alkynoxy, aryloxy, heteroaryloxy and heterocyclyloxy;

$$-\overset{O}{\underset{\|}{S}}-R_{VII-51},$$

wherein $R_{VII-51}$ is selected from the group consisting of alkyl, alkenyl, alkynyl, aryl, heteroaryl, heterocyclyl, haloalkyl, haloalkenyl, haloalkynyl, haloaryl, haloheteroaryl and haloheterocyclyl; and $$-\overset{O}{\underset{\underset{O}{\|}}{\overset{\|}{S}}}-R_{VII-53},$$

wherein $R_{VII-53}$ is selected from the group consisting of alkyl, alkenyl, alkynyl, aryl, heteroaryl and heterocyclyl;

provided that when $R_{VII-5}$ is selected from the group consisting of heterocyclylalkyl and heterocyclylalkenyl, the heterocyclyl radical of the corresponding heterocyclylalkyl or heterocyclylalkenyl is other than δ-lactone; and provided that when $R_{VII-4}$ is aryl, heteroaryl or heterocyclyl, and one of $R_{VII-2}$ and $R_{VII-6}$ is trifluoromethyl, then the other of $R_{VII-2}$ and $R_{VII-6}$ is difluoromethyl.

Compounds of Formula VII and their methods of manufacture are disclosed in PCT Publication No. WO 9941237-A1, which is incorporated herein by reference in its entirety for all purposes.

In a preferred embodiment, the CETP inhibitor of Formula VII is dimethyl 5,5-dithiobis[2-difluoromethyl-4-(2-methylpropyl)-6-(trifluoromethyl)-3-pyridine-carboxylate].

Another class of CETP inhibitors that finds utility with the present invention consists of substituted biphenyls having the Formula VIII

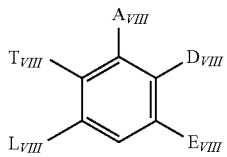

Formula VIII or a pharmaceutically acceptable salt, enantiomers, or stereoisomers thereof, in which $A_{VIII}$ stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII-1}R_{VIII-2}$, wherein $R_{VIII-1}$ and $R_{VIII-2}$ are identical or different and denote hydrogen, phenyl, or straight-chain or branched alkyl with up to 6 carbon atoms, $D_{VIII}$ stands for straight-chain or branched alkyl with up to 8 carbon atoms, which is substituted by hydroxy, $E_{VIII}$ and $L_{VIII}$ are either identical or different and stand for straight-chain or branched alkyl with up to 8 carbon atoms, which is optionally substituted by cycloalkyl with 3 to 8 carbon atoms, or stands for cycloalkyl with 3 to 8 carbon atoms, or $E_{VIII}$ has the above-mentioned meaning and $L_{VIII}$ in this case stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII-3}R_{VIII-4}$, wherein $R_{VIII-3}$ and $R_{VIII-4}$ are identical or different and have the meaning given above for $R_{VIII-1}$ and $R_{VIII-2}$, or $E_{VIII}$ stands for straight-chain or branched alkyl with up to 8 carbon atoms, or stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII-5}R_{VIII-6}$, wherein $R_{VIII-5}$ and $R_{VIII-6}$ are identical or different and have the meaning given above for $R_{VIII-1}$ and $R_{VIII-2}$, and $L_{VIII}$ in this case stands for straight-chain or branched alkoxy with up to 8 carbon atoms or for cycloalkyloxy with 3 to 8 carbon atoms, $T_{VIII}$ stands for a radical of the formula

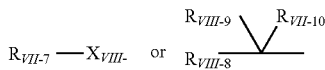

wherein $R_{VIII-7}$ and $R_{VIII-8}$ are identical or different and denote cycloalkyl with 3 to 8 carbon atoms, or aryl with 6 to 10 carbon atoms, or denote a 5- to 7-member aromatic, optionally benzo-condensed, heterocyclic compound with up to 3 heteroatoms from the series S, N and/or O, which are optionally substituted up to 3 times in an identical manner or differently by trifluoromethyl, trifluoromethoxy, halogen, hydroxy, carboxyl, by straight-chain or branched alkyl, acyl, alkoxy, or alkoxycarbonyl with up to 6 carbon atoms each, or by phenyl, phenoxy, or thiophenyl, which can in turn be substituted by halogen, trifluoromethyl, or trifluoromethoxy, and/or the rings are substituted by a group of the formula —$NR_{VIII-11}R_{VIII-12}$, wherein $R_{VIII-11}$ and $R_{VIII-12}$ are identical or different and have the meaning given above for $R_{VIII-1}$, and $R_{VIII-2}$, $X_{VIII}$ denotes a straight or branched alkyl chain or alkenyl chain with 2 to 10 carbon atoms each, which are optionally substituted up to 2 times by hydroxy, $R_{VIII-9}$ denotes hydrogen, and $R_{VIII-10}$ denotes hydrogen, halogen, azido, trifluoromethyl, hydroxy, mercapto, trifluoromethoxy, straight-chain or branched alkoxy with up to 5 carbon atoms, or a radical of the formula —$NR_{VIII-13}R_{VIII-14}$, wherein $R_{VIII-13}$ and $R_{VIII-14}$ are identical or different and have the meaning given above for $R_{VIII-1}$ and $R_{VIII-2}$, or $R_{VIII-9}$ and $R_{VIII-10}$ form a carbonyl group together with the carbon atom.

Compounds of Formula VIII are disclosed in PCT Publication No. WO 9804528, which is incorporated herein by reference in its entirety for all purposes.

Another class of CETP inhibitors that finds utility with the present invention consists of substituted 1,2,4-triazoles having the Formula IX

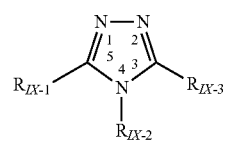

Formula IX or a pharmaceutically acceptable salt or tautomer thereof;

wherein $R_{IX-1}$ is selected from higher alkyl, higher alkenyl, higher alkynyl, aryl, aralkyl, aryloxyalkyl, alkoxyalkyl, alkylthioalkyl, arylthioalkyl, and cycloalkylalkyl;

wherein $R_{IX-2}$ is selected from aryl, heteroaryl, cycloalkyl, and cycloalkenyl, wherein $R_{IX-2}$ is optionally substituted at a substitutable position with one or more radicals independently selected from alkyl, haloalkyl, alkylthio, alkylsulfinyl, alkylsulfonyl, alkoxy, halo, aryloxy, aralkyloxy, aryl, aralkyl, aminosulfonyl, amino, monoalkylamino and dialkylamino; and wherein $R_{IX-3}$ is selected from hydrido, —SH and halo; provided $R_{IX-2}$ cannot be phenyl or 4-methylphenyl when $R_{IX-1}$ is higher alkyl and when $R_{IX-3}$ is BSH.

Compounds of Formula IX and their methods of manufacture are disclosed in PCT Publication No. WO 9914204, which is incorporated herein by reference in its entirety for all purposes.

In a preferred embodiment, the CETP inhibitor is selected from the following compounds of Formula IX:

2,4-dihydro-4-(3-methoxyphenyl)-5-tridecyl-3H-1,2,4-triazole-3-thione;
2,4-dihydro-4-(2-fluorophenyl)-5-tridecyl-3H-1,2,4-triazole-3-thione;
2,4-dihydro-4-(2-methylphenyl)-5-tridecyl-3H-1,2,4-triazole-3-thione;
2,4-dihydro-4-(3-chlorophenyl)-5-tridecyl-3H-1,2,4-triazole-3-thione;
2,4-dihydro-4-(2-methoxyphenyl)-5-tridecyl-3H-1,2,4-triazole-3-thione;
2,4-dihydro-4-(3-methylphenyl)-5-tridecyl-3H-1,2,4-triazole-3-thione;
4-cyclohexyl-2,4-dihydro-5-tridecyl-3H-1,2,4-triazole-3-thione;
2,4-dihydro-4-(3-pyridyl)-5-tridecyl-3H-1,2,4-triazole-3-thione;
2,4-dihydro-4-(2-ethoxyphenyl)-5-tridecyl-3H-1,2,4-triazole-3-thione;
2,4-dihydro-4-(2,6-dimethylphenyl)-5-tridecyl-3H-1,2,4-triazole-3-thione;
2,4-dihydro-4-(4-phenoxyphenyl)-5-tridecyl-3H-1,2,4-triazole-3-thione;
4-(1,3-benzodioxol-5-yl)-2,4-dihydro-5-tridecyl-3H-1,2,4-triazole-3-thione;
4-(2-chlorophenyl)-2,4-dihydro-5-tridecyl-3H-1,2,4-triazole-3-thione;
2,4-dihydro-4-(4-methoxyphenyl)-5-tridecyl-3H-1,2,4-triazole-3-thione;
2,4-dihydro-5-tridecyl-4-(3-trifluoromethylphenyl)-3H-1,2,4-triazole-3-thione;
2,4-dihydro-5-tridecyl-4-(3-fluorophenyl)-3H-1,2,4-triazole-3-thione;
4-(3-chloro-4-methylphenyl)-2,4-dihydro-5-tridecyl-3H-1,2,4-triazole-3-thione;
2,4-dihydro-4-(2-methylthiophenyl)-5-tridecyl-3H-1,2,4-triazole-3-thione;
4-(4-benzyloxyphenyl)-2,4-dihydro-5-tridecyl-3H-1,2,4-triazole-3-thione;
2,4-dihydro-4-(2-naphthyl)-5-tridecyl-3H-1,2,4-triazole-3-thione;
2,4-dihydro-5-tridecyl-4-(4-trifluoromethylphenyl)-3H-1,2,4-triazole-3-thione;
2,4-dihydro-4-(1-naphthyl)-5-tridecyl-3H-1,2,4-triazole-3-thione;
2,4-dihydro-4-(3-methylthiophenyl)-5-tridecyl-3H-1,2,4-triazole-3-thione;
2,4-dihydro-4-(4-methylthiophenyl)-5-tridecyl-3H-1,2,4-triazole-3-thione;
2,4-dihydro-4-(3,4-dimethoxyphenyl)-5-tridecyl-3H-1,2,4-triazole-3-thione;
2,4-dihydro-4-(2,5-dimethoxyphenyl)-5-tridecyl-3H-1,2,4-triazole-3-thione;
2,4-dihydro-4-(2-methoxy-5-chlorophenyl)-5-tridecyl-3H-1,2,4-triazole-3-thione;
4-(4-aminosulfonylphenyl)-2,4-dihydro-5-tridecyl-3H-1,2,4-triazole-3-thione;
2,4-dihydro-5-dodecyl-4-(3-methoxyphenyl)-3H-1,2,4-triazole-3-thione;
2,4-dihydro-4-(3-methoxyphenyl)-5-tetradecyl-3H-1,2,4-triazole-3-thione;
2,4-dihydro-4-(3-methoxyphenyl)-5-undecyl-3H-1,2,4-triazole-3-thione; and
2,4-dihydro-(4-methoxyphenyl)-5-pentadecyl-3H-1,2,4-triazole-3-thione.

Another class of CETP inhibitors that finds utility with the present invention consists of hetero-tetrahydroquinolines having the Formula X

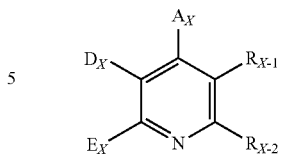

Formula X and pharmaceutically acceptable salts, enantiomers, or stereoisomers or N-oxides of said compounds;
in which
$A_X$ represents cycloalkyl with 3 to 8 carbon atoms or a 5 to 7-membered, saturated, partially saturated or unsaturated, optionally benzo-condensed heterocyclic ring containing up to 3 heteroatoms from the series comprising S, N and/or O, that in case of a saturated heterocyclic ring is bonded to a nitrogen function, optionally bridged over it, and in which the aromatic systems mentioned above are optionally substituted up to 5-times in an identical or different substituents in the form of halogen, nitro, hydroxy, trifluoromethyl, trifluoromethoxy or by a straight-chain or branched alkyl, acyl, hydroxyalkyl or alkoxy each having up to 7 carbon atoms or by a group of the formula $BNR_{X-3}R_{X-4}$,
in which
$R_{X-3}$ and $R_{X-4}$ are identical or different and denote hydrogen, phenyl or straight-chain or branched alkyl having up to 6 carbon atoms,
or
$A_X$ represents a radical of the formula

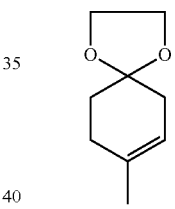

$D_X$ represents an aryl having 6 to 10 carbon atoms, that is optionally substituted by phenyl, nitro, halogen, trifluormethyl or trifluoromethoxy, or it represents a radical of the formula

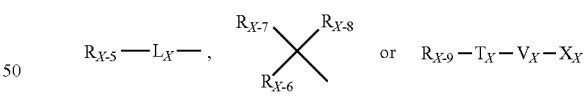

in which
$R_{X-5}$, $R_{X-6}$ and $R_{X-9}$ independently of one another denote cycloalkyl having 3 to 6 carbon atoms, or an aryl having 6 to 10 carbon atoms or a 5- to 7-membered aromatic, optionally benzo-condensed saturated or unsaturated, mono-, bi-, or tricyclic heterocyclic ring from the series consisting of S, N and/or O, in which the rings are substituted, optionally, in case of the nitrogen containing aromatic rings via the N function, with up to 5 identical or different substituents in the form of halogen, trifluoromethyl, nitro, hydroxy, cyano, carbonyl, trifluoromethoxy, straight straight-chain or branched acyl, alkyl, alkylthio, alkylalkoxy, alkoxy, or alkoxycarbonyl each having up to 6 carbon atoms, by aryl or trifluoromethyl-substituted aryl each having 6 to 10 carbon atoms or by an, optionally benzo-condensed, aromatic 5- to 7-membered heterocyclic ring having up to 3 heteroatoms from the series consisting of S, N, and/or O, and/or substituted by a group of the formula $BOR_{X-10}$, $—SR_{X-11}$, $SO_2R_{X-12}$ or $BNR_{X-13}R_{X-14}$, in which $R_{X-10}$, $R_{X-11}$ and $R_{X-12}$ independently from each other denote aryl having 6 to 10 carbon atoms, which is in turn substituted with up to 2 identical or different substituents in the form of phenyl, halogen or a straight-chain or branched alkyl having up to 6 carbon atoms, $R_{X-13}$ and $R_{X-14}$ are identical or different and have the meaning of $R_{X-3}$ and $R_{X-4}$ indicated above, or $R_{X-5}$ and/or $R_{X-6}$ denote a radical of the formula

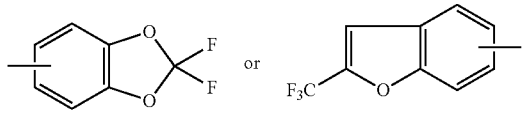

$R_{X-7}$ denotes hydrogen or halogen, and $R_{X-8}$ denotes hydrogen, halogen, azido, trifluoromethyl, hydroxy, trifluoromethoxy, straight-chain or branched alkoxy or alkyl having up to 6 carbon atoms or a radical of the formula $BNR_{X-15}R_{X-16}$, in which $R_{X-15}$ and $R_{X-16}$ are identical or different and have the meaning of $R_{X-3}$ and $R_{X-4}$ indicated above, or $R_{X-7}$ and $R_{X-8}$ together form a radical of the formula $=O$ or $=NR_{X-17}$, in which $R_{X-17}$ denotes hydrogen or straight chain or branched alkyl, alkoxy or acyl having up to 6 carbon atoms, $L_X$ denotes a straight chain or branched alkylene or alkenylene chain having up to 8 carbon atoms, that are optionally substituted with up to 2 hydroxy groups, $T_X$ and $X_X$ are identical or different and denote a straight chain or branched alkylene chain with up to 8 carbon atoms or $T_X$ or $X_X$ denotes a bond, $V_X$ represents an oxygen or sulfur atom or an $BNR_{X-18}$-group, in which $R_{X-18}$ denotes hydrogen or straight chain or branched alkyl with up to 6 carbon atoms or phenyl, $E_X$ represents cycloalkyl with 3 to 8 carbon atoms, or straight chain or branched alkyl with up to 8 carbon atoms, that is optionally substituted by cycloalkyl with 3 to 8 carbon atoms or hydroxy, or represents a phenyl, that is optionally substituted by halogen or trifluoromethyl, $R_{X-1}$ and $R_{X-2}$ together form a straight-chain or branched alkylene chain with up to 7 carbon atoms, that must be substituted by carbonyl group and/or by a radical with the formula

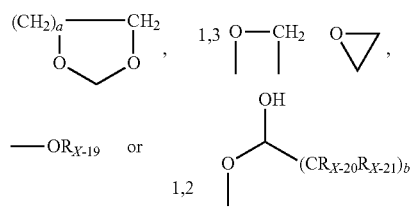

in which a and b are identical or different and denote a number equaling 1,2, or 3, $R_{X-19}$ denotes hydrogen, cycloalkyl with 3 up to 7 carbon atoms, straight chain or branched silylalkyl with up to 8 carbon atoms or straight chain or branched alkyl with up to 8 carbon atoms, that are optionally substituted by hydroxyl, straight chain or branched alkoxy with up to 6 carbon atoms or by phenyl, which in turn might be substituted by halogen, nitro, trifluormethyl, trifluoromethoxy or by phenyl or by tetrazole-substituted phenyl, and alkyl, optionally be substituted by a group with the formula $BOR_{X-22}$, in which $R_{X-22}$ denotes a straight chain or branched acyl with up to 4 carbon atoms or benzyl, or $R_{X-19}$ denotes straight chain or branched acyl with up to 20 carbon atoms or benzoyl, that is optionally substituted by halogen, trifluoromethyl, nitro or trifluoromethoxy, or it denotes straight chain or branched fluoroacyl with up to 8 carbon atoms and 9 fluorine atoms, $R_{X-20}$ and $R_{X-21}$ are identical or different and denote hydrogen, phenyl or straight chain or branched alkyl with up to 6 carbon atoms, or $R_{X-20}$ and $R_{X-21}$ together form a 3- to 6-membered carbocyclic ring, and the carbocyclic rings formed are optionally substituted, optionally also geminally, with up to six identical or different substituents in the form of trifluoromethyl, hydroxy, nitrile, halogen, carboxyl, nitro, azido, cyano, cycloalkyl or cycloalkyloxy with 3 to 7 carbon atoms each, by straight chain or branched alkoxycarbonyl, alkoxy or alkylthio with up to 6 carbon atoms each or by straight chain or branched alkyl with up to 6 carbon atoms, which in turn is substituted with up to 2 identically or differently by hydroxyl, benzyloxy, trifluoromethyl, benzoyl, straight chain or branched alkoxy, oxyacyl or carbonyl with up to 4 carbon atoms each and/or phenyl, which may in turn be substituted with a halogen, trifluoromethyl or trifluoromethoxy, and/or the formed carbocyclic rings are optionally substituted, also geminally, with up to 5 identical or different substituents in the form of phenyl, benzoyl, thiophenyl or sulfonylbenzyl, which in turn are optionally substituted by halogen, trifluoromethyl, trifluoromethoxy or nitro, and/or optionally are substituted by a radical with the formula

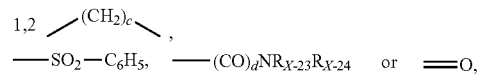

in which c denotes a number equaling 1, 2, 3, or 4, d denotes a number equaling 0 or 1, $R_{X-23}$ and $R_{X-24}$ are identical or different and denote hydrogen, cycloalkyl with 3 to 6 carbon atoms, straight chain or branched alkyl with up to 6 carbon atoms, benzyl or phenyl, that is optionally substituted with up to 2 identically or differently by halogen, trifluoromethyl, cyano, phenyl or nitro, and/or the formed carbocyclic rings are substituted optionally by a spiro-linked radical with the formula

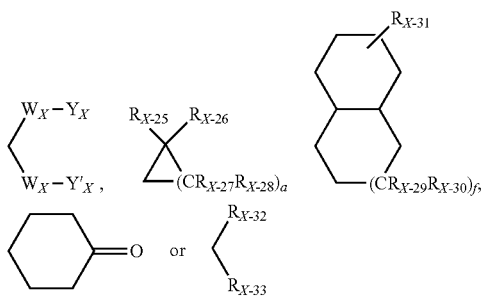

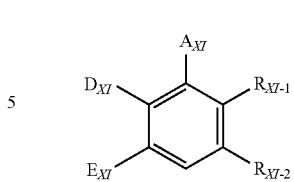

Formula XI in which $W_X$ denotes either an oxygen or a sulfur atom $Y_X$ and $Y'_X$ together form a 2 to 6 membered straight chain or branched alkylene chain, e denotes a number equaling 1, 2, 3, 4, 5, 6, or 7, f denotes a number equaling 1 or 2, $R_{X-25}$, $R_{X-26}$, $R_{X-27}$, $R_{X-28}$, $R_{X-29}$, $R_{X-30}$ and $R_{X-31}$ are identical or different and denote hydrogen, trifluoromethyl, phenyl, halogen or straight chain or branched alkyl or alkoxy with up to 6 carbon atoms each, or $R_{X-25}$ and $R_{X-26}$ or $R_{X-27}$ and $R_{X-28}$ respectively form together a straight chain or branched alkyl chain with up to 6 carbon atoms, or $R_{X-25}$ and $R_{X-26}$ or $R_{X-27}$ and $R_{X-28}$ each together form a radical with the formula

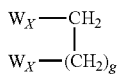

in which $W_X$ has the meaning given above, g denotes a number equaling 1, 2, 3, 4, 5, 6, or 7, $R_{X-32}$ and $R_{X-33}$ form together a 3- to 7-membered heterocycle, which contains an oxygen or sulfur atom or a group with the formula SO, $SO_2$ or

in which $R_{X-34}$ denotes hydrogen, phenyl, benzyl or straight or branched alkyl with up to 4 carbon atoms.

Compounds of Formula X and their methods of manufacture are disclosed in PCT Publication No. WO 9914215, which is incorporated herein by reference in its entirety for all purposes.

In a preferred embodiment, the CETP inhibitor is selected from the following compounds of Formula X:

2-cyclopentyl-5-hydroxy-7,7-dimethyl-4-(3-thienyl)-3-(4-trifluoromethylbenxoyl)-5,6,7,8-tetrahydroquinoline;

2-cyclopentyl-3-[fluoro-(4-trifluoromethylphenyl)methyl]-5-hydroxy-7,7-dimethyl-4-(3-thienyl)-5,6,7,8-tetrahydroquinoline; and 2-cyclopentyl-5-hydroxy-7,7-dimethyl-4-(3-thienyl)-3-(trifluoromethylbenxyl)-5,6,7,8-tetrahydroquinoline.

Another class of CETP inhibitors that finds utility with the present invention consists of substituted tetrahydro naphthalines and analogous compound having the Formula XI and stereoisomers, stereoisomer mixtures, and salts thereof, in which $A_{XI}$ stands for cycloalkyl with 3 to 8 carbon atoms, or stands for aryl with 6 to 10 carbon atoms, or stands for a 5- to 7-membered, saturated, partially unsaturated or unsaturated, possibly benzocondensated, heterocycle with up to 4 heteroatoms from the series S, N and/or O, where aryl and the heterocyclic ring systems mentioned above are substituted up to 5-fold, identical or different, by cyano, halogen, nitro, carboxyl, hydroxy, trifluoromethyl, trifluoro-methoxy, or by straight-chain or branched alkyl, acyl, hydroxyalkyl, alkylthio, alkoxycarbonyl, oxyalkoxycarbonyl or alkoxy each with up to 7 carbon atoms, or by a group of the formula

—$NR_{XI-3}R_{XI-4}$, in which $R_{XI-3}$ and $R_{XI-4}$ are identical or different and denote hydrogen, phenyl, or straight-chain or branched alkyl with up to 6 carbon atoms $D_{XI}$ stands for a radical of the formula

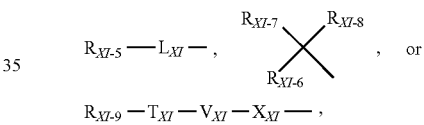

in which $R_{XI-5}$, $R_{XI-6}$ and $R_{XI-9}$, independent of each other, denote cycloalkyl with 3 to 6 carbon atoms, or denote aryl with 6 to 10 carbon atoms, or denote a 5- to 7-membered, possibly benzocondensated, saturated or unsaturated, mono-, bi- or tricyclic heterocycle with up to 4 heteroatoms of the series S, N and/or O, where the cycles are possibly substituted in the case of the nitrogen-containing rings also via the N-function up to 5-fold, identical or different, by halogen, trifluoromethyl. nitro, hydroxy, cyano, carboxyl, trifluoromethoxy, straight-chain or branched acyl, alkyl, alkylthio, alkylalkoxy, alkoxy or alkoxycarbonyl with up to 6 carbon atoms each. by aryl or trifluoromethyl substituted aryl with 6 to 10 carbon atoms each, or by a possibly benzocondensated aromatic 5- to 7-membered heterocycle with up to 3 heteroatoms of the series S, N and/or O, and/or are substituted by a group of the formula

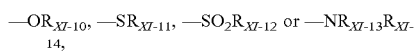

in which $R_{XI-10}$, $R_{XI-11}$ and $R_{XI-12}$, independent of each other, denote aryl with 6 to 10 carbon atoms, which itself is substituted up to 2-fold, identical or different, by phenyl, halogen. or by straight-chain or branched alkyl with up to 6 carbon atoms, $R_{XI-13}$ and $R_{XI-14}$ are identical or different and have the meaning given above for $R_{XI-3}$ and $R_{XI-4}$, or $R_{XI-5}$ and/or $R_{XI-6}$ denote a radical of the formula

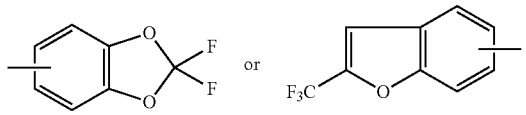

$R_{XI-7}$ denotes hydrogen, halogen or methyl,
and
$R_{XI-8}$ denotes hydrogen, halogen, azido, trifluoromethyl, hydroxy, trifluoromethoxy, straight-chain or branched alkoxy or alkyl with up to 6 carbon atoms each, or a radical of the formula —$NR_{XI-15}R_{X-16}$,
in which
$R_{XI-15}$ and $R_{XI-16}$ are identical or different and have the meaning given above for $R_{XI-3}$ and $R_{XI-4}$,
or
$R_{XI-7}$ and $R_{XI-8}$ together form a radical of the formula =O or =$NR_{XI-17}$, in which
$R_{XI-17}$ denotes hydrogen or straight-chain or branched alkyl, alkoxy or acyl with up to 6 carbon atoms each,
$L_{XI}$ denotes a straight-chain or branched alkylene- or alkenylene chain with up to 8 carbon atoms each, which is possibly substituted up to 2-fold by hydroxy,
$T_{XI}$ and $X_{XI}$ are identical or different and denote a straight-chain or branched alkylene chain with up to 8 carbon atoms, or
$T_{XI}$ and $X_{XI}$ denotes a bond,
$V_{XI}$ stands for an oxygen- or sulfur atom or for an —$NR_{XI-18}$ group, in which
$R_{XI-18}$ denotes hydrogen or straight-chain or branched alkyl with up to 6 carbon atoms, or phenyl,
$E_{XI}$ stands for cycloalkyl with 3 to 8 carbon atoms, or stands for straight-chain or branched alkyl with up to 8 carbon atoms, which is possibly substituted by cycloalkyl with 3 to 8 carbon atoms or hydroxy, or stands for phenyl, which is possibly substituted by halogen or trifluoromethyl,
$R_{XI-1}$ and $R_{XI-2}$ together form a straight-chain or branched alkylene chain with up to 7 carbon atoms, which must be substituted by a carbonyl group and/or by a radical of the formula

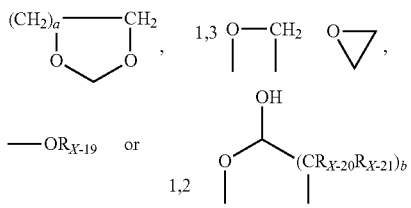

in which
a and b are identical or different and denote a number 1, 2 or 3
$R_{XI-19}$ denotes hydrogen, cycloalkyl with 3 to 7 carbon atoms, straight-chain or branched silylalkyl with up to 8 carbon atoms, or straight-chain or branched alkyl with up to 8 carbon atoms, which is possibly substituted by hydroxy, straight-chain or branched alkoxy with up to 6 carbon atoms, or by phenyl, which itself can be substituted by halogen, nitro, trifluoromethyl, trifluoromethoxy or by phenyl substituted by phenyl or tetrazol, and alkyl is possibly substituted by a group of the formula —$OR_{XI-22}$,
in which
$R_{XI-22}$ denotes straight-chain or branched acyl with up to 4 carbon atoms, or benzyl,
or
$R_{XI-19}$ denotes straight-chain or branched acyl with up to 20 carbon atoms or benzoyl, which is possibly substituted by halogen, trifluoromethyl, nitro or trifluoromethoxy, or denotes straight-chain or branched fluoroacyl with up to 8 carbon atoms and 9 fluorine atoms,
$R_{XI-20}$ and $R_{XI-21}$ are identical or different, denoting hydrogen, phenyl or straight-chain or branched alkyl with up to 6 carbon atoms,
or
$R_{XI-20}$ and $R_{XI-21}$ together form a 3- to 6-membered carbocycle, and, possibly also geminally, the alkylene chain formed by $R_{X-1}$ and $R_{XI-2}$, is possibly substituted up to 6-fold, identical or different, by trifluoromethyl, hydroxy, nitrile, halogen, carboxyl, nitro, azido, cyano, cycloalkyl or cycloalkyloxy with 3 to 7 carbon atoms each, by straight-chain or branched alkoxycarbonyl, alkoxy or alkoxythio with up to 6 carbon atoms each, or by straight-chain or branched alkyl with up to 6 carbon atoms, which itself is substituted up to 2-fold, identical or different. by hydroxyl, benzyloxy, trifluoromethyl, benzoyl, straight-chain or branched alkoxy, oxyacyl or carboxyl with up to 4 carbon atoms each, and/or phenyl—which itself can be substituted by halogen, trifluoromethyl or trifluoromethoxy, and/or the alkylene chain formed by $R_{XI-1}$ and $R_{XI-2}$ is substituted, also geminally, possibly up to 5-fold, identical or different, by phenyl, benzoyl, thiophenyl or sulfobenzyl—which themselves are possibly substituted by halogen, trifluoromethyl, trifluoromethoxy or nitro, and/or the alkylene chain formed by $R_{XI-1}$ and $R_{XI-2}$ is possibly substituted by a radical of the formula

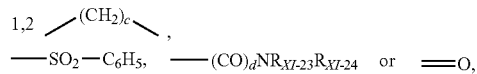

in which
c denotes a number 1, 2, 3 or 4,
d denotes a number 0 or 1,
$R_{XI-23}$ and $R_{XI-24}$ are identical or different and denote hydrogen, cycloalkyl with 3 to 6 carbon atoms, straight-chain or branched alkyl with up to 6 carbon atoms, benzyl or phenyl, which is possibly substituted up to 2-fold. identical or different, by halogen, trifluoromethyl, cyano, phenyl or nitro, and/or the alkylene chain formed by $R_{XI-1}$ and $R_{XI-2}$ is possibly substituted by a spiro-jointed radical of the formula

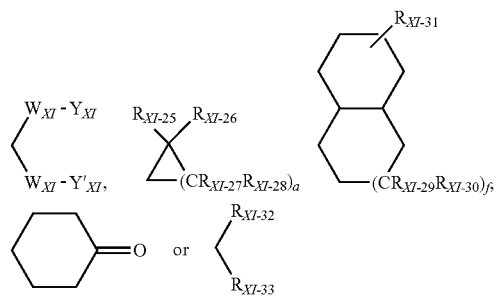

in which $W_{XI}$ denotes either an oxygen or a sulfur atom, $Y_{XI}$ and $Y'_{XI}$ together form a 2- to 6-membered straight-chain or branched alkylene chain, e is a number 1, 2, 3, 4, 5, 6 or 7, f denotes a number 1 or 2, $R_{XI-25}$, $R_{XI-26}$, $R_{XI-27}$, $R_{XI-28}$, $R_{XI-29}$, $R_{XI-30}$ and $R_{XI-31}$ are identical or different and denote hydrogen, trifluoromethyl, phenyl, halogen, or straight-chain or branched alkyl or alkoxy with up to 6 carbon atoms each, or $R_{XI-25}$ and $R_{XI-26}$ or $R_{XI-27}$ and $R_{XI-28}$ together form a straight-chain or branched alkyl chain with up to 6 carbon atoms, or $R_{XI-25}$ and $R_{XI-26}$ or $R_{XI-27}$ and $R_{XI-28}$ together form a radical of the formula

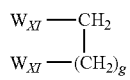

in which $W_{XI}$ has the meaning given above, g is a number 1, 2, 3, 4, 5, 6 or 7, $R_{XI-32}$ and $R_{XI-33}$ together form a 3- to 7-membered heterocycle that contains an oxygen- or sulfur atom or a group of the formula SO, $SO_2$ or $-NR_{XI-34}$, in which $R_{XI-34}$ denotes hydrogen, phenyl, benzyl, or straight-chain or branched alkyl with up to 4 carbon atoms.

Compounds of Formula XI and their methods of manufacture are disclosed in PCT Publication No. WO 9914174, which is incorporated herein by reference in its entirety for all purposes.

Another class of CETP inhibitors that finds utility with the present invention consists of 2-aryl-substituted pyridines having the Formula (XII)

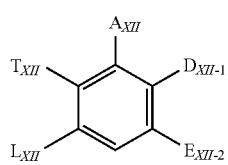

Formula XII or pharmaceutically acceptable salts, enantiomers, or stereoisomers of said compounds, in which $A_{XII}$ and $E_{XII}$ are identical or different and stand for aryl with 6 to 10 carbon atoms which is possibly substituted, up to 5-fold identical or different, by halogen, hydroxy, trifluoromethyl, trifluoromethoxy, nitro or by straight-chain or branched alkyl, acyl, hydroxy alkyl or alkoxy with up to 7 carbon atoms each, or by a group of the formula $-N_{XII-1}R_{XII-2}$, where $R_{XII-1}$ and $R_{XII-2}$ are identical or different and are meant to be hydrogen, phenyl or straight-chain or branched alkyl with up to 6 carbon atoms, $D_{XII}$ stands for straight-chain or branched alkyl with up to 8 carbon atoms, which is substituted by hydroxy, $L_{XII}$ stands for cycloalkyl with 3 to 8 carbon atoms or for straight-chain or branched alkyl with up to 8 carbon atoms, which is possibly substituted by cycloalkyl with 3 to 8 carbon atoms, or by hydroxy, $T_{XII}$ stands for a radical of the formula $R_{XII-3}-X_{XII}-$ or

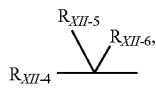

where $R_{XII-3}$ and $R_{XII-4}$ are identical or different and are meant to be cycloalkyl with 3 to 8 carbon atoms, or aryl with 6 to 10 carbon atoms, or a 5- to 7-membered aromatic, possibly benzocondensated heterocycle with up to 3 heteroatoms from the series S, N and/or O, which are possibly substituted. up to 3-fold identical or different, by trifluoromethyl, trifluoromethoxy, halogen, hydroxy, carboxyl, nitro, by straight-chain or branched alkyl, acyl, alkoxy or alkoxycarbonyl with up to 6 carbon atoms each. or by phenyl, phenoxy or phenylthio which in turn can be substituted by halogen. trifluoromethyl or trifluoromethoxy, and/or where the cycles are possibly substituted by a group of the formula $-NR_{XII-7}R_{XII-8}$, where $R_{XII-7}$ and $R_{XII-8}$ are identical or different and have the meaning of $R_{XII-1}$ and $R_{XII-2}$ given above, $X_{XII}$ is a straight-chain or branched alkyl or alkenyl with 2 to 10 carbon atoms each, possibly substituted up to 2-fold by hydroxy or halogen, $R_{XII-5}$ stands for hydrogen, and $R_{XII-6}$ means to be hydrogen, halogen, mercapto, azido, trifluoromethyl, hydroxy, trifluoromethoxy, straight-chain or branched alkoxy with up to 5 carbon atoms, or a radical of the formula $BNR_{XII-9}R_{XII-10}$, where $R_{XII-9}$ and $R_{XII-10}$ are identical or different and have the meaning of $R_{XII-1}$ and $R_{XII-2}$ given above, or $R_{XII-5}$ and $R_{XII-6}$, together with the carbon atom, form a carbonyl group.

Compounds of Formula XII and their methods of manufacture are disclosed in EP 796846-A1, U.S. Pat. No. 6,127,383 and U.S. Pat. No. 5,925,645, all of which are incorporated herein by reference in their entireties for all purposes.

In a preferred embodiment, the CETP inhibitor is selected from the following compounds of Formula XII:

4,6-bis-(p-fluorophenyl)-2-isopropyl-3-[(p-trifluoromethyl-phenyl)-(fluoro)-methyl]-5-(1-hydroxyethyl)pyridine;

2,4-bis-(4-fluorophenyl)-6-isopropyl-5-[4-(trifluoromethyl-phenyl)-fluoromethyl]-3-hydroxymethyl)pyridine; and 2,4-bis-(4-fluorophenyl)-6-isopropyl-5-[2-(3-trifluoromethylphenyl)vinyl]-3-hydroxymethyl)pyridine.

Another class of CETP inhibitors that finds utility with the present invention consists of compounds having the Formula (XIII)

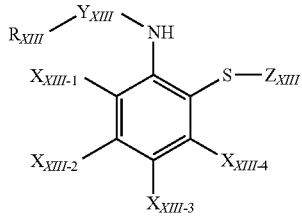

Formula XIII or pharmaceutically acceptable salts, enantiomers, stereoisomers, hydrates, or solvates of said compounds, in which $R_{XIII}$ is a straight chain or branched $C_{1-10}$ alkyl; straight chain or branched $C_{2-10}$ alkenyl; halogenated $C_{1-4}$ lower alkyl; $C_{3-10}$ cycloalkyl that may be substituted; $C_{5-8}$ cycloalkenyl that may be substituted; $C_{3-10}$ cycloalkyl $C_{1-10}$ alkyl that may be substituted; aryl that may be substituted; aralkyl that may be substituted; or a 5- or 6-membered heterocyclic group having 1 to 3 nitrogen atoms, oxygen atoms or sulfur atoms that may be substituted, $X_{XIII-1}$, $X_{XIII-2}$, $X_{XIII-3}$, $X_{XIII-4}$ may be the same or different and are a hydrogen atom; halogen atom; $C_{1-4}$ lower alkyl; halogenated $C_{1-4}$ lower alkyl; $C_{1-4}$ lower alkoxy; cyano group; nitro group; acyl; or aryl, respectively;

$Y_{XIII}$ is —CO—; or $BSO_2$—; and $Z_{XIII}$ is a hydrogen atom; or mercapto protective group.

Compounds of Formula XIII and their methods of manufacture are disclosed in PCT Publication No. WO 98/35937, which is incorporated herein by reference in its entirety for all purposes.

In a preferred embodiment, the CETP inhibitor is selected from the following compounds of Formula XIII:

N,N'-(dithiodi-2,1-phenylene)bis[2,2-dimethyl-propanamide];

N,N'-(dithiodi-2,1-phenylene)bis[1-methyl-cyclohexanecarboxamide];

N,N'-(dithiodi-2,1-phenylene)bis[1-(3-methylbutyl)-cyclopentanecarboxamide];

N,N'-(dithiodi-2,1-phenylene)bis[1-(3-methylbutyl)-cyclohexanecarboxamide];

N,N'-(dithiodi-2,1-phenylene)bis[1-(2-ethylbutyl)-cyclohexanecarboxamide];

N,N'-(dithiodi-2,1-phenylene)bis-tricyclo[3.3.1.1$^{3,7}$]decane-1-carboxamide;

propanethioic acid, 2-methyl-,S-[2-[[[1-(2-ethylbutyl)cyclohexyl]carbonyl]amino]phenyl]ester;

propanethioic acid, 2,2-dimethyl-, S-[2-[[[1-(2-ethylbutyl)cyclohexyl]carbonyl]amino]phenyl]ester; and ethanethioic acid, S-[2-[[[1-(2-ethylbutyl)cyclohexyl]carbonyl]amino]phenyl]ester.

Another class of CETP inhibitors that finds utility with the present invention consists of polycyclic aryl and heteroaryl tertiary-heteroalkylamines having the Formula XIV

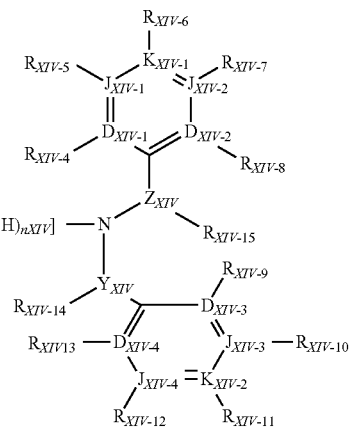

Formula XIV and pharmaceutically acceptable forms thereof, wherein:

$n_{XIV}$ is an integer selected from 0 through 5;

$R_{XIV-1}$ is selected from the group consisting of haloalkyl, haloalkenyl, haloalkoxyalkyl, and haloalkenyloxyalkyl;

$X_{XIV}$ is selected from the group consisting of O, H, F, S, S(O), NH, N(OH), N(alkyl), and N(alkoxy);

$R_{XIV-16}$ is selected from the group consisting of hydrido, alkyl, alkenyl, alkynyl, aryl, aralkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryl, perhaloaralkyl, perhaloaryloxyalkyl, heteroaryl, heteroarylalkyl, monocarboalkoxyalkyl, monocarboalkoxy, dicarboalkoxyalkyl, monocarboxamido, monocyanoalkyl, dicyanoalkyl, carboalkoxycyanoalkyl, acyl, aroyl, heteroaroyl, heteroaryloxyalkyl, dialkoxyphosphonoalkyl, trialkylsilyl, and a spacer selected from the group consisting of a covalent single bond and a linear spacer moiety having from 1 through 4 contiguous atoms linked to the point of bonding of an aromatic substituent selected from the group consisting of $R_{XIV-4}$, $R_{XIV-8}$, $R_{XIV-9}$, and $R_{XIV-13}$ to form a heterocyclyl ring having from 5 through 10 contiguous members with the provisos that said spacer moiety is other than a covalent single bond when $R_{XIV-2}$ is alkyl and there is no $R_{XIV-16}$ wherein X is H or F;

$D_{XIV-1}$, $D_{XIV-2}$, $J_{XIV-1}$, $J_{XIV-2}$ and $K_{XIV-1}$ are independently selected from the group consisting of C, N, O, S and a covalent bond with the provisos that no more than one of $D_{XIV-1}$, $D_{XIV-2}$, $J_{XIV-1}$, $J_{XIV-2}$ and $K_{XIV-1}$ is a covalent bond, no more than one of $D_{XIV-1}$, $D_{XIV-2}$, $J_{XIV-1}$, $J_{XIV-2}$ and $K_{XIV-1}$ is O, no more than one of $D_{XIV-1}$, $D_{XIV-2}$, $J_{XIV-1}$, $J_{XIV-2}$ and $K_{XIV-1}$ is S, one of $D_{XIV-1}$, $D_{XIV-2}$, $J_{XIV-1}$, $J_{XIV-2}$ and $K_{XIV-1}$ must be a covalent bond when two of $D_{XIV-1}$, $D_{XIV-2}$, $J_{XIV-1}$, $J_{XIV-2}$ and $K_{XIV-1}$ are O and S, and no more than four of $D_{XIV-1}$, $D_{XIV-2}$, $J_{XIV-1}$, $J_{XIV-2}$ and $K_{XIV-1}$ are N;

$D_{XIV-3}$, $D_{XIV-4}$, $J_{XIV-3}$, $J_{XIV-4}$ and $K_{XIV-2}$ are independently selected from the group consisting of C, N, O, S and a covalent bond with the provisos that no more than one of $D_{XIV-3}$, $D_{XIV-4}$, $J_{XIV-3}$, $J_{XIV-4}$ and $K_{XIV-2}$ is a covalent bond, no more than one of $D_{XIV-3}$, $D_{XIV-4}$, $J_{XIV-3}$, $J_{XIV-4}$ and $K_{XIV-2}$ is O, no more than one of $D_{XIV-3}$, $D_{XIV-4}$, $J_{XIV-3}$, $J_{XIV-4}$ and $K_{XIV-2}$ is S, one of $D_{XIV-3}$, $D_{XIV-4}$, $J_{XIV-3}$, $J_{XIV-4}$ and $K_{XIV-2}$ must be a covalent bond when two of $D_{XIV-3}$, $D_{XIV-4}$, $J_{XIV-3}$, $J_{XIV-4}$ and $K_{XIV-2}$ are O and S, and no more than four of $D_{XIV-3}$, $D_{XIV-4}$, $J_{XIV-3}$, $J_{XIV-4}$ and $K_{XIV-2}$ and $K_{XIV-2}$ are N;

$R_{XIV-2}$ is independently selected from the group consisting of hydrido, hydroxy, hydroxyalkyl, amino, aminoalkyl, alkylamino, dialkylamino, alkyl, alkenyl, alkynyl, aryl, aralkyl, aralkoxyalkyl, aryloxyalkyl, alkoxyalkyl, heteroaryloxyalkyl, alkenyloxyalkyl, alkylthioalkyl, aralkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, aloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, alkylsulfinylalkyl, alkylsulfonylalkyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsulfonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, and diaralkoxyphosphonoalkyl;

$R_{XIV-2}$ and $R_{XIV-3}$ are taken together to form a linear spacer moiety selected from the group consisting of a covalent single bond and a moiety having from 1 through 6 contiguous atoms to form a ring selected from the group consisting of a cycloalkyl having from 3 through 8 contiguous members, a cycloalkenyl having from 5 through 8 contiguous members, and a heterocyclyl having from 4 through 8 contiguous members;

$R_{XIV-3}$ is selected from the group consisting of hydrido, hydroxy, halo, cyano, aryloxy, hydroxyalkyl, amino, alkylamino, dialkylamino, acyl, sulfhydryl, acylamido, alkoxy, alkylthio, arylthio, alkyl, alkenyl, alkynyl, aryl, aralkyl, aryloxyalkyl, alkoxyalkyl, heteroarylthio, aralkylthio, aralkoxyalkyl, alkylsulfinylalkyl, alkylsulfonylalkyl, aroyl, heteroaroyl, aralkylthioalkyl, heteroaralkylthioalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsulfonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, and diaralkoxyphosphonoalkyl;

$Y_{XIV}$ is selected from a group consisting of a covalent single bond, $(C(R_{XIV-14})_2)_{qXIV}$ wherein $qXIV$ is an integer selected from 1 and 2 and $(CH(R_{XIV-14}))_{gXIV}$—$W_{XIV}$—$(CH(R_{XIV-14}))_{pXIV}$ wherein $gXIV$ and $pXIV$ are integers independently selected from 0 and 1;

$R_{XIV-14}$ is independently selected from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsulfonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_{XIV-9}$ and $R_{XIV-13}$ to form a ring selected from the group consisting of a cycloalkenyl ring having from 5 through 8 contiguous members and a heterocyclyl ring having from 5 through 8 contiguous members and a spacer selected from a moiety having a chain length of 2 to 5 atoms connected to the point of bonding selected from the group consisting of $R_{XIV-4}$ and $R_{XIV-8}$ to form a heterocyclyl having from 5 through 8 contiguous members with the proviso that, when $Y_{XIV}$ is a covalent bond, an $R_{XIV-14}$ substituent is not attached to $Y_{XIV}$;

$R_{XIV-14}$ and $R_{XIV-14}$, when bonded to the different atoms, are taken together to form a group selected from the group consisting of a covalent bond, alkylene, haloalkylene, and a spacer selected from a group consisting of a moiety having a chain length of 2 to 5 atoms connected to form a ring selected from the group of a saturated cycloalkyl having from 5 through 8 contiguous members, a cycloalkenyl having from 5 through 8 contiguous members, and a heterocyclyl having from 5 through 8 contiguous members;

$R_{XIV-14}$ and $R_{XIV-14}$, when bonded to the same atom are taken together to form a group selected from the group consisting of oxo, thiono, alkylene, haloalkylene, and a spacer selected from the group consisting of a moiety having a chain length of 3 to 7 atoms connected to form a ring selected from the group consisting of a cycloalkyl having from 4 through 8 contiguous members, a cycloalkenyl having from 4 through 8 contiguous members, and a heterocyclyl having from 4 through 8 contiguous members;

$W_{XIV}$ is selected from the group consisting of O, C(O), C(S), C(O)N($R_{XIV-14}$), C(S)N($R_{XIV-14}$), ($R_{XIV-14}$)NC(O), ($R_{XIV-14}$)NC(S), S, S(O), S(O)$_2$, S(O)$_2$N($R_{XIV-14}$), ($R_{XIV-14}$)NS(O)$_2$, and N($R_{XIV-14}$) with the proviso that $R_{XIV-14}$ is selected from other than halo and cyano;

$Z_{XIV}$ is independently selected from a group consisting of a covalent single bond, $(C(R_{XIV-15})_2)_{qXIV-2}$ wherein $qXIV-2$ is an integer selected from 1 and 2, $(CH(R_{XIV-15}))_{jXIV}$—W—$(CH(R_{XIV-15}))_{kXIV}$ wherein $jXIV$ and $kXIV$ are integers independently selected from 0 and 1 with the proviso that, when $Z_{XIV}$ is a covalent single bond, an $R_{XIV-15}$ substituent is not attached to $Z_{XIV}$;

$R_{XIV-15}$ is independently selected, when $Z_{XIV}$ is $(C(R_{XIV-15})_2)_{qXIV}$ wherein $_{qXIV}$ is an integer selected from 1 and 2, from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsulfonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_{XIV-4}$ and $R_{XIV-8}$ to form a ring selected from the group consisting of a cycloalkenyl ring having from 5 through 8 contiguous members and a heterocyclyl ring having from 5 through 8 contiguous members, and a spacer selected from a moiety having a chain length of 2 to 5 atoms connected to the point of bonding selected from the group consisting of $R_{XIV-9}$ and $R_{XIV-13}$ to form a heterocyclyl having from 5 through 8 contiguous members;

$R_{XIV-15}$ and $R_{XIV-15}$, when bonded to the different atoms, are taken together to form a group selected from the group consisting of a covalent bond, alkylene, haloalkylene, and a spacer selected from a group consisting of a moiety having a chain length of 2 to 5 atoms connected to form a ring selected from the group of a saturated cycloalkyl having from 5 through 8 contiguous members, a cycloalkenyl having from 5 through 8 contiguous members, and a heterocyclyl having from 5 through 8 contiguous members;

$R_{XIV-15}$ and $R_{XIV-5}$, when bonded to the same atom are taken together to form a group selected from the group consisting of oxo, thiono, alkylene, haloalkylene, and a spacer selected from the group consisting of a moiety having a chain length of 3 to 7 atoms connected to form a ring selected from the group consisting of a cycloalkyl having from 4 through 8 contiguous members, a cycloalkenyl having from 4 through 8 contiguous members, and a heterocyclyl having from 4 through 8 contiguous members;

$R_{XIV-15}$ is independently selected, when $Z_{XIV}$ is $(CH(R_{XIV-15}))_{jXIV}$—W—$(CH(R_{XIV-15}))_{kXIV}$ wherein $_{jXIV}$ and $_{kXIV}$ are integers independently selected from 0 and 1, from the group consisting of hydrido, halo, cyano, aryloxy, carboxyl, acyl, aroyl, heteroaroyl, hydroxyalkyl, heteroaryloxyalkyl, acylamido, alkoxy, alkylthio, arylthio, alkyl, alkenyl, alkynyl, aryl, aralkyl, aryloxyalkyl, alkoxyalkyl, heteroaryloxyalkyl, aralkoxyalkyl, heteroaralkoxyalkyl, alkylsulfonylalkyl, alkylsulfinylalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsulfonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl, a spacer selected from a linear moiety having a chain length of 3 to 6 atoms connected to the point of bonding selected from the group consisting of $R_{XIV-4}$ and $R_{XIV-8}$ to form a ring selected from the group consisting of a cycloalkenyl ring having from 5 through 8 contiguous members and a heterocyclyl ring having from 5 through 8 contiguous members, and a spacer selected from a linear moiety having a chain length of 2 to 5 atoms connected to the point of bonding selected from the group consisting of $R_{XIV-9}$ and $R_{XIV-13}$ to form a heterocyclyl ring having from 5 through 8 contiguous members;

$R_{XIV-4}$, $R_{XIV-5}$, $R_{XIV-6}$, $R_{XIV-7}$, $R_{XIV-8}$, $R_{XIV-9}$, $R_{XIV-10}$, $R_{XIV-11}$, $R_{XIV-12}$, and $R_{XIV-13}$ are independently selected from the group consisting of perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkoxyalkyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkylamidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydroxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the proviso that there are one to five non-hydrido ring substituents $R_{XIV-4}$, $R_{XIV-5}$, $R_{XIV-6}$, $R_{XIV-7}$, and $R_{XIV-8}$ present, that there are one to five non-hydrido ring substituents $R_{XIV-9}$, $R_{XIV-10}$, $R_{XIV-11}$, $R_{XIV-12}$, and $R_{XIV-13}$ present, and $R_{XIV-4}$, $R_{XIV-5}$, $R_{XIV-6}$, $R_{XIV-7}$, $R_{XIV-8}$, $R_{XIV-9}$, $R_{XIV-10}$, $R_{XIV-11}$, $R_{XIV-12}$, and $R_{XIV-13}$ are each independently selected to maintain the tetravalent nature of carbon, trivalent nature of nitrogen, the divalent nature of sulfur, and the divalent nature of oxygen;

$R_{XIV-4}$ and $R_{XIV-5}$, $R_{XIV-5}$ and $R_{XIV-6}$, $R_{XIV-6}$ and $R_{XIV-7}$, $R_{XIV-7}$ and $R_{XIV-8}$, $R_{XIV-8}$ and $R_{XIV-9}$, $R_{XIV-9}$ and $R_{XIV-10}$, $R_{XIV-10}$ and $R_{XIV-11}$, $R_{XIV-11}$ and $R_{XIV-12}$, and $R_{XIV-12}$ and $R_{XIV-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XIV-4}$ and $R_{XIV-5}$, $R_{XIV-5}$ and $R_{XIV-6}$, $R_{XIV-6}$ and $R_{XIV-7}$, and $R_{XIV-7}$ and $R_{XIV-8}$ are used at the same time and that no more than one of the group consisting of spacer pairs $R_{XIV-9}$ and $R_{XIV-10}$, $R_{XIV-10}$ and $R_{XIV-11}$, $R_{XIV-11}$ and $R_{XIV-12}$, and $R_{XIV-12}$ and $R_{XIV-13}$ are used at the same time;

$R_{XIV-4}$ and $R_{XIV-9}$, $R_{XIV-4}$ and $R_{XIV-13}$, $R_{XIV-8}$ and $R_{XIV-9}$, and $R_{XIV-8}$ and $R_{XIV-13}$ are independently selected to form a spacer pair wherein said spacer pair is taken together to form a linear moiety wherein said linear moiety forms a ring selected from the group consisting of a partially saturated heterocyclyl ring having from 5 through 8 contiguous members and a heteroaryl ring having from 5 through 6 contiguous members with the proviso that no more than one of the group consisting of spacer pairs $R_{XIV-4}$ and $R_{XIV-9}$, $R_{XIV-4}$ and $R_{XIV-13}$, $R_{XIV-8}$ and $R_{XIV-9}$, and $R_{XIV-8}$ and $R_{XIV-13}$ is used at the same time.

Compounds of Formula XIV and their methods of manufacture are disclosed in PCT Publication No. WO 00/18721, which is incorporated herein by reference in its entirety for all purposes.

In a preferred embodiment, the CETP inhibitor is selected from the following compounds of Formula XIV:

3-[[3-(3-trifluoromethoxyphenoxy)phenyl][[3-(1,1,2,2-tetrafluoroethoxy)-phenyl]methyl]amino]-1,1,1-trifluoro-2-propanol;

3-[[3-(3-isopropylphenoxy)phenyl][[3-(1,1,2,2-tetrafluoroethoxy)phenyl]-methyl]amino]-1,1,1-trifluoro-2-propanol;

3-[[3-(3-cyclopropylphenoxy)phenyl][[3-(1,1,2,2-tetrafluoroethoxy)phenyl]-methyl]amino]-1,1,1-trifluoro-2-propanol;

3-[[3-(3-(2-furyl)phenoxy)phenyl][[3-(1,1,2,2-tetrafluoroethoxy)phenyl]-methyl]amino]1,1,1-trifluoro-2-propanol;

3-[[3-(2,3-dichlorophenoxy)phenyl][[3-(1,1,2,2-tetrafluoroethoxy)phenyl]-methyl]amino]-1,1,1-trifluoro-2-propanol;

3-[[3-(4-fluorophenoxy)phenyl][[3-(1,1,2,2-tetrafluoroethoxy)phenyl]-methyl]amino]-1,1,1-trifluoro-2-propanol;

3-[[3-(4-methylphenoxy)phenyl][[3-(1,1,2,2-tetrafluoroethoxy)phenyl]-methyl]amino]-1,1,1-trifluoro-2-propanol;

3-[[3-(2-fluoro-5-bromophenoxy)phenyl][[3-(1,1,2,2-tetrafluoroethoxy)phenyl]-methyl]amino]-1,1,1-trifluoro-2-propanol;

3-[[3-(4-chloro-3-ethylphenoxy)phenyl][[3-(1,1,2,2-tetrafluoroethoxy)phenyl]-methyl]amino]-1,1,1-trifluoro-2-propanol;

3-[[3-[3-(1,1,2,2-tetrafluoroethoxy)phenoxy]phenyl][[3-(1,1,2,2-tetrafluoro-ethoxy)phenyl]methyl]amino]-1,1,1-trifluoro-2-propanol;

3-[[3-[3-(pentafluoroethyl)phenoxy]phenyl][[3-(1,1,2,2-tetrafluoroethoxy)-phenyl]methyl]amino]-1,1,1-trifluoro-2-propanol;

3-[[3-(3,5-dimethylphenoxy)phenyl][[3-(1,1,2,2-tetrafluoroethoxy)phenyl]-methyl]amino]-1,1,1-trifluoro-2-propanol;

3-[[3-(3-ethylphenoxy)phenyl][[3-(1,1,2,2-tetrafluoroethoxy)phenyl]-methyl]amino]-1,1,1-trifluoro-2-propanol;

3-[[3-(3-t-butylphenoxy)phenyl][[3-(1,1,2,2-tetrafluoroethoxy)phenyl]-methyl]amino]1,1,1-trifluoro-2-propanol;

3-[[3-(3-methylphenoxy)phenyl][[3-(1,1,2,2-tetrafluoroethoxy)phenyl]-methyl]amino]-1,1,1-trifluoro-2-propanol;

3-[[3-(5,6,7,8-tetrahydro-2-naphthoxy)phenyl][[3-(1,1,2,2-tetrafluoroethoxy)phenyl]methyl]amino]-1,1,1-trifluoro-2-propanol;

3-[[3-(phenoxy)phenyl][[3-(1,1,2,2-tetrafluoroethoxy)phenyl]methyl]amino]-1,1,1-trifluoro-2-propanol;

3-[[3-[3-(N,N-dimethylamino)phenoxy]phenyl][[3-(1,1,2,2-tetrafluoroethoxy)phenyl]methyl]amino]-1,1,1-trifluoro-2-propanol;

3-[[[3-(1,1,2,2-tetrafluoroethoxy)phenyl]methyl][3-[[3-(trifluoromethoxy)-phenyl]methoxy]phenyl]amino]-1,1,1-trifluoro-2-propanol;

3-[[[3-(1,1,2,2-tetrafluoroethoxy)phenyl]methyl][3-[[3-(trifluoromethyl)-phenyl]methoxy]phenyl]amino]-1,1,1-trifluoro-2-propanol;

3-[[[3-(1,1,2,2-tetrafluoroethoxy)phenyl]methyl][3-[[3,5-dimethylphenyl]-methoxy]phenyl]amino]-1,1,1-trifluoro-2-propanol;

3-[[[3-(1,1,2,2-tetrafluoroethoxy)phenyl]methyl][3-[[3-(trifluoromethylthio)-phenyl]methoxy]phenyl]amino]-1,1,-trifluoro-2-propanol;

3-[[[3-(1,1,2,2-tetrafluoroethoxy)phenyl]methyl][3-[[3,5-difluorophenyl]-methoxy]phenyl]amino]-1,1,1-trifluoro-2-propanol;

3-[[[3-(1,1,2,2-tetrafluoroethoxy)phenyl]methyl][3-[cyclohexylmethoxy]-phenyl]amino]-1,1,1-trifluoro-2-propanol;

3-[[3-(2-difluoromethoxy-4-pyridyloxy)phenyl][[3-(1,1,2,2-tetrafluoroethoxy)-phenyl]methyl]amino]-1,1,1-trifluoro-2-propanol;

3-[[3-(2-trifluoromethyl-4-pyridyloxy)phenyl][[3-(1,1,2,2-tetrafluoroethoxy)-phenyl]methyl]amino]-1,1,1-trifluoro-2-propanol;

3-[[3-(3-difluoromethoxyphenoxy)phenyl][[3-(1,1,2,2-tetrafluoroethoxy)-phenyl]methyl]amino]-1,1,1-trifluoro-2-propanol;

3-[[[3-(3-trifluoromethylthio)phenoxy]phenyl][[3-(1,1,2,2-tetrafluoroethoxy)-phenyl]methyl]amino]-1,1,1-trifluoro-2-propanol;

3-[[3-(4-chloro-3-trifluoromethylphenoxy)phenyl][[3-(1,1,2,2-tetrafluoroethoxy)-phenyl]methyl]amino]-1,1,1-trifluoro-2-propanol;

3-[[3-(3-trifluoromethoxyphenoxy)phenyl][[3-(pentafluoroethymethyl]amino]-1,1,1-trifluoro-2-propanol;

3-[[3-(3-isopropylphenoxy)phenyl][[3-(pentafluoroethyl)phenyl]methyl-amino]-1,1,1-trifluoro-2-propanol;

3-[[3-(3-cyclopropylphenoxy)phenyl][[3-(pentafluoroethyl)phenyl]methyl]-amino]-1,1,1-trifluoro-2-propanol;

3-[[3-(3-(2-furyl)phenoxy)phenyl][[3-(pentafluoroethyl)phenyl]methyl]-amino]-1,1,1-trifluoro-2-propanol;

3-[[3-(2,3-dichlorophenoxy)phenyl][[3-(pentafluoroethyl)phenyl]methyl]-amino]-1,1,1-trifluoro-2-propanol;

3-[[3-(4-fluorophenoxy)phenyl][[3-(pentafluoroethyl)phenyl]methyl]amino]-1,1,1-trifluoro-2-propanol;

3-[[3-(4-methylphenoxy)phenyl][[3-(pentafluoroethyl)phenyl]methyl]amino]-1,1,1-trifluoro-2-propanol;

3-[[3-(2-fluoro-5-bromophenoxy)phenyl][[3-(pentafluoroethyl)phenyl]methyl]-amino]-1,1,1-trifluoro-2-propanol;

3-[[3-(4-chloro-3-ethylphenoxy)phenyl][[3-(pentafluoroethyl)phenyl]methyl]-amino]-1,1,1-trifluoro-2-propanol;

3-[[3-[3-(1,1,2,2-tetrafluoroethoxy)phenoxy]phenyl][[3-(pentafluoroethyl)-phenyl]methyl]amino]-1,1,1-trifluoro-2-propanol;

3-[[3-[3-(pentafluoroethyl)phenoxy]phenyl][[3-(pentafluoroethyl)phenyl]-methyl]amino]-1,1,1-trifluoro-2-propanol;

3-[[3-(3,5-dimethylphenoxy)phenyl][[3-(pentafluoroethyl)phenyl]methyl]-amino]-1,1,1-trifluoro-2-propanol;

3-[[3-(3-ethylphenoxy)phenyl][[3-(pentafluoroethyl)phenyl]methyl]amino]-1,1,1-trifluoro-2-propanol;

3-[[3-(3-t-butylphenoxy)phenyl][[3-(pentafluoroethyl)phenyl]methyl]amino]-1,1,1-trifluoro-2-propanol;

3-[[3-(3-methylphenoxy)phenyl][[3-pentafluoroethyl)phenyl]methyl]amino]-1,1,1-trifluoro-2-propanol;

3-[[3-(5,6,7,8-tetrahydro-2-naphthoxy)phenyl][[3-(pentafluoroethyl)phenyl]-methyl]amino]-1,1,1-trifluoro-2-propanol;

3-[[3-(phenoxy)phenyl][[3-(pentafluoroethyl)phenyl]methyl]amino]-1,1,1-trifluoro-2-propanol;

3-[[3-[3-(N,N-dimethylamino)phenoxy]phenyl][[3-(pentafluoroethyl)phenyl]-methyl]amino]-1,1,1-trifluoro-2-propanol;

3-[[[3-(pentafluoroethyl)phenyl]methyl][3-[[3-(trifluoromethoxy)phenyl]-methoxy]phenyl]amino]-1,1,1-trifluoro-2-propanol;

3-[[[3-(pentafluoroethyl)phenyl]methyl][3-[[3-(trifluoromethyl)phenyl]-methoxy]phenyl]amino]-1,1,1-trifluoro-2-propanol;

3-[[[3-(pentafluoroethyl)phenyl]methyl][3-[[3-(trifluoromethylthio)phenyl]-methoxy]phenyl]amino]-1,1,1-trifluoro-2-propanol;

3-[[[3-(pentafluoroethyl)phenyl]methyl][3-[[3,5-difluorophenyl]methoxy]phenyl]amino]-1,1,1-trifluoro-2-propanol;

3-[[[3-(pentafluoroethyl)phenyl]methyl][3-[cyclohexylmethoxy]phenyl]-amino]-1,1,1-trifluoro-2-propanol;

3-[[3-(2-difluoromethoxy-4-pyridyloxy)phenyl][[3-(pentafluoroethyl)phenyl]-methyl]amino]-1,1,1-trifluoro-2-propanol;

3-[[3-(2-trifluoromethyl-4-pyridyloxy)phenyl][[3-(pentafluoroethyl)phenyl]-methyl]amino]-1,1,1-trifluoro-2-propanol;

3-[[3-(3-difluoromethoxyphenoxy)phenyl][[3-(pentafluoroethyl)phenyl]-methyl]amino]-1,1,1-trifluoro-2-propanol;

3-[[[3-(3-trifluoromethylthio)phenoxy]phenyl][[3-(pentafluoroethyl)phenyl]-methyl]amino]-1,1,1-trifluoro-2-propanol;

3-[[3-(4-chloro-3-trifluoromethylphenoxy)phenyl][[3-(pentafluoroethyl)-phenyl]methyl]amino]-1,1,1-trifluoro-2-propanol;

3-[[3-(3-trifluoromethoxyphenoxy)phenyl][[3-(heptafluoropropyl)phenyl]-methyl]amino]-1,1,1-trifluoro-2-propanol;

3-[[3-(3-isopropylphenoxy)phenyl][[3-(heptafluoropropyl)phenyl]methyl]-amino]-1,1,1-trifluoro-2-propanol;

3-[[3-(3-cyclopropylphenoxy)phenyl][[3-(heptafluoropropyl)phenyl]methyl]-amino]-1,1,1-trifluoro-2-propanol;

3-[[3-(3-(2-furyl)phenoxy)phenyl][[3-(heptafluoropropyl)phenyl]methyl]-amino]-1,1,1-trifluoro-2-propanol;

3-[[3-(2,3-dichlorophenoxy)phenyl][[3-(heptafluoropropyl)phenyl]methyl]-amino]-1,1,1-trifluoro-2-propanol;

3-[[3-(4-fluorophenoxy)phenyl][[3-(heptafluoropropyl)phenyl]methyl]amino]-1,1,1-trifluoro-2-propanol;

3-[[3-(4-methylphenoxy)phenyl][[3-(heptafluoropropyl)phenyl]methyl]amino]-1,1,1-trifluoro-2-propanol;

3-[[3-(2-fluoro-5-bromophenoxy)phenyl][[3-(heptafluoropropyl)phenyl]-methyl]amino]-1,1,1-trifluoro-2-propanol;

3-[[3-(4-chloro-3-ethylphenoxy)phenyl][[3-(heptafluoropropyl)phenyl]methyl]-amino]-1,1,1-trifluoro-2-propanol;

3-[[3-[3-(1,1,2,2-tetrafluoroethoxy)phenoxy]phenyl][[3-(heptafluoropropyl)-phenyl]methyl]amino]-1,1,1-trifluoro-2-propanol;

3-[[3-[3-(pentafluoroethyl)phenoxy]phenyl][[3-(heptafluoropropyl)phenyl]-methyl]amino]-1,1,1-trifluoro-2-propanol;

3-[[3-(3,5-dimethylphenoxy)phenyl][[3-(heptafluoropropyl)phenyl]methyl]-amino]-1,1,1-trifluoro-2-propanol;

3-[[3-(3-ethylphenoxy)phenyl][[3-(heptafluoropropyl)phenyl]methyl]amino]-1,1,1-trifluoro-2-propanol;

3-[[3-(3-t-butylphenoxy)phenyl][[3-(heptafluoropropyl)phenyl]methyl]amino]-1,1,1-trifluoro-2-propanol;

3-[[3-(3-methylphenoxy)phenyl][[3-(heptafluoropropyl)phenyl]methyl]amino]-1,1,1-trifluoro-2-propanol;

3-[[3-(5,6,7,8-tetrahydro-2-naphthoxy)phenyl][[3-(heptafluoropropyl)phenyl]-methyl]amino]-1,1,1-trifluoro-2-propanol;

3-[[3-(phenoxy)phenyl][[3-(heptafluoropropyl)phenyl]methyl]amino]-1,1,1-trifluoro-2-propanol;

3-[[3-[3-N,N-dimethylamino)phenoxy]phenyl][[3-(heptafluoropropyl)phenyl]-methyl]amino]-1,1,1-trifluoro-2-propanol;

3-[[[3-(heptafluoropropyl)phenyl]methyl][3-[[3-(trifluoromethoxy)phenyl]-methoxy]phenyl]amino]-1,1,1-trifluoro-2-propanol;

3-[[[3-(heptafluoropropyl)phenyl]methyl][3-[[3-(trifluoromethyl)phenyl]-methoxy]phenyl]amino]-1,1,1-trifluoro-2-propanol;

3-[[[3-(heptafluoropropyl)phenyl]methyl][3-[[3,5-dimethylphenyl]methoxy]-phenyl]amino]-1,1,1-trifluoro-2-propanol;

3-[[[3-(heptafluoropropyl)phenyl]methyl][3-[[3-(trifluoromethylthio)phenyl]-methoxy]phenyl]amino]-1,1,1-trifluoro-2-propanol;

3-[[[3-(heptafluoropropyl)phenyl]methyl][3-[[3,5-difluorophenyl]methoxy]-phenyl]amino]-1,1,1-trifluoro-2-propanol;

3-[[[3-(heptafluoropropyl)phenyl]methyl][3-[cyclohexylmethoxy]phenyl]-amino]-1,1,1-trifluoro-2-propanol;

3-[[3-(2-difluoromethoxy-4-pyridyloxy)phenyl][[3-(heptafluoropropyl)phenyl]-methyl]amino]-1,1,1-trifluoro-2-propanol;

3-[[3-(2-trifluoromethyl-4-pyridyloxy)phenyl][[3-(heptafluoropropyl)phenyl]-methyl]amino]-1,1,1-trifluoro-2-propanol;

3-[[3-(3-difluoromethoxyphenoxy)phenyl][[3-(heptafluoropropyl)phenyl]-methyl]amino]-1,1,1-trifluoro-2-propanol;

3-[[[3-(3-trifluoromethylthio)phenoxy]phenyl][[3-(heptafluoropropyl)phenyl]-methyl]amino]-1,1,1-trifluoro-2-propanol;

3-[[3-(4-chloro-3-trifluoromethylphenoxy)phenyl][[3-(heptafluoropropyl)-phenyl]-methyl]amino]-1,1,1-trifluoro-2-propanol;

3-[[3-(3-trifluoromethoxyphenoxy)phenyl][[2-fluoro-5-(trifluoromethyl)-phenyl]-methyl]amino]-1,1,1-trifluoro-2-propanol;

3-[[3-(3-isopropylphenoxy)phenyl][[2-fluoro-5-(trifluoromethyl)phenyl]-methyl]amino]-1,1,1-trifluoro-2-propanol;

3-[[3-(3-cyclopropylphenoxy)phenyl][[2-fluoro-5-(trifluoromethyl)phenyl]-methyl]amino]-1,1,1-trifluoro-2-propanol;

3-[[3-(3-(2-furyl)phenoxy)phenyl][[2-fluoro-5-(trifluoromethyl)phenyl]-methyl]amino]-1,1,1-trifluoro-2-propanol;

3-[[3-(2,3-dichlorophenoxy)phenyl][[2-fluoro-5-(trifluoromethyl)phenyl]-methyl]amino]-1,1,1-trifluoro-2-propanol;

3-[[3-(4-fluorophenoxy)phenyl][[2-fluoro-5-(trifluoromethyl)phenyl]-methyl]amino]-1,1,1-trifluoro-2-propanol;

3-[[3-(4-methylphenoxy)phenyl][[2-fluoro-5-(trifluoromethyl)phenyl]-methyl]amino]-1,1,1-trifluoro-2-propanol;

3-[[3-(2-fluoro-5-bromophenoxy)phenyl][[2-fluoro-5-(trifluoromethyl)-phenyl]methyl]amino]-1,1,1-trifluoro-2-propanol;

3-[[3-(4-chloro-3-ethylphenoxy)phenyl][[2-fluoro-5-(trifluoromethyl)-phenyl]methyl]amino]-1,1,1-trifluoro-2-propanol;

3-[[3-[3-(1,1,2,2-tetrafluoroethoxy)phenoxy]phenyl][[2-fluoro-5-(trifluoromethyl)phenyl]methyl]amino]-1,1,1-trifluoro-2-propanol;

3-[[3-[3-(pentafluoroethoxy)phenoxy]phenyl][[2-fluoro-5-(trifluoromethyl)-phenyl]-methyl]amino]-1,1,1-trifluoro-2-propanol;

3-[[3-(3,5-dimethylphenoxy)phenyl][[2-fluoro-5-(trifluoromethyl)phenyl]-methyl]amino]-1,1,1-trifluoro-2-propanol;

3-[[3-(3-ethylphenoxy)phenyl][[2-fluoro-5-(trifluoromethyl)phenyl]methyl]-amino]-1,1,1-trifluoro-2-propanol;

3-[[3-(3-t-butylphenoxy)phenyl][[2-fluoro-5-(trifluoromethyl)phenyl]methyl]-amino]-1,1,1-trifluoro-2-propanol;

3-[[3-(3-methylphenoxy)phenyl][[2-fluoro-5-(trifluoromethyl)phenyl]methyl]-amino]-1,1,1-trifluoro-2-propanol;

3-[[3-(5,6,7,8-tetrahydro-2-naphthoxy)phenyl][[2-fluoro-5-(trifluoromethyl)-phenyl]methyl]amino]-1,1,1-trifluoro-2-propanol;

3-[[3-(phenoxy)phenyl][[2-fluoro-5-(trifluoromethyl)phenyl]methyl]amino]-1,1,1-trifluoro-2-propanol;

3-[[3-[3-(N,N-dimethylamino)phenoxy]phenyl][[2-fluoro-5-(trifluoromethyl)-phenyl]methyl]amino]-1,1,1-trifluoro-2-propanol;

3-[[[2-fluoro-5-(trifluoromethyl)phenyl]methyl][3-[[3-(trifluoromethoxy)-phenyl]methoxy]phenyl]amino]-1,1,1-trifluoro-2-propanol;

3-[[[2-fluoro-5-(trifluoromethyl)phenyl]methyl][3-[[3-(trifluoromethyl)-phenyl]methoxy]phenyl]amino]-1,1,1-trifluoro-2-propanol;

3-[[[2-fluoro-5-(trifluoromethyl)phenyl]methyl][3-[[3,5-dimethylphenyl]-methoxy]phenyl]amino]-1,1,1-trifluoro-2-propanol;

3-[[[2-fluoro-5-(trifluoromethyl)phenyl]methyl][3-[[3-(trifluoromethylthio)-phenyl]methoxy]phenyl]amino]-1,1,1-trifluoro-2-propanol;

3-[[[2-fluoro-5-(trifluoromethyl)phenyl]methyl][3-[[3,5-difluorophenyl]-methoxy]phenyl]amino]-1,1,1-trifluoro-2-propanol;

3-[[[2-fluoro-5-(trifluoromethyl)phenyl]methyl][3-[cyclohexylmethoxy]-phenyl]amino]-1,1,1-trifluoro-2-propanol;

3-[[3-(2-difluoromethoxy-4-pyridyloxy)phenyl][[2-fluoro-5-(trifluoromethyl)-phenyl]methyl]amino]-1,1,1-trifluoro-2-propanol;

3-[[3-(2-trifluoromethyl-4-pyridyloxy)phenyl][[2-fluoro-5-(trifluoromethyl)-phenyl]methyl]amino]-1,1,1-trifluoro-2-propanol;

3-[[3-(3-difluoromethoxyphenoxy)phenyl][[2-fluoro-5-(trifluoromethyl)-phenyl]methyl]amino]-1,1,1-trifluoro-2-propanol;

3-[[[3-(3-trifluoromethylthio)phenoxy]phenyl][[2-fluoro-5-(trifluoromethyl)-phenyl]methyl]amino]-1,1,1-trifluoro-2-propanol;

3-[[3-(4-chloro-3-trifluoromethylphenoxy)phenyl][[2-fluoro-5-(trifluoromethyl)phenyl]methyl]amino]-1,1,1-trifluoro-2-propanol;

3-[[3-(3-trifluoromethoxyphenoxy)phenyl][[2-fluoro-4-(trifluoromethyl)-phenyl]methyl]amino]-1,1,1-trifluoro-2-propanol;

3-[[3-(3-isopropylphenoxy)phenyl][[2-fluoro-4-(trifluoromethyl)phenyl]-methyl]amino]-1,1,1-trifluoro-2-propanol;

3-[[3-(3-cyclopropylphenoxy)phenyl][[2-fluoro-4-(trifluoromethyl)phenyl]-methyl]amino]-1,1,1-trifluoro-2-propanol;

3-[[3-(3-(2-furyl)phenoxy)phenyl][[2-fluoro-4-(trifluoromethyl)phenyl]-methyl]amino]-1,1,1-trifluoro-2-propanol;

3-[[3-(2,3-dichlorophenoxy)phenyl][[2-fluoro-4-(trifluoromethyl)phenyl]-methyl]amino]-1,1,1-trifluoro-2-propanol;

3-[[3-(4-fluorophenoxy)phenyl][[2-fluoro-4-(trifluoromethyl)phenyl]-methyl]amino]-1,1,1-trifluoro-2-propanol;

3-[[3-(4-methylphenoxy)phenyl][[2-fluoro-4-(trifluoromethyl)phenyl]-methyl]amino]-1,1,1-trifluoro-2-propanol;

3-[[3-(2-fluoro-5-bromophenoxy)phenyl][[2-fluoro-4-(trifluoromethyl)-phenyl]methyl]amino]-1,1,1-trifluoro-2-propanol;

3-[[3-(4-chloro-3-ethylphenoxy)phenyl][[2-fluoro-4-(trifluoromethyl)-phenyl]methyl]amino]-1,1,1-trifluoro-2-propanol;

3-[[3-[3-(1,1,2,2-tetrafluoroethoxy)phenoxy]phenyl][[2-fluoro-4-(trifluoromethyl)phenyl]methyl]amino]-1,1,1-trifluoro-2-propanol;

3-[[3-[3-(pentafluoroethoxy)phenoxy]phenyl][[2-fluoro-4-(trifluoromethyl)-phenyl]methyl]amino]-1,1,1-trifluoro-2-propanol;

3-[[3-(3,5-dimethylphenoxy)phenyl][[2-fluoro-4-(trifluoromethyl)phenyl]-methyl]amino]-1,1,1-trifluoro-2-propanol;

3-[[3-(3-ethylphenoxy)phenyl][[2-fluoro-4-(trifluoromethyl)phenyl]methyl]-amino]-1,1,1-trifluoro-2-propanol;

3-[[3-(3-t-butylphenoxy)phenyl][[2-fluoro-4-(trifluoromethyl)phenyl]methyl]-amino]-1,1,1-trifluoro-2-propanol;

3-[[3-(3-methylphenoxy)phenyl][[2-fluoro-4-(trifluoromethyl)phenyl]methyl]-amino]-1,1,1-trifluoro-2-propanol;

3-[[3-(5,6,7,8-tetrahydro-2-naphthoxy)phenyl][[2-fluoro-4-(trifluoromethyl)-phenyl]methyl]amino]-1,1,1-trifluoro-2-propanol;

3-[[3-(phenoxy)phenyl][[2-fluoro-4-(trifluoromethyl)phenyl]methyl]amino]-1,1,1-trifluoro-2-propanol;

3-[[3-[3-(N,N-dimethylamino)phenoxy]phenyl][[2-fluoro-4-(trifluoromethyl)-phenyl]methyl]amino]-1,1,1-trifluoro-2-propanol;

3-[[[2-fluoro-4-(trifluoromethyl)phenyl]methyl][3-[[3-(trifluoromethoxy)-phenyl]methoxy]phenyl]amino]-1,1,1-trifluoro-2-propanol;

3-[[[2-fluoro-4-(trifluoromethyl)phenyl]methyl][3-[[3-(trifluoromethyl)-phenyl]methoxy]phenyl]amino]-1,1,1-trifluoro-2-propanol;

3-[[[2-fluoro-4-(trifluoromethyl)phenyl]methyl][3-[[3,5-dimethylphenyl]-methoxy]phenyl]amino]-1,1,1-trifluoro-2-propanol;

3-[[[2-fluoro-4-(trifluoromethyl)phenyl]methyl][3-[[3-(trifluoromethylthio)-phenyl]methoxy]phenyl]amino]-1,1,1-trifluoro-2-propanol;

3-[[[2-fluoro-4-(trifluoromethyl)phenyl]methyl][3-[[3,5-difluorophenyl]-methoxy]phenyl]amino]-1,1,1-trifluoro-2-propanol;

3-[[[2-fluoro-4-(trifluoromethyl)phenyl]methyl][3-[cyclohexylmethoxy]-phenyl]amino]-1,1,1-trifluoro-2-propanol;

3-[[3-(2-difluoromethoxy-4-pyridyloxy)phenyl][[2-fluoro-4-(trifluoromethyl)-phenyl]methyl]amino]-1,1,1-trifluoro-2-propanol;

3-[[3-(2-trifluoromethyl-4-pyridyloxy)phenyl][[2-fluoro-4-(trifluoromethyl)-phenyl]methyl]amino]-1,1,1-trifluoro-2-propanol;

3-[[3-(3-difluoromethoxyphenoxy)phenyl][[2-fluoro-4-(trifluoromethyl)-phenyl]methyl]amino]-1,1,1-trifluoro-2-propanol;

3-[[[3-(3-trifluoromethylthio)phenoxy)phenyl][[2-fluoro-4-(trifluoromethyl)-phenyl]methyl]amino]-1,1,1-trifluoro-2-propanol; and 3-[[3-(4-chloro-3-trifluoromethylphenoxy)phenyl][[2-fluoro-4-(trifluoromethyl)phenyl]methyl]amino]-1,1,1-trifluoro-2-propanol.

Another class of CETP inhibitors that finds utility with the present invention consists of substituted N-Aliphatic-N-Aromatic tertiary-Heteroalkylamines having the Formula XV

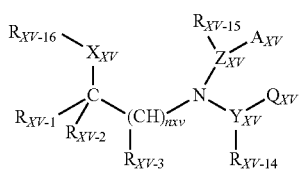

Formula XV and pharmaceutically acceptable forms thereof, wherein:

$n_{XV}$ is an integer selected from 1 through 2;

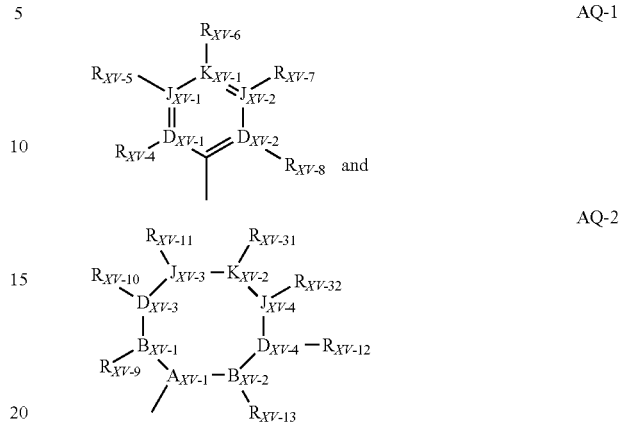

$A_{XV}$ and $Q_{XV}$ are independently selected from the group consisting of —$CH_2(CR_{XV-37}R_{XV-38})_{vXV}$—$(CR_{XV-33}R_{XV-34})_{uXV}$-$T_{XV}$-$(CR_{XV-35}R_{XV-36})_{wXV}$—H, with the provisos that one of $A_{XV}$ and $Q_{XV}$ must be AQ-1 and that one of $A_{XV}$ and $Q_{XV}$ must be selected from the group consisting of AQ-2 and —$CH_2(CR_{XV-37}R_{XV-38})_{vXV}$—$(CR_{XV-33}R_{XV-34})_{uXV}$-$T_{XV}$-$(CR_{XV-35}R_{XV-36})_{wXV}$—H;

$T_{XV}$ is selected from the group consisting of a single covalent bond, O, S, S(O), S(O)$_2$, $C(R_{XV-33})$=$C(R_{XV-35})$, and $$C≡C;$$

$_{vXV}$ is an integer selected from 0 through 1 with the proviso that $_{vXV}$ is 1 when any one of $R_{XV-33}$, $R_{XV-34}$, $R_{XV-35}$, and $R_{XV-36}$ is aryl or heteroaryl;

$_{uXV}$ and $_{wXV}$ are integers independently selected from 0 through 6;

$A_{XV-1}$ is $C(R_{XV-30})$;

$D_{XV-1}$, $D_{XV-2}$, $J_{XV-1}$, $J_{XV-2}$, and $K_{XV-1}$ are independently selected from the group consisting of C, N, O, S and a covalent bond with the provisos that no more than one of $D_{XV-1}$, $D_{XV-2}$, $J_{XV-1}$, $J_{XV-2}$, and $K_{XV-1}$ is a covalent bond, no more than one of $D_{XV-1}$, $D_{XV-2}$, $J_{XV-1}$, $J_{XV-2}$, and $K_{XV-1}$ is O, no more than one of $D_{XV-1}$, $D_{XV-2}$, $J_{XV-1}$, $J_{XV-2}$, and $K_{XV-1}$ is S, one of $D_{XV-1}$, $D_{XV-2}$, $J_{XV-1}$, $J_{XV-2}$, and $K_{XV-1}$ must be a covalent bond when two of $D_{XV-1}$, $D_{XV-2}$, $J_{XV-1}$, $J_{XV-2}$, and $K_{XV-1}$ are O and S, and no more than four of $D_{XV-1}$, $D_{XV-2}$, $J_{XV-1}$, $J_{XV-2}$, and $K_{XV-1}$ are N;

$B_{XV-1}$, $B_{XV-2}$, $D_{XV-3}$, $D_{XV-4}$, $J_{XV-3}$, $J_{XV-4}$, and $K_{XV-2}$ are independently selected from the group consisting of C, $C(R_{XV-30})$, N, O, S and a covalent bond with the provisos that no more than 5 of $B_{XV-1}$, $B_{XV-2}$, $D_{XV-3}$, $D_{XV-4}$, $J_{XV-3}$, $J_{XV-4}$, and $K_{XV-2}$ are a covalent bond, no more than two of $B_{XV-1}$, $B_{XV-2}$, $D_{XV-3}$, $D_{XV-4}$, $J_{XV-3}$, $J_{XV-4}$, and $K_{XV-2}$ are O, no more than two of $B_{XV-1}$, $B_{XV-2}$, $D_{XV-3}$, $D_{XV-4}$, $J_{XV-3}$, $J_{XV-4}$, and $K_{XV-2}$ are S, no more than two of $B_{XV-1}$, $B_{XV-2}$, $D_{XV-3}$, $D_{XV-4}$, $J_{XV-3}$, $J_{XV-4}$, and $K_{XV-2}$ are simultaneously O and S, and no more than two of $B_{XV-1}$, $B_{XV-2}$, $D_{XV-3}$, $D_{XV-4}$, $J_{XV-3}$, $J_{XV-4}$, and $K_{XV-2}$ are N;

$B_{XV-1}$ and $D_{XV-3}$, $D_{XV-3}$ and $J_{XV-3}$, $J_{XV-3}$ and $K_{XV-2}$, $K_{XV-2}$ and $J_{XV-4}$, $J_{XV-4}$ and $D_{XV-4}$, and $D_{XV-4}$ and $B_{XV-2}$ are independently selected to form an in-ring spacer pair wherein said spacer pair is selected from the group consisting of $C(R_{XV-33})$=$C(R_{XV-35})$ and N=N with the provisos that AQ-2 must be a ring of at least five contiguous members, that no more than two of the group of said spacer pairs are simultaneously $C(R_{XV-33})=C(R_{XV-35})$ and that no more than one of the group of said spacer pairs can be N=N unless the other spacer pairs are other than $C(R_{XV-33})=C(R_{XV-35})$, O, N, and S;

$R_{XV-1}$ is selected from the group consisting of haloalkyl and haloalkoxymethyl;

$R_{XV-2}$ is selected from the group consisting of hydrido, aryl, alkyl, alkenyl, haloalkyl, haloalkoxy, haloalkoxyalkyl, perhaloaryl, perhaloaralkyl, perhaloaryloxyalkyl and heteroaryl;

$R_{XV-3}$ is selected from the group consisting of hydrido, aryl, alkyl, alkenyl, haloalkyl, and haloalkoxyalkyl;

$Y_{XV}$ is selected from the group consisting of a covalent single bond, $(CH_2)_q$ wherein q is an integer selected from 1 through 2 and $(CH_2)_j$—O—$(CH_2)_k$ wherein j and k are integers independently selected from 0 through 1;

$Z_{XV}$ is selected from the group consisting of covalent single bond, $(CH_2)_q$ wherein q is an integer selected from 1 through 2, and $(CH_2)_j$—O—$(CH_2)_k$ wherein j and k are integers independently selected from 0 through 1;

$R_{xv-4}$, $R_{xv-8}$, $R_{xv-9}$ and $R_{xv-13}$ are independently selected from the group consisting of hydrido, halo, haloalkyl, and alkyl;

$R_{XV-30}$ is selected from the group consisting of hydrido, alkoxy, alkoxyalkyl, halo, haloalkyl, alkylamino, alkylthio, alkylthioalkyl, alkyl, alkenyl, haloalkoxy, and haloalkoxyalkyl with the proviso that $R_{xv-30}$ is selected to maintain the tetravalent nature of carbon, trivalent nature of nitrogen, the divalent nature of sulfur, and the divalent nature of oxygen;

$R_{XV-30}$, when bonded to $A_{XV-1}$, is taken together to form an intra-ring linear spacer connecting the $A_{XV-1}$-carbon at the point of attachment of $R_{XV-30}$ to the point of bonding of a group selected from the group consisting of $R_{XV-10}$, $R_{XV-11}$, $R_{XV-12}$, $R_{XV-31}$, and $R_{XV-32}$ wherein said intra-ring linear spacer is selected from the group consisting of a covalent single bond and a spacer moiety having from 1 through 6 contiguous atoms to form a ring selected from the group consisting of a cycloalkyl having from 3 through 10 contiguous members, a cycloalkenyl having from 5 through 10 contiguous members, and a heterocyclyl having from 5 through 10 contiguous members;

$R_{XV-30}$, when bonded to $A_{XV-1}$, is taken together to form an intra-ring branched spacer connecting the $A_{XV-1}$-carbon at the point of attachment of $R_{XV-30}$ to the points of bonding of each member of any one of substituent pairs selected from the group consisting of substituent pairs $R_{XV-10}$ and $R_{XV-11}$, $R_{XV-10}$ and $R_{XV-31}$, $R_{XV-10}$ and $R_{XV-32}$, $R_{XV-10}$ and $R_{XV-12}$, $R_{XV-11}$ and $R_{XV-31}$, $R_{XV-11}$ and $R_{XV-32}$, $R_{XV-11}$ and $R_{XV-12}$, $R_{XV-31}$ and $R_{XV-32}$, $R_{XV-31}$ and $R_{XV-12}$, and $R_{XV-32}$ and $R_{XV-12}$ and wherein said intra-ring branched spacer is selected to form two rings selected from the group consisting of cycloalkyl having from 3 through 10 contiguous members, cycloalkenyl having from 5 through 10 contiguous members, and heterocyclyl having from 5 through 10 contiguous members;

$R_{XV-4}$, $R_{XV-5}$, $R_{XV-6}$, $R_{XV-7}$, $R_{XV-8}$, $R_{XV-9}$, $R_{XV-10}$, $R_{XV-11}$, $R_{XV-12}$, $R_{XV-13}$, $R_{XV-31}$, $R_{XV-32}$, $R_{XV-33}$, $R_{XV-34}$, $R_{XV-35}$, and $R_{XV-36}$ are independently selected from the group consisting of hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkylamidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydroxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamino, alkylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the provisos that $R_{XV-4}$, $R_{XV-5}$, $R_{XV-6}$, $R_{XV-7}$, $R_{XV-8}$, $R_{XV-9}$, $R_{XV-10}$, $R_{XV-11}$, $R_{XV-12}$, $R_{XV-13}$, $R_{XV-31}$, $R_{XV-32}$, $R_{XV-33}$, $R_{XV-34}$, $R_{XV-35}$, and $R_{XV-36}$ are each independently selected to maintain the tetravalent nature of carbon, trivalent nature of nitrogen, the divalent nature of sulfur, and the divalent nature of oxygen, that no more than three of the $R_{XV-33}$ and $R_{XV-34}$ substituents are simultaneously selected from other than the group consisting of hydrido and halo, and that no more than three of the $R_{XV-35}$ and $R_{XV-36}$ substituents are simultaneously selected from other than the group consisting of hydrido and halo;

$R_{XV-9}$, $R_{XV-10}$, $R_{XV-11}$, $R_{XV-12}$, $R_{XV-13}$, $R_{XV-31}$, and $R_{XV-32}$ are independently selected to be oxo with the provisos that $B_{XV-1}$, $B_{XV-2}$, $D_{XV-3}$, $D_{XV-4}$, $J_{XV-3}$, $J_{XV-4}$, and $K_{XV-2}$ are independently selected from the group consisting of C and S, no more than two of $R_{XV-9}$, $R_{XV-10}$, $R_{XV-11}$, $R_{XV-12}$, $R_{XV-13}$, $R_{XV-31}$, and $R_{XV-32}$ are simultaneously oxo, and that $R_{XV-9}$, $R_{XV-10}$, $R_{XV-11}$, $R_{XV-12}$, $R_{XV-13}$, $R_{XV-31}$, and $R_{XV-32}$ are each independently selected to maintain the tetravalent nature of carbon, trivalent nature of nitrogen, the divalent nature of sulfur, and the divalent nature of oxygen;

$R_{XV-4}$ and $R_{XV-5}$, $R_{XV-5}$ and $R_{XV-6}$, $R_{XV-6}$ and $R_{XV-7}$, $R_{XV-7}$ and $R_{XV-8}$, $R_{XV-9}$ and $R_{XV-10}$, $R_{XV-10}$ and $R_{XV-11}$, $R_{XV-11}$ and $R_{XV-31}$, $R_{XV-31}$ and $R_{XV-32}$, $R_{XV-32}$ and $R_{XV-12}$, and $R_{XV-12}$ and $R_{XV-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XV-4}$ and $R_{XV-5}$, $R_{XV-5}$ and $R_{XV-6}$, $R_{XV-6}$ and $R_{XV-7}$, $R_{XV-7}$ and $R_{XV-8}$ is used at the same time and that no more than one of the group consisting of spacer pairs $R_{XV-9}$ and $R_{XV-10}$, $R_{XV-10}$ and $R_{XV-11}$, $R_{XV-11}$ and $R_{XV-31}$, $R_{XV-31}$ and $R_{XV-32}$, $R_{XV-32}$ and $R_{XV-12}$, and $R_{XV-12}$ and $R_{XV-13}$ are used at the same time;

$R_{XV-9}$ and $R_{XV-11}$, $R_{XV-9}$ and $R_{XV-12}$, $R_{XV-9}$ and $R_{XV-13}$ $R_{XV-9}$ and $R_{XV-31}$, $R_{XV-9}$ and $R_{XV-32}$, $R_{XV-10}$ and $R_{XV-12}$, $R_{XV-10}$ and $R_{XV-13}$, $R_{XV-10}$ and $R_{XV-31}$, $R_{XV-10}$ and $R_{XV-32}$, $R_{XV-11}$ and $R_{XV-12}$, $R_{XV-11}$ and $R_{XV-13}$, $R_{XV-11}$ and $R_{XV-32}$, $R_{XV-12}$ and $R_{XV-31}$, $R_{XV-13}$ and $R_{XV-31}$, and $R_{XV-13}$ and $R_{XV-32}$ are independently selected to form a spacer pair wherein said spacer pair is taken together to form a linear spacer moiety selected from the group consisting of a covalent single bond and a moiety having from 1 through 3 contiguous atoms to form a ring selected from the group consisting of a cycloalkyl having from 3 through 8 contiguous members, a cycloalkenyl having from 5 through 8 contiguous members, a saturated heterocyclyl having from 5 through 8 contiguous members and a partially saturated heterocyclyl having from 5 through 8 contiguous members with the provisos that no more than one of said group of spacer pairs is used at the same time;

$R_{XV-37}$ and $R_{XV-38}$ are independently selected from the group consisting of hydrido, alkoxy, alkoxyalkyl, hydroxy, amino, thio, halo, haloalkyl, alkylamino, alkylthio, alkylthioalkyl, cyano, alkyl, alkenyl, haloalkoxy, and haloalkoxyalkyl.

Compounds of Formula XV and their methods of manufacture are disclosed in PCT Publication No. WO 00/18723, which is incorporated herein by reference in its entirety for all purposes.

In a preferred embodiment, the CETP inhibitor is selected from the following compounds of Formula XV:

3-[[3-(4-chloro-3-ethylphenoxy)phenyl](cyclohexylmethyl)amino]-1,1,1-trifluoro-2-propanol;
3-[[3-(4-chloro-3-ethylphenoxy)phenyl](cyclopentylmethyl)amino]-1,1,1-trifluoro-2-propanol;
3-[[3-(4-chloro-3-ethylphenoxy)phenyl](cyclopropylmethyl)amino]-1,1,-trifluoro-2-propanol;
3-[[3-(4-chloro-3-ethylphenoxy)phenyl][(3-trifluoromethyl)cyclohexyl-methyl]amino]-1,1,1-trifluoro-2-propanol;
3-[[3-(4-chloro-3-ethylphenoxy)phenyl][(3-pentafluoroethyl)cyclohexyl-methyl]amino]-1,1,1-trifluoro-2-propanol;
3-[[3-(4-chloro-3-ethylphenoxy)phenyl][(3-trifluoromethoxy)cyclohexyl-methyl]amino]-1,1,1-trifluoro-2-propanol;
3-[[3-(4-chloro-3-ethylphenoxy)phenyl][[3-(1,1,2,2-tetrafluoroethoxy)cyclo-hexylmethyl]amino]-1,1,1-trifluoro-2-propanol;
3-[[3-(3-trifluoromethoxyphenoxy)phenyl](cyclohexylmethyl)amino]-1,1,1-trifluoro-2-propanol;
3-[[3-(3-trifluoromethoxyphenoxy)phenyl](cyclopentylmethyl)amino]-1,1,1-trifluoro-2-propanol;
3-[[3-(3-trifluoromethoxyphenoxy)phenyl](cyclopropylmethyl)amino]-1,1,1-trifluoro-2-propanol;
3-[[3-(3-trifluoromethoxyphenoxy)phenyl][(3-trifluoromethyl)cyclohexyl-methyl]amino]-1,1,1-trifluoro-2-propanol;
3-[[3-(3-trifluoromethoxyphenoxy)phenyl]](3-pentafluoroethyl)cyclohexyl-methyl]amino]-1,1,1-trifluoro-2-propanol;
3-[[3-(3-trifluoromethoxyphenoxy)phenyl][(3-trifluoromethoxy)cyclohexyl-methyl]amino]-1,1,1-trifluoro-2-propanol;
3-[[3-(3-trifluoromethoxyphenoxy)phenyl][[3-(1,1,2,2-tetrafluoroethoxy)cyclohexyl-methyl]amino]-1,1,1-trifluoro-2-propanol;
3-[[3-(3-isopropylphenoxy)phenyl](cyclohexylmethyl)amino]-1,1,1-trifluoro-2-propanol:
3-[[3-(3-isopropylphenoxy)phenyl](cyclopentylmethyl)amino]-1,4,1-trifluoro-2-propanol;
3-[[3-(3-isopropylphenoxy)phenyl](cyclopropylmethyl)amino]-1,1,1-trifluoro-2-propanol;
3-[[3-(3-isopropylphenoxy)phenyl][(3-trifluoromethyl)cyclohexyl-methyl]amino]-1,1,1-trifluoro-2-propanol;
3-[[3-(3-isopropylphenoxy)phenyl][(3-pentafluoroethyl)cyclohexyl-methyl]amino]-1,1,1-trifluoro-2-propanol;
3-[[3-(3-isopropylphenoxy)phenyl][(3-trifluoromethoxy)cyclohexyl-methyl]amino]-1,1,1-trifluoro-2-propanol;
3-[[3-(3-isopropylphenoxy)phenyl][3-(1,1,2,2-tetrafluoroethoxy)cyclohexyl-methyl]amino]-1,1,1-trifluoro-2-propanol;
3-[[3-(2,3-dichlorophenoxy)phenyl](cyclohexylmethyl)amino]-1,1,1-trifluoro-2-propanol;
3-[[3-(2,3-dichlorophenoxy)phenyl](cyclopentylmethyl)amino]-1,1,1-trifluoro-2-propanol;
3-[[3-(2,3-dichlorophenoxy)phenyl](cyclopropylmethyl)amino]-1,1,1-trifluoro-2-propanol;
3-[[3-(2,3-dichlorophenoxy)phenyl][(3-trifluoromethyl)cyclohexyl-methyl]amino]-1,1,1-trifluoro-2-propanol;
3-[[3-(2,3-dichlorophenoxy)phenyl][(3-pentafluoroethyl)cyclohexyl-methyl]amino]-1,1,1-trifluoro-2-propanol;
3-[[3-(2,3-dichlorophenoxy)phenyl][(3-trifluoromethoxy)cyclohexyl-methyl]amino]-1,1,1-trifluoro-2-propanol;
3-[[3-(2,3-dichlorophenoxy)phenyl][3-(1,1,2,2-tetrafluoroethoxy)cyclo-hexylmethyl]amino]-1,1,1-trifluoro-2-propanol;
3-[[3-(4-fluorophenoxy)phenyl](cyclohexylmethyl)amino]-1,1,1-trifluoro-2-propanol;
3-[[3-(4-fluorophenoxy)phenyl](cyclopentylmethyl)amino]-1,1,1-trifluoro-2-propanol;
3-[[3-(4-fluorophenoxy)phenyl](cyclopropylmethyl)amino]-1,1,1-trifluoro-2-propanol;
3-[[3-(4-fluorophenoxy)phenyl][(3-trifluoromethyl)cyclohexyl-methyl]amino]-1,1,1-trifluoro-2-propanol;
3-[[3-(4-fluorophenoxy)phenyl][(3-pentafluoroethyl)cyclohexyl-methyl]amino]-1,1,1-trifluoro-2-propanol;
3-[[3-(4-fluorophenoxy)phenyl][(3-trifluoromethoxy)cyclohexyl-methyl]amino]-1,1,1-trifluoro-2-propanol;
3-[[3-(4-fluorophenoxy)phenyl][[3-(1,1,2,2-tetrafluoroethoxy)cyclohexyl]amino]-1,1,1-trifluoro-2-propanol;
3-[[3-(3-trifluoromethoxybenzyloxy]phenyl](cyclohexylmethyl)amino]-1,1,1-trifluoro-2-propanol;
3-[[3-(3-trifluoromethoxybenzyloxy)phenyl](cyclopentylmethyl)amino]-1,1,1-trifluoro-2-propanol;
3-[[3-(3-trifluoromethoxybenzyloxy)phenyl](cyclopropylmethyl)amino]-1,1,1-trifluoro-2-propanol;
3-[[3-(3-trifluoromethoxybenzyloxy)phenyl][(3-trifluoromethyl)cyclohexyl-methyl]amino]-1,1,1-trifluoro-2-propanol;
3-[[3-(3-trifluoromethoxybenzyloxy)phenyl][(3-pentafluoroethyl)cyclohexyl-methyl]amino]-1,1'-trifluoro-2-propanol;
3-[[3-(3-trifluoromethoxybenzyloxy)phenyl][(3-trifluoromethoxy)cyclohexyl-methyl]amino]-1,1,1-trifluoro-2-propanol;
3-[[3-(3-trifluoromethoxybenzyloxy)phenyl][3-(1,1,2,2-tetrafluoroethoxy)-cyclohexyl methyl]amino]-1,1,1-trifluoro-2-propanol;

3-[[3-(3-trifluoromethylbenzyloxy)phenyl](cyclohexylmethyl)amino]-1,1,1-trifluoro-2-propanol;
3-[[3-(3-trifluoromethylbenzyloxy)phenyl](cyclopentylmethyl)amino]-1,1,1-trifluoro-2-propanol;
3-[[3-(3-trifluoromethylbenzyloxy)phenyl](cyclopropylmethyl)amino]-1,1,1-trifluoro-2-propanol;
3-[[3-(3-trifluoromethyl benzyloxy)phenyl][(3-trifluoromethyl)cyclohexyl-methyl]amino]-1,1,1-trifluoro-2-propanol;
3-[[3-(3-trifluoromethyl benzyloxy)phenyl][(3-pentafluoroethyl)cyclohexyl-methyl]amino]-1,1,1-trifluoro-2-propanol;
3-[[3-(3-trifluoromethylbenzyloxy)phenyl][(3-trifluoromethoxy)cyclohexyl-methyl]amino]-1,1,1-trifluoro-2-propanol;
3-[[3-(3-trifluoromethylbenzyloxy)phenyl][3-(1,1,2,2-tetrafluoroethoxy)cyclohexyl-methyl]amino]-1,1,1-trifluoro-2-propanol;
3-[[[(3-trifluoromethyl)phenyl]methyl](cyclohexyl)amino]-1,1,1-trifluoro-2-propanol;
3-[[[(3-pentafluoroethyl)phenyl]methyl](cyclohexyl)amino]-1,1,1-trifluoro-2-propanol;
3-[[[(3-trifluoromethoxy)phenyl]methyl](cyclohexyl)amino]-1,1,1-trifluoro-2-propanol;
3-[[[3-(1,1,2,2-tetrafluoroethoxy)phenyl]methyl](cyclohexyl)amino]-1,1,1-trifluoro-2-propanol;
3-[[[(3-trifluoromethyl)phenyl]methyl](4-methylcyclohexyl)amino]-1,1,1-trifluoro-2-propanol;
3-[[[(3-pentafluoroethyl)phenyl]methyl](4-methylcyclohexyl)amino]-1,1,1-trifluoro-2-propanol;
3-[[[(3-trifluoromethoxy)phenyl]methyl](4-methylcyclohexyl)amino]-1,1,1-trifluoro-2-propanol;
3-[[[3-(1,1,2,2-tetrafluoroethoxy)phenyl]methyl](4-methylcyclohexyl)amino]-1,1,1-trifluoro-2-propanol;
3-[[[(3-trifluoromethyl)phenyl]methyl](3-trifluoromethylcyclohexyl)amino]-1,1,1-trifluoro-2-propanol;
3-[[[(3-pentafluoroethyl)phenyl]methyl](3-trifluoromethylcyclohexyl)amino]-1,1,1-trifluoro-2-propanol;
3-[[[(3-trifluoromethoxy)phenyl]methyl](3-trifluoromethylcyclohexyl)amino]-1,1,1-trifluoro-2-propanol;
3-[[[3-(1,1,2,2-tetrafluoroethoxy)phenyl]methyl](3-trifluoromethylcyclohexyl)amino]-1,1,1-trifluoro-2-propanol;
3-[[[(3-trifluoromethyl)phenyl]methyl][3-(4-chloro-3-ethylphenoxy)cyclo-hexyl]amino]-1,1,1-trifluoro-2-propanol;
3-[[[(3-pentafluoroethyl)phenyl]methyl][3-(4-chloro-3-ethylphenoxy)cyclo-hexyl]amino]-1,1,1-trifluoro-2-propanol;
3-[[[(3-trifluoromethoxy)phenyl]methyl][3-(4-chloro-3-methylphenoxy)cyclo-hexyl]amino]-1,1,1-trifluoro-2-propanol;
3-[[[3-(1,1,2,2-tetrafluoroethoxy)phenyl]methyl][3-(4-chloro-3-ethylphenoxy)-cyclohexyl]amino]-1,1,1-trifluoro-2-propanol;
3-[[[(3-trifluoromethyl)phenyl]methyl](3-phenoxycyclohexyl)amino]-1,1,1-trifluoro-2-propanol;
3-[[[(3-pentafluoroethyl)phenyl]methyl](3-phenoxycyclohexyl)amino]-1,1,1-trifluoro-2-propanol;
3-[[[(3-trifluoromethoxy)phenyl]methyl](3-phenoxycyclohexyl)amino]-1,1,1-trifluoro-2-propanol;
3-[[[3-(1,1,2,2-tetrafluoroethoxy)phenyl]methyl](3-phenoxycyclohexyl)amino]-1,1,1-trifluoro-2-propanol;
3-[[[(3-trifluoromethyl)phenyl]methyl](3-isopropoxycyclohexyl)amino]-1,1,1-trifluoro-2-propanol;
3-[[[(3-pentafluoroethyl)phenyl]methyl](3-isopropoxycyclohexyl)amino]-1,1,1-trifluoro-2-propanol;
3-[[[(3-trifluoromethoxy)phenyl]methyl](3-isopropoxycyclohexyl)amino]-1,1,1-trifluoro-2-propanol;
3-[[[3-(1,1,2,2-tetrafluoroethoxy)phenyl]methyl](3-isopropoxycyclohexyl)-amino]-1,1,1-trifluoro-2-propanol;
3-[[[(3-trifluoromethyl)phenyl]methyl](3-cyclopentyloxycyclohexyl)amino]-1,1,1-trifluoro-2-propanol;
3-[[[(3-pentafluoroethyl)phenyl]methyl](3-cyclopentyloxycyclohexyl)amino]-1,1,1-trifluoro-2-propanol;
3-[[[(3-trifluoromethoxy)phenyl]methyl](3-cyclopentyloxycyclohexyl)amino]-1,1,1-trifluoro-2-propanol;
3-[[[3-(1,1,2,2-tetrafluoroethoxy)phenyl]methyl](3-cyclopentyloxycyclohexyl)-amino]-1,1,1-trifluoro-2-propanol;
3-[[[(2-trifluoromethyl)pyrid-6-yl]methyl](3-isopropoxycyclohexyl)amino]-1,1,1-trifluoro-2-propanol;
3-[[[(2-trifluoromethyl)pyrid-6-yl]methyl](3-cyclopentyloxycyclohexyl)-amino]-1,1,1-trifluoro-2-propanol;
3-[[[(2-trifluoromethyl)pyrid-6-yl]methyl](3-phenoxycyclohexyl)amino]-1,1,1-trifluoro-2-propanol;
3-[[[(2-trifluoromethyl)pyrid-6-yl]methyl](3-trifluoromethylcyclohexyl)amino]-1,1,1-trifluoro-2-propanol;
3-[[[(2-trifluoromethyl)pyrid-6-yl]methyl][3-(4-chloro-3-ethylphenoxy)cyclo-hexyl]amino]-1,1,1-trifluoro-2-propanol;
3-[[[(2-trifluoromethyl)pyrid-6-yl]methyl][3-(1,1,2,2-tetrafluoroethoxy)cyclo-hexyl]amino]-1,1,1-trifluoro-2-propanol;
3-[[[(2-trifluoromethyl)pyrid-6-yl]methyl](3-pentafluoroethylcyclohexyl)-amino]-1,1,1-trifluoro-2-propanol;
3-[[[(2-trifluoromethyl)pyrid-6-yl]methyl](3-trifluoromethoxycyclohexyl)-amino]-1,1,1-trifluoro-2-propanol;
3-[[[(3-trifluoromethyl)phenyl]methyl][3-(4-chloro-3-ethylphenoxy)propyl]-amino]-1,1,1-trifluoro-2-propanol;
3-[[[(3-pentafluoroethyl)phenyl]methyl][3-(4-chloro-3-ethylphenoxy)propyl]-amino]-1,1,1-trifluoro-2-propanol;
3-[[[(3-trifluoromethoxy)phenyl]methyl][3-(4-chloro-3-ethylphenoxy)propyl]-amino]-1,1,1-trifluoro-2-propanol;
3-[[[3-(1,1,2,2-tetrafluoroethoxy)phenyl]methyl][3-(4-chloro-3-ethylphenoxy)-propyl]amino]-1,1,1-trifluoro-2-propanol;
3-[[[(3-trifluoromethyl)phenyl]methyl][3-(4-chloro-3-ethylphenoxy)-2,2-di-fluoropropyl]amino]-1,1,1-trifluoro-2-propanol;
3-[[[(3-pentafluoroethyl)phenyl]methyl][3-(4-chloro-3-ethylphenoxy)-2,2-di-fluoropropyl]amino]-1,1,1-trifluoro-2-propanol;
3-[[[(3-trifluoromethoxy)phenyl]methyl][3-(4-chloro-3-ethylphenoxy)-2,2,-di-fluoropropyl]amino]-1,1,1-trifluoro-2-propanol;
3-[[[3-(1,1,2,2-tetrafluoroethoxy)phenyl]methyl][3-(4-chloro-3-ethylphenoxy)-2,2,-difluoropropyl]amino]-1,1,1-trifluoro-2-propanol;
3-[[[(3-trifluoromethyl)phenyl]methyl][3-(isopropoxy)propyl]amino]-1,1,1-trifluoro-2-propanol;
3-[[[(3-pentafluoroethyl)phenyl]methyl][3-(isopropoxy)propyl]amino]-1,1,1-trifluoro-2-propanol;
3-[[[(3-trifluoromethoxy)phenyl]methyl][3-(isopropoxy)propyl]amino]-1,1,1-trifluoro-2-propanol;
3-[[[3-(1,1,2,2-tetrafluoroethoxy)phenyl]methyl]3-(isopropoxy)propyl]amino]-1,1,1-trifluoro-2-propanol; and
3-[[[3-(1,1,2,2-tetrafluoroethoxy)phenyl]methyl][3-(phenoxy)propyl]amino]-1,1,1-trifluoro-2-propanol.

Another class of CETP inhibitors that finds utility with the present invention consists of (R)-chiral halogenated 1-substituted amino-(n+1)-alkanols having the Formula XVI Formula XVI

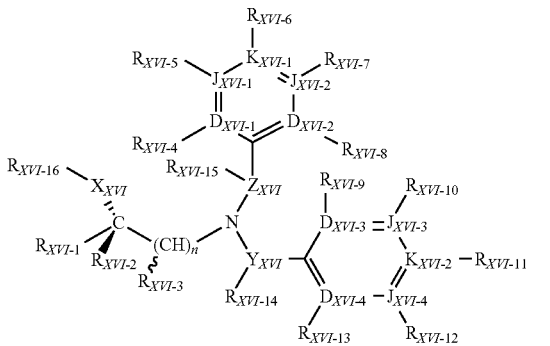

and pharmaceutically acceptable forms thereof, wherein:

$n_{XVI}$ is an integer selected from 1 through 4;

$X_{XVI}$ is oxy;

$R_{XVI-1}$ is selected from the group consisting of haloalkyl, haloalkenyl, haloalkoxymethyl, and haloalkenyloxymethyl with the proviso that $R_{XVI-1}$ has a higher Cahn-Ingold-Prelog stereochemical system ranking than both $R_{XVI-2}$ and $(CHR_{XVI-3})_n$—$N(A_{XVI})Q_{XVI}$ wherein $A_{XVI}$ is Formula XVI-(III) and Q is Formula XVI-(III);

XVI-II

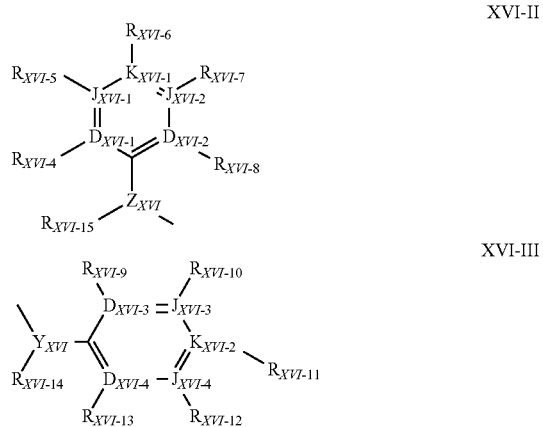

XVI-III $R_{XVI-16}$ is selected from the group consisting of hydrido, alkyl, acyl, aroyl, heteroaroyl, trialkylsilyl, and a spacer selected from the group consisting of a covalent single bond and a linear spacer moiety having a chain length of 1 to 4 atoms linked to the point of bonding of any aromatic substituent selected from the group consisting of $R_{XVI-4}$, $R_{XVI-8}$, $R_{XVI-9}$, and $R_{XVI-13}$ to form a heterocyclyl ring having from 5 through 10 contiguous members;

$D_{XVI-1}$, $D_{XVI-2}$, $J_{XVI-1}$, $J_{XVI-2}$ and $K_{XVI-1}$ are independently selected from the group consisting of C, N, O, S and covalent bond with the provisos that no more than one of $D_{XVI-1}$, $D_{XVI-2}$, $J_{XVI-1}$, $J_{XVI-2}$ and $K_{XVI-1}$ is a covalent bond, no more than one $D_{XVI-1}$, $D_{XVI-2}$, $J_{XVI-1}$, $J_{XVI-2}$ and $K_{XVI-1}$ is be O, no more than one of $D_{XVI-1}$, $D_{XVI-2}$, $J_{XVI-1}$, $J_{XVI-2}$ and $K_{XVI-1}$ is S, one of $D_{XVI-1}$, $D_{XVI-2}$, $J_{XVI-1}$, $J_{XVI-2}$ and $K_{XVI-1}$ must be a covalent bond when two of $D_{XVI-1}$, $D_{XVI-2}$, $J_{XVI-1}$, $J_{XVI-2}$ and $K_{XVI-1}$ are O and S, and no more than four of $D_{XVI-1}$, $D_{XVI-2}$, $J_{XVI-1}$, $J_{XVI-2}$ and $K_{XVI-1}$ is N;

$D_{XVI-3}$, $D_{XVI-4}$, $J_{XVI-3}$, $J_{XVI-4}$ and $K_{XVI-2}$ are independently selected from the group consisting of C, N, O, S and covalent bond with the provisos that no more than one is a covalent bond, no more than one of $D_{XVI-3}$, $D_{XVI-4}$, $J_{XVI-3}$, $J_{XVI-4}$ and $K_{XVI-2}$ is O, no more than one of $D_{XVI-3}$, $D_{XVI-4}$, $J_{XVI-3}$, $J_{XVI-4}$ and $K_{XVI-2}$ is S, no more than two of $D_{XVI-3}$, $D_{XVI-4}$, $J_{XVI-3}$, $J_{XVI-4}$ and $K_{XVI-2}$ is O and S, one of $D_{XVI-3}$, $D_{XVI-4}$, $J_{XVI-3}$, $J_{XVI-4}$ and $K_{XVI-2}$ must be a covalent bond when two of $D_{XVI-3}$, $D_{XVI-4}$, $J_{XVI-3}$, $J_{XVI-4}$ and $K_{XVI-2}$ are O and S, and no more than four of $D_{XVI-3}$, $D_{XVI-4}$, $J_{XVI-3}$, $J_{XVI-4}$ and $K_{XVI-2}$ are N;

$R_{XVI-2}$ is selected from the group consisting of hydrido, aryl, aralkyl, alkyl, alkenyl, alkenyloxyalkyl, haloalkyl, haloalkenyl, halocycloalkyl, haloalkoxy, haloalkoxyalkyl, haloalkenyloxyalkyl, halocycloalkoxy, halocycloalkoxyalkyl, perhaloaryl, perhaloaralkyl, perhaloaryloxyalkyl, heteroaryl, dicyanoalkyl, and carboalkoxycyanoalkyl, with the proviso that $R_{XVI-2}$ has a lower Cahn-Ingold-Prelog system ranking than both $R_{XVI-1}$ and $(CHR_{XVI-3})_n$—$N(A_{XVI})Q_{XVI}$;

$R_{XVI-3}$ is selected from the group consisting of hydrido, hydroxy, cyano, aryl, aralkyl, acyl, alkoxy, alkyl, alkenyl, alkoxyalkyl, heteroaryl, alkenyloxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl, with the provisos that $(CHR_{XVI-3})_n$—$N(A_{XVI})Q_{XVI}$ has a lower Cahn-Ingold-Prelog stereochemical system ranking than $R_{XVI-1}$ and a higher Cahn-Ingold-Prelog stereochemical system ranking than $R_{XVI-2}$;

$Y_{XVI}$ is selected from a group consisting of a covalent single bond, $(C(R_{XVI-14})_2)_q$ wherein q is an integer selected from 1 and 2 and $(CH(R_{XVI-14}))_g$—$W_{XVI}$—$(CH(R_{XVI-14}))_p$ wherein g and p are integers independently selected from 0 and 1;

$R_{XVI-14}$ is selected from the group consisting of hydrido, hydroxy, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$Z_{XVI}$ is selected from a group consisting of a covalent single bond, $(C(R_{XVI-15})_2)_q$, wherein q is an integer selected from 1 and 2, and $(CH(R_{XVI-15}))_j$—$W_{XVI}$—$(CH(R_{XVI-15}))_k$ wherein j and k are integers independently selected from 0 and 1;

$W_{XVI}$ is selected from the group consisting of O, C(O), C(S), C(O)N($R_{XVI-14}$), C(S)N($R_{XVI-14}$), ($R_{XVI-14}$)NC(O), ($R_{XVI-14}$)NC(S), S, S(O), S(O)$_2$, S(O)$_2$N($R_{XVI-14}$), ($R_{XVI-14}$)NS(O)$_2$, and N($R_{XVI-14}$) with the proviso that $R_{XVI-14}$ is other than cyano;

$R_{XVI-15}$ is selected, from the group consisting of hydrido, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$R_{XVI-4}$, $R_{XVI-5}$, $R_{XVI-6}$, $R_{XVI-7}$, $R_{XVI-8}$, $R_{XVI-9}$, $R_{XVI-10}$, $R_{XVI-11}$, $R_{XVI-12}$, and $R_{XVI-13}$ are independently selected from the group consisting of hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkyl, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl, amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydroxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the proviso that $R_{XVI-14}$, $R_{XVI-5}$, $R_{XVI-6}$, $R_{XVI-7}$, $R_{XVI-8}$, $R_{XVI-9}$, $R_{XVI-10}$, $R_{XVI-11}$, $R_{XVI-12}$, and $R_{XVI-13}$ are each independently selected to maintain the tetravalent nature of carbon, trivalent nature of nitrogen, the divalent nature of sulfur, and the divalent nature of oxygen;

$R_{XVI-4}$ and $R_{XVI-5}$, $R_{XVI-5}$ and $R_{XVI-6}$, $R_{XVI-6}$ and $R_{XVI-7}$, $R_{XVI-7}$ and $R_{XVI-8}$, $R_{XVI-9}$ and $R_{XVI-10}$, $R_{XVI-10}$ and $R_{XVI-11}$, $R_{XVI-11}$ and $R_{XVI-12}$, and $R_{XVI-12}$ and $R_{XVI-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XVI-4}$ and $R_{XVI-5}$, $R_{XVI-5}$ and $R_{XVI-6}$, $R_{XVI-6}$ and $R_{XVI-7}$, and $R_{XVI-7}$ and $R_{XVI-8}$ is used at the same time and that no more than one of the group consisting of spacer pairs $R_{XVI-9}$ and $R_{XVI-10}$, $R_{XVI-10}$ and $R_{XVI-11}$, $R_{XVI-11}$ and $R_{XVI-12}$, and $R_{XVI-12}$ and $R_{XVI-13}$ can be used at the same time;

$R_{XVI-4}$ and $R_{XVI-9}$, $R_{XVI-4}$ and $R_{XVI-13}$, $R_{XVI-8}$ and $R_{XVI-9}$, and $R_{XVI-8}$ and $R_{XVI-13}$ is independently selected to form a spacer pair wherein said spacer pair is taken together to form a linear moiety wherein said linear moiety forms a ring selected from the group consisting of a partially saturated heterocyclyl ring having from 5 through 8 contiguous members and a heteroaryl ring having from 5 through 6 contiguous members with the proviso that no more than one of the group consisting of spacer pairs $R_{XVI-4}$ and $R_{XVI-9}$, $R_{XVI-4}$ and $R_{XVI-13}$, $R_{XVI-8}$ and $R_{XVI-9}$, and $R_{XVI-8}$ and $R_{XVI-13}$ is used at the same time.

Compounds of Formula XVI and their methods of manufacture are disclosed in PCT Publication No. WO 00/18724, which is incorporated herein by reference in its entirety for all purposes.

In a preferred embodiment, the CETP inhibitor is selected from the following compounds of Formula XVI:

(2R)-3-[[3-(3-trifluoromethoxyphenoxy)phenyl][[3-(1,1,2,2-tetrafluoroethoxy)phenyl]methyl]amino]-1,1,1-trifluoro-2-propanol;

(2R)-3-[[3-(3-isopropylphenoxy)phenyl][[3-(1,1,2,2-tetrafluoroethoxy)phenyl]-methyl]amino]-1,1,1-trifluoro-2-propanol;

(2R)-3-[[3-(3-cyclopropylphenoxy)phenyl][[3-(1,1,2,2-tetrafluoroethoxy)phenyl]-methyl]amino]-1,1,1-trifluoro-2-propanol;

(2R)-3-[[3-(3-(2-furyl)phenoxy)phenyl][[3-(1,1,2,2-tetrafluoroethoxy)phenyl]-methyl]amino]-1,1,1-trifluoro-2-propanol;

(2R)-3-[[3-(2,3-dichlorophenoxy)phenyl][[3-(1,1,2,2-tetrafluoroethoxy)phenyl]-methyl]amino]-1,1,1-trifluoro-2-propanol;

(2R)-3-[[3-(4-fluorophenoxy)phenyl][[3-(1,1,2,2-tetrafluoroethoxy)phenyl]-methyl]amino]-1,1,1-trifluoro-2-propanol;

(2R)-3-[[3-(4-methylphenoxy)phenyl][[3-(1,1,2,2-tetrafluoroethoxy)phenyl]-methyl]amino]-1,1,1-trifluoro-2-propanol;

(2R)-3-[[3-(2-fluoro-5-bromophenoxy)phenyl][[3-(1,1,2,2-tetrafluoroethoxy)phenyl]-methyl]amino]-1,1,1-trifluoro-2-propanol;

(2R)-3-[[3-(4-chloro-3-ethylphenoxy)phenyl][[3-(1,1,2,2-tetrafluoroethoxy)phenyl]-methyl]amino]-1,1,1-trifluoro-2-propanol;

(2R)-3-[[3-[3-(1,1,2,2-tetrafluoroethoxy)phenoxy]phenyl][[3-(1,1,2,2-tetrafluoro-ethoxy)phenyl]methyl]amino]-1,1,1-trifluoro-2-propanol;

(2R)-3-[[3-[3-(pentafluoroethyl)phenoxy]phenyl][[3-(1,1,2,2-tetrafluoroethoxy)-phenyl]methyl]amino]-1,1,1-trifluoro-2-propanol;

(2R)-3-[[3-(3,5-dimethylphenoxy)phenyl][[3-(1,1,2,2-tetrafluoroethoxy)phenyl]-methyl]amino]-1,1,1-trifluoro-2-propanol;

(2R)-3-[[3-(3-ethylphenoxy)phenyl][[3-(1,1,2,2-tetrafluoroethoxy)phenyl]-methyl]amino]-1,1,1-trifluoro-2-propanol;

(2R)-3-[[3-(3-t-butylphenoxy)phenyl][[3-(1,1,2,2-tetrafluoroethoxy)phenyl]-methyl]amino]-1,1,1-trifluoro-2-propanol;

(2R)-3-[[3-(3-methylphenoxy)phenyl][[3-(1,1,2,2-tetrafluoroethoxy)phenyl]-methyl]amino]-1,1,1-trifluoro-2-propanol;

(2R)-3-[[3-(5,6,7,8-tetrahydro-2-naphthoxy)phenyl][[3-(1,1,2,2-tetrafluoro-ethoxy)phenyl]methyl]amino]-1,1,1-trifluoro-2-propanol;

(2R)-3-[[3-(phenoxy)phenyl][[3-(1,1,2,2-tetrafluoroethoxy)phenyl]methyl]amino]-1,1,1-trifluoro-2-propanol;

(2R)-3-[[3-(N,N-dimethylamino)phenoxy]phenyl][[3-(1,1,2,2-tetrafluoro-ethoxy)phenyl]methyl]amino]-1,1,1-trifluoro-2-propanol;

(2R)-3-[[[3-(1,1,2,2,-tetrafluoroethoxy)phenyl]methyl][3-[[3-(trifluoromethoxy)-phenyl]methoxy]phenyl]amino]-1,1,1-trifluoro-2-propanol;

(2R)-3-[[[3-(1,1,2,2-tetrafluoroethoxy)phenyl]methyl][3-[[3-(trifluoromethyl)phenyl]methoxy]phenyl]amino]-1,1,1-trifluoro-2-propanol;

(2R)-3-[[[3-(1,1,2,2-tetrafluoroethoxy)phenyl]methyl][3-[[3,5-dimethylphenyl]-methoxy]phenyl]amino]-1,1,1-trifluoro-2-propanol;

(2R)-3-[[[3-(1,1,2,2-tetrafluoroethoxy)phenyl]methyl][3-[[3-(trifluoromethylthio)-phenyl]methoxy]phenyl]amino]-1,1,1-trifluoro-2-propanol;

(2R)-3-[[[3-(1,1,2,2-tetrafluoroethoxy)phenyl]methyl][3-[[3,5-difluorophenyl]-methoxy]phenyl]amino]-1,1,1-trifluoro-2-propanol;

(2R)-3-[[[3-(1,1,2,2-tetrafluoroethoxy)phenyl]methyl][3-[cyolohexylmethoxy]-phenyl]amino]-1,1,1-trifluoro-2-propanol;

(2R)-3-[[3-(2-difluoromethoxy-4-pyridyloxy)phenyl][[3-(1,1,2,2-tetrafluoroethoxy)-phenyl]methyl]amino]-1,1,1-trifluoro-2-propanol;

(2R)-3-[[3-(2-trifluoromethyl-4-pyridyloxy)phenyl][[3-(1,1,2,2-tetrafluoroethoxy)-phenyl]methyl]amino]-1,1,1-trifluoro-2-propanol;

(2R)-3-[[3-(3-difluoromethoxyphenoxy)phenyl][[3-(1,1,2,2-tetrafluoroethoxy)-phenyl]methyl]amino]-1,1,1-trifluoro-2-propanol;

(2R)-3-[[[3-(3-trifluoromethylthio)phenoxy]phenyl][[3-(1,1,2,2-tetrafluoroethoxy)-phenyl]methyl]amino]-1,1,1-trifluoro-2-propanol;

(2R)-3-[[3-(4-chloro-3-trifluoromethylphenoxy)phenyl][[3-(1,1,2,2-tetrafluoroethoxy)-phenyl]methyl]amino]-1,1,1-trifluoro-2-propanol;

(2R)-3-[[3-(3-trifluoromethoxyphenoxy)phenyl][[3-(pentafluoroethyl)phenyl]-methyl]amino]-1,1,1-trifluoro-2-propanol;

(2R)-3-[[3-(3-isopropylphenoxy)phenyl][[3-(pentafluoroethyl)phenyl]methyl]-amino]-1,1,1-trifluoro-2-propanol;

(2R)-3-[[3-(3-cyclopropylphenoxy)phenyl][[3-(pentafluoroethyl)phenyl]methyl]-amino]-1,1,1-trifluoro-2-propanol;

(2R)-3-[[3-(3-(2-furyl)phenoxy)phenyl][[3-(pentafluoroethyl)phenyl]methyl]-amino]-1,1,1-trifluoro-2-propanol;

(2R)-3-[[3-(2,3-dichlorophenoxy)phenyl][[3-(pentafluoroethyl)phenyl]methyl]-amino]-1,1,1-trifluoro-2-propanol;

(2R)-3-[[3-(4-fluorophenoxy)phenyl][[3-(pentafluoroethyl)phenyl]methyl]amino]-1,1,1-trifluoro-2-propanol;

(2R)-3-[[3-(4-methylphenoxy)phenyl][[3-(pentafluoroethyl)phenyl]methyl]amino]-1,1,1-trifluoro-2-propanol;

(2R)-3-[[3-(2-fluoro-5-bromophenoxy)phenyl][[3-(pentafluoroethyl)phenyl]methyl]-amino]-1,1,1-trifluoro-2-propanol;

(2R)-3-[[3-(4-chloro-3-ethylphenoxy)phenyl][[3-(pentafluoroethyl)phenyl]methyl]-amino]-1,1,1-trifluoro-2-propanol;

(2R)-3-[[3-[3-(1,1,2,2-tetrafluoroethoxy)phenoxy]phenyl][[3-(pentafluoroethyl)-phenyl]methyl]amino]-1,1,1-trifluoro-2-propanol;

(2R)-3-[[3-[3-(pentafluoroethyl)phenoxy]phenyl][[3-(pentafluoroethyl)phenyl]-methyl]amino]-1,1,1-trifluoro-2-propanol;

(2R)-3-[[3-(3,5-dimethylphenoxy)phenyl][[3-(pentafluoroethyl)phenyl]methyl]-amino]-1,1,1-trifluoro-2-propanol;

(2R)-3-[[3-(3-ethylphenoxy)phenyl][[3-(pentafluoroethyl)phenyl]methyl]amino]-1,1,1-trifluoro-2-propanol;

(2R)-3-[[3-(3-t-butylphenoxy)phenyl][[3-(pentafluoroethyl)phenyl]methyl]amino]-1,1,1-trifluoro-2-propanol;

(2R)-3-[[3-(3-methylphenoxy)phenyl][[3-(pentafluoroethyl)phenyl]methyl]amino]-1,1,1-trifluoro-2-propanol;

(2R)-3-[[3-(5,6,7,8-tetrahydro-2-naphthoxy)phenyl][[3-(pentafluoroethyl)phenyl]-methyl]amino]-1,1,1-trifluoro-2-propanol;

(2R)-3-[[3-(phenoxy)phenyl][[3-(pentafluoroethyl)phenyl]methyl]amino]-1,1,1-trifluoro-2-propanol;

(2R)-3-[[3-[3-(N,N-dimethylamino)phenoxy]phenyl][[3-(pentafluoroethyl)phenyl]-methyl]amino]-1,1,1-trifluoro-2-propanol;

(2R)-3-[[[3-(pentafluoroethyl)phenyl]methyl][3-[[3-(trifluoromethoxy)phenyl]-methoxy]phenyl]amino]-1,1,1-trifluoro-2-propanol;

(2R)-3-[[[3-(pentafluoroethyl)phenyl]methyl][3-[[3-(trifluoromethyl)-phenyl]-methoxy]phenyl]amino]-1,1,1-trifluoro-2-propanol;

(2R)-3-[[[3-(pentafluoroethyl)phenyl]methyl][3-[[3,5-dimethylphenyl]methoxy]-phenyl]amino]-1,1,1-trifluoro-2-propanol;

(2R)-3-[[[3-(pentafluoroethyl)phenyl]methyl][3-[[3-(trifluoromethylthio)phenyl]-methoxy]phenyl]amino]-1,1,1-trifluoro-2-propanol;

(2R)-3-[[[3-(pentafluoroethyl)phenyl]methyl][3-[[3,5-difluorophenyl]methoxy]-phenyl]amino]-1,1,1-trifluoro-2-propanol;

(2R)-3-[[[3-(pentafluoroethyl)phenyl]methyl][3-[cyclohexyl methoxy]phenyl]-amino]-1,1,1-trifluoro-2-propanol;

(2R)-3-[[3-(2-difluoromethoxy-4-pyridyloxy)phenyl][[3-(pentafluoroethyl)phenyl]-methyl]amino]-1,1,1-trifluoro-2-propanol;

(2R)-3-[[3-(2-trifluoromethyl-4-pyridyloxy)phenyl][[3-(pentafluoroethyl)phenyl]-methyl]amino]-1,1,1-trifluoro-2-propanol;

(2R)-3-[[3-(3-difluoromethoxyphenoxy)phenyl][[3-(pentafluoroethyl)phenyl]-methyl]amino]-1,1,1-trifluoro-2-propanol;

(2R)-3-[[[3-(3-trifluoromethylthio)phenoxy]phenyl][[3-(pentafluoroethyl)phenyl]-methyl]amino]-1,1,1-trifluoro-2-propanol;

(2R)-3-[[3-(4-chloro-3-trifluoromethylphenoxy)phenyl][[3-(pentafluoroethyl)-phenyl]methyl]amino]-1,1,1-trifluoro-2-propanol;

(2R)-3-[[3-(3-trifluoromethoxyphenoxy)phenyl][[3-(heptafluoropropyl)phenyl]-methyl]amino]-1,1,1-trifluoro-2-propanol;

(2R)-3-[[3-(3-isopropylphenoxy)phenyl][[3-(heptafluoropropyl)phenyl]methyl]-amino]-1,1,1-trifluoro-2-propanol;

(2R)-3-[[3-(3-cyclopropylphenoxy)phenyl][[3-(heptafluoropropyl)phenyl]methyl]-amino]-1,1,1-trifluoro-2-propanol;

(2R)-3-[[3-(3-(2-furyl)phenoxy)phenyl][[3-(heptafluoropropyl)phenyl]methyl]-amino]-1,1,1-trifluoro-2-propanol;

(2R)-3-[[3-(2,3-dichlorophenoxy)phenyl][[3-(heptafluoropropyl)phenyl]methyl]-amino]-1,1,1-trifluoro-2-propanol;

(2R)-3-[[3-(4-fluorophenoxy)phenyl][[3-(heptafluoropropyl)phenyl]methyl]amino]-1,1,1-trifluoro-2-propanol;

(2R)-3-[[3-(4-methylphenoxy)phenyl][[3-(heptafluoropropyl)phenyl]methyl]amino]-1,1,1,-trifluoro-2-propanol;

(2R)-3-[[3-(2-fluoro-5-bromophenoxy)phenyl][[3-(heptafluoropropyl)phenyl]methyl]-amino]-1,1,1-trifluoro-2-propanol;

(2R)-3-[[3-(4-chloro-3-ethylphenoxy)phenyl][[3-(heptafluoropropyl)phenyl]methyl]-amino]-1,1,1-trifluoro-2-propanol;

(2R)-3-[[3-[3-(1,1,2,2-tetrafluoroethoxy)phenoxy]phenyl][[3-(heptafluoropropyl)-phenyl]methyl]amino]-1,1,1-trifluoro-2-propanol;

(2R)-3-[[3-[3-(pentafluoroethyl)phenoxy]phenyl][[3-(heptafluoropropyl)phenyl]-methyl]amino]-1,1,1-trifluoro-2-propanol;

(2R)-3-[[3-(3,5-dimethylphenoxy)phenyl][[3-(heptafluoropropyl)phenyl]methyl]-amino]-1,1,1-trifluoro-2-propanol;

(2R)-3-[[3-(3-ethylphenoxy)phenyl][[3-(heptafluoropropyl)phenyl]methyl]amino]-1,1,1-trifluoro-2-propanol;

(2R)-3-[[3-(3-t-butylphenoxy)phenyl][[3-(heptafluoropropyl)phenyl]methyl]amino]-1,1,1-trifluoro-2-propanol;

(2R)-3-[[3-(3-methylphenoxy)phenyl][[3-(heptafluoropropyl)phenyl]methyl]amino]-1,1,1-trifluoro-2-propanol;

(2R)-3-[[3-(5,6,7,8-tetrahydro-2-naphthoxy)phenyl][[3-(heptafluoropropyl)phenyl]-methyl]amino]-1,1,1-trifluoro-2-propanol;

(2R)-3-[[3-(phenoxy)phenyl][[3-(heptafluoropropyl)phenyl]methyl]amino]-1,1,1-trifluoro-2-propanol;

(2R)-3-[[3-[3-(N,N-dimethylamino)phenoxy]phenyl][[3-(heptafluoropropyl)phenyl]-methyl]amino]-1,1,1-trifluoro-2-propanol;

(2R)-3-[[[3-(heptafluoropropyl)phenyl]methyl][3-[[3-(trifluoromethoxy)phenyl]-methoxy]phenyl]amino]-1,1,1-trifluoro-2-propanol;

(2R)-3-[[[3-(heptafluoropropyl)phenyl]methyl][3-[[3-(trifluoromethyl)phenyl]-methoxy]phenyl]amino]-1,1,1-trifluoro-2-propanol;

(2R)-3-[[[3-(heptafluoropropyl)phenyl]methyl][3-[[3,5-dimethylphenyl]methoxy]-phenyl]amino]-1,1,1-trifluoro-2-propanol;

(2R)-3-[[[3-(heptafluoropropyl)phenyl]methyl][3-[[3-(trifluoromethylthio)phenyl]-methoxy]phenyl]amino]-1,1,1-trifluoro-2-propanol;

(2R)-3-[[[3-(heptafluoropropyl)phenyl]methyl][3-[[3,5-difluorophenyl]methoxy]-phenyl]amino]-1,1,1-trifluoro-2-propanol;

(2R)-3-[[[3-(heptafluoropropyl)phenyl]methyl][3-[cyclohexylmethoxy]phenyl]-amino]-1,1,1-trifluoro-2-propanol;

(2R)-3-[[3-(2-difluoromethoxy-4-pyridyloxy)phenyl][[3-(heptafluoropropyl)phenyl]-methyl]amino]-1,1,1-trifluoro-2-propanol;

(2R)-3-[[3-(2-trifluoromethyl-4-pyridyloxy)phenyl][[3-(heptafluoropropyl)phenyl]-methyl]amino]-1,1,1-trifluoro-2-propanol;

(2R)-3-[[3-(3-difluoromethoxyphenoxy)phenyl][[3-(heptafluoropropyl)phenyl]-methyl]amino]-1,1,1-trifluoro-2-propanol;

(2R)-3-[[[3-(3-trifluoromethylthio)phenoxy]phenyl][[3-320(heptafluoropropyl)phenyl]-methyl]amino]-1,1,1-trifluoro-2-propanol;

(2R)-3-[[3-(4-chloro-3-trifluoromethylphenoxy)phenyl][[3-(heptafluoropropyl)-phenyl]methyl]amino]-1,1,1-trifluoro-2-propanol;

(2R)-3-[[3-(3-trifluoromethoxyphenoxy)phenyl][[2-fluoro-5-(trifluoromethyl)-phenyl]methyl]amino]-1,1,1-trifluoro-2-propanol;

(2R)-3-[[3-(3-isopropylphenoxy)phenyl][[2-fluoro-5-(trifluoromethyl)phenyl]-methyl]amino]-1,1,1-trifluoro-2-propanol;

(2R)-3-[[3-(3-cyclopropylphenoxy)phenyl][[2-fluoro-5-(trifluoromethyl)phenyl]-methyl]amino]-1,1,1-trifluoro-2-propanol;

(2R)-3-[[3-(3-(2-furyl)phenoxy)phenyl][[2-fluoro-5-(trifluoromethyl)phenyl]-methyl]amino]-1,1,1-trifluoro-2-propanol;

(2R)-3-[[3-(2,3-dichlorophenoxy)phenyl][[2-fluoro-5-(trifluoromethyl)phenyl]-methyl]amino]-1,1,1-trifluoro-2-propanol;

(2R)-3-[[3-(4-fluorophenoxy)phenyl][[2-fluoro-5-(trifluoromethyl)phenyl]-methyl]amino]-1,1,1-trifluoro-3-propanol;

(2R)-3-[[3-(4-methylphenoxy)phenyl][[2-fluoro-5-(trifluoromethyl)phenyl]-methyl]amino]-1,1,1-trifluoro-2-propanol;

(2R)-3-[[3-(2-fluoro-5-bromophenoxy)phenyl][[2-fluoro-5-(trifluoromethyl)-phenyl]methyl]amino]-1,1,1-trifluoro-2-propanol;

(2R)-3-[[3-(4-chloro-3-ethylphenoxy)phenyl][[2-fluoro-5-(trifluoromethyl)-phenyl]methyl]amino]-1,1,1-trifluoro-2-propanol;

(2R)-3-[[3-[3-(1,1,2,2-tetrafluoroethoxy)phenoxy]phenyl][[2-fluoro-5-(trifluoro-methyl)phenyl]methyl]amino]-1,1,1-trifluoro-2-propanol;

(2R)-3-[[3-(3-(pentafluoroethyl)phenoxy)phenyl][[2-fluoro-5-(trifluoromethyl)-phenyl]methyl]amino]-1,1,1-trifluoro-2-propanol;

(2R)-3-[[3-(3,5-dimethylphenoxy)phenyl][[2-fluoro-5-(trifluoromethyl)phenyl]-methyl]amino]-1,1,1-trifluoro-2-propanol;

(2R)-3-[[3-(3-ethylphenoxy)phenyl][[2-fluoro-5-(trifluoromethyl)phenyl]methyl]-amino]-1,1,1-trifluoro-2-propanol;

(2R)-3-[[3-(3-t-butylphenoxy)phenyl][[2-fluoro-5-(trifluoromethyl)phenyl]methyl]-amino]-1,1,1-trifluoro-2-propanol;

(2R)-3-[[3-(3-methylphenoxy)phenyl][[2-fluoro-5-(trifluoromethyl)phenyl]methyl]-amino]-1,1,1-trifluoro-2-propanol;

(2R)-3-[[3-(5,6,7,8-tetrahydro-2-naphthoxy)phenyl][[2-fluoro-5-(trifluoromethyl)-phenyl]methyl]amino]-1,1,1-trifluoro-2-propanol;

(2R)-3-[[3-(phenoxy)phenyl][[2-fluoro-5-(trifluoromethyl)phenyl]methyl]amino]-1,1,1-trifluoro-2-propanol;

(2R)-3-[[3-[3-(N,N-dimethylamino, phenoxy]phenyl][[2-fluoro-5-(trifluoromethyl)-phenyl]methyl]amino]-1,1,1-trifluoro-2-propanol;

(2R)-3-[[[2-fluoro-5-(trifluoromethyl)phenyl]methyl][3-[[3-(trifluoromethoxy)-phenyl]methoxy]phenyl]amino]-1,1,1-trifluoro-3-propanol;

(2R)-3-[[[2-fluoro-5-(trifluoromethyl)phenyl]methyl][3-[[3-(trifluoromethyl)-phenyl]methoxy]phenyl]amino]-1,1,1-trifluoro-2-propanol;

(2R)-3-[[[2-fluoro-5-(trifluoromethyl)phenyl]methyl][3-[[3,5-dimethylphenyl]-methoxy]phenyl]amino]-1,1,1-trifluoro-2-propanol;

(2R)-3-[[[2-fluoro-5-(trifluoromethyl)phenyl]methyl][3-[[3-(trifluoromethylthio)-phenyl]methoxy]phenyl]amino]-1,1,1-trifluoro-2-propanol;

(2R)-3-[[[2-fluoro-5-(trifluoromethyl)phenyl]methyl][3-[[3,5-difluorophenyl]-methoxy]phenyl]amino]-1,1,1-trifluoro-2-propanol;

(2R)-3-[[[2-fluoro-5-(trifluoromethyl)phenyl]methyl][3-[cyclohexylmethoxyl-phenyl]amino]-1,1,1-trifluoro-2-propanol;

(2R)-3-[[3-(2-difluoromethoxy-4-pyridyloxy)phenyl][[2-fluoro-5-(trifluoromethyl)-phenyl]methyl]amino]-1,1,1-trifluoro-2-propanol;

(2R)-3-[[3-(2-trifluoromethyl-4-pyridyloxy)phenyl][[2-fluoro-5-(trifluoromethyl)-phenyl]methyl]amino]-1,1,1-trifluoro-2-propanol;

(2R)-3-[[3-(3-difluoromethoxyphenoxy)phenyl][[2-fluoro-5-(trifluoromethyl)-phenyl]methyl]amino]-1,1,1-trifluoro-2-propanol;

(2R)-3-[[[3-(3-trifluoromethylthio)phenoxy]phenyl][[2-fluoro-5-(trifluoromethyl)-phenyl]methyl]amino]-1,1,1-trifluoro-2-propanol;

(2R)-3-[[3-(4-chloro-3-trifluoromethylphenoxy)phenyl][[2-fluoro-5-(trifluoro-methyl)phenyl]methyl]amino]-1,1,1-trifluoro-2-propanol;
(2R)-3-[[3-(3-trifluoromethoxyphenoxy)phenyl][[2-fluoro-4-(trifluoromethyl)-phenyl]methyl]amino]-1,1,1-trifluoro-2-propanol;
(2R)-3-[[3-(3-isopropylphenoxy)phenyl][[2-fluoro-4-(trifluoromethyl)phenyl]-methyl]amino]-1,1,1-trifluoro-2-propanol;
(2R)-3-[[3-(3-cyclopropylphenoxy)phenyl][[2-fluoro-4-(trifluoromethyl)phenyl]-methyl]amino]-1,1,1-trifluoro-2-propanol;
(2R)-3-[[3-(3-(2-furyl)phenoxy)phenyl][[2-fluoro-4-(trifluoromethyl)phenyl]-methyl]amino]-1,1,1-trifluoro-2-propanol;
(2R)-3-[[3-(2,3-dichlorophenoxy)phenyl][[2-fluoro-4-(trifluoromethyl)phenyl]-methyl]amino]-1,1,1-trifluoro-2-propanol;
(2R)-3-[[3-(4-fluorophenoxy)phenyl][[2-fluoro-4-(trifluoromethyl)phenyl]-methyl]amino]-1,1,1-trifluoro-2-propanol;
(2R)-3-[[3-(4-methylphenoxy)phenyl][[2-fluoro-4-(trifluoromethyl)phenyl]-methyl]amino]-1,1,1-trifluoro-2-propanol;
(2R)-3-[[3-(2-fluoro-5-bromophenoxy)phenyl][[2-fluoro-4-(trifluoromethyl)-phenyl]methyl]amino]-1,1,1-trifluoro-2-propanol;
(2R)-3-[[3-(4-chloro-3-ethylphenoxy)phenyl][[2-fluoro-4-(trifluoromethyl)-phenyl]methyl]amino]-1,1,1-trifluoro-2-propanol;
(2R)-3-[[3-[3-(1,1,2,2-tetrafluoroethoxy)phenoxy]phenyl][[2-fluoro-4-(trifluoromethyl)phenyl]methyl]amino]-1,1,1-trifluoro-2-propanol;
(2R)-3-[[3-[3-(pentafluoroethyl)phenoxy]phenyl][[2-fluoro-4-(trifluoromethyl)-phenyl]methyl]amino]-1,1,1-trifluoro-2-propanol;
(2R)-3-[[3-(3,5-dimethylphenoxy)phenyl][[2-fluoro-4-(trifluoromethyl)phenyl]-methyl]amino]-1,1,1-trifluoro-2-propanol;
(2R)-3-[[3-(3-ethylphenoxy)phenyl][[2-fluoro-4-(trifluoromethyl)phenyl]methyl]-amino]-1,1,1-trifluoro-2-propanol;
(2R)-3-[[3-(3-t-butylphenoxy)phenyl][[2-fluoro-4-(trifluoromethyl)phenyl]methyl]-amino]-1,1,1-trifluoro-2-propanol;
(2R)-3-[[3-(3-methylphenoxy)phenyl][[2-fluoro-4-(trifluoromethyl)phenyl]methyl]-amino]-1,1,1-trifluoro-2-propanol;
(2R)-3-[[3-(5,6,7,8-tetrahydro-2-naphthoxy)phenyl][[2-fluoro-4-(trifluoromethyl)-phenyl]methyl]amino]-1,1,1-trifluoro-2-propanol;
(2R)-3-[[3-(phenoxy)phenyl][[2-fluoro-4-(trifluoromethyl)phenyl]methyl]amino]-1,1,1-trifluoro-2-propanol;
(2R)-3-[[3-[3-(N,N-dimethylamino)phenoxy]phenyl][[2-fluoro-4-(trifluoromethyl)-phenyl]methyl]amino]-1,1,1-trifluoro-2-propanol;
(2R)-3-[[[2-fluoro-4-(trifluoromethyl)phenyl]methyl][3-[[3-(trifluoromethoxy)phenyl]methoxy]phenyl]amino]-1,1,1-trifluoro-2-propanol;
(3R)-3-[[[2-fluoro-4-(trifluoromethyl)phenyl]methyl][3-[[3-(trifluoromethyl)phenyl]methoxy]phenyl]amino]-1,1,1-trifluoro-2-propanol;
(2R)-3-[[[2-fluoro-4-(trifluoromethyl)phenyl]methyl][3-[[3,5-dimethylphenyl]-methoxy]phenyl]amino]-1,1,1-trifluoro-2-propanol;
(2R)-3-[[[2-fluoro-4-(trifluoromethyl)phenyl]methyl][3-[[3-(trifluoromethylthio)-phenyl]methoxy]phenyl]amino]-1,1,1-trifluoro-2-propanol;
(2R)-3-[[[2-fluoro-4-(trifluoromethyl)phenyl]methyl][3-[[3,5-difluorophenyl]-methoxy]phenyl]amino]-1,1,1-trifluoro-2-propanol;
(2R)-3-[[[2-fluoro-4-(trifluoromethyl)phenyl]methyl][3-[cyclohexylmethoxy]-phenyl]amino]-1,1,1-trifluoro-2-propanol;
(2R)-3-[[3-(2-difluoromethoxy-4-pyridyloxy)phenyl][[2-fluoro-4-(trifluoromethyl)-phenyl]methyl]amino]-1,1,1-trifluoro-2-propanol;
(2R)-3-[[3-(2-trifluoromethyl-4-pyridyloxy)phenyl][[2-fluoro-4-(trifluoromethyl)-phenyl]methyl]amino]-1,1,1-trifluoro-2-propanol;
(2R)-3-[[3-(3-difluoromethoxyphenoxy)phenyl][[2-fluoro-4-(trifluoromethyl)-phenyl]methyl]amino]-1,1,1-trifluoro-2-propanol;
(2R)-3-[[[3-(3-trifluoromethylthio)phenoxy]phenyl][[2-fluoro-4-(trifluoromethyl)-phenyl]methyl]amino]-1,1,1-trifluoro-2-propanol; and
(2R)-3-[[3-(4-chloro-3-trifluoromethylphenoxy)phenyl][[2-fluoro-4-(trifluoromethyl)phenyl]methyl]amino]-1,1,1-trifluoro-2-propanol.

Another class of CETP inhibitors that finds utility with the present invention consists of quinolines of Formula XVII

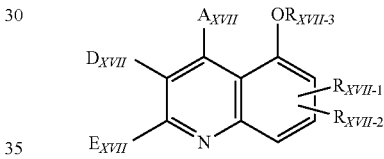

Formula XVII and pharmaceutically acceptable forms thereof, wherein:

$A_{XVII}$ denotes an aryl containing 6 to 10 carbon atoms, which is optionally substituted with up to five identical or different substituents in the form of a halogen, nitro, hydroxyl, trifluoromethyl, trifluoromethoxy or a straight-chain or branched alkyl, acyl, hydroxyalkyl or alkoxy containing up to 7 carbon atoms each, or in the form of a group according to the formula $-NR_{XVII-4}R_{XVII-5}$, wherein $R_{XVII-4}$ and $R_{XVII-5}$ are identical or different and denote a hydrogen, phenyl or a straight-chain or branched alkyl containing up to 6 carbon atoms, $D_{XVII}$ denotes an aryl containing 6 to 10 carbon atoms, which is optionally substituted with a phenyl, nitro, halogen, trifluoromethyl or trifluoromethoxy, or a radical according to the formula

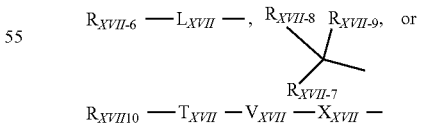

wherein $R_{XVII-6}$, $R_{XVII-7}$, $R_{XVII-10}$ denote, independently from one another, a cycloalkyl containing 3 to 6 carbon atoms, or an aryl containing 6 to 10 carbon atom or a 5- to 7-membered, optionally benzo-condensed, saturated or unsaturated, mono-, bi- or tricyclic heterocycle containing up to 4 heteroatoms from the series of S, N and/or O, wherein the rings are optionally substituted, in the case of the nitrogen-containing rings also via the N function, with up to five identical or different substituents in the form of a halogen, trifluoromethyl, nitro, hydroxyl, cyano, carboxyl, trifluoromethoxy, a straight-chain or branched acyl, alkyl, alkylthio, alkylalkoxy, alkoxy or alkoxycarbonyl containing up to 6 carbon atoms each, an aryl or trifluoromethyl-substituted aryl containing 6 to 10 carbon atoms each, or an optionally benzo-condensed, aromatic 5- to 7-membered heterocycle containing up to 3 heteroatoms from the series of S, N and/or O, and/or in the form of a group according to the formula —$OR_{XVII-11}$, —$SR_{XVII-12}$, —$SO_2R_{XVII-13}$, or —$NR_{XVII-14}R_{XVII-15}$;

$R_{XVII-11}$, $R_{XVII-12}$, and $R_{XVII-13}$ denote, independently from one another, an aryl containing 6 to 10 carbon atoms, which is in turn substituted with up to two identical or different substituents in the form of a phenyl, halogen or a straight-chain or branched alkyl containing up to 6 carbon atoms, $R_{XVII-14}$ and $R_{XVII-15}$ are identical or different and have the meaning of $R_{XVII-4}$ and $R_{XVII-5}$ given above, or $R_{XVII-6}$ and/or $R_{XVII-7}$ denote a radical according to the formula

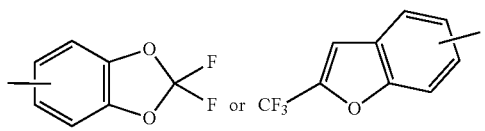

$R_{XVII-8}$ denotes a hydrogen or halogen, and $R_{XVII-9}$ denotes a hydrogen, halogen, azido, trifluoromethyl, hydroxyl, trifluoromethoxy, a straight-chain or branched alkoxy or alkyl containing up to 6 carbon atoms each, or a radical according to the formula $NR_{XVII-16}R_{XVII-17}$, $R_{XVII-16}$ and $R_{XVII-17}$ are identical or different and have the meaning of $R_{XVII-4}$ and $R_{XVII-5}$ above; or $R_{XVII-8}$ and $R_{XVII-9}$ together form a radical according to the formula =O or =$NR_{XVII-18}$;

$R_{XVII-18}$ denotes a hydrogen or a straight-chain or branched alkyl, alkoxy or acyl containing up to 6 carbon atoms each;

$L_{XVII}$ denotes a straight-chain or branched alkylene or alkenylene chain containing up to 8 carbon atoms each, which are optionally substituted with up to two hydroxyl groups;

$T_{XVII}$ and $X_{XVII}$ are identical or different and denote a straight-chain or branched alkylene chain containing up to 8 carbon atoms; or $T_{XVII}$ and $X_{XVII}$ denotes a bond;

$V_{XVII}$ denotes an oxygen or sulfur atom or —$NR_{XVII-19}$;

$R_{XVII-19}$ denotes a hydrogen or a straight-chain or branched alkyl containing up to 6 carbon atoms or a phenyl;

$E_{XVII}$ denotes a cycloalkyl containing 3 to 8 carbon atoms, or a straight-chain or branched alkyl containing up to 8 carbon atoms, which is optionally substituted with a cycloalkyl containing 3 to 8 carbon atoms or a hydroxyl, or a phenyl, which is optionally substituted with a halogen or trifluoromethyl;

$R_{XVII-1}$ and $R_{XVII-2}$ are identical or different and denote a cycloalkyl containing 3 to 8 carbon atoms, hydrogen, nitro, halogen, trifluoromethyl, trifluoromethoxy, carboxy, hydroxy, cyano, a straight-chain or branched acyl, alkoxycarbonyl or alkoxy with up to 6 carbon atoms, or $NR_{XVII-20}R_{XVII-21}$;

$R_{XVII-20}$ and $R_{XVII-21}$ are identical or different and denote hydrogen, phenyl, or a straight-chain or branched alkyl with up to 6 carbon atoms; and or $R_{XVII-1}$ and/or $R_{XVII-2}$ are straight-chain or branched alkyl with up to 6 carbon atoms, optionally substituted with halogen, trifluoromethoxy, hydroxy, or a straight-chain or branched alkoxy with up to 4 carbon atoms, aryl containing 6-10 carbon atoms optionally substituted with up to five of the same or different substituents selected from halogen, cyano, hydroxy, trifluoromethyl, trifluoromethoxy, nitro, straight-chain or branched alkyl, acyl, hydroxyalkyl, alkoxy with up to 7 carbon atoms and $NR_{XVII-22}R_{XVII-23}$;

$R_{XVII-22}$ and $R_{XVII-23}$ are identical or different and denote hydrogen, phenyl or a straight-chain or branched alkyl up to 6 carbon atoms; and/or $R_{XVII-1}$ and $R_{XVII-2}$ taken together form a straight-chain or branched alkene or alkane with up to 6 carbon atoms optionally substituted with halogen, trifluoromethyl, hydroxy or straight-chain or branched alkoxy with up to 5 carbon atoms;

$R_{XVII-3}$ denotes hydrogen, a straight-chain or branched acyl with up to 20 carbon atoms, a benzoyl optionally substituted with halogen, trifluoromethyl, nitro or trifluoromethoxy, a straight-chained or branched fluoroacyl with up to 8 carbon atoms and 7 fluoro atoms, a cycloalkyl with 3 to 7 carbon atoms, a straight chained or branched alkyl with up to 8 carbon atoms optionally substituted with hydroxyl, a straight-chained or branched alkoxy with up to 6 carbon atoms optionally substituted with phenyl which may in turn be substituted with halogen, nitro, trifluoromethyl, trifluoromethoxy, or phenyl or a tetrazol substituted phenyl, and/or an alkyl that is optionally substituted with a group according to the formula —$OR_{XVII-24}$;

$R_{XVII-24}$ is a straight-chained or branched acyl with up to 4 carbon atoms or benzyl.

Compounds of Formula XVII and their methods of manufacture are disclosed in PCT Publication No. WO 98/39299, which is incorporated herein by reference in its entirety for all purposes.

Another class of CETP inhibitors that finds utility with the present invention consists of 4-Phenyltetrahydroquinolines of Formula XVIII

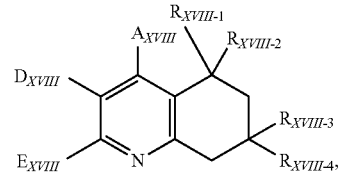

Formula XVIII

N oxides thereof, and pharmaceutically acceptable forms thereof, wherein:

$A_{XVIII}$ denotes a phenyl optionally substituted with up to two identical or different substituents in the form of halogen, trifluoromethyl or a straight-chain or branched alkyl or alkoxy containing up to three carbon atoms;

$D_{XVIII}$ denotes the formula

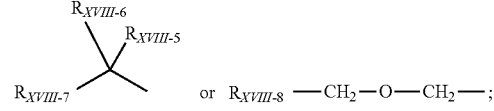

$R_{XVIII-5}$ and $R_{XVIII-6}$ are taken together to form =O; or $R_{XVIII-5}$ denotes hydrogen and $R_{XVIII-6}$ denotes halogen or hydrogen; or $R_{XVIII-5}$ and $R_{XVIII-6}$ denote hydrogen;

$R_{XVIII-7}$ and $R_{XVIII-8}$ are identical or different and denote phenyl, naphthyl, benzothiazolyl, quinolinyl, pyrimidyl or pyridyl with up to four identical or different substituents in the form of halogen, trifluoromethyl, nitro, cyano, trifluoromethoxy, —$SO_2$—$CH_3$ or $N_{XVIII-9}R_{XVIII-10}$;

$R_{XVIII-9}$ and $R_{XVIII-10}$ are identical or different and denote hydrogen or a straight-chained or branched alkyl of up to three carbon atoms;

$E_{XVIII}$ denotes a cycloalkyl of from three to six carbon atoms or a straight-chained or branched alkyl of up to eight carbon atoms;

$R_{XVIII-1}$ denotes hydroxy;

$R_{XVIII-2}$ denotes hydrogen or methyl;

$R_{XVIII-3}$ and $R_{XVIII-4}$ are identical or different and denote straight-chained or branched alkyl of up to three carbon atoms; or $R_{XVIII-3}$ and $R_{XVIII-4}$ taken together form an alkenylene made up of between two and four carbon atoms.

Compounds of Formula XVIII and their methods of manufacture are disclosed in PCT Publication No. WO 99/15504 and U.S. Pat. No. 6,291,477, both of which are incorporated herein by reference in their entireties for all purposes.

The invention is particularly advantageous for the class of drugs which are both acid-sensitive and low-solubility. Exemplary acid-sensitive, low-solubility drugs include (+)-N-{3-[3-(4-fluorophenoxy)phenyl]-2-cyclopenten-1-yl}-N-hydroxyurea; omeprazole; etoposide; famotidine; erythromycin; quinapril; lansoprazole; progabide; as well as CCR1 inhibitors such as quinoxaline-2-carboxylic acid [4(R)-carbamoyl-1(S)-3-fluorobenzyl-2(S),7-dihydroxy-7-methyl-octyl]amide and quinoxaline-2-carboxylic acid [1-benzyl-4-(4,4-difluoro-1-hydroxy-cyclohexyl)-2-hydroxy-4-hydroxycarbamoyl-butyl]-amide.

The invention is useful for improving the intrinsic dissolution rate of compounds selected from the following. The intrinsic dissolution rate is defined as the rate of dissolution of a pure pharmaceutical active ingredient when conditions such as surface area, agitation-stirring speed, pH and ionic-strength of the dissolution medium are kept constant. Intrinsic dissolution rate is further defined as being measured in water at 37° C. using a USP II dissolution apparatus equipped with a Wood's apparatus (Wood, J H; Syarto, J E and Letterman, H: J. Pharm. Sci. 54 (1965), 1068) with a stirring speed of 50 rpm. The intrinsic dissolution rate is defined in terms of mg of drug dissolved per minute from a unit surface area, therefore, the intrinsic dissolution rate is referred to in units of mg/min·cm².

The compositions and methods of the invention are particularly useful for compounds with an intrinsic dissolution rate of preferably less than 0.1 mg/min·cm² and more preferably with less than 0.05 mg/min·cm².

Turning now to the chemical structures of specific CCR1 inhibitors, one class of CCR1 inhibitors that finds utility with the present invention consists of dihydroxyhexanoic acid derivatives having the Formula CCR1-I

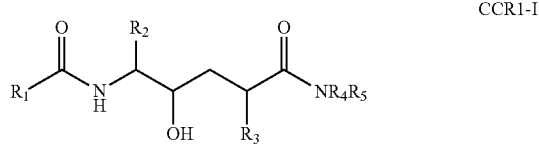

CCR1-I wherein $R_1$ is ($C_2$-$C_9$) heteroaryl optionally substituted with one, two or three substituents independently selected from the group consisting of hydrogen, halo, cyano, ($C_1$-$C_6$)alkyl optionally substituted with one, two or three fluorine atoms, hydroxy, hydroxy-($C_1$-$C_6$)alkyl, ($C_1$-$C_6$)alkoxy, ($C_1$-$C_6$)alkoxy($C_1$-$C_6$)alkyl, HO—(C=O)—, ($C_1$-$C_6$)alkyl-O—(C=O)—, HO—(C=O)—($C_1$-$C_6$)alkyl, ($C_1$-$C_6$)alkyl-O—(C=O)—($C_1$-$C_6$)alkyl, ($C_1$-$C_6$)alkyl-(C=O)—O—, ($C_1$-$C_6$)alkyl-(C=O)—O—($C_1$-$C_6$)alkyl, H(O=C)—, H(O=C)—($C_1$-$C_6$)alkyl, ($C_1$-$C_6$)alkyl(O=C)—, ($C_1$-$C_6$)alkyl(O=C)—($C_1$-$C_6$)alkyl, $NO_2$, amino, ($C_1$-$C_6$)alkylamino, [($C_1$-$C_6$)alkyl]$_2$-amino, amino($C_1$-$C_6$)alkyl, ($C_1$-$C_6$)alkylamino($C_1$-$C_6$)alkyl, [($C_1$-$C_6$)alkyl]$_2$-amino($C_1$-$C_6$)alkyl, $H_2N$—(C=O)—, ($C_1$-$C_6$)alkyl-NH—(C=O)—, [($C_1$-$C_6$)alkyl]$_2N$—(C=O)—, $H_2N$(C=O)—($C_1$-$C_6$)alkyl, ($C_1$-$C_6$)alkyl-HN(C=O)—($C_1$-$C_6$)alkyl, [($C_1$-$C_6$)alkyl]$_2N$—(C=O)—($C_1$-$C_6$)alkyl, H(O=C)—NH—, ($C_1$-$C_6$)alkyl(C=O)—NH, ($C_1$-$C_6$)alkyl(C=O)—[NH]($C_1$-$C_6$)alkyl, ($C_1$-$C_6$)alkyl(C=O)—[N($C_1$-$C_6$)alkyl]($C_1$-$C_6$)alkyl, ($C_1$-$C_6$)alkyl-S—, ($C_1$-$C_6$)alkyl-(S=O)—, ($C_1$-$C_6$)alkyl-$SO_2$—, ($C_1$-$C_6$)alkyl-$SO_2$—NH—, $H_2N$—$SO_2$—, $H_2N$—$SO_2$—($C_1$-$C_6$)alkyl, ($C_1$-$C_6$)alkylHN—$SO_2$—($C_1$-$C_6$)alkyl, [($C_1$-$C_6$)alkyl]$_2N$—$SO_2$—($C_1$-$C_6$)alkyl, $CF_3SO_3$—, ($C_1$-$C_6$)alkyl-$SO_3$—, phenyl, ($C_3$-$C_{10}$)cycloalkyl, ($C_2$-$C_9$)heterocycloalkyl, and ($C_2$-$C_9$)heteroaryl;

wherein $R_2$ is phenyl-($CH_2$)$_m$—, naphthyl-($CH_2$)$_m$—, ($C_3$-$C_{10}$)cycloalkyl-($CH_2$)$_m$—, ($C_1$-$C_6$)alkyl or ($C_2$-$C_9$)heteroaryl-($CH_2$)$_m$—, wherein each of said phenyl, naphthyl, ($C_3$-$C_{10}$)cycloalkyl or ($C_2$-$C_9$)heteroaryl moieties of said phenyl-($CH_2$)$_m$—, naphthyl-($CH_2$)$_m$—, ($C_3$-$C_{10}$)cycloalkyl-($CH_2$)$_m$— or ($C_2$-$C_9$)heteroaryl-($CH_2$)$_m$— groups may optionally be substituted with one, two, or three substituents independently selected from the group consisting of hydrogen, halo, cyano, ($C_1$-$C_6$)alkyl, hydroxy, hydroxy-($C_1$-$C_6$)alkyl, ($C_1$-$C_6$)alkoxy, ($C_1$-$C_6$)alkoxy($C_1$-$C_6$)alkyl, HO—(C=O)—, ($C_1$-$C_6$)alkyl-O—(C=O)—, HO—(C=O)—($C_1$-$C_6$)alkyl, ($C_1$-$C_6$)alkyl-O—(C=O)—($C_1$-$C_6$)alkyl, ($C_1$-$C_6$)alkyl-(C=O)—O—, ($C_1$-$C_6$)alkyl-(C=O)—O—($C_1$-$C_6$)alkyl, H(O=C)—, H(O=C)—($C_1$-$C_6$)alkyl, ($C_1$-$C_6$)alkyl(O=C)—, ($C_1$-$C_6$)alkyl(O=C)—($C_1$-$C_6$)alkyl, $NO_2$, amino, ($C_1$-$C_6$)alkylamino, [($C_1$-$C_6$)alkyl]$_2$-amino, amino($C_1$-$C_6$)alkyl, ($C_1$-$C_6$)alkylamino($C_1$-$C_6$)alkyl, [($C_1$-$C_6$)alkyl]$_2$-amino($C_1$-$C_6$)alkyl, $H_2N$—(C=O)—, ($C_1$-$C_6$)alkyl-NH—(C=O)—, [($C_1$-$C_6$)alkyl]$_2N$—(C=O)—, $H_2N$(C=O)—($C_1$-$C_6$)alkyl, ($C_1$-$C_6$)alkyl-HN(C=O)—($C_1$-$C_6$)alkyl, [($C_1$-$C_6$)alkyl]$_2N$—(C=O)—($C_1$-$C_6$)alkyl, H(O=C)—NH—, ($C_1$-$C_6$)alkyl(C=O)—NH, ($C_1$-$C_6$)alkyl(C=O)—[NH]($C_1$-$C_6$)alkyl, ($C_1$-$C_6$)alkyl(C=O)—[N($C_1$-$C_6$)alkyl]($C_1$-$C_6$)alkyl, ($C_1$-$C_6$)alkyl-S—, ($C_1$-$C_6$)alkyl-(S=O)—, ($C_1$-$C_6$)alkyl-$SO_2$—, ($C_1$-$C_6$)alkyl-$SO_2$—NH—, $H_2N$—$SO_2$—, $H_2N$—$SO_2$—($C_1$-$C_6$)alkyl, ($C_1$-$C_6$)alkylHN—$SO_2$—($C_1$-$C_6$)alkyl, [($C_1$-$C_6$)alkyl]$_2N$—$SO_2$—($C_1$-$C_6$)alkyl, $CF_3SO_3$—, ($C_1$-$C_6$)alkyl-$SO_3$—, phenyl, phenoxy, benzyloxy, ($C_3$-$C_{10}$)cycloalkyl, ($C_2$-$C_9$)heterocycloalkyl, and ($C_2$-$C_9$)heteroaryl;

wherein $R^3$ is hydrogen, ($C_1$-$C_{10}$)alkyl, ($C_3$-$C_{10}$)cycloalkyl-($CH_2$)$_n$—, ($C_2$-$C_9$)heterocycloalkyl-($CH_2$)$_n$—, ($C_2$-$C_9$)heteroaryl-($CH_2$)$_n$— or aryl-($CH_2$)$_n$—; wherein n is an integer from zero to six;

wherein said $R_3$ ($C_1$-$C_{10}$)alkyl group may optionally be substituted with one or more substituents, (preferably from one to three substituents) independently selected from hydrogen, halo, CN, ($C_1$-$C_6$)alkyl, hydroxy, hydroxy-($C_1$-$C_6$)alkyl, ($C_1$-$C_6$)alkoxy, ($C_1$-$C_6$)alkoxy($C_1$-$C_6$)alkyl, HO—(C=O)—, ($C_1$-$C_6$)alkyl-O—(C=O)—, HO—(C=O)—($C_1$-$C_6$)alkyl, ($C_1$-$C_6$)alkyl-O—(C=O)—($C_1$-$C_6$)alkyl, ($C_1$-$C_6$)alkyl-(C=O)—O—, ($C_1$-$C_6$)alkyl-(C=O)—O—

$(C_1-C_6)$alkyl, $H(O=C)-$, $H(O=C)-(C_1-C_6)$alkyl, $(C_1-C_6)$alkyl$(O=C)-$, $(C_1-C_6)$alkyl$(O=C)-(C_1-C_6)$alkyl, $NO_2$, amino, $(C_1-C_6)$alkylamino, $[(C_1-C_6)$alkyl$]_2$-amino, amino$(C_1-C_6)$alkyl, $(C_1-C_6)$alkylamino$(C_1-C_6)$alkyl, $[(C_1-C_6)$alkyl$]_2$-amino$(C_1-C_6)$alkyl, $H_2N-(C=O)-$, $(C_1-C_6)$alkyl-NH$-(C=O)-$, $[(C_1-C_6)$alkyl$]_2N-(C=O)-$, $H_2N(C=O)-(C_1-C_6)$alkyl, $(C_1-C_6)$alkyl-HN$(C=O)-(C_1-C_6)$alkyl, $[(C_1-C_6)$alkyl$]_2N-(C=O)-(C_1-C_6)$alkyl, $H(O=C)-NH-$, $(C_1-C_6)$alkyl$(C=O)-NH$, $(C_1-C_6)$alkyl$(C=O)-[NH](C_1-C_6)$alkyl, $(C_1-C_6)$alkyl$(C=O)-[N(C_1-C_6)$alkyl$](C_1-C_6)$alkyl, $(C_1-C_6)$alkyl-S$-$, $(C_1-C_6)$alkyl-$(S=O)-$, $(C_1-C_6)$alkyl-SO$_2-$, $(C_1-C_6)$alkyl-SO$_2-NH-$, $H_2N-SO_2-$, $H_2N-SO_2-(C_1-C_6)$alkyl, $(C_1-C_6)$alkylHN$-SO_2-(C_1-C_6)$alkyl, $[(C_1-C_6)$alkyl$]_2$N$-SO_2-(C_1-C_6)$alkyl, $CF_3SO_3-$, $(C_1-C_6)$alkyl-SO$_3-$, phenyl, $(C_3-C_{10})$cycloalkyl, $(C_2-C_9)$heterocycloalkyl, and $(C_2-C_9)$heteroaryl; and wherein any of the carbon-carbon single bonds of said $(C_1-C_{10})$alkyl may optionally be replaced by a carbon-carbon double bond;

wherein the $(C_3-C_{10})$cycloalkyl moiety of said $R_3$ $(C_3-C_{10})$cycloalkyl-$(CH_2)_n-$ group may optionally be substituted by one to three substituents independently selected from the group consisting of hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO$-(C=O)-$, $(C_1-C_6)$alkyl-O$-(C=O)-$, HO$-(C=O)-(C_1-C_6)$alkyl, $(C_1-C_6)$alkyl-O$-(C=O)-(C_1-C_6)$alkyl, $(C_1-C_6)$alkyl-$(C=O)-O-$, $(C_1-C_6)$alkyl-$(C=O)-O-(C_1-C_6)$alkyl, $H(O=C)-$, $H(O=C)-(C_1-C_6)$alkyl, $(C_1-C_6)$alkyl$(O=C)-$, $(C_1-C_6)$alkyl$(O=C)-(C_1-C_6)$alkyl, $NO_2$, amino, $(C_1-C_6)$alkylamino, $[(C_1-C_6)$alkyl$]_2$-amino, amino$(C_1-C_6)$alkyl, $(C_1-C_6)$alkylamino$(C_1-C_6)$alkyl, $[(C_1-C_6)$alkyl$]_2$-amino$(C_1-C_6)$alkyl, $H_2N-(C=O)-$, $(C_1-C_6)$alkyl-NH$-(C=O)-$, $[(C_1-C_6)$alkyl$]_2N-(C=O)-$, $H_2N(C=O)-(C_1-C_6)$alkyl, $(C_1-C_6)$alkyl-HN$(C=O)-(C_1-C_6)$alkyl, $[(C_1-C_6)$alkyl$]_2N-(C=O)-(C_1-C_6)$alkyl, $H(O=C)-NH-$, $(C_1-C_6)$alkyl$(C=O)-NH$, $(C_1-C_6)$alkyl$(C=O)-[NH](C_1-C_6)$alkyl, $(C_1-C_6)$alkyl$(C=O)-[N(C_1-C_6)$alkyl$](C_1-C_6)$alkyl, $(C_1-C_6)$alkyl-S$-$, $(C_1-C_6)$alkyl-$(S=O)-$, $(C_1-C_6)$alkyl-SO$_2-$, $(C_1-C_6)$alkyl-SO$_2-NH-$, $H_2N-SO_2-$, $H_2N-SO_2-(C_1-C_6)$alkyl, $(C_1-C_6)$alkyl HN$-SO_2-(C_1-C_6)$alkyl, $[(C_1-C_6)$alkyl$]_2N-SO_2-(C_1-C_6)$alkyl, $CF_3SO_3-$, $(C_1-C_6)$alkyl-SO$_3-$, phenyl, $(C_3-C_{10})$cycloalkyl, $(C_2-C_9)$heterocycloalkyl, and $(C_2-C_9)$heteroaryl;

wherein the $(C_2-C_9)$heterocycloalkyl moiety of said $R_3$ $(C_2-C_9)$heterocycloalkyl-$(CH_2)_n-$ group may contain from one to three heteroatoms independently selected from nitrogen, sulfur, oxygen, $>S(=O)$, $>SO_2$ or $>NR^6$, wherein said $(C_2-C_9)$heterocycloalkyl moiety of said $(C_2-C_9)$heterocycloalkyl-$(CH_2)_n-$ group may optionally be substituted on any of the ring carbon atoms capable of forming an additional bond (preferably one to three substituents per ring) with a substituent independently selected from the group consisting of hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO$-(C=O)-$, $(C_1-C_6)$alkyl-O$-(C=O)-$, HO$-(C=O)-(C_1-C_6)$alkyl, $(C_1-C_6)$alkyl-O$-(C=O)-(C_1-C_6)$alkyl, $(C_1-C_6)$alkyl-$(C=O)-O-$, $(C_1-C_6)$alkyl-$(C=O)-O-(C_1-C_6)$alkyl, $H(O=C)-$, $H(O=C)-(C_1-C_6)$alkyl, $(C_1-C_6)$alkyl$(O=C)-$, $(C_1-C_6)$alkyl$(O=C)-(C_1-C_6)$alkyl, $NO_2$, amino, $(C_1-C_6)$alkylamino, $[(C_1-C_6)$alkyl$]_2$-amino, amino$(C_1-C_6)$alkyl, $(C_1-C_6)$alkylamino$(C_1-C_6)$alkyl, $[(C_1-C_6)$alkyl$]_2$-amino$(C_1-C_6)$alkyl, $H_2N-(C=O)-$, $(C_1-C_6)$alkyl-NH$-(C=O)-$, $[(C_1-C_6)$alkyl$]_2N-(C=O)-$, $H_2N(C=O)-(C_1-C_6)$alkyl, $(C_1-C_6)$alkyl-HN$(C=O)-(C_1-C_6)$alkyl, $[(C_1-C_6)$alkyl$]_2N-(C=O)-(C_1-C_6)$alkyl, $H(O=C)-NH-$, $(C_1-C_6)$alkyl$(C=O)-NH$, $(C_1-C_6)$alkyl$(C=O)-[NH](C_1-C_6)$alkyl, $(C_1-C_6)$alkyl$(C=O)-[N(C_1-C_6)$alkyl$](C_1-C_6)$alkyl, $(C_1-C_6)$alkyl-S$-$, $(C_1-C_6)$alkyl-$(S=O)-$, $(C_1-C_6)$alkyl-SO$_2-$, $(C_1-C_6)$alkyl-SO$_2-NH-$, $H_2N-SO_2-$, $H_2N-SO_2-(C_1-C_6)$alkyl, $(C_1-C_6)$alkylHN$-SO_2-(C_1-C_6)$alkyl, $[(C_1-C_6)$alkyl$]_2N-SO_2-(C_1-C_6)$alkyl, $CF_3SO_3-$, $(C_1-C_6)$alkyl-SO$_3-$, phenyl, $(C_3-C_{10})$cycloalkyl, $(C_2-C_9)$heterocycloalkyl, and $(C_2-C_9)$heteroaryl;

wherein the $(C_2-C_9)$heteroaryl moiety of said $R^3$ $(C_2-C_9)$heteroaryl-$(CH_2)_n-$ group may contain from one to three heteroatoms independently selected from nitrogen, sulfur or oxygen, wherein said $(C_2-C_9)$heteroaryl moiety of said $(C_2-C_9)$heteroaryl-$(CH_2)_n-$ group may optionally be substituted on any of the ring carbon atoms capable of forming an additional bond (preferably one to three substitutents per ring) with a substituent selected from the group consisting of hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO$-(C=O)-$, $(C_1-C_6)$alkyl-O$-(C=O)-$, HO$-(C=O)-(C_1-C_6)$alkyl, $(C_1-C_6)$alkyl-O$-(C=O)-(C_1-C_6)$alkyl, $(C_1-C_6)$alkyl-$(C=O)-O-$, $(C_1-C_6)$alkyl-$(C=O)-O-(C_1-C_6)$alkyl, $H(O=C)-$, $H(O=C)-(C_1-C_6)$alkyl, $(C_1-C_6)$alkyl$(O=C)-$, $(C_1-C_6)$alkyl$(O=C)-(C_1-C_6)$alkyl, $NO_2$, amino, $(C_1-C_6)$alkylamino, $[(C_1-C_6)$alkyl$]_2$-amino, amino$(C_1-C_6)$alkyl, $(C_1-C_6)$alkylamino$(C_1-C_6)$alkyl, $[(C_1-C_6)$alkyl$]_2$-amino$(C_1-C_6)$alkyl, $H_2N-(C=O)-$, $(C_1-C_6)$alkyl-NH$-(C=O)-$, $[(C_1-C_6)$alkyl$]_2N-(C=O)-$, $H_2N(C=O)-(C_1-C_6)$alkyl, $(C_1-C_6)$alkyl-HN$(C=O)-(C_1-C_6)$alkyl, $[(C_1-C_6)$alkyl$]_2N-(C=O)-(C_1-C_6)$alkyl, $H(O=C)-NH-$, $(C_1-C_6)$alkyl$(C=O)-NH$, $(C_1-C_6)$alkyl$(C=O)-[NH](C_1-C_6)$alkyl, $(C_1-C_6)$alkyl$(C=O)-[N(C_1-C_6)$alkyl$](C_1-C_6)$alkyl, $(C_1-C_6)$alkyl-S$-$, $(C_1-C_6)$alkyl-$(S=O)-$, $(C_1-C_6)$alkyl-SO$_2-$, $(C_1-C_6)$alkyl-SO$_2-NH-$, $H_2N-SO_2-$, $H_2N-SO_2-(C_1-C_6)$alkyl, $(C_1-C_6)$alkylHN$-SO_2-(C_1-C_6)$alkyl, $[(C_1-C_6)$alkyl$]_2N-SO_2-(C_1-C_6)$alkyl, $CF_3SO_3-$, $(C_1-C_6)$alkyl-SO$_3-$, phenyl, $(C_3-C_{10})$cycloalkyl, $(C_2-C_9)$heterocycloalkyl, and $(C_2-C_9)$heteroaryl; and wherein said aryl moiety of said $R_3$ aryl-$(CH_2)_n-$ group is optionally substituted phenyl or naphthyl, wherein said phenyl and naphthyl may optionally be substituted with from one to three substituents independently selected from the group consisting of hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO$-(C=O)-$, $(C_1-C_6)$alkyl-O$-(C=O)-$, HO$-(C=O)-(C_1-C_6)$alkyl, $(C_1-C_6)$alkyl-O$-(C=O)-(C_1-C_6)$alkyl, $(C_1-C_6)$alkyl-$(C=O)-O-$, $(C_1-C_6)$alkyl-$(C=O)-O-(C_1-C_6)$alkyl, $H(O=C)-$, $H(O=C)-(C_1-C_6)$alkyl, $(C_1-C_6)$alkyl$(O=C)-$, $(C_1-C_6)$alkyl$(O=C)-(C_1-C_6)$alkyl, $NO_2$, amino, $(C_1-C_6)$alkylamino, $[(C_1-C_6)$alkyl$]_2$-amino, amino$(C_1-C_6)$alkyl, $(C_1-C_6)$alkylamino$(C_1-C_6)$alkyl, $[(C_1-C_6)$alkyl$]_2$-amino$(C_1-C_6)$alkyl, $H_2N-(C=O)-$, $(C_1-C_6)$alkyl-NH$-(C=O)-$, $[(C_1-C_6)$alkyl$]_2N-(C=O)-$, $H_2N(C=O)-(C_1-C_6)$alkyl, $(C_1-C_6)$alkyl-HN$(C=O)-(C_1-C_6)$alkyl, $[(C_1-C_6)$alkyl$]_2N-(C=O)-(C_1-C_6)$alkyl, $H(O=C)-NH-$, $(C_1-C_6)$alkyl$(C=O)-NH$, $(C_1-C_6)$alkyl$(C=O)-[NH](C_1-C_6)$alkyl, $(C_1-C_6)$alkyl$(C=O)-[N(C_1-C_6)$alkyl$](C_1-C_6)$alkyl, $(C_1-C_6)$alkyl-S$-$, $(C_1-C_6)$alkyl-$(S=O)-$, $(C_1-C_6)$alkyl-SO$_2-$, $(C_1-C_6)$alkyl-SO$_2-NH-$, $H_2N-SO_2-$, $H_2N-SO_2-(C_1-C_6)$alkyl, $(C_1-C_6)$alkyl HN$-SO_2-(C_1-C_6)$alkyl, $[(C_1-C_6)$alkyl$]_2N-SO_2-(C_1-C_6)$alkyl, $CF_3SO_3-$, $(C_1-C_6)$alkyl-SO$_3-$, phenyl, $(C_3-C_{10})$cycloalkyl, $(C_2-C_9)$heterocycloalkyl, and $(C_2-C_9)$heteroaryl;

or $R_3$ and the carbon to which it is attached form a five to seven membered carbocyclic ring, wherein any of the carbon atoms of said five membered carbocyclic ring may optionally be substituted with a substituent selected from the group consisting of hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, NO$_2$, amino, $(C_1-C_6)$alkylamino, [$(C_1-C_6)$alkyl]$_2$-amino, amino$(C_1-C_6)$alkyl, $(C_1-C_6)$alkylamino$(C_1-C_6)$alkyl, [$(C_1-C_6)$alkyl]$_2$-amino$(C_1-C_6)$alkyl, H$_2$N—(C=O)—, $(C_1-C_6)$alkyl-NH—(C=O)—, [$(C_1-C_6)$alkyl]$_2$N—(C=O)—, H$_2$N(C=O)—$(C_1-C_6)$alkyl, $(C_1-C_6)$alkyl-HN(C=O)—$(C_1-C_6)$alkyl, [$(C_1-C_6)$alkyl]$_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, H$_2$N—SO$_2$—, H$_2$N—SO$_2$—$(C_1-C_6)$alkyl, $(C_1-C_6)$alkylHN—SO$_2$—$(C_1-C_6)$alkyl, [$(C_1-C_6)$alkyl]$_2$N—SO$_2$—$(C_1-C_6)$alkyl, CF$_3$SO$_3$—, $(C_1-C_6)$alkyl-SO$_3$—, phenyl, $(C_3-C_{10})$cycloalkyl, $(C_2-C_9)$heterocycloalkyl, and $(C_2-C_9)$heteroaryl; wherein one of the carbon-carbon bonds of said five to seven membered carbocyclic ring may optionally be fused to an optionally substituted phenyl ring, wherein said substituents may be independently selected from hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, NO$_2$, amino, $(C_1-C_6)$alkylamino, [$(C_1-C_6)$alkyl]$_2$-amino, amino$(C_1-C_6)$alkyl, $(C_1-C_6)$alkylamino$(C_1-C_6)$alkyl, [$(C_1-C_6)$alkyl]$_2$-amino$(C_1-C_6)$alkyl, H$_2$N—(C=O)—, $(C_1-C_6)$alkyl-NH—(C=O)—, [$(C_1-C_6)$alkyl]$_2$N—(C=O)—, H$_2$N(C=O)—$(C_1-C_6)$alkyl, $(C_1-C_6)$alkyl-HN(C=O)—$(C_1-C_6)$alkyl, [$(C_1-C_6)$alkyl]$_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, H$_2$N—SO$_2$—, H$_2$N—SO$_2$—$(C_1-C_6)$alkyl, $(C_1-C_6)$alkylHN—SO$_2$—$(C_1-C_6)$alkyl, [$(C_1-C_6)$alkyl]$_2$N—SO$_2$—$(C_1-C_6)$alkyl, CF$_3$SO$_3$—, $(C_1-C_6)$alkyl-SO$_3$—, phenyl, $(C_3-C_{10})$cycloalkyl, $(C_2-C_9)$heterocycloalkyl, and $(C_2-C_9)$heteroaryl;

wherein R$_4$ is hydrogen, $(C_1-C_6)$alkyl, hydroxy, $(C_1-C_6)$alkoxy, hydroxy$(C_1-C_6)$alkyl, $(C_1-C_6)$alkoxy(C=O)—, $(C_3-C_{10})$cycloalkyl-$(CH_2)_q$—, $(C_2-C_9)$heterocycloalkyl-$(CH_2)_q$—, $(C_2-C_9)$heteroaryl-$(CH_2)_q$—, phenyl-$(CH_2)_q$—, or naphthyl-$(CH_2)_q$—; wherein said $(C_2-C_9)$heterocycloalkyl, $(C_2-C_9)$heteroaryl, phenyl and naphthyl groups may be optionally substituted with one or two substituents from the group consisting of hydrogen, halo, cyano, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, NO$_2$, amino, $(C_1-C_6)$alkylamino, [$(C_1-C_6)$alkyl]$_2$ amino, amino$(C_1-C_6)$alkyl, $(C_1-C_6)$alkylamino $(C_1-C_6)$alkyl, [$(C_1-C_6)$alkyl]$_2$-amino$(C_1-C_6)$alkyl, H$_2$N—(C=O)—, $(C_1-C_6)$alkyl-NH—(C=O)—, [$(C_1-C_6)$alkyl]$_2$N—(C=O)—, H$_2$N(C=O)—$(C_1-C_6)$alkyl, $(C_1-C_6)$alkyl-HN(C=O)—$(C_1-C_6)$alkyl, [$(C_1-C_6)$alkyl]$_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, H$_2$N—SO$_2$—, H$_2$N—SO$_2$—$(C_1-C_6)$alkyl, $(C_1-C_6)$alkylHN—SO$_2$—$(C_1-C_6)$alkyl, [$(C_1-C_6)$alkyl]$_2$N—SO$_2$—$(C_1-C_6)$alkyl, CF$_3$SO$_3$—, $(C_1-C_6)$alkyl-SO$_3$—, phenyl, $(C_3-C_{10})$cycloalkyl, $(C_2-C_9)$heterocycloalkyl, and $(C_2-C_9)$heteroaryl;

wherein R$_5$ is hydrogen, $(C_1-C_6)$alkyl or amino; or

R$_4$ and R$_5$ together with the nitrogen atom to which they are attached form a $(C_2-C_9)$heterocycloalkyl group optionally substituted with one or two substituents selected from the group consisting of hydrogen, halo, cyano, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, NO$_2$, amino, $(C_1-C_6)$alkylamino, [$(C_1-C_6)$alkyl]$_2$ amino, amino$(C_1-C_6)$alkyl, $(C_1-C_6)$alkylamino $(C_1-C_6)$alkyl, [$(C_1-C_6)$alkyl]$_2$-amino$(C_1-C_6)$alkyl, H$_2$N—(C=O)—, $(C_1-C_6)$alkyl-NH—(C=O)—, [$(C_1-C_6)$alkyl]$_2$N—(C=O)—, H$_2$N(C=O)—$(C_1-C_6)$alkyl, $(C_1-C_6)$alkyl-HN(C=O)—$(C_1-C_6)$alkyl, [$(C_1-C_6)$alkyl]$_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, H$_2$N—SO$_2$—, H$_2$N—SO$_2$—$(C_1-C_6)$alkyl, $(C_1-C_6)$alkyl-HN—SO$_2$—$(C_1-C_6)$alkyl, [$(C_1-C_6)$alkyl]$_2$N—SO$_2$—$(C_1-C_6)$alkyl, CF$_3$SO$_3$—, $(C_1-C_6)$alkyl-SO$_3$—, phenyl, $(C_3-C_{10})$cycloalkyl, $(C_2-C_9)$heterocycloalkyl, and $(C_2-C_9)$heteroaryl;

wherein R$^6$ is hydrogen, $(C_1-C_6)$alkyl, $(C_1-C_6)$alkoxy-$(CH_2)_g$—, $(C_1-C_6)$alkoxy(C=O)—$(CH_2)_g$—, $(C_1-C_6)$alkyl-$(SO_2)$—$(CH_2)_g$—, $(C_6-C_{10})$aryloxy-$(CH_2)_g$—, $(C_6-C_{10})$aryloxy(C=O)—$(CH_2)_g$—, or $(C_6-C_{10})$aryl-$(SO_2)$—$(CH_2)_g$—;

wherein g is an integer from zero to four;

wherein m is an integer from zero to four;

wherein n is an integer from zero to six;

with the proviso that when one of R$^4$ or R$^5$ is hydrogen, and the other of R$^4$ or R$^5$ is $(C_1-C_6)$alkyl; R$^2$ is $(C_3-C_{10})$cycloalkyl or isopropyl and R$^3$ is $(C_3-C_5)$alkyl, phenyl, methylvinyl, dimethylvinyl, halovinyl, hydroxy$(C_1-C_3)$alkyl or amino$(C_1-C_4)$alkyl then R$^1$ must be other than indol-5-yl, 6-azaindol-2-yl, 2,3-dichloro-pyrrol-5-yl, 4-hydroxyquinolin-3-yl, 2-hydroxyquinoxalin-3-yl, 6-azaindolin-3-yl, or optionally substituted indol-2 or 3-yl;

and the pharmaceutically acceptable salts of such compounds.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, cyclohexyl or cycloheptyl) or be linear or branched and contain cyclic moieties. Such alkyl and alkoxy groups may be substituted with one, two or three halogen and/or hydroxy atoms, preferably fluorine atoms.

Unless otherwise indicated, "halogen" includes fluorine, chlorine, bromine, and iodine.

"$(C_3-C_{10})$cycloalkyl" when used herein refers to cycloalkyl groups containing zero to two levels of unsaturation such as cyclopropyl, cyclobutyl, cyclopentyl, cyclopentenyl, cyclohexyl, cyclohexenyl, 1,3-cyclohexadiene, cycloheptyl, cycloheptenyl, bicyclo[3.2.1]octane, norbornanyl, and the like.

"($C_2$-$C_9$)heterocycloalkyl" when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, and the like. One of ordinary skill in the art will understand that the connection of said ($C_2$-$C_9$)heterocycloalkyl rings is through a carbon or a $sp^3$ hybridized nitrogen heteroatom.

"($C_2$-$C_9$)heteroaryl" when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl, and the like. One of ordinary skill in the art will understand that the connection of said ($C_2$-$C_9$) heterocycloalkyl rings is through a carbon atom or a $sp^3$ hybridized nitrogen heteroatom.

"Aryl" when used herein refers to phenyl or naphthyl.

"Protected amine" and "protected amino" refers to an amine group with one of the hydrogen atoms replaced with a protecting group (P). Any suitable protecting group may be used for amine protection. Suitable protecting groups include carbobenzyloxy, t-butoxy carbonyl (BOC) or 9-fluorenyl-methylenoxy carbonyl.

Compounds of Formula CCR1-I and their methods of manufacture are disclosed in commonly assigned U.S. patent application Ser. No. 09/380,269, filed Feb. 5, 1998, U.S. patent application Ser. No. 09/403,218, filed Jan. 18, 1999, PCT Publication No. WO98/38167, and PCT Publication No. WO99/40061, all of which are incorporated herein by reference in their entireties for all purposes.

In a preferred embodiment, the CCR1 inhibitor is selected from one of the following compounds of Formula CCR1-I:

quinoxaline-2-carboxylic acid 4(R)-carbamoyl-1(S)-(3-chloro-benzyl)-2(S),7-dihydroxy-7-methyl-octyl]-amide;
7,8-difluoro-quinoline-3-carboxylic acid (1S)-benzyl-4(R)-carbamoyl-2(S),7-dihydroxy-7-methyl-octyl)-amide;
6,7,8-trifluoro-quinoline-3-carboxylic acid (1(S)-benzyl-4(R)-carbamoyl-2(S),7-dihydroxy-7-methyl-octyl)-amide;
quinoxaline-2-carboxylic acid [4(R)-carbamoyl-1(S)-(3-fluoro-benzyl)-2(S),7-dihydroxy-7-methyl-octyl]-amide;
quinoxaline-2-carboxylic acid (1(S)-benzyl-2(S),7-dihydroxy-4(R)-hydroxycarbamoyl-7-methyl-octyl)-amide;
quinoxaline-2-carboxylic acid [4(R)-carbamoyl-1(S)-(2-chloro-benzyl)-2(S),7-dihydroxy-7-methyl-octyl]-amide;
quinoxaline-2-carboxylic acid [1(S)-(2-fluoro-benzyl)-2(S),7-dihydroxy-4(R)-hydroxycarbamoyl-7-methyl-octyl]-amide;
quinoxaline-2-carboxylic acid [4(R)-carbamoyl-1(S)-(2-fluoro-benzyl)-2(S),7-dihydroxy-7-methyl-octyl]-amide;
quinoxaline-2-carboxylic acid [1(S)-(3,4-difluoro-benzyl)-2(S),7-dihydroxy-4(R)-hydroxycarbamoyl-7-methyl-octyl]-amide;
quinoxaline-2-carboxylic acid [4(R)-carbamoyl-1(S)-(3,4-difluoro-benzyl)-2(S),7-dihydroxy-7-methyl-octyl]-amide;
quinoxaline-2-carboxylic acid (4(R)-carbamoyl-2(S),7-dihydroxy-7-methyl-1(S)-naphthalen-1-ylmethyl-octyl)-amide;
7,8-difluoro-quinoline-3-carboxylic acid 1(S)-benzyl-2(S)-hydroxy-7-methyl-4(R)-methylcarbamoyl-octyl)-amide;
8-fluoro-quinoline-3-carboxylic acid 1(S)-benzyl-2(S)-hydroxy-7-methyl-4(R)-methylcarbamoyl-octyl)-amide;
quinoxaline-2-carboxylic acid [4(R)-carbamoyl-7-fluoro-1-(3(S)-fluoro-benzyl)-2(S)-hydroxy-7-methyl-octyl]-amide;
quinoxaline-2-carboxylic acid [4(R)-carbamoyl-1-(2(S)-fluoro-benzyl)-2(S)-hydroxy-7-methyl-octyl]-amide;
quinoxaline-2-carboxylic acid [1(S)-benzyl-4(S)-carbamoyl-4(S)-(2,6-dimethyl-tetrahydro-pyran-4-yl)-2(S)-hydroxy-butyl]-amide;
quinoxaline-2-carboxylic acid 1(S)-benzyl-4(R)-carbamoyl-7-fluoro-2(S)-hydroxy-7-methyl-octyl)-amide;
quinoxaline-2-carboxylic acid 1(S)-benzyl-5-cyclohexyl-2(S)-hydroxy-4(R)-methylcarbamoyl-pentyl)-amide;
quinoxaline-2-carboxylic acid 1(S)-cyclohexylmethyl-2(S)-hydroxy-7-methyl-4(R)-methylcarbamoyl-octyl)-amide;
quinoxaline-2-carboxylic acid [1(S)-benzyl-2(S)-hydroxy-4(S)-hydroxycarbamoyl-4-(1-hydroxy-4-methyl-cyclohexyl)-butyl]-amide;
quinoxaline-2-carboxylic acid [1(S)-benzyl-4(S)-(4,4-difluoro-1-hydroxy-cyclohexyl)-2(S)-hydroxy-4-hydroxycarbamoyl-butyl]-amide;
quinoxaline-2-carboxylic acid [1(S)-benzyl-4(S)-carbamoyl-4(S)-(4,4-difluoro-cyclohexyl)-2(S)-hydroxy-butyl]-amide;
quinoline-3-carboxylic acid (1(S)-benzyl-4(S)-carbamoyl-4-cyclohexyl-2(S)-hydroxy-butyl)-amide;
quinoxaline-2-carboxylic acid (4(R)-carbamoyl-2(S)-hydroxy-7-methyl-1(S)-thiophen-2-ylmethyl-octyl)-amide;
quinoxaline-2-carboxylic acid 1(S)-benzyl-4(R)-carbamoyl-7-chloro-2(S)-hydroxy-oct-6-enyl)-amide;
quinoxaline-2-carboxylic acid 1(S)-benzyl-4(R)-carbamoyl-2(S)-hydroxy-5-phenyl-pentyl)-amide;
N-1(S)-benzyl-4(R)-carbamoyl-7-fluoro-2(S)-hydroxy-7-methyl-octyl)-5,6-dichloro-nicotinamide;
quinoxaline-2-carboxylic acid (4(R)-carbamoyl-2(S)-hydroxy-7-methyl-1(S)-thiazol-4(R)-ylmethyl-octyl)-amide;
benzothiazole-2-carboxylic acid 1(S)-benzyl-4(R)-carbamoyl-7-fluoro-2(S)-hydroxy-7-methyl-octyl)-amide; and
benzofuran-2-carboxylic acid 1(S)-benzyl-4(R)-carbamoyl-7-fluoro-2(S)-hydroxy-7-methyl-octyl)-amide.

In another preferred embodiment, the CCR1 compound has a formula Ia-1:

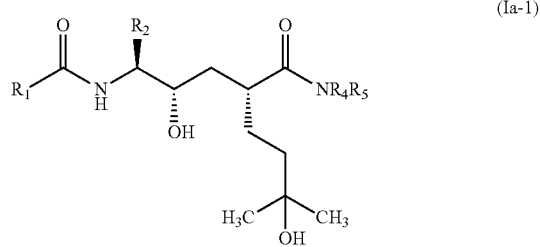

(Ia-1)

wherein the substituents are as defined above.

In a preferred method of making the compound Ia-1, the reaction is started with Scheme 1. In the herein described processes, the substituents are as defined for CCR1-I, and the following:

$R_7$ is hydroxy, $(C_1-C_6)$alkyl, or phenyl wherein the phenyl group unsubstituted or substituted with one, two, or three $(C_1-C_6)$alkyl, hydroxy, or halogen groups;

$R_8$ is hydroxy or halogen;

$R_9$ is phenyl, naphthyl, $(C_3-C_{10})$cycloalkyl, $(C_1-C_6)$alkyl or $(C_2-C_9)$heteroaryl, wherein each of said phenyl, naphthyl, $(C_3-C_{10})$cycloalkyl or $(C_2-C_9)$heteroaryl groups may be unsubstituted or substituted with one, two, or three substituents independently selected from the group consisting of halogen, cyano, and $(C_1-C_6)$alkyl;

P is a protecting group;

X is hydroxy or halogen; and q is 0, 1, 2, 3, or 4.

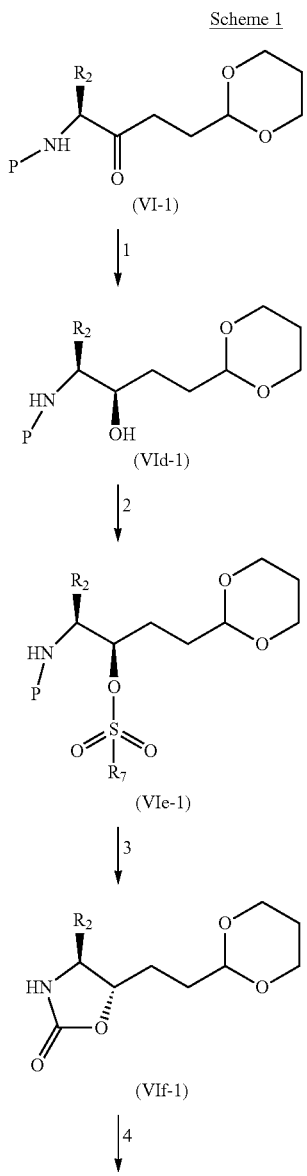

Scheme 1

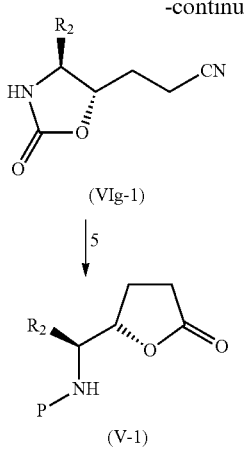

In scheme 1 step 1, a compound of the formula (VI-1) is reduced with a reducing agent under heat to form a compound of the formula (VId-1). In one embodiment, the reducing agent is aluminum triisopropoxide and isopropanol. Preferably, the temperature is maintained above room temperature, more preferably between about 60° C. and about 82° C. The product alcohol can be isolated by either cooling the reaction mixture to room temperature, diluting with more isopropanol and collecting the crystalline material or by cooling the reaction to room temperature and adding 1N HCL and water and collecting the crystalline material.

Step 2 of scheme 1 includes reacting a compound of the formula $R_7$—$SO_2$—X and a compound of the formula (VId-1) in the presence of a base to form the compound of the formula (VIe-1). Any amine base is suitable, including pyridine, triethylamine, N-methylmayholine, and diisoyropylethylamine. In one embodiment, $R_7$—$SO_2$—$R_8$ is p-toluenesulfonic acid, methanesulfonic acid, sulfuric acid, or methanesulfonyl chloride. In another embodiment, the conversion of hydroxy dioxane (VId-1) to dioxane oxazolidinone (VIe-1) can be achieved by treatment of the hydroxy dioxane (VId-1) with methanesulfonyl chloride and triethylamine in tetrahydrofuran solution and heating the mixture to cause the cyclization of the mesylate formed in situ to the oxazolidinone.

In step 3 of scheme 1, a compound of the formula (VIf-1) may be formed by heating the compound of the formula (VIe-1). The reaction may proceed by dissolving compound VIe-1 in a solvent such as pyridine or N-methyl imidazole and heating the mixture for several hours at temperature from about 50° C. to about 100° C.; preferably at about 80° C. The mesylate (VIf-1) may be recovered by extraction into an organic solvent such as ethyl acetate and removal of the amine solvents by extraction of the solution with aqueous acid.

Step 4 of scheme 1 depicts reacting hydroxylamine hydrochloride, a compound of the formula $R_7$—$SO_2$—X, and a compound of the formula (VIf-1) to form a compound of the formula (VIg-1). In one embodiment, $R_7$—$SO_2$—X is p-toluenesulfonic acid, methanesulfonic acid, sulfuric acid, or methanesulfonyl chloride. The reaction may occur in a solvent, such as methanol. In one embodiment, the reaction occurs in methanol with tosic acid at reflux for 8 to 24 hours. The resulting nitrile oxazolidinone contains a small amount of the corresponding ethyl ester which is not removed since it also is converted to the desired lactone in subsequent steps.

Step 5 of scheme 1 includes a) hydrolyzing a compound of the formula (VIg-1) with an aqueous solution in the presence of a base, b) protecting the amine group of the compound so formed, and c) cyclizing the compound so formed with heat and an acid catalyst. In one embodiment, the compound VIg-1 is hydrolyzed with sodium hydroxide. The pH is adjusted to approximately 10 and tetrahydrofuran and BOC dicarbonate are added. This provides the protected hydroxy acid, which may be heated in 10% acetic acid and toluene to provide the protected amine lactone (V-1).

The compound of formula (V-1) may also be produced according to scheme 2.

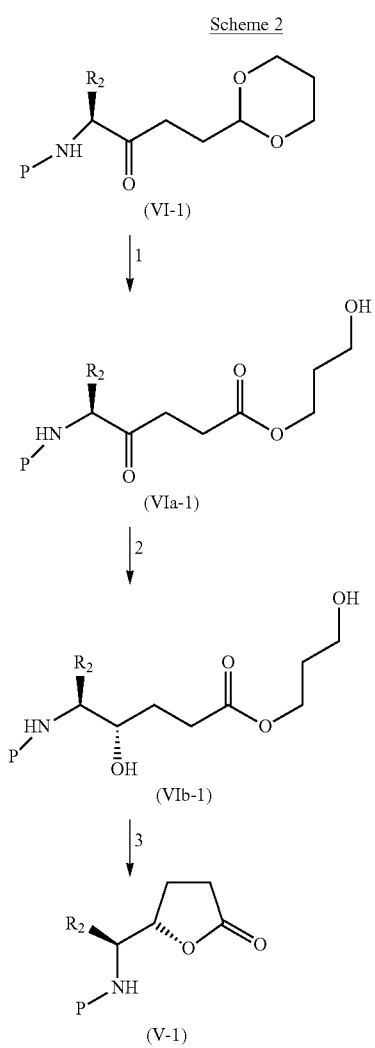

In step 1 of scheme 2, a compound of the formula (VI-1) may be reacted with ozone to for a compound of the formula (VIa-1). The compound VI-1 may be present in a solvent, such as ethyl acetate, and the ozone introduced through sparging at a temperature below room temperature, preferably at about −15° C., until the starting dioxane ketone is substantially reacted. Any excess ozone may be removed by bubbling nitrogen through the solution. The resulting crude ketone ester mixture may be isolated after treatment with aqueous sodium bisulfite to remove any hydroperoxides.

Alternatively, in step 1 of scheme 2, the compound of the formula (VIa-1) may be formed by reacting hypochlorous acid and a compound of the formula (VI-1). Such an oxidation reaction typically produces chlorinated forms of the compound VIa-1 as side products in addition to the compound VIa-1. This oxidation reaction proceeds by mixing the compound VI-1 in solvent, such as acetic acid and/or acetone, and adding sodium hypochlorite, while keeping the mixture at a low temperature, preferably at or below about 0° C.

As a means to convert the side product chlorinated forms of the compound VIa-1 to compounds of the formula V-1, the compounds formed from the hypochlorous acid oxidation reaction may optionally be hydrogenated by reaction with hydrogen in the presence of a catalyst. The hydrogenation may include introducing the products from the hypochlorous acid oxidation reaction into a solvent system of tetrahydrofuran and water, followed by addition of a Pd/C catalyst. The resulting mixture is subjected to hydrogen above atmospheric pressure and temperature. In one embodiment, the pressure is about 80 pounds per square inch and the temperature is maintained from about 60° C. to about 70° C. until the reaction is substantially complete.

In step 2 of scheme 2, the compound of the formula (VIb-1) may be formed by reacting a silyating agent and a compound of the formula (VIa-1) and reacting the compound so formed with a reducing agent. In one embodiment, the reducing agent is N-selectride. In another embodiment, the silyating agent is 1,1,1,3,3,3-hexamethyl-disilazane. The reduction reaction may occur at temperatures below about 0° C., preferably below about −20° C., more preferably below about −50° C. In addition, the reducing agent may be present in slight excess.

In step 3 of scheme 2, the compound of the formula (V-1) is formed by heating a compound of the formula (VIb-1) in the presence of an acid catalyst, such as acetic acid. In one embodiment, the cyclization reaction occurs by introducing the compound VIb-1 into a solvent mixture, such as toluene and 10% acetic acid, at the solvent reflux temperature for 8 to 16 hours. This provides the desired lactone as a crystalline solid after work up.

One method of making the compound of the formula (VI-1) is by reacting a compound of the formula (VII-1)

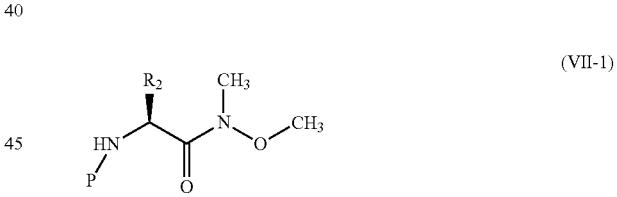

with a Grinard reagent formed in situ by addition of 2-(2-bromo-ethyl)-[1,3]dioxane to a mixture comprising magnesium and the compound of the formula (VII-1). In one embodiment, the mixture further comprises methyl magnesium chloride and/or methyl magnesium bromide in a solvent. Any exotherm formed from the reaction may be controlled by the rate of addition of the bromide.

The compound of the formula (VII-1) may be formed by coupling N,O-dimethylhydroxylamine hydrochloride and a compound of the formula (VIII-1)

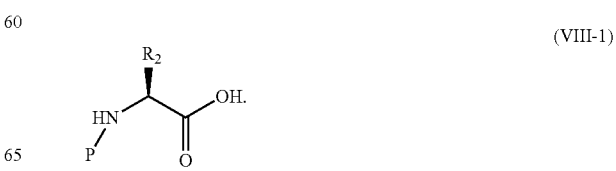

This coupling reaction may be performed by mixed anhydride procedure. In one mixed anhydride procedure, compound VIII-1 is combined with methylene chloride and N-methylmorpholine is added followed by isobutyl chloroformate. In a separate mixture, a slurry of N,O-dimethylhydroxylamine hydrochloride is treated with N-methylmorpholine. The two reaction mixtures are combined and then quenched with a solution of citric acid in water. This procedure preferably operates at a temperature below about 20° C., more preferably below about 0° C.

Compounds of formula (V-1) may be used to produce compounds of the formula (IVa1-1) according to scheme 3:

Scheme 3

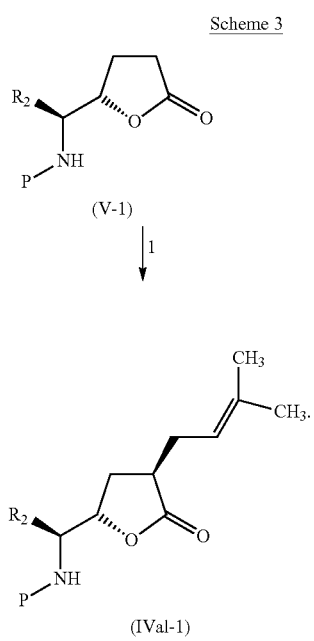

(V-1)

↓ 1

(IVa1-1)

In step 1 of scheme 3, the compound of the formula (IVa1-1) may be formed by reacting 4-halo-2-methyl-2-butene and a compound of the formula (V-1) in the presence of a base. Exemplary bases include lithium-dialkyl amides such as lithium N-isopropyl-N-cyclohexylamide, lithium bis(trimethylsilyl)amide, lithium di-isopropylamide, and potassium hydride. Suitable solvents include aprotic polar solvents such as ethers (such as tetrahydrofuran, glyme or dioxane), benzene, or toluene, preferably tetrahydrofuran. The aforesaid reaction is conducted at a temperature from about −78° C. to about 0° C., preferably at about −78° C. In one embodiment, alkylation of the lactone (V-1) is accomplished by reacting the lactone (V-1) with lithium bis(trimethylsilyl)amide and dimethylallyl bromide in tetrahydrofuran at a temperature from about −78° C. to about −50° C. Reaction times range from several hours or if an additive such as dimethyl imidazolidinone is present, the reaction may be complete in minutes.

Compounds of formula (IVa1-1) may be used to produce compounds of the formula (Ia-1) according to scheme 4:

Scheme 4

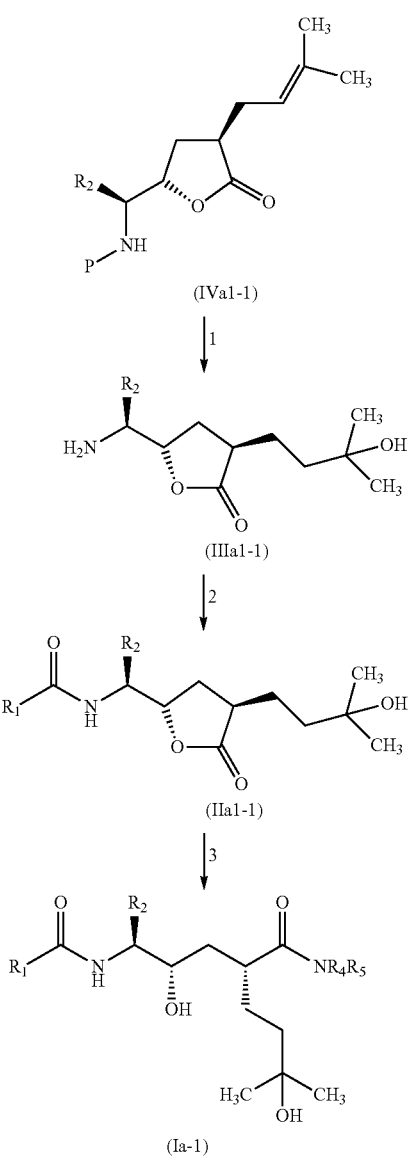

(IVa1-1)

↓ 1

(IIIa1-1)

↓ 2

(IIa1-1)

↓ 3

(Ia-1)

In step 1 of scheme 4, a compound of the formula (IIIa1-1) is formed by reacting a compound of the formula (IVa1-1) with phosphoric acid. Preferably, this reaction occurs in any suitable solvent, such as non-alcoholic solvents. Two preferred solvents include tetrahydrofuran and dichloroethane. The reaction may take place at any suitable temperature, preferably from about −25° C. to about 120° C., more preferably from about 15° C. to about 40° C. Reaction time is dependent on temperature and batch size, amount other factors, but typically reaction time is from about 2 hours to about 14 hours.

Step 2 of scheme 4 depicts coupling a compound IIIa1-1 with a compound having the formula $R_1$—CO—X to form a compound having the formula (IIa1-1). This coupling reaction is generally conducted at a temperature from about −30° C. to about 80° C., preferably from about 0° C. to about 25° C. The coupling reaction may occur with a coupling reagent that activates the acid functionality. Exemplary coupling reagents include dicyclohexylcarbodiimide/hydroxybenzotriazole (DCC/HBT), N-3-dimethylaminopropyl-N'-ethylcarbodiimide (EDC/HBT), 2-ethyoxy-1-ethoxycarbonyl-1,2-dihydroquinoline (EEDQ), carbonyl diimidazole (CDI), and diethylphosphorylcyanide. The coupling is conducted in an inert solvent, preferably an aprotic solvent, such as tetrahydrofuran, acetonitirile, dichloromethane, chloroform, or N,N-dimethylformamide. One preferred solvent is tetrahydrofuran. In one embodiment, quinoxaline acid is combined with CDI in anhydrous tetrahydrofuran and heated to provide the acyl imidazole. Compound IIIa1-1 is added to the acyl imidazole at room temperature to form the compound IIa1-1.

Step 3 of scheme 4 includes reacting the compound of formula IIa1-1 with an amine having a formula $NHR_4R_5$ to form a compound of the formula (Ia-1). In one embodiment, the amine is ammonia either anhydrous in an organic solvent or as an aqueous solution of ammonium hydroxide added to a polar solvent at a temperature from about −10° C. to about 35° C., preferably at about 30° C. Suitable solvents include, alcohols, such as methanol, ethanol, or butanols; ethers such as tetrahydrofuran, glyme or dioxane; or a mixture thereof, including aqueous mixtures. Preferably the solvent is methanol. In one embodiment, the compound IIa1-1 is dissolved in methanol which has been saturated with ammonia gas. In another embodiment, the compound IIa1-1 in methanol is treated with ammonium hydroxide in tetrahydrofuran at room temperature.

Scheme 5 represents an alternative method to form compounds of formula Ia-1 from compounds of formula IVa1-1.

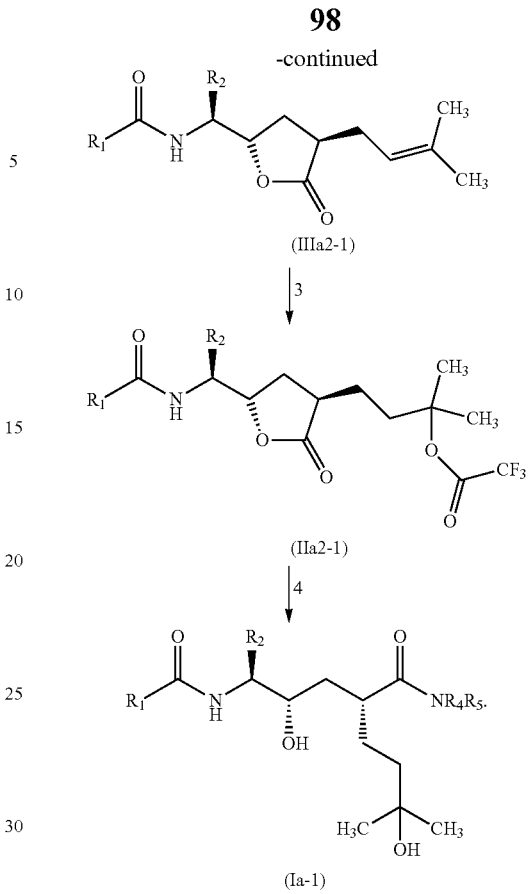

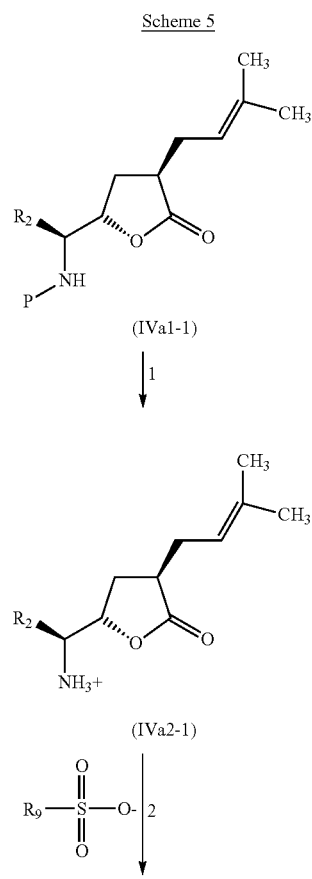

In step 1 of scheme 5, a compound of the formula (IVa1-1) is reacted with a compound of the formula $R_9$—$SO_2$—X to form a compound of the formula (IVa2-1). Any suitable acidic deprotection reaction may be performed. In one example, an excess of p-toluenesulfonic acid hydrate in ethyl acetate is introduced to the compound IVa1-1 at room temperature. Suitable solvents include ethyl acetate, alcohols, tetrahydrofuran, and mixtures thereof. The reaction may proceed at ambient or elevated temperatures. Typically, the reaction is substantially complete within two and twelve hours. The resulting compound IVa2-1 may be crystallized and separated from the reaction mixture, and may be further purified to remove impurities by recrystallization from hot ethyl acetate.

In step 2 of scheme 5, the compound IVa2-1 may be coupled with a compound having the formula $R_1$—CO—X to form a compound of the formula (IIIa2-1). This coupling reaction is generally conducted at a temperature from about −30° C. to about 80° C., preferably from about 0° C. to about 25° C. The coupling reaction may occur with a coupling reagent that activates the acid functionality. Exemplary coupling reagents include dicyclohexylcarbodiimide/hydroxybenzotriazole (DCC/HBT), N-3-dimethylaminopropyl-N'-ethylcarbodiimide (EDC/HBT), 2-ethyoxy-1-ethoxycarbonyl-1,2-dihydroquinoline (EEDQ), carbonyl diimidazole (CDI)/dimethylaminopyridine (DMAP), and diethylphosphorylcyanide. The coupling is conducted in an inert solvent, preferably an aprotic solvent, such as acetonitirile, dichloromethane, chloroform, or N,N-dimethylformamide. One preferred solvent is methylene chloride. In one embodiment, quinoxaline acid is combined with methylene chloride, oxalyl chloride and a catalytic amount of N,N-dimethylformamide to form an acid chloride complex. The compound IVa2-1 is added to the acid chloride complex followed by triethylamine at a temperature from about 00° C. to about 25° C. to form the compound IIIa2-1.

Step 3 of scheme 5 includes reacting a compound IIIa2-1 with trifluoroacetic acid to produce a compound of the formula (IIa2-1). In one embodiment, the hydration with trifluoroacetic acid occurs in methylene chloride solution at room temperature. The hydration may take several hours to complete at room temperature. A catalytic amount of sulfuric acid can be added to the reaction solution to increase the rate of reaction.

Step 4 of scheme 5 includes reacting the compound of formula IIa2-1 with an amine having a formula $NHR_4R_5$ to form a compound of the formula (Ia-1). In one embodiment, the amine is ammonia either anhydrous in an organic solvent or as an aqueous solution of ammonium hydroxide added to a polar solvent at a temperature from about −10° C. to about 35° C., preferably at about 30° C. Suitable solvents include, alcohols, such as methanol, ethanol, or butanols; ethers such as tetrahydrofuran, glyme or dioxane; or a mixture thereof, including aqueous mixtures. Preferably the solvent is methanol. In one embodiment, the compound IIa2-1 is dissolved in methanol which has been saturated with ammonia gas. In another embodiment, the compound IIa2-1 in methanol is treated with ammonium hydroxide in tetrahydrofuran at room temperature.

Neutral Dispersion Polymers

The neutral polymers suitable for use in the dispersions of the present invention are pharmaceutically acceptable and should be inert, in the sense that they do not chemically react with the drug in an adverse manner when present in the composition. The polymer should also have an aqueous-solubility of at least 0.1 mg/mL over at least a portion of the pH range of 1-8.

The polymer is "neutral," meaning that the dispersion polymer possesses substantially no acidic functional groups. By "substantially no acidic functional groups" is meant that the number of acidic groups covalently attached to the polymer is less than about 0.05 milliequivalents per gram of polymer. Preferably, the number is less than about 0.02 milliequivalents per gram of polymer. By "acidic groups" is meant functional groups that, when attached to the polymer, have $pK_a$ values in a humid or aqueous environment of about 5 or less. Preferably, the $pK_a$ value of the functional groups on the neutral polymer is greater than about 6. Thus, the neutral polymers may contain ionic groups as long as the groups are not acidic.

However, for many drugs, particularly those that are also sensitive to basic conditions, e.g., "base-sensitive drugs," it is preferred that the neutral polymers be substantially non-ionizable. By "substantially nonionizable" is meant that the number of "ionizable groups" covalently attached to the polymer is less than about 0.05 milliequivalents per gram of polymer and preferably less than about 0.02 milliequivalents per gram of polymer. "Ionizable groups" are those that are at least about 10% ionized over at least a portion of the physiologically relevant pH 1 to 8 range and thus such groups have $pK_a$ values of about 0 to 9.

The neutral dispersion polymer may be cellulosic or non-cellulosic. A preferred class of neutral cellulosic dispersion polymers are those with at least one ester- and/or ether-linked substituent in which the polymer has a degree of substitution of at least 0.05 for each substituent. It should be noted that in the polymer nomenclature used herein, ether-linked substituents are recited prior to "cellulose" as the moiety attached to the ether group; for example, "methyl cellulose" has a methyl moiety ether-linked to the polymer. In contrast, ester-linked substituents are recited after "cellulose" as the carboxylate; for example, "cellulose acetate" has an acetate moiety ester-linked to the polymer.

It should also be noted that a polymer name such as "cellulose acetate butyrate" refers to any of the family of cellulosic polymers that have acetate and butyrate groups attached via ester linkages to a significant fraction of the cellulosic polymer's hydroxyl groups. Generally, the degree of substitution of each substituent group can range from about 0.05 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been butyrate substituted, the butyrate degree of substitution is 3. Also included within each polymer family type are cellulosic polymers that have additional substituents added in relatively small amounts that do not substantially alter the performance of the polymer.

Polymer substituents may be either non-ionizable or ionizable; however, the ionizable groups may not be acidic groups. Exemplary ether-linked non-ionizable substituents include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked non-ionizable groups include: alkylate groups, such as acetate, propionate, butyrate, etc.; and arylate groups such as phenylate. However, when ester-linked non-ionizable groups are included, the polymer may need to include a sufficient amount of a hydrophilic substituent so that the polymer has at least some water solubility at any physiologically relevant pH of from 1 to 8. In the case of neutral dispersion polymers, such hydrophilic substituents may consist of non-acidic ionizable groups such as amino-functionalized groups or phenolate groups. In the case of non-ionizable neutral dispersion polymers, such hydrophilic groups are non-ionizable substituents such as alcohol, ether or ester groups.

Exemplary neutral non-ionizable cellulosic polymers that may be used to form the dispersion include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

Exemplary neutral, but ionizable cellulosic polymers, include aminoethyl cellulose, aminoethyl cellulose acetate, hydroxypropyl amino ethyl cellulose and hydroxybenzyl cellulose.

Another class of neutral dispersion polymers is non-cellulosic, neutral polymers. Such polymers may be either non-ionizable or ionizable. Exemplary non-ionizable, neutral polymers include vinyl polymers and copolymers having substituents of hydroxyl, alkylacyloxy, and cyclicamido. Exemplary non-cellulosic, neutral polymers include hydroxyethyl methacrylate, polyvinylhydroxyethyl ether, polyethylene glycol, and polyoxyethylene-polyoxypropylene block copolymers also known as poloxamers.

Exemplary ionizable neutral polymers include amine-functionalized polyacrylates and polymethacrylates, some of which are also sold as EUDRAGITS manufactured by Rohm Tech Inc., and neutral proteins.

A preferred subset of neutral polymers are those that are also concentration-enhancing. Dispersion polymers that are both neutral and also concentration-enhancing are generally amphiphilic in that they possess substituents that are relatively hydrophobic and substituents that are relatively hydrophilic.

Amphiphilic cellulosics may be prepared by substituting the cellulose at any or all of the 3 hydroxyl substituents present on each saccharide repeat unit with at least one relatively hydrophobic substituent. Hydrophobic substituents may be essentially any substituent that, if substituted to a high enough level or degree of substitution, can render the cellulosic polymer essentially aqueous insoluble. Hydrophilic regions of the polymer can be either those portions that are relatively unsubstituted, since the unsubstituted hydroxyls are themselves relatively hydrophilic, or those regions that are substituted with hydrophilic substituents. Examples of hydrophobic substitutents include ether-linked alkyl groups such as methyl, ethyl, propyl, butyl, etc.; or ester-linked alkyl groups such as acetate, propionate, butyrate, etc.; and ether- and/or ester-linked aryl groups such as phenyl, benzoate, or phenylate. As discussed above, hydrophilic substituents may consist of non-acidic ionizable groups such as amino-functionalized groups or phenolate groups. In the case of non-ionizable neutral dispersion polymers, such hydrophilic groups are non-ionizable substituents such as alcohol, ether or ester groups.

Exemplary amphiphilic polymers include non-ionizable cellulosics such as hydroxypropyl methyl cellulose, hydroxyethyl methyl cellulose and hydroxyethyl acetate; non-acidic ionizable cellulosics such as amino ethyl cellulose acetate and hydroxybenzyl cellulose; and non-ionizable non-cellulosics such as polyvinylpyrrolidone ethylene/vinyl alcohol copolymers and polyoxyethylene-polyoxypropylene block copolymers (also referred to as poloxamers); and ionizable non-cellulosics such as amine-functionalized polyacrylates and polymethacrylates. When the amphiphilic polymer is hydroxypropyl methyl cellulose, it is preferred that it is provided in a grade that possesses a dynamic viscosity that is 60 mPa-s or less, more preferably 10 mPa-s or less and most preferably between 1 mPa-s and 6 mPa-s, when measured in a 2% weight/volume solution at 20° C.

A preferred class of neutral non-cellulosic polymers are comprised of vinyl copolymers of a hydrophilic, hydroxyl-containing repeat unit and a hydrophobic, alkyl- or aryl-containing repeat unit. Such neutral vinyl copolymers are termed "amphiphilic hydroxyl-functional vinyl copolymers." Amphiphilic hydroxyl-functional vinyl copolymers are exceptional in that they are both non-ionic and yet, surprisingly, when used as dispersion polymers for low-solubility drugs, yield solid amorphous dispersions that provide high levels of drug concentration enhancement when dosed to an aqueous environment of use. Such polymers may be used with any low-solubility drug, and not simply acid-sensitive drugs.

Dispersions of such copolymers are believed to provide high concentration enhancements due to the amphiphilicity of these copolymers which provide both sufficient hydrophobic groups to interact with the hydrophobic, low-solubility drugs and also sufficient hydrophilic groups to have sufficient aqueous solubility for good dissolution. The copolymeric structure of the amphiphilic hydroxyl-functional vinyl copolymers also allows their hydrophilicity and hydrophobicity to be adjusted to maximize performance with a specific low-solubility drug.

The preferred copolymers have the general structure:

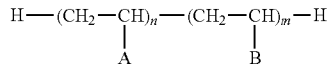

wherein A and B represent "hydrophilic, hydroxyl-containing" and "hydrophobic" substituents, respectively, and n and m represent the average number of hydrophilic vinyl repeat units and average number of hydrophobic vinyl repeat units respectively per polymer molecule. Copolymers may be block copolymers, random copolymers or they may have structures anywhere between these two extremes. The sum of n and m is generally from about 50 to about 20,000 and therefore the polymers have molecular weights from about 2,500 to about 1,000,000 daltons.

The hydrophilic, hydroxyl-containing repeat units, "A," may simply be hydroxyl (—OH) or it may be any short-chain, 1 to 6 carbon, alkyl with one or more hydroxyls attached thereto. The hydroxyl-substituted alkyl may be attached to the vinyl backbone via carbon-carbon or ether linkages. Thus, exemplary "A" structures include, in addition to hydroxyl itself, hydroxymethyl, hydroxyethyl, hydroxypropyl, hydroxymethoxy, hydroxyethoxy and hydroxypropoxy.

The hydrophobic substituent, "B," may simply be: hydrogen (—H), in which case the hydrophobic repeat unit is ethylene; an alkyl or aryl substituent with up to 12 carbons attached via a carbon-carbon bond such as methyl, ethyl or phenyl; an alkyl or aryl substituent with up to 12 carbons attached via an ether linkage such as methoxy, ethoxy or phenoxy; an alkyl or aryl substituent with up to 12 carbons attached via an ester linkage such as acetate, propionate, butyrate or benzoate. The amphiphilic hydroxyl-functional vinyl copolymers of the present invention may be synthesized by any conventional method used to prepare substituted vinyl copolymers. Some substituted vinyl copolymers such as polyvinyl alcohol/polyvinyl acetate are well known and commercially available.

A particularly convenient subclass of amphiphilic hydroxyl-functional vinyl copolymers to synthesize are those where the hydrophobic substituent "B" comprises the hydrophilic substituent "A" to which an alkylate or arylate group is attached via an ester link-age to one or more of the hydroxyls of A. Such copolymers may be synthesized by first forming the homopolymer of the hydrophobic vinyl repeat unit having the substituent B, followed by hydrolysis of a portion of the ester groups to convert a portion of the hydrophobic repeat units to hydrophilic, hydroxyl-containing repeat units having the substituent A. For example, partial hydrolysis of the homopolymer, polyvinylbutyrate, yields the copolymer, vinylalcohol/vinylbutyrate copolymer for which A is hydroxyl (—OH) and B is butyrate (—OOC—CH$_2$—CH$_2$—CH$_3$).

For all types of copolymers, the value of n must be sufficiently large relative to the value of m that the resulting copolymer is at least partially water soluble. Although the value of the ratio, n/m varies depending on the identity of A and B, it is generally at least about 1 and more commonly about 2 or more. The ratio n/m can be as high as 200. When the copolymer is formed by hydrolysis of the hydrophobic homopolymer, the relative values of n and m are typically reported in "percent hydrolysis," which is the fraction (expressed as a percent) of the total repeat units of the copolymer that are in the hydrolyzed or hydroxyl form. The percent hydrolysis, H, is given as H=100*

$$\left(\frac{n}{n+m}\right)$$

Thus, vinylbutyrate/vinylalcohol copolymer (formed by hydrolysis of a portion of the butyrate groups) having a percent hydrolysis of 75% has an n/m ratio of 3.

A particularly preferred family of amphiphilic hydroxyl-functional vinyl copolymers are those where A is hydroxyl and B is acetate. Such copolymers are termed vinylacetate/vinylalcohol copolymers. Some commercial grades are also sometimes referred to simply as polyvinylalcohol. However, the true homopolymer, polyvinylalcohol is not amphiphilic, is almost entirely water insoluble, and is not a part of this invention. Preferred vinylacetate/vinylalcohol copolymers are those where H is between about 67% and 99.5%, or n/m has a value between about 2 and 200. The preferred average molecular weight is between about 2500 and 1,000,000 daltons and more preferably between about 3000 and about 100,000 daltons.

In order to form dispersions that have a high level of concentration and bioavailability enhancement, it is important that the identity of A and B, the n/m value, and average molecular weight be chosen such that the polymers are sufficiently hydrophobic that they strongly interact with the hydrophobic, low-solubility drug and yet are still significantly water soluble. Typically good results are obtained when the aqueous solubility of the copolymer at 37° C. is between about 0.04 and 10.0 wt % and preferably between about 0.1 and 2.0 wt %.

While specific polymers are discussed as being suitable for use in the compositions of the present invention, blends of such polymers may also be suitable. Thus the term "polymer" is intended to include blends of polymers in addition to a single species of polymer.

Concentration Enhancement

As described above, it is often preferred that the neutral dispersion polymer is also concentration-enhancing. The neutral concentration-enhancing dispersion polymers improve the concentration of a low-solubility drug in a use environment, and thereby preferably improve bioavailability of the drug.

The term "concentration-enhancing" means that the polymer is present in a sufficient amount in the composition so as to improve the concentration of the drug in a use environment relative to a control composition free from the concentration-enhancing polymer. As used herein, a "use environment" can be either the in vivo environment of the GI tract, subdermal, intranasal, buccal, intrathecal, ocular, intraaural, subcutaneous spaces, vaginal tract, arterial and venous blood vessels, pulmonary tract or intramuscular tissue of an animal, such as a mammal and particularly a human, or the in vitro environment of a test solution, such as phosphate buffered saline (PSB) or a Model Fasted Duodenal (MFD) solution. Concentration enhancement may be determined through either in vitro dissolution tests or through in vivo tests. It has been determined that enhanced drug concentration in in vitro dissolution tests in Model Fasted Duodenal (MFD) solution or Phosphate Buffered Saline (PBS) is a good indicator of in vivo performance and bioavailability. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. An appropriate MFD solution is the same PBS solution wherein additionally is present 7.3 mM sodium taurocholic acid and 1.4 mM of 1-palmitoyl-2-oleyl-sn-glycero-3-phosphocholine. In particular, a composition containing a concentration-enhancing polymer may be dissolution-tested by adding it to MFD or PBS solution and agitating to promote dissolution.

In one aspect, a composition containing a concentration-enhancing polymer of the present invention provides a Maximum Drug Concentration (MDC) that is at least 1.25-fold the MDC provided by a control composition. In other words, if the MDC provided by the control composition is 100 □g/mL, then a composition of the present invention containing a concentration-enhancing polymer provides an MDC of at least 125 □g/mL. More preferably, the MDC of drug achieved with the compositions of the present invention are at least 2-fold, even more preferably at least 3-fold, and most preferably at least 10-fold that of the control composition.

The appropriate control composition depends on whether a dispersion polymer is being tested, or whether a composition comprised of a mixture of a dispersion and concentration-enhancing polymer is being tested. Where the composition is simply the dispersion itself, and the dispersion polymer is being tested to determine whether it is a concentration-enhancing polymer, the control composition is conventionally the undispersed drug alone (e.g., typically, the crystalline drug alone in its most thermodynamically stable crystalline form, or in cases where a crystalline form of the drug is unknown, the control may be the amorphous drug alone) or the drug plus a weight of inert diluent equivalent to the weight of polymer in the test composition. By inert is meant that the diluent is not concentration-enhancing. Where the composition is comprised of a mixture of a dispersion and additional concentration-enhancing polymer, the control composition is the dispersion alone without any additional concentration-enhancing polymer.

Alternatively, the compositions containing concentration-enhancing polymers of the present invention provide in an aqueous use environment a concentration versus time Area Under The Curve (AUC), for any period of at least 90 minutes between the time of introduction into the use environment and about 270 minutes following introduction to the use environment that is at least 1.25-fold that of an appropriate control composition. More preferably, the AUC achieved with the compositions of the present invention are at least 2-fold, more preferably at least 3-fold, and most preferably at least 10-fold that of a control composition.

Alternatively, the compositions of the present invention containing concentration-enhancing polymers, when dosed orally to a human or other animal, provide an AUC in drug concentration in the blood plasma or serum that is at least 1.25-fold that observed when an appropriate control composition is dosed. Preferably, the blood AUC is at least 2-fold, more preferably at least 3-fold, that of an appropriate control composition. Thus, the compositions that, when evaluated, meet either the in vitro or the in vivo, or both, performance criteria are a part of this invention.

A typical in vitro test to evaluate enhanced drug concentration can be conducted by (1) administering with agitation a sufficient quantity of test composition (for example, the dispersion of the low-solubility drug and neutral polymer) in a test medium, such that if all of the drug dissolved, the theoretical concentration of drug would exceed the equilibrium concentration of the drug by a factor of at least 2; (2) adding an appropriate amount of control composition to an equivalent amount of test medium; and (3) determining whether the measured MDC and/or AUC of the test composition in the test medium is at least 1.25-fold that provided by the control composition. The concentration of dissolved drug is typically measured as a function of time by sampling the test medium and plotting drug concentration in the test medium vs. time so that the MDC and/or AUC can be ascertained. In conducting such a dissolution test, the amount of test composition or control composition used is an amount such that if all of the drug dissolved, the drug concentration would be at least 2-fold to 100-fold that of the solubility (that is, the equilibrium concentration), of the drug. For some dispersions of a very low-solubility drug and neutral polymer, it may be necessary to administer an even greater amount of the dispersion to determine the MDC.

To avoid drug particulates which would give an erroneous determination, the test solution is either filtered or centrifuged. "Dissolved drug" is typically taken as that material that either passes a 0.45 μm syringe filter or, alternatively, the material that remains in the supernatant following centrifugation. Filtration can be conducted using a 13 mm, 0.45 μm polyvinylidine difluoride syringe filter sold by Scientific Resources under the trademark TITAN®. Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (±10-40%) than that obtained with the filter specified above but will still allow identification of preferred dispersions. It is recognized that this definition of "dissolved drug" encompasses not only monomeric solvated drug molecules but also a wide range of species such as polymer/drug assemblies that have submicron dimensions such as drug aggregates, aggregates of mixtures of polymer and drug, micelles, polymeric micelles, colloidal particles or nanocrystals, polymer/drug complexes, and other such drug-containing species that are present in the filtrate or supernatant in the specified dissolution test.

Alternatively, the concentration-enhancing polymer results in improved bioavailability. Relative bioavailability of the drug in the compositions of the present invention can be tested in vivo in animals or humans using conventional methods for making such a determination. An in vivo test, such as a crossover study, may be used to determine whether a composition provides an enhanced relative bioavailability compared with a control. In an in vivo crossover study a "test composition" of drug and concentration-enhancing polymer is dosed to half a group of test subjects and, after an appropriate washout period (e.g., one week) the same subjects are dosed with a "control composition" that comprises an equivalent quantity of drug as the "test composition." The other half of the group is dosed with the control composition first, followed by the test composition. The relative bioavailability is measured as the concentration in the blood (serum or plasma) versus time area under the curve (AUC) determined for the test composition divided by the AUC in the blood provided by the control composition. Preferably, this test/control ratio is determined for each subject, and then the ratios are averaged over all subjects in the study. In vivo determinations of AUC can be made by plotting the serum or plasma concentration of drug along the ordinate (y-axis) against time along the abscissa (x-axis). Generally, the values for AUC represent a number of values taken from all of the subjects in a patient test population averaged over the entire test population.

A preferred embodiment of the invention is one in which the relative bioavailability of the test composition is at least 1.25 relative to a control composition as described above. (That is, the AUC in the blood provided by the test composition is at least 1.25-fold the AUC provided by the control composition.) An even more preferred embodiment of the invention is one in which the relative bioavailability of the test composition is at least 2.0, more preferably at least 3, relative to a control composition of the drug but with no polymer present, as described above. The determination of AUCs is a well-known procedure and is described, for example, in Welling, "Pharmacokinetics Processes and Mathematics," ACS Monograph 185 (1986).

Often the enhancement in drug concentration or relative bioavailability that is observed increases as the drug:polymer ratio decreases from a value of about 1 (50 wt % drug) to a value of about 0.11 (10 wt % drug). The drug:polymer ratio that yields optimum results varies from drug to drug and is best determined in in vitro dissolution tests and/or in vivo bioavailability tests. However, the amount of polymer that can be used in a dosage form is often limited by the total mass requirements of the dosage form. For example, when oral dosing to a human is desired, at low drug-to-polymer ratios the total mass of drug and polymer may be unacceptably large for delivery of the desired dose in a single tablet or capsule. Thus, it is often necessary to use drug-to-polymer ratios that are less than optimum in specific dosage forms to provide a sufficient drug dose in a dosage form that is small enough to be easily delivered to a use environment.

Improved Chemical Stability

When the compositions of the present invention comprise dispersions of acid-sensitive drug and neutral polymer(s), such compositions provide improved chemical stability of the drug relative to a control composition comprised of an equivalent quantity of drug dispersed in an acidic dispersion polymer. The acidic dispersion polymer used in the control composition may be any polymer suitable for determining whether the drug is acid-sensitive that meets the definition of an "acidic polymer." Convenient acidic dispersion polymers for use in the control composition include HPMCAS, CAP and HPMCP. A composition of the present invention will meet the chemical stability requirements discussed below relative to at least one control dispersion of drug and either HPMCAS, HPMCP, or CAP.

A relative degree of improvement in chemical stability of an acid-sensitive drug in a test composition may be determined by taking the ratio of the degree of degradation of the drug in a control composition and the degree of degradation of the drug in a test composition under the same storage conditions for the same storage time period. The test composition is simply the composition of acid-sensitive drug, neutral polymer and optional additional excipients of the present invention. The control composition is the same as the test composition with the exception that an acidic dispersion polymer (that is, either HPMCAS, HPMCP or CAP) replaces the neutral dispersion polymer. For example, where the degree of degradation of a drug in a test composition comprised of an acid-sensitive drug and a neutral polymer is 1 wt %, and the degree of degradation of a control composition comprised of an equivalent quantity of drug and HPMCAS is 5 wt %, the relative degree of improvement is 5 wt %/1 wt % equals 5.0. For dispersions of acid-sensitive drugs and neutral polymers of the present invention, the relative degree of improvement is at least 1.25. Preferably, the relative degree of improvement is at least 3, more preferably at least 5, and even more preferably at least 10. In fact, some compositions of the present invention may achieve a relative degree of improvement greater than 100.

The particular storage conditions and time of storage may be chosen as convenient depending on the degree of acid-sensitivity of the drug, the particular acidic polymer used in the control dispersion, and the ratio of drug to polymer in the dispersion. Where the drug is particularly acid-sensitive, or where the dispersion has a low ratio of drug to polymer, then shorter storage time periods may be used. Where the rate of drug degradation is linear, the relative degree of improvement will be independent of the storage time. However, where the rate of drug degradation is non-linear under controlled storage conditions, the stability test used to compare the test dispersion with the control dispersion is preferably chosen such that the degree of degradation is sufficiently large that it may be accurately measured. Typically, the time period is chosen so as to observe a degree of degradation in the control composition of at least 0.1 wt % to 0.2 wt %. However, the time period is not so long that the ratio of drug to polymer changes substantially. Typically, the time period is such that the observed degree of degradation for the test composition is less than 50 wt % and preferably less than 20 wt %. When rate of drug degradation in the control composition is relatively slow, the test is preferably conducted over a long enough period of time under controlled storage conditions to allow a meaningful comparison of the stability of the test dispersion with the control dispersion.

A stability test which may be used to test whether a dispersion meets the chemical stability criteria described above is storage of the test dispersion and the control dispersion for six months at 40° C. and 75% RH. A relative degree of improvement may become apparent within a shorter time, such as three to five days, and shorter storage times may be used for some very acid-sensitive drugs. When comparing dispersions under storage conditions which approximate ambient conditions, e.g., 30° C. and 60% RH, the storage period may need to be several months up to two years.

In addition, it is preferred that the dispersions comprising acid-sensitive drug and neutral polymer(s) result in drug stability such that the acid-sensitive drug has a degree of degradation of less than about 2 wt %, more preferably less than about 0.5 wt %, and most preferably less than about 0.1 wt % when stored at 40° C. and 75% RH for six months, or less than 2 wt %, more preferably 0.5 wt %, and more preferably 0.1 wt %, when stored at 30° C. and 60% RH for one year. Nevertheless, the compositions of the present invention may have a degree of degradation that is much greater than the preferred values, so long as the dispersion achieves the degree of improvement relative to a control composition as described above.

Preparation of Dispersions

Dispersions of the drugs and neutral dispersion polymer may be made according to any known process which results in at least a "major portion" (meaning at least 60 wt %) of the drug being in the amorphous state. Such processes include mechanical, thermal and solvent processes. Exemplary mechanical processes include milling and extrusion; melt processes include high temperature fusion, solvent modified fusion and melt-congeal processes; and solvent processes include non-solvent precipitation, spray coating and spray-drying. See, for example, U.S. Pat. No. 5,456,923 and U.S. Pat. No. 5,939,099 which describe formation of dispersions via extrusion processes; U.S. Pat. No. 5,340,591 and U.S. Pat. No. 4,673,564 which describe forming dispersions by milling processes; and U.S. Pat. No. 5,707,646 and U.S. Pat. No. 4,894,235 which describe the formation of dispersions via melt/congeal processes, the disclosures of which are incorporated by reference.

While the drug in its pure state may be crystalline or amorphous, at least a major portion of the drug in the dispersion is amorphous. By "amorphous" is meant simply that the drug is in a non-crystalline state. As used herein, the term "a major portion" of the drug means that at least 60% of the drug in the dispersion is in the amorphous form, rather than the crystalline form. In general, a drug is more reactive in its amorphous state relative to its crystalline state and so the need to use a neutral dispersion polymer to prevent degradation of acid-sensitive drug increases as the fraction of drug in the amorphous state increases. It has also been found that the aqueous concentration of the drug in a use environment tends to improve as the fraction of drug present in the amorphous state in the dispersion increases. Accordingly, a "major portion" of the drug in the dispersion is amorphous and preferably the drug in the dispersion is substantially amorphous. As used herein, a "major portion" and "substantially amorphous" mean that the amount of the drug in crystalline form does not exceed about 40 wt % and about 25 wt %, respectively. More preferably, the drug in the dispersion is "almost completely amorphous," meaning that the amount of drug in the crystalline form does not exceed 10 wt %. Amounts of crystalline drug may be measured by powder X-ray diffraction, Scanning Electron Microscope (SEM) analysis, differential scanning calorimetry (DSC), or any other standard quantitative measurement.

The amorphous drug can exist as a pure phase, as a solid solution of drug homogeneously distributed throughout the polymer or any combination of these states or those states that lie intermediate between them. In cases where the drug is a low-solubility drug and concentration or bioavailability enhancement is desired, the dispersion is preferably "substantially homogeneous" so that the amorphous drug is dispersed as homogeneously as possible throughout the polymer. Dispersions of the present invention that are substantially homogeneous generally are more physically stable and have improved concentration-enhancing properties and, in turn improved bioavailability, relative to nonhomogeneous dispersions. As used herein, "substantially homogeneous" means that the drug present in relatively pure amorphous domains within the solid dispersion is relatively small, on the order of less than 20%, and preferably less than 10% of the total amount of drug.

While the dispersion may have some drug-rich domains, it is preferred that the dispersion itself have a single glass transition temperature ($T_g$) which demonstrates that the dispersion is substantially homogeneous. This contrasts with a simple physical mixture of pure amorphous drug particles and pure amorphous polymer particles which generally display two distinct $T_g$s, one that of the drug and one that of the polymer. $T_g$ as used herein is the characteristic temperature where a glassy material, upon gradual heating, undergoes a relatively rapid (e.g., 10 to 100 seconds) physical change from a glass state to a rubber state. Almost completely amorphous, substantially homogeneous dispersions may be made by any of the processes discussed above.

To obtain the maximum level of concentration and bioavailability enhancement, particularly upon storage for long times prior to use, it is preferred that the drug remain, to the extent possible, in the amorphous state. The inventors have found that this is best achieved when the glass-transition temperature, $T_g$, of the amorphous dispersion is substantially above the storage temperature of the dispersion. In particular, it is preferable that the $T_g$ of the amorphous dispersion is at least 40° C. and preferably at least 60° C. Since the $T_g$ is a function of the water content of the dispersion which in turn is a function of the RH to which the dispersion is exposed, these $T_g$ values refer to the $T_g$ of the dispersion containing water in an amount that is in equilibrium with the RH equivalent to that found during storage. For those aspects of the invention in which the dispersion is a solid, substantially amorphous dispersion of drug in the dispersion polymer and in which the drug itself has a relatively low $T_g$ (about 70° C. or less) it is preferred that the dispersion polymer have a $T_g$ of at least 40° C., preferably at least 70° C. and more preferably greater than 100° C. Exemplary high $T_g$ polymers include hydroxypropyl cellulose and hydroxypropyl methyl cellulose. Since conversion of amorphous drug to the crystalline state is related to the relative values of (1) the $T_g$ of the dispersion (at the storage RH) and (2) the storage temperature, solid amorphous dispersions of the present invention may tend to remain in the amorphous state for longer periods when stored at relatively low temperatures and low relative humidities. In addition, packaging of such dispersions so as to prevent absorption of water or inclusion of a water absorbing material such as a desiccant to also prevent or retard water absorption can lead to a higher $T_g$ during storage, thereby helping to retain the amorphous state. Likewise, storage at lower temperatures can also improve the retention of the amorphous state.

Turning now to particular methods, when either the neutral polymer or the drug has a relatively low melting point, typically less than about 200° C. and preferably less than about 160° C., extrusion or melt-congeal processes that provide heat and/or mechanical energy are often suitable for forming almost completely amorphous dispersions. Often, when the drug has significant solubility in the dispersion material, such methods may also make substantially homogeneous dispersions. For example, 10 wt % drug and 90 wt % polyvinyl pyrrolidone (PVP) may be dry blended, with or without the addition of water, and the blend fed to a twin-screw extrusion device. The processing temperature may vary from about 50° C. up to about 200° C. depending on the melting point of the drug and polymer, which is a function of the polymer grade chosen and the amount of water, if any, added. Generally, the higher the melting point of the drug and polymer, the higher the processing temperature. Generally, the lowest processing temperature that produces a satisfactory dispersion (almost completely amorphous and substantially homogeneous) is chosen.

A method for forming dispersions that is often preferred is "solvent processing," which consists of dissolution of the drug and one or more neutral polymers in a common solvent. The term "solvent" is used broadly and includes mixtures of solvents. "Common" here means that the solvent, which can be a mixture of compounds, will simultaneously dissolve both the drug and the polymer(s).

After both the drug and polymer(s) have been dissolved, the solvent is removed by evaporation or by mixing with a non-solvent. Exemplary processes are spray-drying, spray-coating (pan-coating, fluidized bed coating, etc.), vacuum evaporation, precipitation by mixing of the polymer and drug solution with a non-solvent such as $CO_2$, hexane, or heptane, and processes that combine solvents with heat and mechanical energy such as extrusion processes that include the use of a solvent as a processing aid or even wet granulation processes as long as such processes result in at least a major portion of the drug being amorphous. Preferably, removal of the solvent is rapid and results in a solid dispersion which is substantially homogeneous. In substantially homogeneous dispersions, the drug is dispersed as homogeneously as possible throughout the polymer and can be thought of as a solid solution of drug dispersed in the polymer(s). When the resulting dispersion constitutes a solid solution of drug in polymer, the dispersion may be thermodynamically stable, meaning that the concentration of drug in the polymer is at or below its equilibrium value, or it may be considered a supersaturated solid solution where the drug concentration in the dispersion polymer(s) is above its equilibrium value.

The solvent may be removed through the process of spray-drying. The term spray-drying is used conventionally and broadly refers to processes involving breaking up liquid mixtures into small droplets (atomization) and rapidly removing solvent from the mixture in a container (spray-drying apparatus) where there is a strong driving force for evaporation of solvent from the droplets. The strong driving force for solvent evaporation is generally provided by maintaining the partial pressure of solvent in the spray-drying apparatus well below the vapor pressure of the solvent at the temperature of the drying droplets. This is accomplished by either (1) maintaining the pressure in the spray-drying apparatus at a partial vacuum (e.g., 0.01 to 0.50 atm); (2) mixing the liquid droplets with a warm drying gas; or (3) both. In addition, at least a portion of the heat required for evaporation of solvent may be provided by heating the spray solution.

Solvents suitable for spray-drying can be any organic compound in which the drug and polymer are mutually soluble. Preferably, the solvent is also volatile with a boiling point of 150° C. or less. In addition, the solvent should have relatively low toxicity and be removed from the dispersion to a level that is acceptable according to The International Committee on Harmonization (ICH) guidelines. Removal of solvent to this level may require a processing step such as tray-drying or fluidized-bed drying subsequent to the spray-drying or spray-coating process. Preferred solvents include alcohols such as methanol, ethanol, n-propanol, iso-propanol, and butanol; ketones such as acetone, methyl ethyl ketone and methyl iso-butyl ketone; esters such as ethyl acetate and propylacetate; and various other solvents such as acetonitrile, methylene chloride, toluene, and 1,1,1-trichloroethane. Lower volatility solvents such as dimethyl acetamide or dimethylsulfoxide can also be used. Mixtures of solvents, such as 50% methanol and 50% acetone, can also be used, as can mixtures with water as long as the polymer and drug are sufficiently soluble to make the spray-drying process practicable. In particular, when the neutral polymer is relatively hydrophilic such as hydroxypropyl methyl cellulose (HPMC), or certain amphiphilic hydroxyl-functional vinyl copolymers, it is often preferred to use a mixture of an organic solvent and water to ensure that both drug and polymer are simultaneously soluble.

Generally, the temperature and flow rate of the drying gas is chosen so that the polymer/drug-solution droplets are dry enough by the time they reach the wall of the apparatus that they are essentially solid, and so that they form a fine powder and do not stick to the apparatus wall. The actual length of time to achieve this level of dryness depends on the size of the droplets. Droplet sizes generally range from 1 μm to 500 μm in diameter, with 5 to 200 μm being more typical. The large surface-to-volume ratio of the droplets and the large driving force for evaporation of solvent leads to actual drying times of a few seconds or less, and more typically less than 0.1 second. This rapid drying is often critical to the particles maintaining a uniform, homogeneous dispersion instead of separating into drug-rich and polymer-rich phases. As above, to get large enhancements in concentration and bioavailability it is often necessary to obtain as homogeneous of a dispersion as possible. Solidification times should be less than 100 seconds, preferably less than a few seconds, and more preferably less than 1 second. In general, to achieve this rapid solidification of the drug/polymer solution, it is preferred that the size of droplets formed during the spray-drying process are less than about 500 μm in diameter, and preferably less than about 300 μm. The resultant solid particles thus formed are generally less than about 300 μm in diameter.

Following solidification, the solid powder typically stays in the spray-drying chamber for about 5 to 60 seconds, further evaporating solvent from the solid powder. The final solvent content of the solid dispersion as it exits the dryer should be low, since this reduces the mobility of drug molecules in the dispersion, thereby improving its stability. Generally, the solvent content of the dispersion as it leaves the spray-drying chamber should be less than about 10 wt % and preferably less than about 3 wt %. In some cases, it may be preferable to spray a solvent or a solution of a polymer or other excipient into the spray-drying chamber to form granules, so long as the dispersion is not adversely affected.

Spray-drying processes and spray-drying equipment are described generally in Perry's *Chemical Engineers' Handbook*, Sixth Edition (R. H. Perry, D. W. Green, J. O. Maloney, eds.) McGraw-Hill Book Co. 1984, pages 20-54 to 20-57. More details on spray-drying processes and equipment are reviewed by Marshall "Atomization and Spray-Drying," 50 *Chem. Eng. Prog. Monogr. Series* 2 (1954).

The solid amorphous dispersions formed from a low-solubility drug and an amphiphilic hydroxyl-functional vinyl copolymer are preferably almost completely amorphous and substantially homogenous. Such almost completely amorphous, substantially homogenous dispersions are generally more physically stable (that is, resist phase separation or crystallization upon storage), and show higher levels of concentration enhancement. As with the dispersions of other embodiments of the invention, such dispersions may in principle be formed by any known process, including mechanical, thermal and solvent processes. However, "solvent processing" is preferred for forming dispersions of amphiphilic hydroxyl-functional vinyl copolymers because when properly performed, solvent processing tends to produce dispersions in which the drug is almost completely amorphous and in which the dispersion is substantially homogeneous.

In order to achieve such preferred dispersions, a copolymer type and solvent must be chosen to yield a solution in which the amphiphilic, hydroxyl-functional vinyl copolymer and low-solubility drug are both soluble and preferably highly soluble. Preferably, both the copolymer and low-solubility drug each have solubilities in the solvent at 37° C. of at least 0.5 wt % and preferably at least 2.0 wt % and more preferably at least 5.0 wt %.

In order to have the drug and copolymer both have such high solubilities in the solvent while the polymer is also sufficiently soluble in aqueous solution, the polymer molecular weight must generally not be too high and the polymer must have the correct n/m values. For example it has been found that for vinylacetate/vinylalcohol copolymers that n/m values are preferably between about 2 and 100 and molecular weights are preferably less than about 50,000 daltons.

In addition, the solvent is preferably chosen such that the lesser of either (1) the polymer solubility or (2) the product of the drug solubility and the ratio of the polymer to drug in the final dispersion, is high and is preferably maximized. To achieve this, it is often desirable to use blends of two or more solvents. In particular, a blend of water and an organic solvent is often preferred. Exemplary preferred solvents are mixtures of water and alcohols such as methanol, ethanol, n-propanol, iso-propanol and the isomers of butanol.

In addition it is preferable for the solvent processing to be conducted such that solvent is removed rapidly so that the polymer-drug solution solidifies rapidly. Thus solvent processes such as spray-coating and spray-drying are preferred.

In addition, to achieve rapid solvent removal, and to keep the residual solvent level in the dispersion low (preferably less than about 5 wt %), a relatively volatile solvent is chosen. Preferably the boiling points of the solvents are less than about 150° C. and more preferably less than about 125° C. When the solvent is a mixture of solvents, up to about 40% of the solvent may comprise a low volatility solvent. When the dispersion polymer is a vinylacetate/vinylalcohol copolymer of the preferred type described earlier, preferred solvents include mixtures of methanol and water.

Returning to dispersions generally, the amount of polymer relative to the amount of drug present in the dispersions of the present invention depends on the drug and polymer and may vary widely from a drug-to-polymer weight ratio of from 0.01 to about 4 (e.g., 1 wt % drug to 80 wt % drug). However, in most cases it is preferred that the drug-to-polymer ratio is greater than about 0.05 (4.8 wt % drug) and less than about 2.5 (71 wt % drug).

In addition to the drug and polymer(s), the dispersions of the present invention may include optional additional ingredients. One optional additional ingredient is a buffer. Buffers suitable for use in the dispersions of the present invention are preferably basic. Buffers are particularly preferred for dispersions of neutral polymers and drugs that have a high degree of acid-sensitivity. The buffers may reduce the risk of drug degradation due to the presence of acidic species in the dispersion, elsewhere in the composition, or acidic or basic species formed during storage. The compositions preferably provide improved chemical stability relative to dispersions that are free from the buffer.

Exemplary buffers that may be used in the dispersions of the present invention include sodium acetate, ammonium acetate, sodium carbonate, sodium bicarbonate, disodium hydrogen phosphate and trisodium phosphate. It is generally preferred that the buffer be chosen such that it maintains the pH at the optimum value during storage to minimize degradation reactions. For most acid-sensitive drugs, the preferred pH value is greater than about 6. Since many dispersion polymers such as cellulosics are also base-sensitive, it is generally preferred that the buffer be chosen to maintain the dispersion pH between about 6 and 10. In cases where the acid-sensitive drug is also a base-sensitive drug, it is often preferred to maintain the dispersion pH between about 6 and about 8. To accomplish this, it is sometimes desirable for the buffer to be a blend of protonated and deprotonated material, where the $pK_a$ of the protonated material is near the desired dispersion pH. Such buffers may comprise from 0.1 to 20 wt % of the dispersion.

Alternatively, the dispersion may include basic excipients such as mono-, di- or tri-ethanolamine, or glucoseamine, which may comprise from 0.1 to 20 wt % of the dispersion. Such basic excipients may be used to control the dispersion pH as described above.

Mixtures of Dispersions and
Concentration-Enhancing Polymer

A separate embodiment of the invention comprises a combination of (1) a dispersion of an acid-sensitive, low-solubility drug and neutral dispersion polymer(s) and (2) a second polymer that is concentration-enhancing. The dispersion is free from at least a portion of the second polymer, and is preferably substantially free from the second polymer. By "substantially free" is meant that the dispersion and the second polymer are not mixed at the molecular level to form a dispersion containing the second polymer. While a small amount of the second polymer may be incorporated into the dispersion as a result of processing, nevertheless the drug in the dispersion meets the chemical stability requirements discussed above for dispersions of acid-sensitive drugs and neutral polymers notwithstanding the presence of the second polymer in the composition. The neutral dispersion polymer optionally may also be concentration-enhancing.

The compositions of this aspect of the present invention are generally physical combinations comprising the dispersion and the second polymer. "Combination" as used herein means that the dispersion and second polymer may be in physical contact with each other or in close proximity but without the necessity of being physically mixed at the molecular level (i.e., a dispersion). The dispersion and concentration-enhancing polymer may be in different regions of the composition. For example, the solid composition may be in the form of a multi-layer tablet, as known in the art, wherein one or more layers comprises the dispersion and one or more different layers comprises the second polymer. Yet another example may constitute a coated tablet wherein either the dispersion or the second polymer or both may be present in the tablet core and the coating may comprise the second polymer. Alternatively, the combination can be in the form of a simple dry physical mixture wherein both the dispersion and the second polymer are mixed in particulate form and wherein the particles of each, regardless of size, retain the same individual physical properties that they exhibit in bulk. Any conventional method used to mix the dispersion and second polymer together such as physical mixing and dry or wet granulation, which does not convert the dispersion and the second polymer to another molecular dispersion, may be used.

Alternatively, the dispersion and second polymer may be co-administered, meaning that the dispersion may be administered separately from, but within the same general time frame as, the second polymer. Thus, a dispersion may, for example, be administered in its own dosage form which is taken at approximately the same time as the second polymer which is in a separate dosage form. If administered separately, it is generally preferred to administer both the dispersion and the second polymer within 60 minutes of each other, so that the two are present together in the use environment. When not administered approximately simultaneously (e.g., within a minute or two of each other), the second polymer is preferably administered prior to the dispersion.

The second polymer may be any concentration-enhancing polymer, such as those described above in connection with the neutral dispersion polymers. As described above, the inventors have found that ionizable, cellulosic polymers, particularly those that are acidic cellulosic enteric polymers, provide superior enhancement in aqueous concentration of the drug in a use environment relative to other polymers, and are therefore preferred in the absence of their reactivity with the drug. Many of these ionizable, cellulosic polymers have acidic functional groups and therefore are inappropriate for use as a dispersion polymer with acid-sensitive drugs. However, the concentration-enhancing advantage provided by such ionizable concentration-enhancing polymers may be achieved by simply combining such a polymer as the second polymer with a pre-formed dispersion of the acid-sensitive drug and a neutral polymer in a fashion that does not alter the neutral characteristic of the pre-formed dispersion.

A preferred class of concentration-enhancing polymers suitable for use as the second polymer comprises ionizable cellulosic polymers with at least one ester- and/or ether-linked substituent in which the polymer has a degree of substitution of at least 0.05 for each substituent. Particularly preferred hydrophilic substituents for use in making ionizable polymers are those that are ether- or ester-linked acidic ionizable groups such as carboxylic acids, thiocarboxylic acids and sulfonates, and groups that may be non-acidic such as substituted phenoxy groups, amines, and phosphates. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid, etc.; thiocarboxylic acids, such as thioacetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary ester linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as amino salicylic acid; amines, such as natural or synthetic amino acids, such as alanine or phenylalanine; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer aqueous soluble at least at pH values where any ionizable groups are ionized. In some cases, the aromatic group may itself be ionizable, such as phthalate or trimellitate substituents.

Exemplary ionizable cellulosic concentration-enhancing polymers that are at least partially ionized at physiologically relevant pHs include: hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Another class of concentration-enhancing polymers suitable for use with the present invention comprises ionizable non-cellulosic polymers. Exemplary polymers of this type that are generally acidic include carboxylic acid-functionalized vinyl polymers, such as the carboxylic acid functionalized polymethacrylates and carboxylic acid functionalized polyacrylates such as the EUDRAGITS® manufactured by Rohm Tech Inc., of Malden, Mass., and acidic proteins.

A preferred class of concentration-enhancing polymers comprises polymers that are "amphiphilic" in nature, meaning that the polymer has hydrophobic and hydrophilic portions. The hydrophobic portion may comprise groups such as aliphatic or aromatic hydrocarbon groups. The hydrophilic portion may comprise either ionizable or non-ionizable groups that are capable of hydrogen bonding such as hydroxyls, carboxylic acids, esters, amines or amides.

Amphiphilic polymers are preferred because it is believed that such polymers may tend to have relatively strong interactions with the drug and may promote the formation of various types of polymer/drug assemblies in the use environment. Ionizable polymers, and particularly those that have a significant level of carboxylic acid functional groups (e.g., acidic polymers) typically show the greatest concentration and bioavailability enhancements and therefore are preferred for use with low-solubility drugs. However, they may not form a part of the dispersion when the drug is acid-sensitive. Thus, a particularly preferred composition is one in which an acid-sensitive drug is dispersed in a neutral or non-ionizable polymer and an ionizable or acidic polymer is added such that it is not part of the dispersion.

In addition, ionic, and in particular acidic polymers, are thought to show desirable concentration-enhancement properties due to the repulsion of the like charges of the ionized groups of such polymers. This repulsion may serve to limit the size of the polymer/drug assemblies to the nanometer or submicron scale. For example, while not wishing to be bound by a particular theory, such polymer/drug assemblies may comprise hydrophobic drug clusters surrounded by the polymer with the polymer's hydrophobic regions turned inward towards the drug and the hydrophilic regions of the polymer turned outward toward the aqueous environment. Alternatively, depending on the specific chemical nature of the drug, the ionized functional groups of the polymer may associate, for example, via ion pairing or hydrogen bonds, with ionic or polar groups of the drug. In the case of ionizable polymers, the hydrophilic regions of the polymer would include the ionized functional groups. Such polymer/drug assemblies in solution may well resemble charged polymeric micellar-like structures. In any case, regardless of the mechanism of action, the inventors have observed that such amphiphilic polymers, particularly ionizable cellulosic polymers, have been shown to improve the maximum drug concentration (MDC) and/or area under the curve (AUC) of the drug in aqueous solution relative to control compositions free from such polymers.

Surprisingly, such amphiphilic polymers can greatly enhance the maximum concentration of drug obtained when the drug is dosed to a use environment. In addition, such amphiphilic polymers may interact with the drug to prevent the precipitation or crystallization of the drug from solution despite its concentration being substantially above its equilibrium concentration.

Exemplary ionizable cellulosic polymers that meet the definition of amphiphilic, having hydrophilic and hydrophobic regions, include polymers such as cellulose acetate phthalate and cellulose acetate trimellitate where the cellulosic repeat units that have one or more acetate substituents are hydrophobic relative to those that have no acetate substituents or have one or more ionized phthalate or trimellitate substituents.

A particularly desirable subset of cellulosic ionizable concentration-enhancing polymers are those that possess both a carboxylic acid functional aromatic substituent and an alkylate substituent and thus are amphiphilic. Exemplary polymers include cellulose acetate phthalate, methyl cellulose acetate phthalate, ethyl cellulose acetate phthalate, hydroxypropyl cellulose acetate phthalate, hydroxylpropyl methyl cellulose phthalate, hydroxypropyl methyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Another particularly desirable subset of cellulosic ionizable polymers are those that possess a non-aromatic carboxylate substituent. Exemplary polymers include hydroxypropyl methyl cellulose acetate succinate, hydroxypropyl methyl cellulose succinate, hydroxypropyl cellulose acetate succinate, hydroxyethyl methyl cellulose acetate succinate, hydroxyethyl methyl cellulose succinate, and hydroxyethyl cellulose acetate succinate.

Non-cellulosic polymers that are amphiphilic are copolymers of a relatively hydrophilic and a relatively hydrophobic monomer. Examples include acrylate and methacrylate copolymers. Exemplary commercial grades of such copolymers include the EUDRAGITS, which are copolymers of methacrylates and acrylates. Another suitable class of amphiphilic copolymers are the amphiphilic hydroxyl-functional vinyl copolymers described previously.

Excipients and Dosage Forms

Although the key ingredients present in the compositions of the present invention are simply the dispersion and optional non-dispersion concentration-enhancing polymer(s), the inclusion of other excipients in the composition may be useful. These excipients may be utilized with the drug and polymer composition in order to formulate the composition into tablets, capsules, suppositories, suspensions, powders for suspension, creams, transdermal patches, depots, and the like. The composition of drug and polymer can be added to other dosage form ingredients in essentially any manner that does not substantially alter the drug. The excipients may be either physically mixed with the dispersion and/or included within the dispersion. However, where the drug is acid-sensitive, acidic excipients should not be added to the dispersion unless neutralized.

One very useful class of excipients is surfactants. Suitable surfactants include fatty acid and alkyl sulfonates; commercial surfactants such as benzalkonium chloride (HYAMINE® 1622, available from Lonza, Inc., Fairlawn, N.J.); dioctyl sodium sulfosuccinate, DOCUSATE SODIUM™ (available from Mallinckrodt Spec. Chem., St. Louis, Mo.); polyoxyethylene sorbitan fatty acid esters (TWEEN®, available from ICI Americas Inc., Wilmington, Del.; LIPOSORB® P-20 available from Lipochem Inc., Patterson N.J.; CAPMUL® POE-0 available from Abitec Corp., Janesville, Wis.), and natural surfactants such as sodium taurocholic acid, 1-palmitoyl-2-oleoyl-sn-glycero-3-phosphocholine, lecithin, and other phospholipids and mono- and diglycerides. Preferably, the surfactants are not acidic. In cases where the surfactant is acidic, such as fatty acids, the salts of the acids are preferred. Thus, sodium dodecanate is preferred relative to dodecanoic acid. Such materials can advantageously be employed to increase the rate of dissolution by facilitating wetting, thereby increasing the maximum dissolved concentration, and also to inhibit crystallization or precipitation of drug by interacting with the dissolved drug by mechanisms such as complexation, formation of inclusion complexes, formation of micelles or adsorbing to the surface of solid drug, crystalline or amorphous. These surfactants may comprise up to 5 wt % of the composition.

The addition of pH modifiers such as acids, bases, or buffers may also be beneficial, retarding the dissolution of the composition (e.g., acids such as citric acid or succinic acid when the concentration-enhancing polymer is anionic) or, alternatively, enhancing the rate of dissolution of the composition (e.g., bases such as sodium acetate or amines when the polymer is anionic). Of course, where the drug is acid-sensitive, pH modifiers should not be added to the dispersion except as discussed above in connection with including buffers or basic excipients within the dispersion.

Conventional matrix materials, complexing agents, solubilizers, fillers, disintegrating agents (disintegrants), or binders may also be added as part of the composition itself or added by granulation via wet or mechanical or other means. These materials may comprise up to 90 wt % of the composition.

Examples of matrix materials, fillers, or diluents include lactose, mannitol, xylitol, microcrystalline cellulose, calcium diphosphate, dicalcium phosphate and starch.

Examples of disintegrants include sodium starch glycolate, sodium alginate, carboxy methyl cellulose sodium, methyl cellulose, and croscarmellose sodium, and cross-linked forms of polyvinyl pyrrolidone such as those sold under the trade name CROSPOVIDONE (available from BASF Corporation).

Examples of binders include methyl cellulose, microcrystalline cellulose, starch, and gums such as guar gum, and tragacanth.

Examples of lubricants include magnesium stearate, calcium stearate, and stearic acid.

Examples of preservatives include sulfites (an antioxidant), benzalkonium chloride, methyl paraben, propyl paraben, benzyl alcohol and sodium benzoate.

Examples of suspending agents or thickeners include xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, and titanium dioxide.

Examples of anticaking agents or fillers include silicon oxide and lactose.

Examples of solubilizers include ethanol, propylene glycol or polyethylene glycol.

Other conventional excipients may be employed in the compositions of this invention, including those excipients well-known in the art. Generally, excipients such as pigments, lubricants, flavorants, and so forth may be used for customary purposes and in typical amounts without adversely affecting the properties of the compositions. These excipients may be utilized in order to formulate the composition into tablets, capsules, suspensions, powders for suspension, creams, transdermal patches, and the like.

The compositions of the present invention may be delivered by a wide variety of routes, including, but not limited to, oral, nasal, rectal, vaginal, subcutaneous, intravenous, and pulmonary. Generally, the oral route is preferred.

Compositions of this invention may also be used in a wide variety of dosage forms for administration of drugs. Exemplary dosage forms are powders or granules that may be taken orally either dry or reconstituted by addition of water or other liquids to form a paste, slurry, suspension or solution; tablets; capsules; multiparticulates; and pills. Various additives may be mixed, ground, or granulated with the compositions of this invention to form a material suitable for the above dosage forms.

The compositions of the present invention may be formulated in various forms such that they are delivered as a suspension of particles in a liquid vehicle. Such suspensions may be formulated as a liquid or paste at the time of manufacture, or they may be formulated as a dry powder with a liquid, typically water, added at a later time but prior to oral administration. Such powders that are constituted into a suspension are often termed sachets or oral powder for constitution (OPC) formulations. Such dosage forms can be formulated and reconstituted via any known procedure. The simplest approach is to formulate the dosage form as a dry powder that is reconstituted by simply adding water and agitating. Alternatively, the dosage form may be formulated as a liquid and a dry powder that are combined and agitated to form the oral suspension. In yet another embodiment, the dosage form can be formulated as two powders which are reconstituted by first adding water to one powder to form a solution to which the second powder is combined with agitation to form the suspension.

Generally, it is preferred that the dispersion of drug be formulated for long-term storage in the dry state as this promotes the chemical and physical stability of the drug.

A preferred additive to such formulations is additional concentration-enhancing polymer which may act as a thickener or suspending agent as well as to enhance the concentration of drug in the environment of use and may also act to prevent or retard precipitation or crystallization of drug from solution. Such preferred additives are hydroxyethyl cellulose, hydroxypropyl cellulose, and hydroxypropyl methyl cellulose. In particular, the salts of carboxylic acid functional polymers such as cellulose acetate phthalate, hydroxypropyl methyl cellulose acetate succinate, and carboxymethyl cellulose are useful in this regard. Such polymers may be added in their salt forms or the salt form may be formed in situ during reconstitution by adding a base such as trisodium phosphate and the acid form of such polymers.

In some cases, the overall dosage form or particles, granules or beads that make up the dosage form may have superior performance if coated with an enteric polymer to prevent or retard dissolution until the dosage form leaves the stomach. Exemplary enteric coating materials include hydroxypropyl methyl cellulose acetate succinate, hydroxypropyl methyl cellulose phthalate, cellulose acetate phthalate, cellulose acetate trimellitate, carboxylic acid-functionalized polymethacrylates, and carboxylic acid-functionalized polyacrylate.

Compositions of this invention may be administered in a controlled release dosage form. In one such dosage form, the composition of the drug and polymer is incorporated into an erodible polymeric matrix device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or "matrix" that entraps the dispersion of drug and polymer. The aqueous-swollen matrix gradually erodes, swells, disintegrates or dissolves in the environment of use, thereby controlling the release of the dispersion to the environment of use. Examples of such dosage forms are disclosed more fully in commonly assigned pending U.S. patent application Ser. No. 09/495,059 filed Jan. 31, 2000 which claimed the benefit of priority of provisional patent application Ser. No. 60/119, 400 filed Feb. 10, 1999, the relevant disclosure of which is herein incorporated by reference.

Alternatively, the compositions of the present invention may be administered by or incorporated into a non-erodible matrix device.

Alternatively, the compositions of the invention may be delivered using a coated osmotic controlled release dosage form. This dosage form has two components: (a) the core which contains an osmotic agent and the dispersion of drug and concentration-enhancing polymer; and (b) a non-dissolving and non-eroding coating surrounding the core, the coating controlling the influx of water to the core from an aqueous environment of use so as to cause drug release by extrusion of some or all of the core to the environment of use. The osmotic agent contained in the core of this device may be an aqueous-swellable hydrophilic polymer, osmogen, or osmagent. The coating is preferably polymeric, aqueous-permeable, and has at least one delivery port. Examples of such dosage forms are disclosed more fully in commonly assigned pending U.S. patent application Ser. No. 09/495,061 filed Jan. 31, 2000 which claimed the benefit of priority of provisional Patent Application Ser. No. 60/119, 406 filed Feb. 10, 1999, the relevant disclosure of which is herein incorporated by reference.

Alternatively, the compositions may be delivered via a coated hydrogel controlled release form having at least two components: (a) a core comprising the dispersion of the present invention and a hydrogel, and (b) a coating through which the dispersion has passage when the dosage form is exposed to a use environment. Examples of such dosage forms are more fully disclosed in commonly assigned European Patent EP0378404, the relevant disclosure of which is herein incorporated by reference.

Alternatively, the drug mixture of the invention may be delivered via a coated hydrogel controlled release dosage form having at least three components: (a) a composition containing the dispersion, (b) a water-swellable composition wherein the water-swellable composition is in a separate region within a core formed by the drug-containing composition and the water-swellable composition, and (c) a coating around the core that is water-permeable, water-insoluble, and has at least one delivery port therethrough. In use, the core imbibes water through the coating, swelling the water-swellable composition and increasing the pressure within the core, and fluidizing the dispersion-containing composition. Because the coating remains intact, the dispersion-containing composition is extruded out of the delivery port into an environment of use. Examples of such dosage forms are more fully disclosed in commonly assigned pending U.S. patent application Ser. No. 09/745,095 filed Dec. 20, 2000, which claimed the benefit of priority of provisional patent application 60/171,968 filed Dec. 23, 1999, the relevant disclosure of which is herein incorporated by reference.

Alternatively, the compositions may be administered as multiparticulates. Multiparticulates generally refer to dosage forms that comprise a multiplicity of particles that may range in size from about 10 □m to about 2 mm, more typically about 100 □m to 1 mm in diameter. Such multiparticulates may be packaged, for example, in a capsule such as a gelatin capsule or a capsule formed from an aqueous-soluble polymer such as HPMCAS, HPMC or starch or they may be dosed as a suspension or slurry in a liquid.

Such multiparticulates may be made by any known process, such as wet- and dry-granulation processes, extrusion/spheronization, roller-compaction, melt-congealing processes or by spray-coating seed cores. For example, in wet- and dry-granulation processes, the composition of drug and concentration-enhancing polymer is prepared as described above. This composition is then granulated to form multiparticulates of the desired size. Other excipients, such as a binder (e.g., microcrystalline cellulose), may be blended with the composition to aid in processing and forming the multiparticulates. In the case of wet granulation, a binder such as microcrystalline cellulose may be included in the granulation fluid to aid in forming a suitable multiparticulate.

In any case, the resulting particles may themselves constitute the multiparticulate dosage form or they may be coated by various film-forming materials such as enteric polymers or water-swellable or water-soluble polymers, or they may be combined with other excipients or vehicles to aid in dosing to patients.

Compositions of the present invention may be used to treat any condition which is subject to treatment by administering a drug.

Other features and embodiments of the invention will become apparent from the following examples which are given for illustration of the invention rather than for limiting its intended scope.

EXAMPLES

Examples 1-2

This example discloses solid amorphous dispersions of an acid-sensitive, low-solubility drug and neutral polymer. For Example 1, a dispersion of quinoxaline-2-carboxylic acid [4(R)-carbamoyl-1(S)-3-fluorobenzyl)-2(S),7-dihydroxy-7-methyl-octyl]amide (Drug 1) and the neutral polymer hydroxypropyl methyl cellulose (HPMC E3 Prem) was made by preparing a solution containing 0.125 wt % Drug 1 and 0.375 wt % HPMC in methanol, and spraying the solution into a drying chamber using an atomizing spray nozzle as described below. For Example 2, a dispersion of Drug 1 with the neutral polymer polyvinyl pyrollidone (PVP—Plasdone K-29/32 available from ISP Technologies Inc., Wayne, N.J.) was made by preparing a solution containing 0.33 wt % Drug 1 and 1.0 wt % PVP in acetone/methanol (9/1, wt/wt), and spray-drying the solution as described below.

For Control C1, a dispersion of Drug 1 with hydroxy propyl methyl cellulose acetate succinate, LF-grade (HPMCAS-LF) (with about 14-18 wt % or 350-450 meq of succinate groups per mol of polymer) was made by preparing a solution containing 0.33 wt % Drug 1 and 1.0 wt % HPMCAS-LF in acetone, and spray-drying the solution as described below.

For Examples 1 and 2, and Control C1, the solutions were spray-dried by pumping the solution into a "mini" spray-dryer apparatus via a Cole Parmer 74900 series rate-controlling syringe pump at a rate of 1.3 mL/min. The drug/polymer solution was atomized through a Spraying Systems Co. two-fluid nozzle, Model No. SU1A using a heated stream of nitrogen (100 □C). The spray solution was sprayed into an 11-cm diameter stainless steel chamber. The resulting solid amorphous dispersions containing 25 wt % Drug 1 were collected on filter paper, dried under vacuum, and stored in a dessicator. Table 1 summarizes the spray-drying variables.

TABLE 1

| Ex. | Drug Mass (mg) | Drug No. | Polymer Mass (mg) | Polymer | Solvent Mass (g) | Solvent (wt/wt) |
|---|---|---|---|---|---|---|
| 1 | 50 | 1 | 150 | HPMC | 40 | Methanol |
| 2 | 50 | 1 | 150 | PVP | 15 | Acetone/methanol (9/1) |
| C1 | 50 | 1 | 150 | HPMCAS | 15 | Acetone |

Example 3

In this example the chemical stability of the dispersions of Examples 1 and 2 was assessed by monitoring the potency of the drug before and after exposure to increased temperatures and relative humidity (RH) in accelerated-aging studies. Dispersions of Examples 1 and 2, and Control C1, were placed in two controlled atmosphere chambers: one chamber maintained at 70° C. (no RH control); the second chamber maintained at 40° C. and 75% RH. Potencies of the dispersions before and after storage were determined using HPLC. A Kromasil $C_4$ HPLC column was used with a mobile phase of 45 vol % of 0.2 vol % $H_3PO_4$, and 55 vol % acetonitrile. UV detection was measured at 245 nm. Drug 1 potency was the percent of the total HPLC peak area corresponding to the theoretical amount of drug originally present in the dispersion prior to storage based on the amount of drug present in the initial solutions before spray-drying. The results are shown in Table 2 below.

TABLE 2

| Ex. | Aqueous Soluble Polymer | Drug 1 Conc. in the Dispersion (wt %) | Pot. Before Storage (wt %) | Pot. Day 4 at 70° C. (wt %) | Degree of Degradation Day 4 at 70° C. (wt %) | Pot. Day 14 at 40° C./75% RH (wt %) | Degree of Degradation Day 14 at 40° C./75% RH (wt %) |
|---|---|---|---|---|---|---|---|
| 1 | HPMC | 25 | 100 | 100 | <1 | 100 | <1 |
| 2 | PVP | 25 | 100 | 100 | <1 | 99 | 1 |
| C1 | HPMCAS-LF | 25 | 94 | <1 | >93 | <1 | >93 |

As the data show, the dispersions of Examples 1 and 2 formed with neutral polymers were much more chemically stable than the control dispersion C1 formed from HPMCAS. In fact, the dispersions of both Example 1 and Example 2 had a relative degree of improvement when compared with the control C1 of greater than 93 after only two weeks at 40° C./75% RH.

Example 4

In this example the dispersions of Examples 1 and 2 were tested to show that the dispersions provided concentration-enhancement of the drug in aqueous solution. For Control C2, the crystalline form of the drug alone was used without further processing. For this test, 7.2 mg of the dispersions of Examples 1 and 2, and 3.6 mg of Control C2, was added to respective microcentrifuge tubes. The tubes were placed in a 37° C. temperature-controlled bath, and 1.8 mL phosphate buffered saline (PBS) at pH 6.5 and 290 mOsm/kg was added to each. The samples were quickly mixed using a vortex mixer for about 60 seconds. The samples were centrifuged at 13,000 G at 37° C. for 1 minute. The resulting supernatant solutions were then sampled and diluted 1:6 (by volume) with methanol and then analyzed by high-performance liquid chromatography (HPLC). The contents of the tubes were mixed on the vortex mixer and allowed to stand undisturbed at 37° C. until the next sample was taken. Samples were collected at 4, 10, 20, 40, 90, and 1200 minutes. The results are shown in Table 3.

TABLE 3

| Example | Time (min) | [Drug 1] (µg/mL) | AUC (min*µg/mL) |
|---|---|---|---|
| 1 | 0 | 0 | 0 |
|  | 4 | 863 | 1,700 |
|  | 10 | 895 | 7,000 |
|  | 20 | 885 | 15,900 |
|  | 40 | 925 | 34,000 |
|  | 90 | 907 | 79,800 |
|  | 1200 | 926 | 1,097,100 |
| 2 | 0 | 0 | 0 |
|  | 4 | 923 | 1,800 |
|  | 10 | 928 | 7,400 |
|  | 20 | 913 | 16,600 |
|  | 40 | 947 | 35,200 |
|  | 90 | 927 | 82,100 |
|  | 1200 | 929 | 1,112,100 |
| C2 | 0 | 0 | 0 |
|  | 4 | 274 | 600 |
|  | 10 | 266 | 2,200 |
|  | 20 | 338 | 5,200 |
|  | 40 | 289 | 11,500 |
|  | 90 | 300 | 26,200 |
|  | 1200 | 303 | 360,800 |

The concentrations of Drug 1 obtained in these samples were used to determine the values of the maximum drug concentration between 0 and 90 minutes ($C_{max90}$) and the area under the curve from 0 to 90 minutes ($AUC_{90}$). The results are shown in Table 4.

TABLE 4

| Example | $C_{max90}$ (μg/mL) | $AUC_{90}$ (min*μg/mL) |
|---|---|---|
| 1 | 925 | 79,800 |
| 2 | 947 | 82,000 |
| C2 | 338 | 26,200 |

As can be seen from the data, the neutral polymers HPMC and PVP are both concentration-enhancing polymers in the dispersions of Examples 1 and 2. The Drug 1 and HPMC dispersion of Example 1 provided a $C_{max90}$ that was 2.7-fold, and an $AUC_{90}$ that was 3.0-fold, that of the control C2, while the PVP Drug 1 dispersion of Example 2 provided a $C_{max90}$ that was 2.8-fold, and an $AUC_{90}$ that was 3.1-fold, that of Control C2.

Example 5

The dispersion of Example 2 was stored for 1.5 years at room temperature (sealed), and then analyzed for Drug 1 potency by HPLC using the method described in Example 3. Results are shown in Table 5.

TABLE 5

| Ex. | Polymer | Drug 1 Conc. in the Dispersion (wt %) | Potency Before Storage (wt %) | Potency After 1.5 yrs at room temp./sealed (wt %) |
|---|---|---|---|---|
| 2 | PVP | 25 | 100 | 100 |

As the data show, the dispersion of Example 2 formed with PVP is chemically stable for extended duration under ambient conditions. This data is consistent with the results of accelerated storage stability tests for the dispersion of Example 2 (stored at 70° C. and 40° C./75% RH) shown in Example 3 (Table 2).

In vitro dissolution tests were performed for the dispersion of Example 2 before and after 1.5 years storage, using the procedure described in Example 4, with the following exceptions: 7.2 mg of the dispersion of Example 2 was used in initial dissolution tests, and 5.4 mg of Example 2 was used in dissolution tests after 1.5 years storage. The results are reported as a percentage of the total dose dissolved, to facilitate comparison. The results are shown in Table 6.

TABLE 6

| Time (min) | Initial Drug 1 Concentration (% dissolved) | Drug 1 Concentration After 1.5 yrs Storage (% dissolved) |
|---|---|---|
| 0 | 0 | 0 |
| 4 | 91 | 95 |
| 10 | 92 | 90 |
| 20 | 90 | 87 |
| 40 | 94 | 88 |
| 90 | 92 | 98 |
| 1200 | 92 | 89 |

As can be seen from the data, the dissolution performance of the dispersion of Example 2 was maintained after 1.5 years storage, indicating that the dispersion is physically stable and Drug 1 is chemically stable for at least 1.5 years at ambient conditions.

Examples 6-9

These examples disclose additional dispersions of Drug 1 prepared with the dispersion polymers HPMC, Eudragit® E100 (available from Rohm America Inc., Piscataway, N.J.), and an HPMC/Eudragit® E100 mixture. Eudragit E100 is a polymethacrylate polymer which contains basic groups. Examples 6 through 9 were prepared by spray-drying a solution of Drug 1 and polymer, as described in Example 1. For Example 6, the solution consisted of 1.25 wt % Drug 1 and 3.75 wt % HPMC in methanol/water (9/1, wt/wt). For Example 7, the solution consisted of 0.25 wt % Drug 1 and 4.75 wt % HPMC in methanol/water (9/1, wt/wt). For Example 8, the solution consisted of 1.25 wt % Drug 1 and 3.75 wt % Eudragit® E100 in methanol/acetone (1/1, wt/wt). For Example 9, the solution consisted of 1.25 wt % Drug 1 and 3.75 wt % HPMC/Eudragit (1/1 wt/wt) in methanol/water (9/1, wt/wt). The solution variables are summarized in Table 7.

For Control C3, the solution consisted of 1.25 wt % Drug 1 and 3.75 wt % HPMCAS-HF (HF grade) and methanol.

TABLE 7

| Ex. | Drug Mass (mg) | Drug No. | Polymer Mass (mg) | Polymer | Solvent Mass (g) | Solvent (wt/wt) |
|---|---|---|---|---|---|---|
| 6 | 50 | 1 | 150 | HPMC | 4 | methanol/water (9/1) |
| 7 | 50 | 1 | 950 | HPMC | 30 | methanol/water (9/1) |
| 8 | 125 | 1 | 375 | Eudragit | 10 | acetone/methanol (1/1) |
| 9 | 250 | 1 | 375/375 | HPMC/Eudragit | 20 | methanol/water (9/1) |
| C3 | 50 | 1 | 150 | HPMCAS-HF | 4 | methanol |

Example 10

In this example the chemical stability of the dispersions of Examples 6-9 was assessed. Dispersions were stored under elevated temperature and humidity conditions to increase the rate of physical changes occurring in the materials in order to simulate a longer storage interval in a typical storage environment. Drug purity was determined using HPLC as in Example 3. Results of purity analysis of the dispersions of Drug 1 after various storage intervals under various storage conditions are shown in Table 8.

TABLE 8

| Ex. | Aqueous-Soluble Polymer | Drug 1 Conc. in the Dispersion (wt %) | Potency Day 5 at 40° C./75 RH (wt %) | Degree of Degradation Day 5 (wt %) |
|---|---|---|---|---|
| 6 | HPMC | 25 | 97.3 | 2.7 |
| 7 | HPMC | 5 | 96.3 | 3.7 |
| 8 | Eudragit | 25 | 95.6 | 4.4 |
| 9 | HPMC/Eudragit | 25 | 97.9 | 2.1 |
| C3 | HPMCAS-HF | 25 | 60 | 40 |

The chemical stability of the acid-sensitive drug in dispersions of Examples 6-9 containing neutral polymers were all significantly improved in comparison to the stability of dispersions of the control C3 having the acidic polymer HPMCAS-HF. The relative degree of improvement compared with the control C3 was 14.8 for Example 6, 10.8 for Example 7, 9.1 for Example 8, and 19.0 for Example 9.

Examples 11-12

These examples disclose dispersions of Drug 1 in a neutral polymer with added buffer. Examples 11 and 12 were prepared with Drug 1, as described in Example 1, with the following exceptions: for Example 11, the solution to be spray-dried consisted of 1.25 wt % Drug 1, 0.513 wt % sodium acetate, and 3.75 wt % HPMC in methanol/water (9/1); and for Example 12, the solution consisted of 1.25 wt % Drug 1, 0.32 wt % sodium bicarbonate, and 3.75 wt % HPMC in methanol/water (9/1). The solution variables are summarized in Table 9.

TABLE 9

| Ex. | Drug Mass (mg) | Excipient | Excipient Mass (mg) | Polymer | Polymer Mass (mg) | Solvent (wt/wt) | Solvent Mass (g) |
|---|---|---|---|---|---|---|---|
| 11 | 125 | NaOAc | 51.4 | HPMC | 375 | MeOH/water (9/1) | 10 |
| 12 | 125 | NaHCO$_3$ | 32 | HPMC | 375 | MeOH/water (9/1) | 10 |

Example 13

Chemical stability of the acid-sensitive Drug 1 in the dispersions of Examples 11 and 12 containing buffers was determined by measuring the drug purity before and after storage for Examples 11 and 12, and Control C3. Dispersions were stored under elevated temperature and humidity conditions to increase the rate of changes occurring in the materials in order to simulate a longer storage interval in a typical storage environment. Drug purity was determined using HPLC. Results of analysis of dispersions of Examples 11 and 12 after five days at 40° C./75% RH are shown in Table 10.

TABLE 10

| Ex. | Aqueous-Soluble Polymer/Buffer | Drug 1 Conc. in the Dispersion (wt %) | Potency Day 5 at 40° C./75% RH (%) | Degree of Degradation (%) |
|---|---|---|---|---|
| 11 | HPMC/NaOAc | 23 | 97.79 | 2.2 |
| 12 | HPMC/NaHCO$_3$ | 24 | 95.65 | 4.3 |
| C3 | HPMCAS-HF | 25 | 60 | 40 |

The stability of the dispersions with neutral polymers containing buffers was significantly improved in comparison to the stability of the dispersion with HPMCAS-HF. The relative degree of improvement after five days compared with the Control C3 was 18.2 for Example 11, and 9.3 for Example 12.

Example 14

This example discloses dispersions of a second acid-sensitive drug, quinoxaline-2-carboxylic acid [1-benzyl-4-(4,4-difluoro-cyclohexyl)-2-hydroxy-4-hydroxycarbamoyl-butyl]-amide (Drug 2). For Example 14, a dispersion of Drug 2 and PVP was made by first preparing a solution containing 0.030 wt % drug and 0.27 wt % PVP in methanol/acetone (1/9 wt/wt), and then spraying the solution into a drying chamber using an atomizing spray nozzle in the manner described in Example 1.

For Control C4, a dispersion of Drug 2 and HPMCAS-LF was made by preparing a solution containing 0.030 wt % Drug 2 and 0.27 wt % HPMCAS-LF in acetone, and spray-drying as described above. For Control C5, a dispersion of Drug 2 with the acidic polymer hydroxypropyl methyl cellulose phthalate (HPMCP) was made by preparing a solution containing 0.030 wt % drug and 0.27 wt % HPMCP in acetone, and spray-drying as described above. Table 11 summarizes the solution variables.

TABLE 11

| Ex. | Drug Mass (mg) | Drug No. | Polymer Mass (mg) | Polymer | Solvent Mass (g) | Solvent (wt/wt) |
|---|---|---|---|---|---|---|
| 14 | 3 | 2 | 27 | PVP | 10 | methanol/acetone (1/9) |
| C4 | 3 | 2 | 27 | HPMCAS | 10 | acetone |
| C5 | 3 | 2 | 27 | HPMCP | 10 | acetone |

Example 15

This example assesses the stability of the dispersion of Example 14. The dispersions of Example 14 and Controls C4 and C5 were stored in controlled atmosphere chambers for 7 days at room temperature and 0% RH. Potencies of the dispersions before and after storage were determined using HPLC as in Example 3, with the following exceptions. An HP ODS Hypersil column was used with a mobile phase of 60 vol % 0.02M KH$_2$PO$_4$ (pH 3.0) and 40 vol % acetonitrile. UV detection was measured at 248 nm. The results are shown in Table 12 below.

TABLE 12

| Ex. | Aqueous-Soluble Polymer | Drug 2 Conc. In the Dispersion (wt %) | Potency Day 7 at room temp/0% RH (wt %) | Degree of Degradation (wt %) |
|---|---|---|---|---|
| 14 | PVP | 10 | 84 | 16 |
| C4 | HPMCAS-LF | 10 | 45 | 55 |
| C5 | HPMCP | 10 | 53 | 47 |

As the data show, the dispersion of Example 14 comprised of the acid-sensitive drug and neutral polymer PVP had improved chemical stability relative dispersions formed using either of the acidic polymers HPMCAS-LF or HPMCP. Example 14 had a relative degree of improvement when compared with control C4 of 3.4, and a relative degree of improvement when compared with control C5 of 2.9.

Example 16

This example measures' the concentration-enhancing properties of the PVP dispersion of Example 14. Dissolution tests were performed, as described in Example 4 with the following exceptions: the PBS solution contained 7.3 mM sodium taurocholic acid and 1.4 mM 1-palmitoyl-2-oleyl-sn-glycero-3-phosphocholine (model fasted duodenal (MFD) solution). 1.8 mg of dispersion was added to 1.8 mL of test media. For Control C6, 0.18 mg of the crystalline form of the Drug 2 alone was used without further processing and added to 1.8 mL of MFD solution. The results are shown in Table 13 below.

TABLE 13

| Example | Time (min) | Drug 2 (µg/mL) | AUC (min*□g/mL) |
|---|---|---|---|
| 14 | 0 | 0 | 0 |
|  | 4 | 57 | 100 |
|  | 10 | 55 | 500 |
|  | 20 | 55 | 1,000 |
|  | 40 | 52 | 2,100 |
|  | 90 | 54 | 4,700 |
| C6 | 0 | 0 | 0 |
|  | 4 | 2 | 0 |
|  | 10 | 4 | 0 |
|  | 20 | 4 | 100 |
|  | 40 | 4 | 100 |
|  | 90 | 7 | 400 |

The concentrations of Drug 2 obtained in these samples were used to determine the values of $C_{max90}$ and $AUC_{90}$. The results are shown in Table 14. As can be seen from the data, dispersions of Example 14 provided an 8-fold improvement in $C_{max90}$ and a 12-fold improvement in $AUC_{90}$.

TABLE 14

| Example | $C_{max90}$ (µg/mL) | $AUC_{90}$ (min*µg/mL) |
|---|---|---|
| 14 | 57 | 4700 |
| C6 | 7 | 400 |

Examples 17-18

These examples disclose dispersions of a third acid-sensitive drug, quinoxaline-2-carboxylic acid [1-benzyl-4-(4,4-difluoro-1-hydroxy-cyclohexyl)-2-hydroxy-4-hydroxycarbamoyl-butyl]-amide (Drug 3). For Example 17, a dispersion of Drug 3 and HPMC was made by preparing a solution containing 0.050 wt % Drug 3 and 0.45 wt % HPMC in methanol, and spraying the solution into a drying chamber using an atomizing spray nozzle, as described in Example 1. For Example 18, a dispersion of Drug 3 with PVP was made by preparing a solution containing 0.030 wt % Drug 3 and 0.27 wt % PVP in methanol/acetone (1/9 wt/wt), and spray-drying as described above.

For Control C7, a dispersion of Drug 3 and HPMCAS-LF was made by preparing a solution containing 0.030 wt % drug and 0.27 wt % HPMCAS-LF in acetone, and spray-drying as described above. For Control C8, a dispersion of Drug 3 and HPMCP was made by preparing a solution containing 0.030 wt % drug and 0.27 wt % HPMCP in acetone, and spray-drying as described above. Table 15 summarizes the spray-drying variables.

TABLE 15

| Ex. | Drug Mass (mg) | Drug No. | Polymer Mass (mg) | Polymer | Solvent Mass (g) | Solvent (wt/wt) |
|---|---|---|---|---|---|---|
| 17 | 5 | 3 | 45 | HPMC | 10 | methanol |
| 18 | 3 | 3 | 27 | PVP | 10 | acetone/methanol (9/1) |
| C7 | 3 | 3 | 27 | HPMCAS-LF | 10 | acetone |
| C8 | 3 | 3 | 27 | HPMCP | 10 | acetone |

Example 19

This example demonstrates the relative chemical stability of the dispersions of Examples 17 and 18. The dispersions of Examples 17 and 18, and Controls C7 and C8, were placed in controlled atmosphere chambers for 6 days at room temperature and 0% RH (the HPMC dispersion of Example 16 was stored for 4 days). Potencies of the dispersions before and after storage were determined using HPLC, using the method described in Example 15 above. The results are shown in Table 16 below.

TABLE 16

| Ex. | Aqueous-Soluble Polymer | Drug 3 Conc. in the Dispersion (wt %) | Potency Day 6 at room temp/0% RH (wt %) | Degree of Degradation (wt %) |
|---|---|---|---|---|
| 17 | HPMC | 10 | 92 (4 days) | 8 |
| 18 | PVP | 10 | 95 | 5 |
| C7 | HPMCAS-LF | 10 | 46 | 54 |
| C8 | HPMCP | 10 | 56 | 44 |

The data show that dispersions of the acid-sensitive drug and neutral polymers were more stable than dispersions formed with the acidic polymers HPMCAS-LF and HPMCP. The dispersion of Example 18 had a relative degree of improvement of 10.8 when compared with the control C7, and 8.8 when compared with the control C8.

Example 20

This example demonstrates the concentration enhancement provided by the dispersion of Example 18. Dissolution tests were performed, as described in Example 4 with the following exceptions: samples were tested in MFD Solution, and 1.8 mg of dispersion was added to 1.8 mLs of MFD Solution. Control C9 was simply 0.18 mg of the crystalline Drug 3 alone add to 1.8 mL of MFD solution. The results are shown in Table 17 below.

TABLE 17

| Example | Time (min) | Drug 3 (µg/mL) | AUC (min*□g/mL) |
|---|---|---|---|
| 17 | 0 | 0 | 0 |
|  | 4 | 88 | 200 |
|  | 10 | 83 | 700 |
|  | 20 | 80 | 1,500 |
|  | 40 | 79 | 3,100 |
|  | 90 | 77 | 7,000 |
| C9 | 0 | 0 | 0 |
|  | 4 | 4 | 0 |
|  | 10 | 6 | 0 |
|  | 20 | 8 | 100 |
|  | 40 | 11 | 300 |
|  | 90 | 13 | 900 |

The concentrations of Drug 3 obtained in these samples were used to determine the values of $C_{max90}$ and $AUC_{90}$. The results are shown in Table 18.

TABLE 18

| Example | $C_{max90}$ (μg/mL) | $AUC_{90}$ (min*μg/mL) |
|---|---|---|
| 18 | 88 | 7100 |
| C9 | 13 | 900 |

As can be seen from the data, dispersions of Drug 3, an acid-sensitive drug, and the neutral polymer, PVP, provided concentration-enhancement in an aqueous environment of use. The dispersion of Example 18 provided a $C_{max90}$ that was 6.8-fold, and an $AUC_{90}$ that was 7.9-fold that of the control C9.

Examples 21-29

These examples disclose dispersions formed from various low-solubility drugs and neutral amphiphilic, hydroxyl-functional vinyl copolymers, particularly vinyl acetate/vinyl alcohol copolymers (hereinafter "VAVAC"). For Examples 21 to 24, the dispersions were made using Drug 1. For Examples 25 to 27, the dispersions were made using 5-chloro-1H-indole-2-carboxylic acid [(1S)-benzyl-3-((3R,4S)-dihydroxypyrrolidin-1-yl)-(2R)-hydroxy-3-oxypropyl] amide ("Drug 4"). For Examples 28 to 29, the dispersions were made using (+)-N-{3-[3-(4-fluorophenoxy)phenyl]-2-cyclopenten-1-yl}-N-hydroxyurea ("Drug 5").

Several different grades of VAVAC were used. For Examples 23, 25 and 28, the VAVAC, referred to herein as "VAVAC-20%," was 80% hydrolyzed (meaning that about 20% of the vinyl repeat units were acetylated), and had an average molecular weight of 9,000-10,000 daltons. The VAVAC-20% was supplied by Aldrich Chemical Company of lot #36,062-7.

For Examples 21, 26 and 29, the VAVAC, referred to herein as "VAVAC-12%," was approximately 88% hydrolyzed (approximately 11-13% of the repeat units were acetylated), and had an average molecular weight of 13,000-23,000 daltons. VAVAC-12% was supplied by Aldrich Chemical Company, lot #36,317-0.

For Examples 22, 24 and 27, the VAVAC, referred to herein as "VAVAC-2%," was 98% hydrolyzed (approximately 2% of the repeat units were acetylated) and had an average molecular weight of 13,000-23,000 daltons. VAVAC-2% was supplied by Aldrich Chemical Company, lot #34,840-6.

To form the dispersions of Examples 21-29, solutions containing drug and polymer in a solvent were spray-dried by pumping each solution into a "mini" spray-drier apparatus as described in Example 1.

Table 19 summarizes the variables for the solutions of Examples 21-29.

TABLE 19

| Ex. | Drug | Drug Mass (mg) | Drug Conc.* (%) | Polymer | Polymer Mass (mg) | Spray Solvent (wt/wt) | Solvent Mass (g) |
|---|---|---|---|---|---|---|---|
| 21 | 1 | 62 | 25 | VAVAC-12% | 186 | MeOH/H20 (4/1) | 18 |
| 22 | 1 | 692 | 75 | VAVAC-2% | 231 | MeOH/H20 (1/1) | 50 |
| 23 | 1 | 664 | 50 | VAVAC-20% | 664 | MeOH/H20 (4/1) | 105 |
| 24 | 1 | 522 | 25 | VAVAC-2% | 1565 | MeOH/H20 (4/1) | 110 |
| 25 | 4 | 110 | 25 | VAVAC-20% | 330 | MeOH/H20 (4/1) | 33.8 |
| 26 | 4 | 126 | 25 | VAVAC-12% | 376 | MeOH/H20 (1.8/1) | 50 |
| 27 | 4 | 78 | 25 | VAVAC-2% | 233 | MeOH/H20 (1/1) | 20.6 |
| 28 | 5 | 37 | 10 | VAVAC-20% | 330 | MeOH/H20 (4/1) | 33.8 |
| 29 | 5 | 42 | 10 | VAVAC-12% | 376 | MeOH/H20 (1.8/1) | 50 |

*Drug concentration in the final dispersion.

Example 30

In this example the chemical stability of the dispersions of Examples 23 and 24 was assessed. The dispersions were stored for three weeks at 40° C. and 75% RH, then analyzed for Drug 1 potency by HPLC using the method described in Example 3. Results are shown in Table 20, as are the results for Control C1, a dispersion of Drug 1 and the acidic polymer HPMCAS-LF (prepared in Example 1).

TABLE 20

| Ex. | Polymer | Drug 1 Conc. in the Dispersion (wt %) | Pot. Before Storage (%) | Potency After 3 weeks @ 40° C./75 RH (%) | Degree of Degradation @ 3 wks (wt %) | Relative Degree of Improvement |
|---|---|---|---|---|---|---|
| 23 | VAVAC-20% | 50 | 98 | 97 | 3 | >33 |
| 24 | VAVAC-2% | 25 | 98 | 96 | 4 | >25 |
| C1 | HPMCAS-LF | 25 | 94 | <1* | >99* | — |

*Values were obtained after 2 weeks.

As the data show, the dispersions of Examples 23 and 24 formed with VAVAC have improved chemical stability when compared with Control C1, showing a relative degree of improvement of >33 for Example 23 and >25 for Example 24.

Example 31

In vitro dissolution tests were performed for Examples 21-24, using the procedure described in Example 4, with the following exceptions: 14.4 mg of the dispersions of Example 21, 4.8 mg of the dispersion Example 22, 7.2 mg of the dispersion of Example 23, and 14.4 mg of the dispersion of Example 24 were added to respective tubes. 1.8 mL of PBS was added to each tube to achieve a theoretical total Drug 1 concentration of approximately 2000 μg/mL if all of the drug were to dissolve completely. For comparison, a Control C10 of 1.8 mg of crystalline Drug 1 was added to 1.8 mL of PBS. The results are shown in Table 21.

TABLE 21

| Example | Time (min) | Drug 1 Concentration (µg/mL) | AUC (min*µg/mL) |
|---|---|---|---|
| 21 | 0 | 0 | 0 |
|  | 4 | 1554 | 3,100 |
|  | 10 | 1860 | 13,300 |
|  | 20 | 1474 | 30,000 |
|  | 40 | 744 | 52,200 |
|  | 90 | 685 | 87,900 |
|  | 180 | 632 | 147,200 |
|  | 1200 | 580 | 790,000 |
| 22 | 0 | 0 | 0 |
|  | 4 | 809 | 1,600 |
|  | 10 | 1019 | 7,100 |
|  | 20 | 1162 | 18,000 |
|  | 40 | 1211 | 41,700 |
|  | 90 | 1273 | 103,835 |
|  | 1200 | 1117 | 1,430,292 |
| 23 | 0 | 0 | 0 |
|  | 4 | 1698 | 3,400 |
|  | 10 | 1685 | 13,500 |
|  | 20 | 1076 | 27,400 |
|  | 40 | 608 | 44,200 |
|  | 90 | 552 | 73,200 |
|  | 1200 | 499 | 656,500 |
| 24 | 0 | 0 | 0 |
|  | 4 | 1081 | 2,200 |
|  | 10 | 1279 | 9,200 |
|  | 20 | 1334 | 22,300 |
|  | 40 | 1342 | 49,100 |
|  | 90 | 662 | 99,200 |
|  | 1200 | 478 | 731,900 |
| C10 | 0 | 0 | 0 |
|  | 4 | 241 | 500 |
|  | 10 | 256 | 2,000 |
|  | 20 | 299 | 4,700 |
|  | 40 | 260 | 10,300 |
|  | 90 | 295 | 25,500 |
|  | 180 | 298 | 49,400 |
|  | 1200 | 313 | 361,000 |

The concentrations of Drug 1 obtained in these samples were used to determine the values of $C_{max90}$ and $AUC_{90}$. The results are shown below in Table 22.

TABLE 22

| Example | $C_{max90}$ (µg/mL) | $AUC_{90}$ (min*µg/mL) |
|---|---|---|
| 21 | 1860 | 87,900 |
| 22 | 1273 | 103,800 |
| 23 | 1698 | 73,200 |
| 24 | 1342 | 99,200 |
| C10 | 299 | 25,500 |

As can be seen from the data, the dispersions of Examples 21-24 provided concentration-enhancement over that of Control C10 (crystalline Drug 1 alone). Example 21 provided a $C_{max90}$ that was 6.2-fold and an $AUC_{90}$ that was 3.4-fold that of Control C10; Example 22 provided a $C_{max90}$ that was 4.3-fold, and an $AUC_{90}$ that was 4.1-fold that of the Control C10; Example 23 provided a $C_{max90}$ that was 5.7-fold and an $AUC_{90}$ that was 2.9-fold that of Control C10; and Example 24 provided a $C_{max90}$ that was 4.5-fold and an $AUC_{90}$ that was 3.9-fold that of Control C10.

Example 32

This example demonstrates a composition comprising a dispersion of an acid-sensitive drug and a neutral polymer mixed with an acidic concentration-enhancing polymer, namely HPMCAS-HF. Example 32 was prepared by mixing the dispersion of Example 21 with HPMCAS-HF. An in vitro dissolution test was performed using the procedure described in Example 4, with the following exceptions: 14.4 mg of the dispersion of Example 21 and 14.4 mg of HPMCAS-HF were added to 1.8 mL of PBS solution for a total theoretical Drug 1 concentration of approximately 2000 µg/mL if all of the drug were to dissolve completely. The results are shown in Table 23.

TABLE 23

| Example | Time (min) | Drug 1 Concentration (µg/mL) | AUC (min*µg/mL) |
|---|---|---|---|
| 32 | 0 | 0 | 0 |
|  | 4 | 1365 | 2,700 |
|  | 10 | 1441 | 11,100 |
|  | 20 | 1399 | 25,300 |
|  | 40 | 1577 | 55,100 |
|  | 90 | 1541 | 133,100 |
|  | 180 | 1648 | 276,600 |
|  | 1200 | 1863 | 2,021,700 |

The concentrations of Drug 1 obtained in these samples were used to determine the values of $C_{max90}$ and $AUC_{90}$. The results are shown below in Table 24.

TABLE 24

| Example | $C_{max90}$ (µg/mL) | $AUC_{90}$ (min*µg/mL) |
|---|---|---|
| 32 | 1577 | 133,100 |
| 21 | 1860 | 87,900 |

As can be seen from the data, the composition of Example 32 (i.e., the dispersion of Example 21 and HPMCAS) had an improved $AUC_{90}$ relative to the dispersion of Example 21 alone. Results of dissolution tests for Example 21 were shown previously in Table 22, however, they are shown again in Table 24 for comparison.

Example 33

In vitro dissolution tests were performed for Examples 25-27 using the procedure described in Example 4, with the following exceptions: 14.4 mg each of the dispersions of Examples 25-27 were added to separate, respective centrifuge tubes. 1.8 mL PBS was added to each tube. For comparison, Control C11 was prepared consisting of 3.6 mg of crystalline Drug 4 added to 1.8 mL PBS. Drug 4 concentration in the samples was determined using HPLC. A Zorbax SB $C_{18}$ HPLC column was used with a mobile phase of 35 vol. % water and 65 vol. % methanol. UV detection was measured at 297 nm. The results are shown in Table 25.

TABLE 25

| Example | Time (min) | [Drug 4] (µg/mL) | AUC (min*µg/mL) |
|---|---|---|---|
| 25 | 0 | 0 | 0 |
|  | 4 | 1580 | 3,200 |
|  | 10 | 1581 | 12,600 |
|  | 20 | 1570 | 28,400 |
|  | 40 | 1594 | 60,000 |
|  | 90 | 1476 | 136,000 |
|  | 1200 | 248 | 1,093,600 |
| 26 | 0 | 0 | 0 |
|  | 4 | 1957 | 3,900 |

TABLE 25-continued

| Example | Time (min) | [Drug 4] (µg/mL) | AUC (min*µg/mL) |
|---|---|---|---|
| | 10 | 1993 | 15,800 |
| | 20 | 1948 | 35,500 |
| | 40 | 1980 | 74,700 |
| | 90 | 1959 | 173,200 |
| | 1200 | 163 | 1,350,900 |
| 27 | 0 | 0 | 0 |
| | 4 | 735 | 1,500 |
| | 10 | 733 | 5,900 |
| | 20 | 707 | 13,100 |
| | 40 | 691 | 27,100 |
| | 90 | 676 | 61,200 |
| | 1200 | 147 | 518,000 |
| C11 | 0 | 0 | 0 |
| | 4 | 131 | 300 |
| | 10 | 114 | 1,000 |
| | 20 | 124 | 2,200 |
| | 40 | 107 | 4,500 |
| | 90 | 126 | 10,300 |
| | 1200 | 72 | 120,200 |

The concentrations of Drug 4 obtained in these samples were used to determine the values of $C_{max90}$ and $AUC_{90}$. The results are shown below in Table 26.

TABLE 26

| Example | $C_{max90}$ (µg/mL) | $AUC_{90}$ (min*µg/mL) |
|---|---|---|
| 25 | 1594 | 136,800 |
| 26 | 1993 | 173,200 |
| 27 | 735 | 61,200 |
| C11 | 131 | 10,300 |

As can be seen from the data, the dispersions of Examples 25-27 provided concentration-enhancement over that of Control C11, the crystalline Drug 4 alone. The dispersion of Example 25 provided a $C_{max90}$ that was 12-fold and an $AUC_{90}$ that was 13-fold that of Control C11; Example 26 provided a $C_{max90}$ that was 15-fold and an $AUC_{90}$ that was 17-fold that provided by Control C11; and Example 27 provided a $C_{max90}$ that was 6-fold, and an $AUC_{90}$ that was 6-fold that of Control C11.

Example 34

In vitro dissolution tests were performed for Examples 28-29, using the procedure described in Example 4, with the following exceptions: 9 mg each of the dispersions of Examples 28-29 were added to separate respective centrifuge tubes. 1.8 mL of MFD solution was then added to each tube. For comparison, Control C12 was prepared consisting of 0.36 mg of crystalline Drug 5 added to 1.8 mL of MFD solution for a total theoretical concentration of 200 µg/mL if all of the drug dissolved. Drug 5 concentration in the samples was determined using HPLC. A Waters Symmetry $C_{18}$ HPLC column was used with a mobile phase of 50 vol. % (0.3 vol. % glacial acetic acid, 0.2 vol. % TEA in water) and 50 vol. % acetonitrile. UV detection was measured at 260 nm. The results are shown in Table 27.

TABLE 27

| Example | Time (min) | Drug 5 Concentration (µg/mL) | AUC (min*µg/mL) |
|---|---|---|---|
| 28 | 0 | 0 | 0 |
| | 4 | 211 | 400 |
| | 10 | 180 | 1,600 |
| | 20 | 168 | 3,300 |
| | 40 | 155 | 6,600 |
| | 90 | 144 | 14,000 |
| | 1200 | 139 | 171,100 |
| 29 | 0 | 0 | 0 |
| | 4 | 210 | 400 |
| | 10 | 192 | 1,600 |
| | 20 | 186 | 3,500 |
| | 40 | 175 | 7,100 |
| | 90 | 169 | 15,700 |
| | 1200 | 155 | 195,500 |
| C12 | 0 | 0 | 0 |
| | 4 | 9 | 0 |
| | 10 | 15 | 100 |
| | 20 | 21 | 300 |
| | 40 | 27 | 800 |
| | 90 | 32 | 2,200 |
| | 1200 | 42 | 43,300 |

The concentrations of Drug 5 obtained in these samples were used to determine the values of $C_{max90}$ and $AUC_{90}$. The results are shown below in Table 28. While the amount of Drug 5 used in the Control C12 was less than the amount of Drug 5 in the test compositions of Examples 28 and 29, nevertheless a sufficient amount of Drug 5 in excess of the solubility of Drug 5 was used in Control C12 in order to provide an accurate measure of the performance of Examples 28 and 29 relative to crystalline drug.

TABLE 28

| Example | $C_{max90}$ (µg/mL) | $AUC_{90}$ (min*µg/mL) |
|---|---|---|
| 28 | 211 | 14,000 |
| 29 | 210 | 15,700 |
| C12 | 32 | 2,200 |

As can be seen from the data, the dispersions of Examples 28-29 provided concentration-enhancement over that of crystalline Drug 5 alone. Example 28 provided a $C_{max90}$ that was 6.6-fold and an $AUC_{90}$ that was 6.4-fold that of Control C12; and Example 29 provided a $C_{max90}$ that was 6.6-fold and an $AUC_{90}$ that was 7.1-fold that provided by Control C12.

Examples 35-38

Examples 35 and 36 were dispersions of Drug 4 prepared with the dispersion polymers PVP and HPMC respectively. For Examples 37 and 38, dispersions of Drug 5 and the polymers PVP and HPMC were prepared. To form the dispersions of Examples 35-38, solutions containing drug and polymer in a solvent were spray-dried by pumping each solution into a "mini" spray-drier apparatus as described in Example 1. Table 29 summaries the variables for the solutions used to prepare Examples 35-38.

TABLE 29

| Ex. | Drug | Drug Mass (mg) | Drug Conc.* (%) | Polymer | Polymer Mass (mg) | Spray Solvent (wt/wt) | Solvent Mass (g) |
|---|---|---|---|---|---|---|---|
| 35 | 4 | 50 | 25 | PVP | 150 | acetone | 15 |
| 36 | 4 | 50 | 25 | HPMC | 150 | MeOH/water (9/1) | 15 |
| 37 | 5 | 50 | 10 | PVP | 450 | Acetone | 80 |
| 38 | 5 | 50 | 10 | HPMC | 450 | MeOH/acetone (1/1) | 80 |

*Drug concentration in the final dispersion

Example 39

In vitro dissolution tests were performed for Examples 35-38, using the procedures described in Example 4, with the following exceptions: 14.4 mg each of Example 35 and 36 were added to separate respective test tubes to which 1.8 mL of PBS solution was added, so that the total theoretical Drug 4 concentration was approximately 200 µg/mL if all of Drug 4 were to dissolve completely; 3.6 mg each of Examples 37 and 38 were added in separate respective test tubes to 1.8 mL of MFD solution, to provide a total theoretical Drug 5 concentration of approximately 20 µg/mL if all of Drug 5 were to dissolve completely. Drug 4 concentration in the samples was determined as in Example 33. Drug 5 concentration in the samples was determined as in Example 34. The results are shown in Table 30.

TABLE 30

| Example | Time (min) | [Drug 4] (µg/mL) | AUC (min*µg/mL) |
|---|---|---|---|
| 35 | 0 | 0 | 0 |
|  | 4 | 771 | 1,500 |
|  | 10 | 773 | 6,200 |
|  | 20 | 781 | 13,900 |
|  | 40 | 753 | 29,300 |
|  | 90 | 703 | 65,700 |
|  | 1200 | 540 | 755,500 |
| 36 | 0 | 0 | 0 |
|  | 4 | 420 | 1,000 |
|  | 10 | 422 | 3,400 |
|  | 20 | 429 | 7,600 |
|  | 40 | 447 | 16,400 |
|  | 90 | 447 | 38,700 |
|  | 1200 | 319 | 463,900 |
| 37 | 0 | 0 | 0 |
|  | 4 | 121 | 200 |
|  | 10 | 113 | 900 |
|  | 20 | 111 | 7,100 |
|  | 40 | 111 | 4,300 |
|  | 90 | 120 | 10,100 |
|  | 1200 | 106 | 135,500 |
| 38 | 0 | 0 | 0 |
|  | 4 | 429 | 900 |
|  | 10 | 347 | 3,200 |
|  | 20 | 280 | 6,300 |
|  | 40 | 229 | 11,400 |
|  | 90 | 257 | 23,600 |
|  | 1200 | 164 | 237,200 |

The concentrations of Drug 4 and Drug 5 obtained in these samples were used to determine the values of $C_{max90}$ and $AUC_{90}$. The results for dispersions containing Drug 4 are shown below in Table 31, and for dispersions containing Drug 5 in Table 32.

TABLE 31

| Example | $C_{max90}$ | $AUC_{90}$ |
|---|---|---|
| 35 | 781 | 65,700 |
| 36 | 447 | 38,700 |
| C11 | 131 | 10,300 |

TABLE 32

| Example | $C_{max90}$ | $AUC_{90}$ |
|---|---|---|
| 37 | 121 | 10,100 |
| 38 | 429 | 23,600 |
| C12 | 32 | 2,200 |

As can been seen from the data, the dispersions of Examples 35 and 36 provided superior concentration-enhancement relative to the Control C11 and Examples 37 and 38 provided superior concentration-enhancement relative to the Control C12.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method of making a solid amorphous dispersion pharmaceutical composition, the method comprising:
   (i) providing a drug to be in the pharmaceutical composition, the drug having a solubility in aqueous solution of up to about 1 to 2 mg/ml at any pH from 1 to 8;
   (ii) determining whether the drug is acid sensitive by determining whether, when said drug is administered to an acidic aqueous solution having a pH from 1-4, the concentration of said drug decreases by at least 1 wt % within 24 hours after administration;
   (iii) combining the drug, if determined to be acid sensitive, with a solvent, a neutral concentration-enhancing dispersion polymer selected from the group consisting of hydroxypropyl methylcellulose (HPMC) and hydroxypropyl methylcellulose acetate (HPMCA) and with an excipient selected from the group consisting of a base and a basic buffer, to form a solution; and
   (iv) spray drying the solution to form a substantially homogeneous solid amorphous dispersion that provides improved chemical stability relative to a first control composition comprised of either an equivalent quantity of a dispersion of said drug and an acidic polymer or of an equivalent quantity of a dispersion of said drug and said neutral polymer but free from said base and said buffer.

2. The method of claim 1 wherein the drug is determined to have a degree of degradation of at least 0.01% when the drug is stored in said control acidic dispersion for a period of six months at 40° C. and 75% relative humidity.

3. The method of claim 2 wherein the drug is determined to have a degree of degradation of at least 0.1% when in the control acidic dispersion.

4. The method of claim 1 wherein said drug is determined to have a relative degree of improvement in chemical stability of at least 1.25 when spray dried to form the solid amorphous dispersion formed by the method of claim 1.

5. The method of claim 4 wherein said relative degree of improvement is at least 3.

6. The method of claim 1 wherein said drug in said composition has a relative degree of improvement in chemical stability of at least 1.25 when stored at 40° C. and 75% relative humidity for a period of six months.

7. The method of claim 1 wherein said drug has a dose-to-aqueous solubility ratio of at least 10 mL.

8. The method of claim 1 wherein said dispersion polymer is present in a sufficient amount so that said dispersion provides a relative bioavailability that is at least 1.25 relative to a second control composition comprising an equivalent quantity of said acid sensitive drug and is free from said polymer.

9. The method of claim 8 wherein said relative bioavailability is at least 2 relative to said second control composition.

10. The method of claim 1 wherein said basic buffer is selected from the group consisting of sodium acetate, ammonium acetate, sodium carbonate, sodium bicarbonate, disodium hydrogen phosphate, trisodium phosphate, and mixtures thereof.

11. The method of claim 1 wherein said basic buffer comprises at least 10 wt % of said dispersion.

12. The method of claim 11 wherein the formed solid amorphous dispersion has a pH from about 6 to about 10.

13. The method of claim 1 wherein when the composition formed includes an excipient which is a base, the solid amorphous dispersion formed has a pH of from about 6 to about 10.

14. The method of claim 1 further comprising making the solid amorphous dispersion to have a glass transition temperature intermediate between that of pure amorphous drug and pure polymer.

15. A process for making a solid amorphous dispersion comprising:
   (a) providing a drug having a solubility in aqueous solution of up to about 1 to 2 mg/ml at any pH from 1 to 8
   (a) determining whether the drug is acid sensitive based on whether, when the drug is administered to an acidic aqueous solution having a pH from 1-4, the concentration of the drug in the solution decreases by about 1 wt % within 24 hours after administration;
   (b) mixing the drug, that is determined to be acid sensitive with
      (i) a solvent;
      (ii) a neutral concentration-enhancing dispersion polymer; and
      (iii) an excipient selected from the group consisting of a base and a basic buffer to form a solution of the acid sensitive drug, the dispersion polymer and the excipient;
   (c) breaking up the solution into small droplets, wherein said droplets range in size from 1 to 500 μm;
   (d) directing said droplets and a drying gas into a drying chamber to cause evaporation of a sufficient amount of the solvent from said droplets to cause solidification of said droplets in less than 100 seconds to form said solid amorphous dispersion;
   wherein said solid amorphous dispersion is substantially homogeneous; and
   wherein said composition provides improved chemical stability relative to a control composition comprised of either an equivalent quantity of a dispersion of said drug and an acidic polymer or of an equivalent quantity of a dispersion of said drug and said neutral polymer but free from said base and said buffer.

16. A method for making a solid amorphous dispersion pharmaceutical composition comprising:
   (a) determining that a drug is acid-sensitive such that degradation occurs when dispersed in a pharmaceutical composition;
   (b) mixing the acid-sensitive drug with a neutral concentration-enhancing dispersion polymer selected from the group consisting of HPMC and HPMCA, a solvent, and an excipient selected from the group consisting of a base and a buffer to form a solution;
   (c) spray-drying the solution to form a solid amorphous dispersion that is substantially homogeneous;
   (d) wherein the acid-sensitive drug has a minimum solubility in aqueous solution of less than 1 mg/ml at a pH of from about 1 to about 8 when in the absence of the polymer; and
   (e) wherein the solid amorphous dispersion pharmaceutical composition provides improved chemical stability relative to a control composition comprised of either an equivalent quantity of a dispersion of the acid-sensitive drug and an acidic polymer or of an equivalent quantity of a dispersion of the drug and the neutral polymer but free from the base and the buffer.

17. The method of claim 16 wherein the step of determining that a drug is acid-sensitive further comprises administering a first portion of the drug to an acidic aqueous solution having a pH from 1-4, and determining the drug is acid sensitive when the concentration of the drug decreases by at least 1 wt % within 24 hours after administration.

18. The method of claim 16 wherein the spray drying further comprises breaking up the solution into small droplets, wherein said droplets range in size from 1 to 500 μm.

19. The method of claim 18 wherein the spray drying further comprises directing the droplets and a drying gas into a drying chamber to cause evaporation of a sufficient amount of solvent from the droplets to cause solidification of the droplets in less than 100 seconds to form the solid amorphous dispersion.

* * * * *